US011384138B2

(12) United States Patent
Anderson et al.

(10) Patent No.: US 11,384,138 B2
(45) Date of Patent: Jul. 12, 2022

(54) METHODS OF GENERATING ANTIBODIES

(71) Applicant: Rutgers, The State University of New Jersey, New Brunswick, NJ (US)

(72) Inventors: Stephen Anderson, Princeton, NJ (US); Elliot Campbell, Somerset, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 706 days.

(21) Appl. No.: 15/753,321

(22) PCT Filed: Aug. 18, 2016

(86) PCT No.: PCT/US2016/047620
§ 371 (c)(1),
(2) Date: Feb. 18, 2018

(87) PCT Pub. No.: WO2017/031353
PCT Pub. Date: Feb. 23, 2017

(65) Prior Publication Data

US 2018/0244759 A1 Aug. 30, 2018

Related U.S. Application Data

(60) Provisional application No. 62/207,022, filed on Aug. 19, 2015.

(51) Int. Cl.

| | |
|---|---|
| ***C07K 16/10*** | (2006.01) |
| ***C07K 16/20*** | (2006.01) |
| ***C07K 16/38*** | (2006.01) |
| ***C07K 16/00*** | (2006.01) |
| ***A61K 9/00*** | (2006.01) |
| ***C07K 1/04*** | (2006.01) |
| ***C07K 16/06*** | (2006.01) |

(52) U.S. Cl.
CPC ........ *C07K 16/1045* (2013.01); *A61K 9/0019* (2013.01); *C07K 1/047* (2013.01); *C07K 16/00* (2013.01); *C07K 16/065* (2013.01); *C07K 16/205* (2013.01); *C07K 16/38* (2013.01); *C07K 2317/14* (2013.01); *C07K 2317/33* (2013.01); *C07K 2317/92* (2013.01); *Y02A 50/30* (2018.01)

(58) Field of Classification Search
None
See application file for complete search history.

(56) References Cited

U.S. PATENT DOCUMENTS

| | | | | |
|---|---|---|---|---|
| 8,501,193 | B1 | 8/2013 | Drevet et al. | |
| 2002/0183484 | A1 | 12/2002 | Torres | |
| 2011/0301101 | A1* | 12/2011 | Xia .......................... | A61P 31/14 514/21.3 |
| 2015/0037371 | A1 | 2/2015 | Landry | |

FOREIGN PATENT DOCUMENTS

| | | | | |
|---|---|---|---|---|
| JP | 2010-510994 | A | 4/2010 | |
| WO | 2005097179 | A2 | 10/2005 | |
| WO | WO-2006044410 | A2 * | 4/2006 | ........... C07K 14/005 |
| WO | 2008/064488 | A1 | 6/2008 | |

OTHER PUBLICATIONS

Hemmer et al. International Immunology, 12, 3, 2000, 375-383.*
Yang et al. Journal of Biomolecular Structure and Dynamics, 2013 vol. 31, No. 9, 982-992.*
Mohan et al. Biochemistry 2009, 48, 1390-1398.*
Carmicle et al.,"Antigen Three-dimensional Structure Guides the Processing and Presentation of Helper T-cell Epitopes", Molecular Immunology, vol. 44, pp. 1159-1168, (2007).
Creighton, Thomas E., "Proteins: Structures and Molecular Principles." Proteins: Structures and Molecular Principles, W. H. Freeman and Company, 1984, pp. 286-295.
D. Mirano-Bascos et al: "Influence of Disulfide-Stabilized Structure on the Specificity of Helper T-Cell and Antibody Responses to HIV Envelope Glycoprotein gp120", Journal of Virology., vol. 84, No. 7, Jan. 20, 2010 (Jan. 20, 2010), pp. 3303-3311, XP055309173, US ISSN: 0022-538X, DOI: 10.1128/JVI.02242-09; p. 3307-p. 3309.
Delamarre et al., "Differential Lysosomal Proteolysis in Antigen-Presenting Cells Determines Antigen Fate", Science, vol. 307, pp. 1630-1635, (2005).
Delamarre et al., "Enhancing Immunogenicity by Limiting Susceptibility to Lysosomal Proteolysis", The Journal of Experimental Medicine, vol. 203, No. 9, pp. 2049-2055, (2006).
Dill et al., "The Protein-Folding Problem, 50 Years on", Science, vol. 338, pp. 1042-1046, (2012).
Fersht et al., "Protein Folding and Unfolding at Atomic Resolution", Cell, vol. 108, pp. 573-582, (2002).
Hartman et al., "A Reductionist Cell-free Major Histocompatibility Complex Class II Antigen Processing System Identifies Immunodominant Epitopes", Nature Medicine, vol. 16, No. 11, pp. 1333-1341, (2010).
Hastings et al., "GILT: Shaping the MHC Class II-restricted Peptidome and CD4+ T Cell-mediated Immunity", Frontiers in Immunology, vol. 4, Article 429, pp. 1-7, (2013).
Hong et al., "Methods for Measuring the Thermodynamic Stability of Membrane Proteins", Methods in Enzymology, vol. 455, pp. 213-236, (2009).

(Continued)

*Primary Examiner* — Michael L Borin
(74) *Attorney, Agent, or Firm* — McNeill Baur PLLC

(57) ABSTRACT

The invention describes a method of generating antibodies to a mixture of peptidogenic proteins wherein the peptidogenic protein has altered conformational dynamics as compared to a starting protein and wherein the peptidogenic protein has a similar conformation to the starting protein. The peptidogenic proteins can be used to induce an immune response, which can lead to the generation of antibodies and/or can be used to vaccinate a mammal.

18 Claims, No Drawings

Specification includes a Sequence Listing.

(56) References Cited

OTHER PUBLICATIONS

Hutchings et al., "Therapeutic Antibodies Directed at G Protein-coupled Receptors", Landes Bioscience, vol. 2, Issue 6, pp. 594-606, (2010).
Kim et al., "Crevice-forming Mutants of Bovine Pancreatic Trypsin Inhibitor: Stability Changes and New Hydrophobic Surface", Protein Science, vol. 2, pp. 588-596, (1993).
Loladze et al., "Thermodynamic Consequences of Burial of Polar and Non-polar Amino Acid Residues in the Protein Interior". Journal of Molecular Biology, vol. 320, pp. 343-357, (2002).
Lori et al.,"Effect of Single Amino Acid Substitution Observed in Cancer on Pim-1 Kinase Thermodynamic Stability and Structure", Plos One, vol. 8, Issue 6, pp. 1-11, (2013).
Magliery et al., "Protein Stability by Number: High-throughput and Statistical Approaches to One of Protein Science's Most Difficult Problems", Current Opinion in Chemical Biology, vol. 15(3), pp. 443-451, (2011).
Morris et al., "Overview of Protein Folding Mechanisms: Experimental and Theoretical Approaches to Probing Energy Landscapes", Current Protocols in Protein Science, Unit 28.2, pp. 1-22, (2012).
Nguyen Hong-Nam P et al: "Conformational instability governed by disulfide bonds partitions the dominant from subdominant helper T-cell responses specific for HIV-1 envelope glycoprotein gp120," Vaccine, vol. 33, No. 25, May 2, 2015 (May 2, 2015), pp. 2887-2896, XP029241333, ISSN: 0264-410X, DOI: 10.1016/J.VACCINE.2015.04.082; the whole document.
Ohkuri et al., "A Protein's Conformational Stability is an Immunologically Dominant Factor: Evidence That Free-Energy Barriers for Protein Unfolding Limit the Immunogenicity of Foreign Proteins", The Journal of Immunology, vol. 185, pp. 4199-4205, (2010).
Porta et al., "Rational Engineering of Recombinant Picomavirus Capsids to Produce Safe, Protective Vaccine Antigen", PLOS Pathogens, vol. 9, Issue 3, pp. 1-8, (2013).
Robert Thai et al: "Antigen Stability Controls Antigen Presentation", Journal of Biological Chemistry, vol. 279, No. 48, Nov. 26, 2004 (Nov. 26, 2004), pp. 50257-50266, XP055309174, US ISSN: 0021-9258, DOI: 10.1074/jbc.M405738200; p. 50260-p. 50263.
Sahin et al., "mRNA-based Therapeutics—Developing a New Class of Drugs", Nature Reviews, vol. 13, pp. 759-780, (2014).
Schliehe et al., "Stable Antigen is Most Effective for Eliciting CD8+ T-Cell Responses After DNA Vaccination and Infection with Recombinant Vaccinia Virus In Vivo", Journal of Virology, vol. 86, No. 18, pp. 9782-9793, (2012).
So et al., "Contribution of Conformational Stability of Hen Lysozyme to Induction of Type 2 T-helper Immune Responses", Immunology, vol. 104, pp. 259-268, (2001).
Tekalign Deressa et al: "Structural Integrity of the Antigen Is a Determinant for the Induction of T-Helper Type-1 Immunity in Mice by Gene Gun Vaccines against *E.coli* Beta-Galactosidase", Plos One, vol. 9, No. 7, Jul. 15, 2014 (Jul. 15, 2014), page e102280, XP055309170, DOI: 10.1371/journal.pone.0102280 the whole document.
Thomas et al., "Effect of Single-point Mutations on the Stability and Immunogenicity of a Recombinant Ricin A Chain Subunit Vaccine Antigen", Human Vaccines & Immunotherapeutics, vol. 9, Issue 4, pp. 744-752, (2013).
Written Opinion and International Search Report for PCT/US2016/047620 dated Oct. 24, 2016.
Wu et al., "Phase 1 Trial of Malaria Transmission Blocking Vaccine Candidates Pfs25 and Pvs25 Formulated with Montanide ISA 51", Plos One, vol. 3, Issue 7, pp. 1-9, (2008).
Yu et al.,"Vaccination of Malignant Glioma Patients with Peptide-pulsed Dendritic Cells Elicits Systemic Cytotoxicity and Intracranial T-cell Infiltration", Cancer Research, vol. 61, pp. 842-847, (2001).
Transmittal and International Preliminary Report on Patentability dated Mar. 1, 2018 received in PCT/US2016/047620.
Database UniProtKB—P03441 (HEMA_I79A0) Feb. 2, 2018, "Influenza A virus (strain A/Bangkok/1/1979 H3N2)", Database accession No. P03441.
Database UniProtKB—P05961 (POL_HV1 MN) Feb. 2, 2018, "Human Immunodeficiency Virus Type 1 Group M Subtype B (Isolate MN) (HIV-1)", Database Accession No. P05961.
EPO Office Action dated Dec. 10, 2020 received in corresponding EP Application 16757810.3.
Japanese National Phase PCT Laid-Open Publication No. 2007-530647 (translator's note: an English language member of the same patent family: U.S. Pat. No. 8,501,193).
Japanese Office Action for Japanese Patent Application No. 2018-508678 dated Sep. 22, 2020, and English translation.
Scheiblhofer et al., "Influence of Protein Fold Stability Immunogenicity and its Implications for Vaccine Design", Expert Review of Vaccines, vol. 16, No. 5, pp. 479-489, (2017).
Davenport et al., "Isolate-Specific Differences in the Conformational Dynamics and Antigenicity of HIV-1 gp120," J. Virol., 87(19): 10855-10873 (2013).
Macraild et al., "Conformational Dynamics and Antigenicity in the Disordered Malaria Antigen Merozoite Surface Protein 2," PLoS ONE 10(3): e0119899 (18 pages) (2015).
Thai et al., "Antigen Stability Controls Antigen Presentation," J. Biol. Chem., 279(48): 50257-50266 (2004).

* cited by examiner

METHODS OF GENERATING ANTIBODIES

CROSS-REFERENCE TO RELATED APPLICATIONS

This Application claims priority to U.S. Provisional Application 62/207,022, filed Aug. 19, 2015, which is incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Aug. 16, 2016, is named Combined_SA_01_PCT_ST25_V2.txt and is 10,883,263 bytes in size.

INTRODUCTION

Methods for making antibodies have been around for over 100 years and are routinely used by the skilled artisan. See, for example, Morrison et al., Science 229:1202 (1985); Oi et al., BioTechniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985). Improved methods for generating antibodies have extended these initial methods and have been used to generate many of the therapeutic antibodies now being sold commercially. For example, technologies such as phage display and transgenic mice, that is, mice containing the human immunoglobulin genes, have been used to generate fully human antibodies. However, certain antigens continue to challenge a researcher's ability to raise antibodies even when using the most current techniques.

To induce a cell-mediated immune response within the human body, foreign proteins are broken down into smaller peptides, usually between 8-24 amino acids in length, and are bound to MHC molecules, for display on the surface of antigen presenting cells. The MHC-bound peptides are presented to T-cells to trigger a cell mediated immune response.

The three-dimensional (3D) structure of proteins has been implicated as a factor in proteolytic processing and presentation of epitopes (see, Carmicle et al., Molecular Immunology (2007) vol. 44: 1159-1168). Moreover, Ohkuri et al. (see, Okhuri et al., J. Immunol., (2010), vol. 185: 4199-4205) agreed that conformational stability of a protein is an immunologically dominant factor. However, there is no consensus regarding exactly how the 3D structure affects the immune response.

Delamarre et al. (see, Delamarre et al., JEM, (2006), vol 203: 2049-2055) found that less digestible forms of proteins that were less susceptible to digestion via lysosomal proteolysis were more immunogenic, and therefore, concluded that increasing protein stability improved the immune response. For example, Delamarre et al. showed that the immunogenicity of protein antigens can be improved by reducing susceptibility to proteolysis. Similarly, Mirano-Bascos et al. (see, Mirano-Bascos et al., J. of Virology, (2010), vol. 84: 3303-3311) mutated cysteine residues to prevent each of three disulfide bonds from forming, and determined that the CD4+ T-cell response was broadly reduced for all three variants. Mirano-Bascos et al. similarly concluded that global destabilization of the 3-D structure of a protein reduced antigenic presentation and led to a suppressed immune response. In other studies, such as for example, Nguyen et al., Vaccine, (2015), vol. 33: 2887-2896, outer domain disulfide bonds were deleted with the expectation that such deletions would improve antigenic presentation. Instead, a typical pattern of epitope dominance was observed and the authors concluded that it may not be possible to generate a substantially stronger immune response.

Other groups similarly conclude that protein stabilization is needed for an immune response. For example, Deressa et al., (see, Deressa et al., PLOS, (2014), vol. 9: 1-12) concluded that even minor modifications in the amino acid sequence of an antigen caused fundamental quantitative and qualitative changes in the immune response. Likewise, Porta et al. (see, Porta et al., PLOS, (2013), vol. 9: 1-8) reported that stability is needed for inducing an immune response. Other groups such as Thomas (see, Thomas et al., Human Vaccines & Immunotherapeutics, (2013), vol. 9:744-752) similarly concluded that increasing thermal stability for peptides elicited a better immune response.

In contrast, other groups such as So (see, So et al., Immunology, (2001), vol. 104: 259-268) report conflicting results. So et al. investigated the effect of crosslinking (e.g., removing cross-links and adding crosslinks) on the magnitude of in vivo T-cell responses and found that removing such crosslinks led to better antigen processing and an improved immune response. Similarly, Thai et al., J. Biol. Chem. (2004) vol. 279: 50257-50266) reported mutating surface accessible residues to decrease stability and increase conformational dynamics to increase the immunogenicity of the protein antigen. Thai et al. is also directed towards administration of single antigens.

There is no consensus on whether removing or adding crosslinks improves or inhibits antigen processing. Accordingly, it is unclear in the art as to whether increasing or decreasing protein stability would lead to an improved immune response comprising a broad, diverse array of antibodies.

Thus, there continues to be a need to develop new and improved methods of generating antibodies which can provide a different and broader repertoire of antibodies than previously obtained.

SUMMARY OF THE INVENTION

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject.

As described herein, the invention is directed towards a method of triggering an immune response wherein said method comprises designing a mixture of peptidogenic proteins derived from a starting protein, wherein the peptidogenic proteins have altered conformational dynamics as compared to the starting protein and wherein the peptidogenic proteins are similar in conformation to the starting protein, introducing the peptidogenic proteins to an animal and generating an immune response. The peptidogenic proteins can be introduced into the animals directly (by, for instance, inoculation or immunization) or can be expressed in vivo by polynucleotides that have been introduced into the animal and which encode the peptidogenic proteins. Upon expression of these peptidogenic proteins, the immune response is triggered to generate antibodies both to the peptidogenic proteins and to the original starting protein.

In preferred embodiments, the conformational dynamics of a starting protein are preferably altered by altering the thermodynamic stability of the starting protein. In further preferred embodiments, the conformational dynamics of the starting protein are altered by replacing at least one non-surface amino acid residue of a starting protein to modify the peptidogenicity of the protein. Methods of altering conformational dynamics include, but are not limited to, examining a model of the 3-D structure (experimental or predicted based on homology) of the starting protein, identifying non-surface amino acid residues of the starting protein and replacing at least one non-surface amino acid residue in the starting protein to generate the peptidogenic protein, and/or by comparing the pattern of conserved amino acid homology across proteins orthologous to the starting protein from different species to provisionally identify non-surface amino acid residues of the starting protein (e.g., conserved hydrophobic residues) and replacing at least one non-surface amino acid residue in the starting protein to generate the peptidogenic protein. Other methods of predicting or empirically discovering non-surface (i.e., buried) amino acid residues can also be used. These methods also include using bioinformatics tools that predict secondary structures and/or identify disordered regions of a starting protein to identify at least one non-surface amino acid residue within these structures or ordered regions for replacement, and replacing the at least one non-surface amino acid residue to generate the peptidogenic protein (see, e.g., Cheng et al., Nucleic Acids Res (2005) 33:W72-6; Huang et al. (2014), DisMeta: A Meta Server for Construct Design and Optimization In Chen editor, *Structural Genomics*, Humana Press pp. 3-16). In some embodiments, substitutions in disordered regions are avoided. For example, disorder predictors could be used to identify ordered/structured regions in order to select ordered regions in which to make mutations (Id.). Still other methods include using biochemical experiments to identify core residues, such as through alanine scanning of hydrophobic residues or comparable methods, to identify at least one non-surface amino acid residue within these structures or regions for replacement, and replacing the at least one non-surface amino acid residue to generate the peptidogenic protein. Accordingly, in some embodiments, residues for replacement can be identified based on known structures, and in other embodiments, residues for replacement can be identified based on conserved hydrophobic residues.

In preferred embodiments a non-surface amino acid residue is replaced with a smaller amino acid residue. In further preferred embodiments, the smaller amino acid is an alanine or glycine. In other preferred embodiments, at least 2, 3, 4, 5, 6, 7, 8, 9 or 10 amino acids are replaced in the starting protein. In still other preferred embodiments, at least 10 amino acids, at least 20 amino acids, at least 30 amino acids, at least 40 amino acids, or at least 50 amino acids are replaced in the starting protein. In still other preferred embodiments, multiple amino acid replacements are distributed across a mixture of proteins. For example, in one embodiment, to mutate 10 different residues, the starting protein is mutated 10 different times to generate 10 different peptidogenic proteins, each with a single amino acid replacement. Each of the ten proteins are mixed together to inoculate the animal. In some cases, wild type starting protein, i.e. the protein with no mutations, is part of the mixture. In further preferred embodiments, at least one disulfide bond is eliminated in the starting protein, such as, for example, replacing the cysteines with alanines, serines, and/or glycines, etc. In further preferred embodiments, both cysteines involved in the formation of the at least one disulfide bond in the starting protein are replaced with alanines, serines, and/or glycines, or preferably with alanines or glycines, etc. In further preferred embodiments, the conformational dynamics of the starting protein is altered by replacing (a) at least one threonine with a valine, alanine, glycine or serine; or (b) at least one cysteine with alanine, valine, glycine, serine or threonine; or (c) at least one valine with alanine, glycine, leucine or isoleucine; or (d) at least one leucine with alanine, valine, glycine, or isoleucine; or (e) at least one isoleucine with alanine, valine, leucine, or glycine; or (f) at least one proline, methionine, phenylalanine, tyrosine, or tryptophan with alanine, valine, leucine, isoleucine, or glycine; or (g) at least one aspartic acid or asparagine with glycine, serine, threonine, alanine, valine, leucine, or isoleucine; or (h) at least one glutamic acid or glutamine with aspartic acid, asparagine, glycine, serine, threonine, alanine, valine, leucine, or isoleucine; or (i) at least one lysine with arginine, histidine, glycine, serine, threonine, alanine, valine, methionine, leucine, or isoleucine; or (j) at least one arginine with lysine, histidine, glycine, serine, threonine, alanine, valine, methionine, leucine, or isoleucine; or (k) at least one histidine with lysine, arginine, glycine, serine, threonine, alanine, valine, glutamine, asparagine, leucine, or isoleucine; or (l) at least one alanine with a glycine; or (m) at least one residue with a non-natural amino acid; and/or (n) any of the above combinations.

In still further preferred embodiments, the conformational dynamics of the starting protein is altered by replacing: (a) at least one tryptophan with tyrosine, phenylalanine, methionine, histidine, isoleucine, leucine, valine, alanine or glycine; or (b) at least one tyrosine with phenylalanine, methionine, histidine, isoleucine, leucine, valine, alanine or glycine; or (c) at least one phenylalanine with tyrosine, methionine, histidine, isoleucine, leucine, valine, alanine or glycine; or (d) at least one proline with methionine, leucine, isoleucine, valine, alanine, or glycine; or (e) at least one histidine with phenylalanine, tyrosine, methionine, isoleucine, leucine, valine, alanine, glycine, lysine, arginine, serine, threonine, asparagine, or glutamine; or (f) at least one methionine with isoleucine, leucine, valine, alanine or glycine; or (g) at least one isoleucine with leucine, valine, alanine or glycine; or (h) at least one leucine with isoleucine, valine, alanine or glycine; or (i) at least one valine with alanine, glycine, leucine, or isoleucine; or (j) at least one cysteine with alanine, valine, glycine, serine or threonine; or (k) at least one aspartic acid with glutamic acid, glutamine, asparagine, glycine, serine, threonine, alanine, valine, leucine, or isoleucine; or (l) at least one glutamic acid with aspartic acid, glutamine, asparagine, glycine, serine, threonine, alanine, valine, leucine, or isoleucine; or (m) at least one alanine with a glycine or proline; or (n) at least one serine with alanine or glycine; or (o) at least one glycine with alanine or proline; or (p) at least one lysine with arginine, histidine, glycine, serine, threonine, alanine, valine, methionine, leucine or isoleucine; or (q) at least one asparagine with glycine, alanine, serine, threonine, valine, leucine, isoleucine, glutamine, aspartic acid or glutamic acid; or (r) at least one glutamine with glycine, alanine, serine, threonine, valine, leucine, isoleucine, glutamine, aspartic acid, glutamic acid, or histidine; or (s) at least one arginine with lysine, histidine, glycine, serine, threonine, alanine valine, methionine, leucine, or isoleucine; or (t) at least one threonine with valine, alanine, glycine or serine; or (u) a hydrophobic residue with a smaller, similar hydrophobic residue; or (v) at least one residue with a non-natural amino acid; or (w) any of the above combinations. A combinatorial approach may be used to determine optimal substitutions to increase peptidogenicity.

In preferred embodiments, the change in conformational dynamics of the peptidogenic protein is measured by a change in melting temperature as compared to the starting protein and/or by measuring a change in Gibbs free energy of stabilization. Preferred methods of measuring Gibbs free energy include, but are not limited to, denaturant modulated equilibrium unfolding. Preferred denaturants are urea and/or guanidinium hydrochloride. Alternatively, changes in conformational dynamics can be assayed by detecting a change in a proteolytic sensitivity assay, such as, for example, by measuring digestion with cathepsins and/or other proteases and then analyzing the mixture by mass spectrometry (MS) or sodium dodecylsulfate polyacrylamide gel electrophoresis (SDS-PAGE).

In preferred embodiments, determining whether peptidogenic proteins have a similar conformation to the starting protein can be measured by a cross-reacting antibody that binds to a 3D conformational epitope (often a discontinuous epitope) on both the peptidogenic proteins and the starting protein. Methods for measuring antibody binding include, but are not limited to an immunoprecipitation assay, surface plasma resonance, isothermal titration calorimetry, oblique-incidence reflective difference (OI-RD), western blots, radioimmunoassays, ELISA (enzyme linked immunosorbent assay), "sandwich" immunoassays, gel diffusion precipitin reactions, immunodiffusion assays, agglutination assays, complement-fixation assays, immunoradiometric assays, fluorescent immunoassays, and/or protein A immunoassays.

In further preferred embodiments, a test for measuring cross-reactivity is by a binding assay. In further preferred embodiment, the antibody binding (including a cross-reacting antibody) to a peptidogenic protein has a dissociation constant (KD) of less than or equal to $10^{-9}$M, of less than or equal to $10^{-8}$M, less than or equal to $10^{-7}$M, and/or less than or equal to $10^{-6}$M.

In preferred embodiments, the starting protein is selected from an envelope glycoprotein of the human immunodeficiency virus (HIV), HIV gp120, HIV gp41, HIV gp160, an ebola antigen, a hepatitis C virus (HCV) antigen, a hepatitis B virus (HBV) antigen, a Middle Eastern Respiratory Syndrome coronavirus (MERS-CoV) antigen, a Zika virus antigen, an influenza virus antigen, a viral antigen, a malaria antigen, a bacterial antigen, a parasitic antigen, an allergen, a venom, a toxin, or a tumor-associated antigen, a transmembrane domain protein, an ion channel protein, and/or a G-protein coupled receptor.

In further preferred embodiments, the tumor associated antigen is selected from MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, GAGE-I, GAGE-2, GAGE-3, GAGE-4, GAGE-5, GAGE-6, GAGE-7, GAGE-8, BAGE-I, RAGE-1, LB33/MUM-1, PRAME, NAG, MAGE-Xp2 (MAGE-B2), MAGE-Xp3 (MAGE-B3), MAGE-Xp4 (MAGE-B4), MAGE-C1/CT7, MAGE-C2, NY-ESO-I, LAGE-I, SSX-I, SSX-2(HOM-MEL-40), SSX-3, SSX-4, SSX-5, SCP-I and XAGE, melanocyte differentiation antigens, p53, ras, CEA, MUC1, PMSA, PSA, tyrosinase, Melan-A, MART-1, gp100, gp75, alpha-actinin-4, Bcr-Abl fusion protein, Casp-8, beta-catenin, cdc27, cdk4, cdkn2a, coa-1, dek-can fusion protein, EF2, ETV6-AML1 fusion protein, LDLR-fucosyltransferaseAS fusion protein, HLA-A2, HLA-A11, hsp70-2, KIAAO205, Mart2, Mum-2, and 3, neo-PAP, myosin class I, OS-9, pml-RAR alpha fusion protein, PTPRK, K-ras, N-ras, Triosephosphate isomerase, GnTV, Herv-K-mel, NA-88, SP17, and TRP2-Int2, (MART-I), E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, alpha-fetoprotein, 13HCG, BCA225, BTAA, CA 125, CA 15-3 (CA 27.29\BCAA), CA 195, CA 242, CA-50, CAM43, CD68\KP1, CO-029, FGF-5, G250, Ga733 (EpCAM), HTgp-175, M344, MA-50, MG7-Ag, MOV18, NB\170K, NY-CO-1, RCAS1, SDCCAG16, TA-90 (Mac-2 binding protein\cyclophilin C-associated protein), TAAL6, TAG72, TLP, TPS, tyrosinase related proteins, TRP-1, TRP-2, and cytomegalovirus phosphoprotein 65 (pp65).

In another preferred embodiment, the peptidogenic protein is a protein that is part of a complex. For example, buried interfacial residues may be targeted for amino acid substitution, in e.g., proteins such as gp120, which is an envelope glycoprotein that forms a trimeric complex and is involved in HIV infection.

In a preferred embodiment, the mixture of polynucleotides encoding the peptidogenic proteins can be synthesized in vitro. The polynucleotides can also preferably comprise either DNA or mRNA. In preferred embodiments, the polynucleotides are in vitro transcribed (IVT) mRNA. The mRNA, including the IVT mRNA, can further comprise a poly(A) tail and/or a 5' cap. In another preferred embodiment, the mRNA can be translated in vitro to produce the peptidogenic proteins, including by use of coupled in vitro transcription/translation (IVTT).

The mixture of polynucleotides can comprise sequences encoding different peptidogenic proteins derived from either the same starting protein or from multiple starting proteins. In further preferred embodiments, the polynucleotides can be associated with a targeting component that targets the polynucleotides to a cell or organ. Alternatively, the polynucleotides can be unassociated with a targeting component. The polynucleotides encoding the peptidogenic proteins may also comprise a vector sequence.

Mixtures of these polynucleotides as well as animals (genetically modified or not genetically modified) expressing mixtures of polynucleotides are also contemplated. In preferred embodiments, the animal is a mammal and in further preferred embodiments, the mammal is a human, a mouse, a rabbit, a llama, or a cow.

In further preferred embodiments, the method induces an immune response. The immune response can occur in vivo, ex vivo and/or in vitro.

The polynucleotides encoding the peptidogenic proteins, including, but not limited to mixtures of polynucleotides, can be delivered to the animal by injection. In preferred embodiments, the injection occurs in the muscle of the animal. The delivery of the polynucleotides to the animal can be used for vaccination purposes, in research, or antibody development.

In further preferred embodiments, the antibody produced by the described methods is recovered and isolated. In preferred embodiments, the antibody is a fully human antibody, a chimeric antibody, a single-chain antibody, a camelid antibody, a humanized antibody, a polyclonal antibody or a monoclonal antibody. In preferred embodiments, the polyclonal antibody is further fractionated into single, isolated antibody species. In other preferred embodiments, the produced antibody is affinity matured, such as, for example, by phage display, yeast display, ribosome display or by a panning technique.

Also contemplated are polynucleotides that encode the antibodies produced by the methods described herein. These antibody encoding polynucleotides can also comprise a heterologous promoter and/or a vector sequence.

The peptidogenic proteins and/or the mixtures of polynucleotides encoding the peptidogenic proteins can also be used to vaccinate a mammal. In preferred embodiments, the vaccine is a cancer vaccine, an HIV vaccine, an HCV vaccine, an HBV vaccine, an influenza virus vaccine, a MERS-CoV vaccine, a Zika vaccine, a malaria vaccine, and/or an ebola virus vaccine comprising the peptidogenic proteins.

In further preferred embodiments, the invention is a method of processing a peptidogenic protein wherein the method comprises introducing to an antigen presenting cell a peptidogenic protein, wherein the peptidogenic protein has altered conformational dynamics as compared to a starting protein and wherein the peptidogenic protein has a similar conformation to the starting protein; and permitting the antigen presenting cell to process and display T cell epitopes derived from the peptidogenic protein.

In preferred embodiments, the antigen presenting cell is a dendritic cell, a B cell, a monocyte or a macrophage. In further preferred embodiments, the method is carried out in vitro or ex vivo. In further preferred embodiments, the antigen presenting cell is transfected with a polynucleotide encoding the peptidogenic protein(s) and/or placed in contact with the peptidogenic protein(s). In further preferred embodiments the antigen presenting cell undergoes phagocytosis or pinocytosis of the peptidogenic protein(s) or polynucleotide(s).

DETAILED DESCRIPTION OF THE INVENTION

Overview

We describe herein a novel method of generating an immune response, including enhancing the generation of antibodies by using a protein's "peptidogenic potential" via altering the conformational dynamics of a starting protein while maintaining that protein's 3-D conformation. These peptidogenic proteins can then be used to mount an immune response, used as a vaccine and/or to generate antibodies.

Thus, the invention is directed to a method of triggering an immune response wherein said method comprises designing a mixture of peptidogenic proteins derived from a starting protein, wherein the peptidogenic proteins have altered conformational dynamics as compared to the starting protein and wherein the peptidogenic proteins are similar in conformation to the starting protein, introducing the peptidogenic proteins to an animal and generating an immune response. The peptidogenic proteins can be introduced into the animals directly (by, for instance, inoculation or immunization) or can be expressed in vivo by polynucleotides that have been introduced into the animal and which encode the peptidogenic proteins. Upon expression of these peptidogenic proteins, the immune response is triggered to generate antibodies preferably to both the peptidogenic proteins and to the original starting protein.

Introduction of the polynucleotides can occur, for example, by either directly or after first performing ex vivo transfection of dendritic cells. Additionally, polynucleotides encoding the peptidogenic proteins can be generated and introduced into an animal. The peptidogenic proteins can then be produced in the animal to generate antibodies to the peptidogenic proteins. The methods described herein have the potential to profoundly impact the immunogenicity of proteins. Preferred biophysical and biochemical properties that are altered in the protein, include, but are not limited to conformational dynamics of a protein, the thermodynamic stability, MHC-II binding, and/or the protease susceptibility of the starting protein. The methods described herein can also be used to simultaneously produce cross-reacting antibodies to different peptidogenic proteins (either derived from the same or different starting proteins) which has the potential to profoundly change the way in which antibodies are currently being generated as the repertoire of antibodies that can be obtained by a single injection in an animal has the potential to streamline antibody development and vaccination efficacy.

We have recognized that the conformational dynamics of a protein are critical for the ability of the protein to mount an immune response. The propensity of an antigen to efficiently yield peptide fragments in vivo after immunization we have termed "peptidogenicity." Having the ability to alter the conformational dynamics of a starting protein to design a mixture of peptidogenic proteins which can be administered directly as a protein mixture or simultaneously expressed in an animal by a mixture of polynucleotides has the potential to generate a broad repertoire of antibodies with a single injection in a cost effective manner.

Thus, as disclosed herein, immunizing an animal with a mixture of peptidogenic proteins can robustly stimulate the immune system, generating stronger and/or better immune responses when placed in contact with an antigen presenting cell.

The immunization with a mixture (or combinatorial cocktail) of peptidogenic proteins is advantageous due to the complexity of the proteolytic attack on the protein antigen(s) that produces the peptides. For example, providing multiple different peptidogenic proteins having different amino acid sequences creates an environment where the "tuning mutation(s)" optimal for the production of a given peptide (T cell epitope) in the right time frame may be different from the mutations optimal for production of another peptide. For example, some cells, such as dendritic cells, mediate T-cell responses during an activation phase. If these cells are presented with antigens outside of this activation window (e.g., before or after activation) then a T-cell response may not be triggered. Thus, T-cells need to be presented with antigens at the appropriate time, which is governed by rates of protein degradation (e.g., proteolysis) in the antigen presenting cell, to trigger an immune response. By giving the antigens as mixtures, a multiplicity of different peptidogenic proteins can be endocytosed by a single cell, which theoretically maximizes the diversity of the peptides produced and displayed by that cell. Alternatively, by giving the antigens as mixtures, a multiplicity of different peptidogenic proteins can be endocytosed by multiple cells, which theoretically maximizes the diversity of the peptides produced and displayed by these cells. Additionally, the peptidogenic proteins having increased conformational dynamics may lead to an improved MHC class II binding which is expected to maximize the immune response. For example, for proteins that are relatively non-immunogenic and/or are not good vaccine components because of being too stable, and thus protease degradation is inhibited and subsequent peptide presentation is thereby impoverished resulting in attenuation of the immune response in adaptive immunity, such proteins could be altered as described herein to generate a mixture of peptidogenic proteins with altered conformational dynamics while maintaining a similar conformation as compared to the starting protein.

In preferred embodiments, a starting protein, also referred to as a test starting protein, can be systematically mutated to alter the thermodynamic stability of the starting protein, without significantly altering the three-dimensional structure of the corresponding folded protein, to generate peptidogenic proteins having increased peptidogenicity while displaying essentially the same 3D (conformational) surface epitopes as the starting protein.

Thus, increasing the immunogenicity of a starting protein by altering its conformational dynamics to produce numerous peptidogenic proteins which can then be simultaneously introduced into an animal will generate a robust immune response and has the potential to raise a broader repertoire of polyclonal antibodies which can be further fractionated (for example, by molecularly cloning via their respective encoding mRNAs) into single isolated species.

Definitions

Unless defined otherwise, all technical and scientific terms used herein have the same meaning as commonly understood by those of ordinary skill in the art, such as in the arts of peptide chemistry, cell culture and phage display, nucleic acid chemistry and biochemistry. Standard techniques are used for molecular biology, genetic and biochemical methods (see Sambrook et al., Molecular Cloning: A Laboratory Manual, 3rd ed., 2001, Cold Spring Harbor Laboratory Press, Cold Spring Harbor, N.Y.; Ausubel et al., Short Protocols in Molecular Biology (1999) $4^{th}$ ed., John Wiley & Sons, Inc.), which are incorporated herein by reference.

As used herein, "peptidogenicity" refers to the propensity of a protein to efficiently yield a robust set of diverse peptides which can be used to yield an immune response. Various assays exist for measuring peptidogenicity (see, for example, So et al., FIGS. 2c-d; Thai et al., FIG. 7c-f; and Delamarre et al., FIGS. 1b-c, 4b-c and 5a-b).

As used herein, a "peptidogenic protein" refers to a mutated protein that has been modified in its amino acid sequence to alter its conformational dynamics as compared to the starting protein sequence while maintaining a similar conformation to the starting protein.

As used herein, "non-surface residues" are residues that are not surface accessible with regard to the 3D structure of a protein, e.g., residues that are buried within the interior of the 3D structure of the native protein. In preferred embodiments, "non-surface" residues are defined by the method of Lee and Richards (see, e.g., Lee B et al., J. Mol. Biol. (1971); 55(3):379-IN4. doi:http://dx.doi.org/10.1016/0022-2836(71)90324-X.), where the relative solvent accessibility of the residue in the native protein is less than 50%, less than 40%, less than 30%, less than 25%, less than 20%, less than 10%, less than 5%, or 0%, or by the same method where the difference between the absolute solvent accessible surface area and the surface area in the fully extended Ala-X-Ala tripeptide (see, e.g., Gready J E et al., Protein Science. (1997); 6(5):983-98. doi: 10.1002/pro.5560060504.) is greater than 40 $Å^2$, greater than 50 $Å^2$, greater than 60 $Å^2$, greater than 70 $Å^2$, greater than 80 $Å^2$, greater than 90 $Å^2$, greater than 100 $Å^2$, greater than 110 $Å^2$, or greater than 120 $Å^2$. In further preferred embodiments, "non-surface" residues are defined as residues with a solvent accessible surface area of less than 10 $Å^2$, less than 5 $Å^2$, less than 2.5 $Å^2$, or less than 1 $Å^2$, as calculated by a structural analysis software package familiar to those skilled in the art (e.g. UCSF Chimera (see, e.g., Pettersen E F et al., J. Comput. Chem. (2004); 25(13):1605-12. Epub 2004 Jul. 21.), PyMol (see, e.g., Schrodinger, LLC. The PyMOL Molecular Graphics System, Version 1.8. 2015.), etc.

As used herein, a "starting protein" or "test starting protein" refers to the amino acid sequence of the "original" or "reference" protein that is used to derive the peptidogenic protein. In some examples, the "starting protein" can be a peptidogenic protein that has been further modified.

As used herein, an "immune response" refers to the humoral immune response and/or the cell-mediated immune response that is triggered by an antigen presenting cell after processing a protein. In the humoral immune response, B lymphocytes produce antibodies that react with native, unprocessed antigens. These antigen-antibody reactions may in some cases involve cell-surface antigens that activate the complement cascade, which causes the lysis of cells bearing those antigens. In the cell-mediated immune response, T lymphocytes mobilize macrophages in the presence of processed peptide antigens recognized as foreign. Activated T lymphocytes can also attack cells bearing foreign antigens directly.

As used herein, an "antigen presenting cell" refers to a cell that can break down ("process") a protein into peptides and present the peptides, in conjunction with the MHC allele, preferably major HLA complex class I or class II molecules, on the cell surface. Examples of antigen presenting cells include, but are not limited to dendritic cells, macrophages, B cells, and monocytes.

As used herein, "conformational dynamics" is defined as the phenomena related conformational changes and flexibility of a protein structure in the spatial arrangement of atoms or groups of atoms with respect to each other in a protein molecule. Conformational dynamics include "breathing" motions and involve the vibration, bending, twisting, rotation, and other allowed modes of movement of the atoms joined by the covalent bonds in the protein molecule, governed by intrinsic restoring forces but modulated by non-covalent interactions such as hydrogen bonds, van der Waals forces, and electrostatic interactions. These motions can subtly change the geometry of the protein on a subpicosecond timescale and can result in a vast diversity of conformational states on a time-scale of microseconds to milliseconds. Conformational molecular dynamics of proteins is often studied using computer simulations. See, for example, Shaw et al (2010) *Science* 330, 341. Also as used herein, the conformational dynamics of a starting protein can be altered by chemical modifications, amino acid substitutions, and other mutations such as deletions, insertion, truncations, or any combination thereof, etc. By stating that the conformational dynamics of the peptidogenic protein is varied with regard to the wild type protein, it is meant that the one or more amino acid substitutions of the peptidogenic protein results in altered conformational dynamics as compared to the wild type protein.

As used herein, "thermodynamic stability" is defined in terms of a chemical system where no or minimal energy is either released or consumed, and thus no or minimal changes in thermal energy are present and the system is in its lowest energy state under a given set of experimental conditions. Also as used herein, a "decrease in thermodynamic stability" or "decreased thermodynamic stability" means that the parameters pertaining to thermodynamic stability of the peptidogenic protein are attenuated as compared to those of the starting protein measured under the same conditions, and this decrease can be achieved in the peptidogenic protein by, but not limited to, alterations to the molecular structure of the starting protein via chemical modifications, amino acid substitutions, and other genetic mutations. Methods of measuring a decrease in thermodynamic stability are known in the art and described herein, and include protocols incorporating the measurement of parameters such as melting temperature and urea- or guanidinium hydrochloride-induced equilibrium unfolding (denaturation). These parameters are typically arrived at by monitoring the protein unfolding reaction as a function temperature or denaturant concentration under conditions of equilibrium or quasi-equilibrium. Methods for monitoring the unfolding reaction by measuring the concentration of the unfolded state relative to that of the folded state include, but are not limited to, UV absorption, fluorescence, and circular dichroism. This approach allows the calculation of a stabilization free energy (Gibbs free energy) of the mutant protein relative to the stabilization free energy of the starting protein measured under the same conditions. The difference in free energy is typically denoted by $\Delta\Delta G=\Delta G_{mutant}-\Delta G_{standard(e.g.,\ wt)}$, where $\Delta G_{mutant}$ and $\Delta G_{standard(e.g.,\ wt)}$ are the stabilization free energies of the mutant and "standard" (e.g., wt or wild type) proteins, respectively, and MG is the difference. $\Delta\Delta G>0$ indicates a mutant protein that is less stable than the standard protein, and $\Delta\Delta G<0$ indicates a mutant protein that is more stable than the standard protein.

As used herein, a peptidogenic protein has a "similar conformation" to a starting protein if the 3-D structure is sufficiently maintained after mutating non-surface residues of the protein (and, consequently, potentially modifying its overall conformational dynamics) to allow for an antibody to cross react with both the peptidogenic protein and the starting protein. "Cross-reactivity" can be measured by a binding assay as described herein or as is well known in the art and is measured as a "binding affinity" which is based on dissociation constants ($K_D$), off rates ($k_{off}$), and/or on rates ($k_{on}$). The peptidogenic protein does not need to have an identical 3-D structure as the starting protein; just a sufficiently similar structure displaying similar 3D conformational epitopes (including discontinuous epitopes), that will allow for an antibody to recognize both proteins, even though the binding affinities may be nonidentical.

In the present invention, the term "antibody," refers to immunoglobulin molecules and immunologically active portions of immunoglobulin molecules, i.e., molecules that contain an antigen binding site that immunospecifically binds the peptidogenic protein and/or the starting protein. As such, the term antibody encompasses not only whole antibody molecules, but also antibody fragments as well as variants (including derivatives such as fusion proteins) of antibodies and antibody fragments. Examples of molecules which are described by the term "antibody" in this application include, but are not limited to: single chain Fvs (scFvs), Fab fragments, Fab' fragments, $F(ab')_2$, disulfide linked Fvs (sdFvs), Fvs, and fragments comprising or alternatively consisting of, either a VL or a VH domain. The term "single chain Fv" or "scFv" as used herein refers to a polypeptide comprising a VL domain of an antibody linked to a VH domain of an antibody. See Carter (2006) Nature Rev. Immunol. 6:243.

Additionally, antibodies of the invention include, but are not limited to, monoclonal, multi-specific, bi-specific, human, humanized, mouse, or chimeric antibodies, single chain antibodies, camelid antibodies, Fab fragments, F(ab') fragments, anti-idiotypic (anti-Id) antibodies (including, e.g., anti-Id antibodies to antibodies of the invention), domain antibodies and epitope-binding fragments of any of the above. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule.

Most preferably, the antibodies are human antibodies. As used herein, "human" antibodies include antibodies having the amino acid sequence of a human immunoglobulin and include antibodies isolated from human immunoglobulin libraries and xenomice or other organisms that have been genetically engineered to produce human antibodies. For a detailed discussion of a few of the technologies for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598; and Lonberg and Huszar, Int. Rev. Immunol. 13:65-93 (1995).

Human antibodies or "humanized" chimeric monoclonal antibodies can be produced using techniques described herein or otherwise known in the art. For example, methods for producing chimeric antibodies are known in the art. See, for review the following references: Morrison, Science 229:1202 (1985); Oi et al., BioTechniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985).

The antibodies of the present invention may be monovalent, bivalent, trivalent or multivalent. For example, monovalent scFvs can be multimerized either chemically or by association with another protein or substance. A scFv that is fused to a hexahistidine tag or a Flag tag can be multimerized using Ni-NTA agarose (Qiagen) or using anti-Flag antibodies (Stratagene, Inc.).

The antibodies of the present invention may be monospecific, bispecific, trispecific or of greater multispecificity. Multispecific antibodies may be specific for the peptidogenic protein, for more than one peptidogenic protein, for the starting protein, or they may be specific for both the peptidogenic protein and/or the starting protein and a heterologous epitope, such as a heterologous polypeptide or solid support material. See, e.g., PCT publications WO 93/17715; WO 92/08802; WO 91/00360; WO 92/05793; Tutt, et al., J. Immunol. 147:60-69 (1991); U.S. Pat. Nos. 4,474,893; 4,714,681; 4,925,648; 5,573,920; 5,601,819; Kostelny et. al., J. Immunol. 148:1547-1553 (1992).

The term "fragment" as used herein refers to a polypeptide comprising an amino acid sequence of at least 5 amino acid residues, at least 10 amino acid residues, at least 15 amino acid residues, at least 20 amino acid residues, at least 25 amino acid residues, at least 30 amino acid residues, at least 35 amino acid residues, at least 40 amino acid residues, at least 45 amino acid residues, at least 50 amino acid residues, at least 60 amino residues, at least 70 amino acid residues, at least 80 amino acid residues, at least 90 amino acid residues, at least 100 amino acid residues, at least 125 amino acid residues, at least 150 amino acid residues, at least 175 amino acid residues, at least 200 amino acid residues, or at least 250 amino acid residues, of the amino acid sequence of the peptidogenic protein or starting protein. In some embodiments, a fragment may also refer to a polypeptide comprising an amino acid sequence of about 8 to 24 amino acid residues, or about 5 to 30 amino acid residues.

The term "fusion protein" as used herein refers to a polypeptide that comprises, or alternatively consists of, an amino acid sequence of the peptidogenic protein, the starting protein, and/or the antibody raised against the peptidogenic protein and an amino acid sequence of one or more heterologous peptides and/or polypeptides. For vaccine applications, the heterologous polypeptide sequence fused to the peptidogenic protein is preferably from a viral protein.

The term "host cell" as used herein refers to the particular subject cell transfected with a nucleic acid molecule and the progeny or potential progeny of such a cell. Progeny may not be identical to the parent cell transfected with the nucleic acid molecule due to mutations or environmental influences or developmental steps that may occur in succeeding generations or integration of the nucleic acid molecule into the host cell genome.

A "conservative amino acid substitution" is one in which the amino acid residue is replaced with an amino acid residue having a side chain with a similar chemical nature (e.g., size, charge, steric features [e.g., beta-branched vs. non-beta-branched], polarity [hydrophilic vs. hydrophobic], aromatic vs. non-aromatic, etc.). Whether or not a particular substitution is deemed "conservative" may also depend on the structural context in the folded protein in which a substitution occurs. Amino acid side chains may be chemically similar in one respect but chemically dissimilar in another, and the context may determine which of these properties dominates in terms of how "conservative" (i.e., least disruptive) that particular substitution is. Families of amino acid residues having chemically similar side chains have been defined in the art. These families include amino acids with basic side chains (e.g., lysine, arginine), acidic side chains (e.g., aspartic acid, glutamic acid), uncharged polar side chains (e.g., asparagine, glutamine, serine, threonine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Some side chains have a hybrid character that is pH-dependent in physiologically relevant pH ranges. For example, histidine (pKa~6) becomes more positively-charged (basic) below pH 6, and polar but substantially uncharged at pH 7.5 and above. Cysteine (pKa~8.5) is substantially uncharged (and not particularly polar) below pH 8, but negatively charged (and acidic) at pH 9. The tyrosine phenolic side chain is also partially ionized and negatively charged at higher pH. Moreover, the local electrostatic environment (context) of the rest of the protein can shift these effective pH values substantially. Moreover, an acidic protein cysteine thiolate side chain can react, via thiol-disulfide exchange involving an intermediary disulfide-containing compound such as oxidized glutathione, with another protein cysteine thiol to form an intramolecular disulfide bond; such bonds are highly hydrophobic (non-polar). Additionally, both naturally occurring and/or non-naturally occurring amino acids can be used in the peptidogenic proteins.

Mutations can be introduced in a site-directed fashion or randomly along all or part of the coding sequence. Libraries of mutants can be designed to introduce a single amino acid substitution, two amino acid substitutions, three amino acid substitutions, four amino acid substitutions, and so forth, up to nineteen amino acid substitutions at a given residue site. In still other embodiments, libraries of mutants can be designed to introduce more than nineteen amino acid substitutions (including natural and non-natural amino acids) at a given residue site. In addition, libraries can be combinatorially designed to simultaneously produce multiple mutations at two sites, three sites, four sites, and so on. Following mutagenesis, the encoded protein may routinely be expressed and the conformational dynamics of the encoded protein and/or peptidogenicity can be determined using techniques described herein or by routinely modifying techniques known in the art. The resultant mutant proteins can be screened and evaluated for altered thermodynamic stability or for peptidogenicity or for similar conformation to the starting protein. Alternatively, the expressed protein "output" from the designed library can be used to immunize an animal without prior screening for protein properties.

As used herein, the "patient" or "subject suitable for treatment" may be a mammal, such as a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon, rhesus macaque), an ape (e.g. gorilla, chimpanzee, orangutan, gibbon), or a human. In other embodiments, non-human mammals, especially mammals that are conventionally used as models for demonstrating therapeutic efficacy in humans (e.g. murine, primate, porcine, canine, camels, llamas, or rabbits) may be employed.

Other aspects and embodiments of the invention provide the aspects and embodiments described herein with the term "comprising" replaced by the term "consisting of" and the aspects and embodiments described above with the term "comprising" replaced by the term "consisting essentially of".

As used herein, "and/or" is to be taken as specific disclosure of each of the two or more specified features or components with or without the others. For example "A, B and/or C" is to be taken as specific disclosure of each (i) A, (ii) B, (iii) C, (iv) A and B, (v) A and C, (vi) B and C and (vii) A and B and C, just as if each is set out individually.

Methods of Altering the Conformational Dynamics of a Protein

A peptidogenic protein can be generated using standard molecular biology mutagenesis techniques well known in the art. For example, the peptidogenic protein can be generated by random mutagenesis as is well known in the art, such as, for example, by error-prone PCR, random nucleotide insertion or deletion or other methods prior to recombination.

To generate the peptidogenic protein, protein engineering may be employed. Recombinant DNA technology known to those skilled in the art can be used to create peptidogenic proteins including single or multiple amino acid substitutions, deletions, insertions, or fusion proteins. Such peptidogenic proteins may be screened for those that have altered conformational dynamics while maintaining a similar conformation to the starting protein as described herein.

For example, to increase the conformational dynamics of the peptidogenic protein, the following table, Table 1, shows the average change in Gibbs free energy for exemplary amino acid substitutions in a range of proteins, derived from Tables 1 and 2 of Loladze et al., J. Mol. Biol. 320, 343-357 (2002) [note: this paper uses a non-standard convention when expressing Gibbs free energies between mutant and wild type proteins, namely using negative values to indicate destabilization ($\Delta\Delta G=\Delta G(\text{mutant})-\Delta G(\text{WT})$); the standard convention is that positive changes indicate destabilization ($\Delta\Delta G=\Delta G(\text{WT})-\Delta G(\text{mutant})$, see paragraph 0040 above)]. For example, Val and Leu (and the other larger non-polar amino acid residues) can be substituted with smaller ones such as Ala, Thr, Asn, and/or Gly. In addition, the buried site of Glu in the native protein structure, can be substituted with Leu, Val, Asn, Thr, Ser, Ala, and/or Gly. The types of single site amino acid substitutions shown generally have little impact on the overall conformation of the starting protein.

TABLE 1

| Amino Acid Substitution (multiple positions in various proteins) | Average Gibbs Free Energy difference between mutant and wild type at core residues within a protein ΔΔG (kJ/mol) |
|---|---|
| Val -> Ala | −12.1(±3.3) |
| Val -> Thr | −11.3(±3.7) |
| Val -> Asn | −21.5(±1.0) |
| Leu -> Ala | −14.2(±4.2) |

Another illustrative paper describing destabilizing mutations in the core of a protein that increase conformational dynamics is Kim et al (1993) Protein Sci. 2:588-596. In this work, the authors show that the mutations Phe22→Ala (2.1 kcal/mol), Tyr23→Ala (7.0 kcal/mol), Tyr35→Gly (5.7 kcal/mol), Asn43→Gly (6.0 kcal/mol), and Phe45→Ala (7.2 kcal/mol) destabilize bovine pancreatic trypsin inhibitor (BPTI) at pH 3.5 by the respective amounts shown in parentheses, without seriously disrupting the overall 3D structure of BPTI.

In addition, genetic deletions, insertions, inversions, repeats, and type substitutions selected according to general rules known in the art should have little effect on activity. For example, guidance concerning how to make phenotypically silent amino acid substitutions is provided in Bowie, J. U. et at., "Deciphering the Message in Protein Sequences: Tolerance to Amino Acid Substitutions," Science 247:1306-1310 (1990), wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selections or screens to identify sequences that maintain functionality.

As the authors state, these studies have revealed that proteins are surprisingly tolerant of amino acid substitutions. The authors further indicate which amino acid changes are likely to be permissive at a certain position of the protein. For example, most buried amino acid residues require non-polar side chains, whereas few features of surface side chains are generally conserved. Other such phenotypically silent substitutions are described in Bowie, J. U. et al., supra, and the references cited therein. Typically seen as conservative substitutions are the replacements, one for another, among the aliphatic amino acids Ala, Val, Leu and Ile; interchange of the hydroxyl-bearing residues, Ser and Thr; exchange of the acidic residues, Asp and Glu; substitution between the sidechain amide-bearing residues, Asn and Gln; exchange of the basic amino acids, Lys and Arg; and replacements among the aromatic residues, Phe and Tyr.

In preferred embodiments, the conformational dynamics of the starting protein is altered by replacing: (a) at least one threonine with a valine, alanine, glycine or serine; or (b) at least one cysteine with alanine, valine, glycine, serine or threonine; or (c) at least one valine with alanine, glycine, leucine or isoleucine; or (d) at least one leucine with alanine, valine, glycine, or isoleucine; or (e) at least one isoleucine with alanine, valine, isoleucine, or glycine; or (f) at least one proline, methionine, phenylalanine, tyrosine, or tryptophan with alanine, valine, leucine, isoleucine, or glycine; or (g) at least one aspartic acid with glutamic acid, glutamine, asparagine, glycine, serine, threonine, alanine, valine, leucine, isoleucine; or (h) at least one glutamic acid with aspartic acid, glutamine, asparagine, glycine, serine, threonine, alanine, valine, leucine, or isoleucine; or (i) at least one lysine with arginine, histidine, glycine, serine, threonine, alanine, valine, leucine, or isoleucine; or (j) at least one arginine with lysine, histidine, glycine, serine, threonine, alanine, valine, leucine, or isoleucine; or (k) at least one histidine with lysine, arginine, glycine, serine, threonine, alanine, valine, leucine, isoleucine, or glutamine; or (l) at least one alanine with a glycine or proline; or (m) at least one asparagine with a glycine, alanine, serine, threonine, glutamine, aspartic acid, or glutamic acid; or (n) at least one glutamine with a glycine, alanine, serine, threonine, asparagine, aspartic acid, glutamic acid, or histidine; or (o) at least one glycine with an alanine or proline; or (p) at least one residue with a non-natural amino acid; or (q) any combination of (a)-(p). In still further preferred embodiments, the conformational dynamics of the starting protein is altered by replacing: (a) at least one tryptophan with tyrosine, phenylalanine, methionine, histidine, isoleucine, leucine, valine, alanine or glycine; or (b) at least one tyrosine with phenylalanine, methionine, histidine, isoleucine, leucine, valine, alanine or glycine; or (c) at least one phenylalanine with tyrosine, methionine, histidine, isoleucine, leucine, valine, alanine or glycine; or (d) at least one proline with methionine, leucine, isoleucine, valine, alanine, or glycine; or (e) at least one histidine with phenylalanine, tyrosine, methionine, isoleucine, leucine, valine, alanine, glycine, lysine, arginine, serine, threonine, asparagine, or glutamine; or (f) at least one methionine with isoleucine, leucine, valine, alanine or glycine; or (g) at least one isoleucine with leucine, valine, alanine or glycine; or (h) at least one leucine with isoleucine, valine, alanine or glycine; or (i) at least one valine with alanine, glycine, leucine, or isoleucine; or (j) at least one cysteine with alanine, valine, glycine, serine or threonine; or (k) at least one aspartic acid with glutamic acid, glutamine, asparagine, glycine, serine, threonine, alanine, valine, leucine, or isoleucine; or (l) at least one glutamic acid with aspartic acid, glutamine, asparagine, glycine, serine, threonine, alanine, valine, leucine, or isoleucine; or (m) at least one alanine with a glycine or proline; or (n) at least one serine with alanine or glycine; or (o) at least one glycine with alanine or proline; or (p) at least one lysine with arginine, histidine, glycine, serine, threonine, alanine, valine, methionine, leucine or isoleucine; or (q) at least one asparagine with glycine, alanine, serine, threonine, valine, leucine, isoleucine, glutamine, aspartic acid or glutamic acid; or (r) at least one glutamine with glycine, alanine, serine, threonine, valine, leucine, isoleucine, glutamine, aspartic acid, glutamic acid, or histidine; or (s) at least one arginine with lysine, histidine, glycine, serine, threonine, alanine valine, methionine, leucine, or isoleucine; or (t) at least one threonine with valine, alanine, glycine or serine; or (u) a hydrophobic residue with a smaller, similar hydrophobic residue; or (v) at least one residue with a non-natural amino acid; or (w) any of the above combinations. In some embodiments, hydrophobic resides are targeted for replacement.

Amino acids in the starting protein that are essential for function, conformation, and/or structure and positioned on the protein surface vs. internal can be identified by methods known in the art, such as site-directed mutagenesis or alanine-scanning mutagenesis (Cunningham and Wells, Science 244: 1081-1085 (1989)). The latter procedure introduces single alanine mutations at every residue in the molecule. The resulting mutant molecules are then tested for those having altered conformational dynamics while maintaining a similar conformation to the starting protein.

In an additional embodiment, the amino acid sequence of the starting protein has one or more amino acids (for example, 1, 2, 3, 4, 5, 6, 7, 8, 9, 10, 15, 20, 30 or 50 amino acids) replaced with the substituted amino acids as described above (either conservative or non-conservative substitutions) to produce the peptidogenic protein. For example, substitutions in positions not involving a starting protein's activity and/or internal to the protein structure can be readily made. Sites that are critical for ligand-receptor binding can also be determined by structural analysis such as crystallization, nuclear magnetic resonance or photoaffinity labeling (Smith et al., J. Mol. Biol. 224:899-904 (1992); and de Vos et al. Science 255:306-312 (1992)).

Recombinant DNA technology that employs combinatorial mutagenesis and synthetic DNA synthesis approaches known to those skilled in the art can also be used to create a peptidogenic protein including single or multiple amino acid substitutions, deletions, additions or fusion proteins. Such modified polypeptides may be then screened for altered conformational dynamics while maintaining a similar conformation as the starting protein.

Thus, a peptidogenic protein can be made where one or more amino acid residues are deleted, added, or substituted to generate peptidogenic proteins having altered conformation dynamics. For example, residues in the hydrophobic "core" of the protein can be substituted with non-polar residues having smaller side chains (supra) in order to create cavities in the core and disrupt the packing, and cysteine residues can be deleted or substituted with other amino acid residues in order to eliminate disulfide bridges (which are often found in protein cores). In some embodiments, at least one disulfide bond is eliminated in the starting protein, such as, for example, replacing the cysteines with alanines, serines, and/or glycines, etc. In further preferred embodiments, both cysteines involved in the formation of the at least one disulfide bond are replaced with alanines, serines, and/or glycines, or preferably with alanines or glycines, etc.

The peptidogenic proteins are preferably provided in an isolated form, and preferably are substantially purified. Additionally, the peptidogenic proteins would display a stable 3D conformational epitope for B-cell activation while synthesized peptides (such as by chemical synthesis) can be co-administered, which could optimize the epitopes for MHC-II presentation. Alternatively, the peptidogenic proteins and peptides can be expressed by a mixture of polynucleotides. In still other embodiments, peptidogenic proteins can be combined with a wild type starting protein and synthetic peptide(s) to elicit an immune response.

In some embodiments, the rate of polypeptide degradation may be adjusted in order to produce an optimal mix of peptides, and in the right time frame, to allow maximal diversity of the displayed peptides on the antigen presenting cells.

Immunization with mixtures (such as combinatorial cocktails) of antigens is advantageous due to the complexity of the proteolytic attack on the protein antigen(s) that produce the peptides for display. Thus, the "tuning mutation(s)" optimal for the production of a given peptide (T cell epitope) in the right time frame may be different from the mutations optimal for production of another peptide. By giving the antigens as mixtures, a multiplicity of different mutant proteins may be endocytosed by a single cell or multiple cells, which maximizes the diversity of the peptides produced and displayed by that cell.

Combinatorial immunization, in which subjects are immunized with two or more distinct antigens that have the same overall surface features (i.e. cross-reacting B-cell epitopes) but with different conformational dynamics, enriches the diversity of T-cell epitopes. This combinatorial approach, which includes hundreds or even thousands of different immunogens in a single inoculation (both protein-based and nucleotide-based) may vastly increase the B-cell epitope repertoire, since every molecule in the mix can contribute to one or more unique T-cell epitopes while maintaining a wild type-like conformation. In some aspects, because the wild-type configuration is maintained, the B-cell epitope repertoire is biased towards the most stable (and presumably wild type-like) molecules in the ensemble.

Peptidogenic Protein has a Similar Conformation as a Starting Protein

The operational test of whether the peptidogenic protein has a "similar conformation to the starting protein" is whether or not a cross-reacting antibody, especially an antibody that recognizes a conformational (3D) epitope, specifically binds to both the peptidogenic protein and the starting protein. In the present invention "cross-reactivity" or a "cross-reacting antibody" is defined in terms of "binding affinity" which can be measured based on dissociation constant ($K_D$), off rate ($k_{off}$), and/or on rate ($k_{on}$).

For example, a cross-reacting antibody binds to both the peptidogenic protein and the starting protein at a dissociation constant or $K_D$ less than or equal to $5\times10^{-6}$ M, $10^{-6}$ M, $5\times10^{-7}$ M, $10^{-7}$ M, $5\times10^{-8}$ M, or $10^{-8}$ M. Even more preferably, a cross-reacting antibody binds to both the peptidogenic protein and the starting protein at a dissociation constant $K_D$ less than or equal to $5\times10^{-9}$M, $10^{-9}$M, $5\times10^{-10}$M, $10^{-10}$ M, $5\times10^{-11}$M, $10^{-11}$ M, $5\times10^{-12}$M, $10^{-12}$M, $5\times10^{-13}$ M, $10^{-13}$ M, $5\times10^{-14}$M, or $10^{-14}$ M. The invention encompasses a dissociation constant or $K_D$ for the peptidogenic protein and/or the starting protein that is within any one of the ranges that are between each of the individual recited values. Additionally, it is specifically contemplated that the $K_D$ for the antibody that binds to a peptidogenic protein may not be identical to its $K_D$ with respect to the starting protein, and in preferred embodiments, the $K_D$ for the antibody that hinds to the peptidogenic protein is less than the $K_D$ for its binding to the starting protein. It is understood that, operationally, $K_D$ in this case refers to the functional affinity of the antibody for the antigen. Functional or "apparent" affinity may be enhanced in multivalent antibodies that contain multiple interacting sites (e.g., Fab arms) that can bind to the antigen ("avidity effect").

Additionally, a cross-reacting antibody binds to both the peptidogenic protein and the starting protein with an off rate ($k_{off}$) of less than or equal to $5\times10^{-2}$ $sec^{-1}$, $10^{-2}$ $sec^{-1}$, $5\times10^{-3}$ $sec^{-1}$ or $10^{-3}$ $sec^{-1}$. More preferably, a cross-reacting antibody binds to both the peptidogenic protein and the starting protein at off rate ($k_{off}$) of less than or equal to $5\times10^{-4}$ $sec^{-1}$, $10^{-1}$ $sec^{-1}$, $5\times10^{-5}$ $sec^{-1}$, or $10^{-5}$ $sec^{-1}$, $5\times10^{-1}$ $sec^{-1}$, $10^{-6}$ $sec^{-1}$, $5\times10^{-7}$ $sec^{-1}$ or $10^{-7}$ $sec^{-1}$. The invention encompasses an off rate ($k_{off}$) for the peptidogenic protein and/or the starting protein that is within any one of the ranges that are between each of the individual recited values. Additionally, it is specifically contemplated that the $k_{off}$ of the antibody for the peptiflogenic protein may not be identical to the $k_{off}$ of the starting protein, and in preferred embodiments, the ($k_{off}$) for the binding of the antibody to the peptidogenic protein is greater than the ($k_{off}$) for the binding of the antibody to the starting protein.

Assays to test for the cross-reactivity are described herein or are known in the art. For example, binding assays may be performed in solution (e.g., Houghten, Bio/Techniques 13:412-421(1992)), on beads (e.g., Lam, Nature 354:82-84 (1991)), on chips (e.g., Fodor, Nature 364:555-556 (1993)), on bacteria (e.g., U.S. Pat. No. 5,223,409), on spores (e.g., U.S. Pat. Nos. 5,571,698; 5,403,484; and 5,223,409), on plasmids (e.g., Cull et al., Proc. Natl. Acad. Sci. USA 89:1865-1869 (1992)) or on phage (e.g., Scott and Smith, Science 249:386-390 (1990); Devlin, Science 249:404-406 (1990); Cwirla et al., Proc. Natl. Acad. Sci. USA 87:6378-6382 (1990); and Felici, J. Mol. Biol. 222:301-310 (1991)). Examples of such assays are described further below in the Examples.

Use of the Peptidogenic Protein to Generate Antibodies

The peptidogenic protein can be used to generate antibodies by methods well known by the skilled artisan, such as, for example, methods described in the art. See, for instance, Sutcliffe et al., supra; Wilson et al., supra; Chow et al., Proc. Natl. Acad. Sci. USA 82:910-914 (1985); and Bittle et al., J. Gen. Virol. 66:2347-2354 (1985). If in vivo immunization is used, animals may be immunized with a peptidogenic protein and/or a polynucleotide encoding the peptidogenic protein described herein.

Animals such as rabbits, rats, mice, llamas, camels, and/or cows can be immunized with the peptidogenic protein and/or a polynucleotide encoding the peptidogenic protein. For instance, intraperitoneal and/or intradermal injection of emulsions containing about 100 micrograms of a peptidogenic protein or carrier protein and Freund's adjuvant or any other adjuvant known for stimulating an immune response may be used. Several booster injections may be needed, for instance, at intervals of about two weeks, to provide a useful titer of anti-peptidogenic protein antibody which can be detected, for example, by ELISA assay using free peptidogenic protein adsorbed, directly or indirectly (e.g., via a biotinylated AviTag), to a solid surface. The titer of anti-peptidogenic protein antibodies in serum from an immunized animal may be increased by selection of anti-peptidogenic protein antibodies, for instance, by adsorption to the peptidogenic protein on a solid support and elution of the selected antibodies according to methods well known in the art. Such selections could also be done using the starting protein.

Additionally, antibodies generated by the disclosed methods can be affinity matured using display technology, such as for example, phage display, yeast display or ribosome display. In one example, single chain antibody molecules ("scFvs") displayed on the surface of phage particles are screened to identify those scFvs that immunospecifically bind to the peptidogenic protein and/or the starting protein. The present invention encompasses both scFvs and portions thereof that are identified to immunospecifically bind to the peptidogenic protein and/or the starting protein. Such scFvs can routinely be "converted" to immunoglobulin molecules by inserting, for example, the nucleotide sequences encoding the VH and/or VL domains of the scFv into an expression vector containing the constant domain sequences and engineered to direct the expression of the immunoglobulin molecule.

Recombinant expression of an antibody raised using the peptidogenic protein and/or a polynucleotide encoding the peptidogenic protein of the invention (including scFvs and other molecules comprising, or alternatively consisting of, antibody fragments or variants thereof (e.g., a heavy or light chain of an antibody of the invention or a portion thereof or a single chain antibody of the invention)), requires construction of an expression vector(s) containing a polynucleotide that encodes the antibody or fragment or variant thereof. Once a polynucleotide encoding an antibody molecule (e.g., a whole antibody, a heavy or light chain of an antibody, or variant or portion thereof (preferably, but not necessarily, containing the heavy or light chain variable domain)), of the invention has been obtained, the vector(s) for the production of the antibody molecule may be produced by recombinant DNA technology using techniques well known in the art. Thus, methods for preparing an antibody by expressing a polynucleotide containing an antibody encoding nucleotide sequence are described herein. Methods which are well known to those skilled in the art can be used to construct expression vectors containing antibody coding sequences (as well as the coding sequences for the peptidogenic protein) and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding either the peptidogenic protein or an antibody raised to the peptidogenic protein (e.g., a whole antibody, a heavy or light chain of an antibody, a heavy or light chain variable domain of an antibody, or a portion thereof, or a heavy or light chain CDR, a single chain Fv, or fragments or variants thereof), operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy chain, the entire light chain, or both the entire heavy and light chains.

The expression vector(s) can be transferred to a host cell by conventional techniques and the transfected cells are then cultured by conventional techniques to produce either the peptidogenic protein or the antibody that has been raised against a peptidogenic protein. Thus, the invention includes host cells containing polynucleotide(s) encoding the peptidogenic protein or an antibody raised against the peptidogenic protein (e.g., whole antibody, a heavy or light chain thereof, or portion thereof, or a single chain antibody of the invention, or a fragment or variant thereof), operably linked to a heterologous promoter. In preferred embodiments, for the expression of entire antibody molecules, vectors encoding both the heavy and light chains may be co-expressed in the host cell for expression of the entire immunoglobulin molecule, as detailed below.

A variety of host-expression vector systems may be utilized to express the peptidogenic protein or the antibody raised to the peptidogenic protein. Such host-expression systems represent vehicles by which the coding sequences of interest may be produced and subsequently purified, but also represent cells which may, when transformed or transfected, with the appropriate nucleotide coding sequences, express the peptidogenic protein or the antibody raised to the peptidogenic protein. These include, but are not limited to, microorganisms such as bacteria (e.g., *E. coli, B. subtilis*) transformed with recombinant bacteriophage DNA, plasmid DNA or cosmid DNA expression vectors containing sequences; yeast (e.g., *Saccharomyces, Pichia*) transformed with recombinant yeast expression vectors containing coding sequences; insect cell systems infected with recombinant virus expression vectors (e.g., baculovirus) containing coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, are used for the expression of either the peptidogenic protein or a recombinant antibody molecule. For example, mammalian cells such as Chinese hamster ovary cells (CHO), in conjunction with a vector such as the major intermediate early gene promoter element from human cytomegalovirus is an effective expression system (Foecking et al., Gene 45:101 (1986); Cockett et al., Bio/Technology 8:2 (1990)).

In bacterial systems, a number of expression vectors may be advantageously selected depending upon the intended use. For example, when a large quantity of a protein (whether a peptidogenic protein or an antibody raised against the peptidogenic protein) is to be produced, vectors which direct the expression of high levels of fusion protein products that are readily purified may be desirable. Such vectors include, but are not limited to, the *E. coli* expression vector pUR278 (Ruther et al., EMBO 1. 2:1791 (1983)), in which the coding sequence may be ligated individually into the vector in frame with the lac Z coding region so that a fusion protein is produced; pIN vectors (Inouye & Inouye, Nucleic Acids Res. 13:3101-3109 (1985); Van Heeke & Schuster, J. Biol. Chem. 24:5503-5509 (1989)); and the like. pGEX vectors may also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or Factor Xa protease cleavage sites so that the cloned target gene product can be released from the GST moiety.

In an insect system, *Autographa californica* nuclear polyhedrosis virus (AcNPV) may be used as a vector to express a peptidogenic protein or an antibody raised against the peptidogenic protein. The virus grows in *Spodoptera frugiperda* cells. Coding sequences may be cloned individually into non-essential regions (for example, the polyhedrin gene) of the virus and placed under control of an AcNPV promoter (for example, the polyhedrin promoter).

In mammalian host cells, a number of viral-based expression systems may be utilized. In cases where an adenovirus is used as an expression vector, the coding sequence of interest may be ligated to an adenovirus transcription/translation control complex, e.g., the late promoter and tripartite leader sequence. This chimeric gene may then be inserted in the adenovirus genome by in vitro or in vivo recombination.

Insertion in a non-essential region of the viral genome (e.g., region E1 or E3) will result in a recombinant virus that is viable and capable of expressing the peptidogenic protein or an antibody raised against the peptidogenic protein in infected hosts (e.g., see Logan & Shenk, Proc. Natl. Acad. Sci. USA 8 1:355-359 (1984)).

Specific initiation signals may also be required for efficient translation of inserted coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner et al., Methods in Enzymol. 153:51-544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed, to this end, eukaryotic host cells which possess the cellular machinery for proper processing of the primary transcript, glycosylation, and phosphorylation of the gene product may be used. Such mammalian host cells include, but are not limited to, CHO, VERY, BHK, Hela, COS, NSO, MDCK, 293, 3T3, W138, and in particular, breast cancer cell lines such as, for example, BT483, Hs578T, HTB2, BT2O and T47D, and normal mammary gland cell line such as, for example, CRL7O3O and HsS78Bst.

For long-term, high-yield production of recombinant proteins, stable expression is preferred. For example, cell lines which stably express the peptidogenic protein or an antibody raised against the peptidogenic protein may be engineered. Rather than using expression vectors which contain viral origins of replication, host cells can be transformed with a polynucleotide controlled by appropriate expression control elements (e.g., promoter, enhancer, sequences, transcription terminators, polyadenylation sites, etc.), and a selectable marker. Following the introduction of the foreign polynucleotide, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the peptidogenic protein or an antibody raised against the peptidogenic protein.

A number of selection systems may be used, including but not limited to, the herpes simplex virus thymidine kinase (Wigler et al., Cell 11:223 (1977)), hypoxanthineguanine phosphoribosyltransferase (Szybalska & Szybalski, Proc. Natl. Acad. Sci. USA 48:202 (1992)), and adenine phosphoribosyltransferase (Lowy et al., Cell 22:8 17 (1980)) genes can be employed in tk-, hgprt- or aprt-cells, respectively. Also, antimetabolite resistance can be used as the basis of selection for the following genes: dhfr, which confers resistance to methotrexate (Wigler et al., Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 (Goldspiel et al., Clinical Pharmacy, 12: 488-505 (1993); Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62: 191-217 (1993); TIB TECH 11(5):155-2 15 (May; 1993)); and hygro, which confers resistance to hygromycin (Santerre et al., Gene 30:147 (1984)). Methods commonly known in the art of recombinant DNA technology may be routinely applied to select the desired recombinant clone, and such methods are described, for example; in Ausubel et al. (eds.), Current Protocols in Molecular Biology, John Wiley & Sons, N.Y. (1993); Kriegler, Gene Transfer and Expression, A Laboratory Manual, Stockton Press, N Y (1990); and in Chapters 12 and 13, Dracopoli et al. (eds), Current Protocols in Human Genetics, John Wiley & Sons, N.Y. (1994); Colberre-Garapin et al., J. Mol. Biol. 150:1 (1981).

The expression levels of a peptidogenic protein or an antibody raised against the peptidogenic protein can be increased by vector amplification (for a review, see Bebbington and Hentschel, *The use of vectors based on gene amplification for the expression of cloned genes in mammalian cells in DNA cloning*, Vol. 3. (Academic Press, New York, 1987)). When a marker in the vector system expressing a peptidogenic protein or an antibody raised against the peptidogenic protein is amplifiable, an increase in the level of inhibitor present in the host cell culture will increase the number of copies of the marker gene. Since the amplified region is associated with the coding sequence, production of the peptidogenic protein or an antibody raised against the peptidogenic protein will also increase (Crouse et al., Mol. Cell. Biol. 3:257 (1983)).

Other elements that can be included in vector sequences include heterologous signal peptides (secretion signals), membrane anchoring sequences, introns, alternative splice sites, translation start and stop signals, inteins, biotinylation sites and other sites promoting post-translational modifications, purification tags, sequences encoding fusions to other proteins or peptides, separate coding regions separated by internal ribosome reentry sites, sequences encoding "marker" proteins that, for example, confer selectability (e.g., antibiotic resistance) or sortability (e.g., fluorescence), modified nucleotides, and other known polynucleotide cis-acting features not limited to these examples.

In the case of antibodies, the host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain is preferably placed before the heavy chain to avoid an excess of toxic free heavy chain (Proudfoot, Nature 322:52 (1986); Kohler, Proc. Natl. Acad. Sci. USA 77:2 197 (1980)). The coding sequences for the heavy and light chains may comprise cDNA or genomic DNA or synthetic DNA sequences.

Once a peptidogenic protein or an antibody raised against the peptidogenic protein has been produced by recombinant expression, it may be purified by any method known in the art for purification of a protein, for example, by chromatography (e.g., ion exchange, affinity (particularly by Protein A affinity and immunoaffinity for the specific antigen), and sizing column chromatography), centrifugation, differential solubility, or by any other standard technique for the purification of proteins. Further, a peptidogenic protein or an antibody raised against the peptidogenic protein may be fused to heterologous polypeptide sequences described herein or otherwise known in the art to facilitate purification.

In one example, the peptidogenic protein or the antibody raised to the peptidogenic protein described herein may be fused with the constant domain of immunoglobulins (IgA, IgE, IgG, IgM), or portions thereof (CH1, CH2, CH3, or any combination thereof and portions thereof), or albumin (including but not limited to recombinant human albumin or fragments or variants thereof (see, e.g., U.S. Pat. No. 5,876,969, issued Mar. 2, 1999, EP Patent 0 413 622, and U.S. Pat. No. 5,766,883, issued Jun. 16, 1998), resulting in chimeric polypeptides. Such fusion proteins may facilitate purification and may increase half-life in vivo. This has been shown for chimeric proteins consisting of the first two domains of the human CD4-polypeptide and various domains of the constant regions of the heavy or light chains of mammalian immunoglobulins. See, e.g., EP 394,827; Traunecker et al., Nature, 331:84-86 (1988). Enhanced delivery of an antigen across the epithelial barrier to the immune system has been demonstrated for antigens (e.g., insulin) conjugated to an FcRn binding partner such as IgG or Fe fragments (see, e.g., PCT Publications WO 96/22024 and WO 99/04813). IgG Fusion proteins that have a disulfide-linked dimeric structure due to the IgG portion disulfide bonds have also been found to be more efficient in binding and neutralizing other molecules than monomeric polypeptides or fragments thereof alone. See, e.g., Fountoulakis et al., J. Biochem., 270:3958-3964 (1995). Nucleic acids encoding the peptidogenic protein or antibodies described herein can also be recombined with a gene of interest as an epitope tag (e.g., the hemagglutinin ("HA") tag or flag tag) to aid in detection and purification of the expressed polypeptide. For example, a system described by Janknecht et al. allows for the ready purification of non-denatured fusion proteins expressed in human cell lines (Janknecht et al., 1991, Proc. Natl. Acad. Sci. USA 88:8972-897). In this system, the gene of interest is subcloned into a vaccinia recombination plasmid such that the open reading frame of the gene is translationally fused to an amino-terminal tag consisting of six histidine residues. The tag serves as a matrix-binding domain for the fusion protein. Extracts from cells infected with the recombinant vaccinia virus are loaded onto Ni2+ nitriloacetic acid-agarose column and histidine-tagged proteins can be selectively eluted with imidazole-containing buffers.

Vaccination

A mixture of peptidogenic proteins and/or polynucleotides encoding the peptidogenic proteins can be used to vaccinate an animal. This vaccination may lead to the raising of antibodies to the peptidogenic proteins. A subject suitable for treatment as described above may be a mammal, such as a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon, rhesus macaque), an ape (e.g. gorilla, chimpanzee, orangutan, gibbon), or a human. In some preferred embodiments, the subject is a human. In other embodiments, non-human mammals, especially mammals that are conventionally used as models for demonstrating therapeutic efficacy in humans (e.g. murine, primate, porcine, canine, or rabbit animals) may be employed.

In some embodiments, the peptidogenic proteins are chimeric fusion proteins, e.g., a viral protein that has been fused to another protein, that are used for vaccines.

A vaccination strategy can be based on repetitive administration of the peptidogenic proteins and/or polynucleotides encoding the peptidogenic proteins to the subject as described herein to enable the development of memory B cells and memory T cells against the peptidogenic protein. Vaccination can be conducted either prophylactically or therapeutically. The peptidogenic proteins can be derived from either the same starting protein or from multiple starting proteins. While prophylactic vaccination strategies aim to stimulate the subject's immune system in developing preventive adaptive immunity to a pathogen, the goal of therapeutic vaccination strategy is conducted after the disease has been already established or to improve a clinical situation, present in the subject.

Proteolytic processing involves antigens such as peptidogenic proteins being processed in Antigen Presenting Cells after endocytosis and fusion of the endosome with a lysosome. The endosome then merges with an exocytic vesicle from the Golgi apparatus containing class II MHC molecules, to which the resultant peptides bind. The MHC-peptide complex then trafficks to the plasma membrane where the antigen is available for display to $CD4^+$ T cells. Any limitation of the proteolytic processing of the peptidogenic proteins could promote a narrowing of the diversity of the peptide products, which would give the class II MHC molecules fewer options among which to select stable binding partners, and this could exacerbate the phenomenon of immunodominant determinants Heightened immunodominance would in turn increase the proportion of non-responders in the population, because immune responsiveness is governed by the genetics of class II MHC alleles. Hence, vaccines using a mixture of peptidogenic proteins and/or polynucleotides encoding the peptidogenic proteins described herein should increase the variety of antigen peptides resulting from intra-endosomal proteolytic processing and therefore would be expected to increase the effectiveness of the vaccine.

Introduction into Animals Polynucleotides Encoding Peptidogenic Proteins

Polynucleotides encoding the peptidogenic proteins can also be directly introduced into animals. See, for example, U.S. Pat. Nos. 5,676,954; 6,875,748; 5,661,133; Sahin et al., Nat Rev Drug Discov, 2014 October; 13(10):759-80; Kariko et al., Mol Ther, 2008 November; 16(11):1833-40; Kariko et al., Nucleic Acid Res, 2011, November; 39(21):e142; U.S. Pat. No. 6,511,832. In one example, polynucleotides, such as a DNA sequences encoding a mixture of peptidogenic proteins are directly injected into a host animal and the polynucleotides enter into the nucleus to be transcribed to mRNA in order to produce the peptidogenic proteins.

Similarly, the polynucleotides can also be mRNA sequences, such as an in vitro transcribed mRNA (IVT mRNA). Essentially, synthetic mRNAs can be engineered to express peptidogenic proteins, and ideally, the mRNA is translated in the cell's cytoplasm without entering the nucleus. In the cytoplasm, the mRNA is decoded by ribosomes and is translated into the peptidogenic proteins.

In either method, the peptidogenic proteins are then processed and used to generate antibodies, much like immunization with a protein. The polynucleotides encoding the peptidogenic proteins can be synthesized using the genetic codon degeneracy and standard DNA synthesis techniques. Mixtures of different polynucleotides encoding the same peptidogenic protein, different peptidogenic proteins derived from the same starting protein, and/or different peptidogenic proteins derived from different starting proteins can be used.

Mammals that can be used to raise antibodies, include but are not limited to rabbits, rats, mice, llamas, and/or cows. The polynucleotides disclosed herein can be injected into the animals via intramuscular, intradermal, intranasal, subcutaneous, intravenous, intratracheal, and intrathecal deliveries. This method of raising antibodies allows for the concurrent production of many species of antibodies as compared to conventional methodology, substantially increasing the repertoire of antibodies produced.

Formulations

A pharmaceutical composition may comprise the peptidogenic proteins described herein, polynucleotides encoding the peptidogenic proteins, or an antibody raised to the peptidogenic protein along with one or more pharmaceutically acceptable carriers, adjuvants, excipients, diluents, fillers, buffers, stabilizers, preservatives, lubricants, or other materials well known to those skilled in the art. Suitable materials will be sterile and pyrogen-free, with a suitable isotonicity and stability. Examples include sterile saline (e.g. 0.9% NaCl), water, dextrose, glycerol, ethanol or the like or combinations thereof. Such materials should be non-toxic and should not interfere with the efficacy of the active compound. The precise nature of the carrier or other material will depend on the route of administration, which may be by bolus, infusion, injection or any other suitable route, as discussed below. The composition may further contain auxiliary substances such as wetting agents, emulsifying agents, pH buffering agents or the like. Suitable carriers, excipients, etc. can be found in standard pharmaceutical texts, for example, Remington's Pharmaceutical Sciences, 18th edition, Mack Publishing Company, Easton, Pa., 1990.

The term "pharmaceutically acceptable" as used herein pertains to compounds, materials, compositions, and/or dosage forms which are, within the scope of sound medical judgment, suitable for use in contact with the tissues of a subject (e.g., human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

In some embodiments, the peptidogenic proteins, the polynucleotides encoding the peptidogenic proteins or an antibody raised to the peptidogenic protein may be provided in a lyophilized form for reconstitution prior to administration. For example, lyophilized reagents may be re-constituted in sterile water and mixed with saline prior to administration to a subject.

Additionally, "cocktails" of the peptidogenic proteins, the polynucleotides encoding the peptidogenic proteins, or an antibody raised to the peptidogenic protein are specifically contemplated. For example, a mixture of different peptidogenic proteins or polynucleotides encoding different peptidogenic proteins derived from the same starting protein can be used to mount an immune response. Alternatively, a mixture of different peptidogenic proteins or polynucleotides encoding different peptidogenic proteins derived from different starting materials may also be used to mount an immune response.

The formulations may conveniently be presented in unit dosage form and may be prepared by any methods well known in the art of pharmacy. Such methods include the step of bringing into association the active compound with the carrier which constitutes one or more accessory ingredients. In general, the formulations are prepared by uniformly and intimately bringing into association the active compound with liquid carriers or finely divided solid carriers or both, and then if necessary shaping the product.

Formulations may be in the form of liquids, solutions, suspensions, emulsions, elixirs, syrups, tablets, lozenges, granules, powders, capsules, cachets, pills, ampoules, suppositories, pessaries, ointments, gels, pastes, creams, sprays, mists, foams, lotions, oils, boluses, electuaries, or aerosols.

Optionally, other therapeutic or prophylactic agents may be included in a pharmaceutical composition or formulation.

Treatment may be any treatment and therapy, whether of a human or an animal (e.g. in veterinary applications), in which some desired therapeutic effect is achieved, for example, the inhibition or delay of the progress of the condition, and includes a reduction in the rate of progress, a halt in the rate of progress, amelioration of the condition, cure or remission (whether partial or total) of the condition, preventing, delaying, abating or arresting one or more symptoms and/or signs of the condition or prolonging survival of a subject or patient beyond that expected in the absence of treatment.

Treatment as a prophylactic measure (i.e. prophylaxis) is also included. For example, a subject susceptible to or at risk of the occurrence or re-occurrence of the disease may be treated as described herein. Such treatment may prevent or delay the occurrence or re-occurrence of the disease in the subject.

The term "therapeutically-effective amount" as used herein, pertains to that amount of the peptidogenic protein or an antibody raised to the peptidogenic protein which is effective for producing some desired therapeutic effect, commensurate with a reasonable benefit/risk ratio.

It will be appreciated that appropriate dosages of the peptidogenic protein or an antibody raised to the peptidogenic protein can vary from patient to patient. Determining the optimal dosage will generally involve the balancing of the level of therapeutic benefit against any risk or deleterious side effects of the administration. The selected dosage level will depend on a variety of factors including, but not limited to, the route of administration, the time of administration, the rate of excretion of the active compound, other drugs, compounds, and/or materials used in combination, and the age, sex, weight, condition, general health, and prior medical history of the patient. The amount of peptidogenic protein, polynucleotide encoding the peptidogenic protein, or an antibody raised to the peptidogenic protein and route of administration will ultimately be at the discretion of the physician, although generally the dosage will be to achieve concentrations of the active compound at a site of therapy without causing substantial harmful or deleterious side-effects.

In general, a suitable dose of the peptidogenic protein or an antibody raised to the peptidogenic protein is in the range of about 100 μg to about 250 mg per kilogram body weight of the subject per day. Where the peptidogenic protein or an antibody raised to the peptidogenic protein is a salt, an ester, prodrug, or the like, the amount administered is calculated on the basis of the parent compound and so the actual weight to be used is increased proportionately.

Administration in vivo can be effected in one dose, continuously or intermittently (e.g., in divided doses at appropriate intervals). Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the physician.

By "simultaneous" administration, it is meant that the peptidogenic proteins, the polynucleotides encoding the peptidogenic proteins, or an antibody raised to the peptidogenic protein are administered to the subject in a single dose by the same route of administration.

By "separate" administration, it is meant that the peptidogenic proteins, the polynucleotides encoding the peptidogenic proteins, or an antibody raised to the peptidogenic protein are administered to the subject by two different routes of administration which occur at the same time. This may occur for example where one agent is administered by infusion or parenterally and the other is given orally during the course of the infusion or parenteral administration.

By "sequential" it is meant that the peptidogenic proteins, the polynucleotides encoding the peptidogenic proteins, or an antibody raised to the peptidogenic protein are administered at different points in time, provided that the activity of the first administered agent is present and ongoing in the subject at the time the second agent is administered. Preferably, a sequential dose will occur such that the second of the two agents is administered within 48 hours, preferably within 24 hours, such as within 12, 6, 4, 2 or 1 hour(s) of the first agent.

Multiple doses of the peptidogenic proteins, the polynucleotides encoding the peptidogenic proteins and/or an antibody raised to the peptidogenic protein may be administered. For example 2, 3, 4, 5 or more than 5 doses may be administered after administration of the peptidogenic proteins, the polynucleotides encoding the peptidogenic proteins, and/or an antibody raised to the peptidogenic protein. The administration of the peptidogenic proteins, the polynucleotides encoding the peptidogenic proteins, and/or an antibody raised to the peptidogenic protein may continue for sustained periods of time after initial administration. For example treatment with the peptidogenic proteins, the polynucleotides encoding the peptidogenic proteins, or an antibody raised to the peptidogenic protein may be continued for at least 1 week, at least 2 weeks, at least 3 weeks, at least 1 month or at least 2 months. Treatment with the peptidogenic proteins, the polynucleotides encoding the peptidogenic proteins, or an antibody raised to the peptidogenic protein may be continued for as long as is necessary to achieve a therapeutic response.

The peptidogenic proteins, the polynucleotides encoding the peptidogenic proteins, or an antibody raised to the peptidogenic protein and compositions comprising these molecules may be administered to a subject by any convenient route of administration, whether systemically/peripherally or at the site of desired action, including but not limited to, oral (e.g. by ingestion); and parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot, for example, subcutaneously or intramuscularly. Usually administration will be by the intravenous route, although other routes such as intraperitoneal, subcutaneous, transdermal, oral, nasal, intramuscular or other convenient routes are not excluded.

The pharmaceutical compositions comprising the peptidogenic protein, the polynucleotides encoding the peptidogenic proteins or an antibody raised to the peptidogenic protein may be formulated in suitable dosage unit formulations appropriate for the intended route of administration.

Formulations suitable for oral administration (e.g. by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by conventional means, e.g., compression or molding, optionally with one or more accessory ingredients. Compressed tablets may be prepared by compressing in a suitable machine the active compound in a free-flowing form such as a powder or granules, optionally mixed with one or more binders (e.g. povidone, gelatin, acacia, sorbitol, tragacanth, hydroxypropylmethyl cellulose); fillers or diluents (e.g. lactose, microcrystalline cellulose, calcium hydrogen phosphate); lubricants (e.g. magnesium stearate, talc, silica); disintegrants (e.g. sodium starch glycolate, cross-linked povidone, cross-linked sodium carboxymethyl cellulose); surface-active or dispersing or wetting agents (e.g. sodium lauryl sulfate); and preservatives (e.g. methyl p-hydroxybenzoate, propyl p-hydroxybenzoate, sorbic acid). Molded tablets may be made by molding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with an enteric coating, to provide release in parts of the gut other than the stomach.

Formulations suitable for parenteral administration (e.g. by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilizers, bacteriostats, and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer's Solution, or Lactated Ringer's Injection. Typically, the concentration of the active compound in the solution is from about 1 ng/ml to about 10 μg/ml, for example from about 10 ng/ml to about 1 μg/ml, from about 1 μg/ml to about 10 mg/ml, from about 10 μg/ml to about 1 mg/ml, from about 1 mg/ml to about 20 mg/ml, from about 10 mg/ml to about 120 mg/ml, or any other concentration suitable for administration of biological drugs (e.g., proteins, antibodies, etc.). The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the active compound to blood components or one or more organs.

Compositions comprising the peptidogenic proteins, the polynucleotides encoding the peptidogenic proteins and/or an antibody raised to the peptidogenic protein may be prepared in the form of a concentrate for subsequent dilution, or may be in the form of divided doses ready for administration. Alternatively, the reagents may be provided separately within a kit, for mixing prior to administration to a human or animal subject.

The peptidogenic proteins, the polynucleotides encoding the peptidogenic proteins, and/or an antibody raised to the peptidogenic protein may be administered alone or in combination with other treatments, either simultaneously or sequentially dependent upon the individual circumstances. For example, peptidogenic proteins, the polynucleotides encoding the peptidogenic proteins, or an antibody raised to the peptidogenic protein as described herein may be administered in combination with one or more additional active compounds.

Various further aspects and embodiments of the present invention will be apparent to those skilled in the art in view of the present disclosure.

It is to be understood that the application discloses all combinations of any of the above aspects and embodiments described above with each other, unless the context demands otherwise. Similarly, the application discloses all combinations of the preferred and/or optional features either singly or together with any of the other aspects, unless the context demands otherwise.

Modifications of the above embodiments, further embodiments and modifications thereof will be apparent to the skilled person on reading this disclosure, and as such these are within the scope of the present invention. All documents and sequence database entries mentioned in this specification are incorporated herein by reference in their entirety for all purposes. The invention is further described below, with reference to the following examples.

EXAMPLES

Example 1: Generating Peptidogenic Antigens

To generate peptidogenic proteins, a starting protein can be modified at its core residues (e.g., one or more mutations) to alter its conformational dynamics. Multiple different peptidogenic proteins can be designed and expressed to immunize animals, such as rabbits, to generate a polyclonal antibody response. Alternatively, polynucleotides encoding the peptidogenic proteins can be directly administered to the animals to generate the peptidogenic proteins in vivo. The response will be monitored by two complementary and mutually reinforcing methods (Georgiou et al, 2014; FIG. 2): (a) purifying B cells from the blood, spleen, and bone marrow of immunized animals, isolating cDNA from mRNA encoding the variable regions of the heavy and light chains, and analyzing this repertoire via deep DNA sequencing; and (b) immunoaffinity purifying from immune sera polyclonal Fab or (Fab')2 fragments using antigen attached to a solid support, digesting the eluted Fab/(Fab')2s with proteases, and sequencing the resultant peptides using LC/MS/MS.

Specifically, challenging test animals (rabbits) with a variety of peptidogenic proteins (or polynucleotides encoding the peptidogenic proteins) where the conformation is similar to the starting protein, but the conformational dynamics of the peptidogenic protein is varied, can be performed. Using next-generation DNA sequencing technology, the humoral response in the animal can be comprehensively characterized Immunoglobulin V-regions from B lymphocytes can be cloned and subjected to massively parallel deep sequencing (5-8). In conjunction with this, polyclonal antibodies from the same test animal can be purified by immunoaffinity chromatography, then protease-digested and subjected to LC-MS/MS to determine the peptide sequences (9, 10). Comparisons of these two datasets illuminate the repertoire of individual antibodies comprising the polyclonal response (9).

For example, small mammalian proteins that have been extremely well-characterized biophysically can be used as test antigens. Preferred examples, include, but are not limited to bovine pancreatic trypsin inhibitor and/or Alzheimer's amyloid precursor protein Kunitz domain. Alternatively, antigens relevant to unmet vaccine needs, such as for example, *P. falciparum* sporozoite antigens can also be generated and tested in this method. Additionally, optimization (or re-optimization) of synthetic vaccines with respect to conformational dynamics of the component proteins (perhaps replacing a single component with a combinatory cocktail of several versions of the same antigen with different core destabilizing mutations) can also be generated. Testing these new vaccines in clinical trials could involve monitoring of the vaccinated individuals using similar DNA sequence analyses of blood-derived B-cell V-region repertoires and proteomic characterization of immunoaffinity-purified polyclonal antibody peptides, similar to the procedures described above.

Other preferred examples of antigens that can be used according to embodiments of the invention described herein, include, but are not limited to antigens or antigens derived from, malarial polypeptides such as thrombospondin-related adhesive protein (TRAP) and/or apical membrane antigen 1 (AMA1), human immunodeficiency virus (HIV) gp120 and gp41, hepatitis C (HCV) envelope glycoproteins E1 and E2, Middle East respiratory syndrome coronavirus (MERS-CoV) Spike glycoprotein, human influenza virus hemagglutinin (HA) and neuraminidase, hepatitis B virus (HBV) capsid core, as well as antigens from related viruses that infect apes, monkeys, birds, pigs, camels, and other animals.

In preferred embodiments, any one of the *P. falciparum* protein antigens listed in the following Table 2 can be used as a starting protein to derive the peptidogenic protein. Additionally, multiple antigens listed in Table 2 can be used as the starting proteins to derive multiple different peptidogenic proteins to be used as a vaccine, generate an immune response, including the raising of antibodies.

TABLE 2

| Gene | Predicted Size | Paralogs | Predicted SP Cleavage Site | Gene | Predicted Size | Paralogs | Predicted SP Cleavage Site |
|---|---|---|---|---|---|---|---|
| MAL13P1.225 | 157 | | 23/24 | PFI0880C | 396 | | 25/26 |
| PF13_0203 | 158 | | 22/23 | PF11_0251 | 421 | | 22/23 |
| PF11_0164 | 195 | PFC0795C | 21/22 | PFC0065C | 437 | PF08_0022, PF14_0015 | 31/32 |
| PFL0375W | 209 | | 16/17 | PFC0925W | 492 | | 30/31 |
| PFI1270W | 217 | | 20/21 | MAL13P1.121 | 565 | | 34/35 |
| PF10_0104 | 223 | | 22/23 | PF13_0133 | 590 | | 33/34 |
| PF13_0128 | 230 | | 18/19 | PFL2015W | 676 | | 27/28 |
| PF11_0058 | 233 | | 35/36 | PFD0440W | 693 | | 25/26 |
| PFA0490W | 234 | | 29/30 | PFC0330W | 699 | | 26/27 |
| PF07_0087 | 244 | | 26/27 | PFD0430C | 840 | | 24/25 |
| PFB0570W | 250 | | 21/22 | PF14_0462 | 851 | PFC0550W | 28/29 |
| PF13_0180 | 258 | PFL0740C | 19/20 | PF07_0100 | 1032 | | 35/36 |
| PF11_0065 | 282 | | 23/24 | MAL7P1.23 | 1183 | | 30/31 |
| PF14_0678 | 287 | | 21/22 | PFL1835W | 1188 | | 26/27 |
| PF13_0125 | 292 | | 19/20 | PF07_0047 | 1229 | PFF0940C | 35/36 |
| PF13_0141 | 316 | PFF0895W | 20/21 | PF14_0250 | 1320 | | 28/29 |
| PF14_0117 | 327 | PFI1775W, PFL2530W | 22/23 | PFE0905W | 1379 | | 24/25 |
| PF11_0098 | 343 | | 26/27 | PFA0180W | 1472 | | 31/32 |
| PF14_0660 | 358 | | 23/24 | PFL1210W | 1696 | | 25/26 |
| PFD0240C | 378 | | 20/21 | PF14_0363 | 1922 | | 26/27 |
| PFE0080C | 398 | | 21/22 | PFB0400W | 2508 | | 34/35 |
| PFA0660W | 402 | PFB0090C, PFB0595W, PFE0055C | 34/35 | PFI0920C | 577 | | 26/27 |
| PF11_0352 | 423 | | 23/24 | PF14_0094 | 768 | | 22/23 |
| PF11_0055 | 424 | | 21/22 | PFA0125C | 1567 | | 26/27 |
| PFB0475C | 446 | | 22/23 | PF10_0372 | 120 | | 25/26 |
| PF11_0302 | 452 | | 21/22 | PFL2315C | 137 | | 28/29 |
| PFA0210C | 466 | | 23/24 | MAL13P1.271 | 181 | | 36/37 |
| PF07_0089 | 467 | | 16/17 | MAL7P1.31 | 236 | | 20/21 |
| PF14_0060 | 475 | | 16/17 | PF10_0317 | 263 | PF14_0653 | 35/36 |
| MAL8P1.17 | 483 | | 24/25 | PF07_0070 | 322 | | 19/20 |
| MAL7P1.77 | 522 | | 23/24 | MAL7P1.64 | 357 | | 28/29 |
| PF11_0099 | 540 | | 33/34 | PFI0935W | 370 | | 21/22 |
| PF07_0068 | 546 | | 22/23 | PFA0160C | 434 | | 22/23 |
| PF13_0201 | 574 | | 25/26 | PFB0465C | 457 | | 27/28 |
| PF07_0094 | 579 | | 17/18 | PF10_0208 | 627 | | 23/24 |
| PF07_0006 | 594 | MAL8P1.143 | 22/23 | PFB0760W | 686 | | 25/26 |
| PFL0770W | 618 | PF07_0073 | 20/21 | MAL13P1.206 | 687 | | 26/27 |
| PFI1645C | 642 | PF13_0262 | 18/19 | PF14_0541 | 717 | | 15/16 |
| PF14_0166 | 674 | | 25/26 | PFL0790W | 870 | | 21/22 |
| PFE0815W | 681 | | 24/25 | PFL2410W | 1039 | | 24/25 |
| PF11_0174 | 700 | | 27/28 | PF14_0440 | 1191 | | 23/24 |
| PFE0475W | 722 | PFB0525W | 21/22 | PF11_0333 | 1503 | | 25/26 |
| PF11_0074 | 743 | | 17/18 | PF10_0242 | 1541 | | 20/21 |
| PFL1385C | 743 | | 23/24 | PFC0590C | 1816 | | 20/21 |
| PF14_0102 | 782 | | 22/23 | PF14_0342 | 1898 | | 27/28 |
| PF11_0212 | 791 | | 20/21 | MAL7P1.92 | 2543 | PFI0550W | 22/23 |
| PF07_0129 | 811 | | 21/22 | PF14_0593 | 1357 | | 18/19 |
| PFL2570W | 816 | | 22/23 | MAL13P1.49 | 144 | | 24/25 |
| PFL1070C | 821 | | 28/29 | MAL13P1.172 | 260 | | 26/27 |
| PFB0695C | 888 | | 32/33 | PF08_0006 | 272 | | 19/20 |
| PF11_0175 | 906 | PF08_0063 | 26/27 | PFD1035W | 328 | | 37/38 |
| MAL13P1.22 | 912 | | 15/16 | PF11_0052 | 336 | | 24/25 |
| PFL0035C | 926 | | 27/28 | MAL13P1.79 | 383 | | 19/20 |
| PFI0685W | 955 | | 18/19 | PF10_0295 | 426 | | 23/24 |
| PFD0425W | 984 | | 21/22 | PFL1745C | 459 | | 22/23 |
| PF14_0293 | 992 | | 24/25 | PF14_0677 | 467 | | 24/25 |

TABLE 2-continued

| Gene | Predicted Size | Paralogs | Predicted SP Cleavage Site | Gene | Predicted Size | Paralogs | Predicted SP Cleavage Site |
|---|---|---|---|---|---|---|---|
| PF14_0344 | 993 | | 20/21 | PFL0600W | 558 | | 23/24 |
| PFL0560C | 1024 | | 20/21 | PF08_0108 | 573 | PF14_0281 | 26/27 |
| PF07_0035 | 1248 | | 20/21 | PF08_0081 | 577 | | 18/19 |
| PFL1675C | 1256 | | 21/22 | PF14_0620 | 858 | | 25/26 |
| PFC0435W | 1294 | | 19/20 | PFE0710W | 867 | | 21/22 |
| PFI1445W | 1364 | | 19/20 | PF11_0270 | 1013 | | 20/21 |
| PF13_0354 | 1408 | | 23/24 | MAL7P1.149 | 1051 | | 19/20 |
| PFC0110W | 1416 | MAL7P1.229, PFA0125C, PFD1155W | 24/25 | PFC0810C | 1119 | | 22/23 |
| PFC0120W | 1417 | | 24/25 | PF14_0249 | 1169 | | 25/26 |
| PF08_0078 | 1419 | | 20/21 | PF13_0116 | 1258 | | 19/20 |
| PF14_0614 | 1502 | | 16/17 | MAL13P1.60 | 1260 | | 25/26 |
| PF14_0051 | 1515 | | 26/27 | PF11_0246 | 1336 | | 23/24 |
| PF11_0076 | 1988 | | 22/23 | PFL2505C | 2215 | | 21/22 |
| MAL13P1.262 | 2006 | | 21/22 | PFB0405W | 3135 | | 20/21 |
| PFC0640W | 2114 | | 26/27 | PF11_0256 | 608 | | 17/18 |
| PFL2520W | 2792 | MAL13P1.176, PF13_0198 | 24/25 | PF08_0047 | 613 | | 28/29 |
| PFC0282W | 116 | | 23/24 | PFC0835C | 440 | | 22/23 |
| PF08_0004 | 137 | | 25/26 | PFI0605C | 446 | | 20/21 |
| PF11_0224 | 162 | | 22/23 | PF10_0127 | 499 | | 16/17 |
| PF13_0272 | 208 | | 22/23 | PF11_0344 | 622 | | 24/25 |
| MAL13P1.171 | 211 | | 20/21 | PF10_0130 | 628 | | 25/26 |
| PFE1340W | 214 | | 27/28 | PFL2395C | 639 | PF14_0428 | 28/29 |
| PF14_0369 | 235 | | 20/21 | PF08_0008 | 738 | | 21/22 |
| PF14_0178 | 259 | | 22/23 | PF14_0201 | 966 | | 22/23 |
| PFL0870W | 352 | | 24/25 | PFI1475W | 1720 | | 19/20 |
| PFC0210C | 397 | | 18/19 | PF13_0182 | 1838 | | 26/27 |
| PFI0500W | 432 | | 28/29 | PF14_0495 | 2189 | | 20/21 |
| PF11_0069 | 276 | | 25/26 | PF13_0277 | 2068 | | 22/23 |
| PFD0355C | 286 | | 32/33 | | | | |

To alter the conformational dynamics of a starting protein, the following changes in Gibbs Free Energy, shown in Table 3 below, can be considered:

TABLE 3

| Amino Acid Substitution (multiple positions in various proteins) | Average Gibbs Free Energy difference between mutant and wild type at core residues within a protein ΔΔG (kJ/mol) |
|---|---|
| Val -> Ala | −12.1(±3.3) |
| Val -> Thr | −11.3(±3.7) |
| Val -> Asn | −21.5(±1.0) |
| Leu -> Ala | −14.2(±4.2) |

As discussed in Loladze et al (J. Mol. Biol. 320, 343-357 (2002)), the following amino acid substitutions can decrease the thermodynamic stability (e.g., reflected in the Gibbs free energy) and alter the conformational dynamics of a starting protein. For example, Val and Leu (and other larger non-polar amino acid residues) can be substituted with smaller ones such as Ala, Thr, Asn, and/or Gly. In addition, the buried site of Glu in the starting protein, can be substituted with Leu, Val, Asn, Thr, Ser, Ala, and/or Gly. These single site amino acid substitutions are expected to generate peptidogenic proteins with lower stability but a similar conformation to the starting protein.

Alternatively, the conformational dynamics of the starting protein is altered by replacing (a) at least one threonine with a valine, alanine, glycine or serine; or (b) at least one cysteine with alanine, valine, glycine, serine or threonine; or (c) at least one valine with alanine, glycine, leucine or isoleucine; or (d) at least one leucine with alanine, valine, glycine, or isoleucine; or (e) at least one isoleucine with alanine, valine, leucine, or glycine; or (f) at least one proline, methionine, phenylalanine, tyrosine, or tryptophan with alanine, valine, leucine, isoleucine, or glycine; or (g) at least one aspartic acid or asparagine with glycine, serine, threonine, alanine, valine, leucine, isoleucine; or (h) at least one glutamic acid or glutamine with aspartic acid, asparagine, glycine, serine, threonine, alanine, valine, leucine, or isoleucine; or (i) at least one lysine with arginine, histidine, glycine, serine, threonine, alanine, valine, methionine, leucine, or isoleucine; or (j) at least one arginine with lysine, histidine, glycine, serine, threonine, alanine, valine, methionine, leucine, or isoleucine; or (k) at least one histidine with lysine, arginine, glycine, serine, threonine, alanine, valine, glutamine, asparagine, leucine, or isoleucine; or (l) at least one alanine with a glycine; or (m) at least one residue with a non-natural amino acid; and/or (n) any of the above combinations.

In still further preferred embodiments, the conformational dynamics of the starting protein is altered by replacing: (a) at least one tryptophan with tyrosine, phenylalanine, methionine, histidine, isoleucine, leucine, valine, alanine or glycine; or (b) at least one tyrosine with phenylalanine, methionine, histidine, isoleucine, leucine, valine, alanine or glycine; or (c) at least one phenylalanine with tyrosine, methionine, histidine, isoleucine, leucine, valine, alanine or glycine; or (d) at least one proline with methionine, leucine, isoleucine, valine, alanine, or glycine; or (e) at least one histidine with phenylalanine, tyrosine, methionine, isoleucine, leucine, valine, alanine, glycine, lysine, arginine, serine, threonine, asparagine, or glutamine; or (f) at least one methionine with isoleucine, leucine, valine, alanine or glycine; or (g) at least one isoleucine with leucine, valine, alanine or glycine; or (h) at least one leucine with isoleucine, valine, alanine or glycine; or (i) at least one valine with alanine, glycine, leucine, or isoleucine; or (j) at least one cysteine with alanine, valine, glycine, serine or threonine; or (k) at least one aspartic acid with glutamic acid, glutamine, asparagine, glycine, serine, threonine, alanine, valine, leucine, or isoleucine; or (l) at least one glutamic acid with aspartic acid, glutamine, asparagine, glycine, serine, threonine, alanine, valine, leucine, or isoleucine; or (m) at least one alanine with a glycine or proline; or (n) at least one serine with alanine or glycine; or (o) at least one glycine with alanine or proline; or (p) at least one lysine with arginine, histidine, glycine, serine, threonine, alanine, valine, methionine, leucine or isoleucine; or (q) at least one asparagine with glycine, alanine, serine, threonine, valine, leucine, isoleucine, glutamine, aspartic acid or glutamic acid; or (r) at least one glutamine with glycine, alanine, serine, threonine, valine, leucine, isoleucine, glutamine, aspartic acid, glutamic acid, or histidine; or (s) at least one arginine with lysine, histidine, glycine, serine, threonine, alanine valine, methionine, leucine, or isoleucine; or (t) at least one threonine with valine, alanine, glycine or serine; or (u) a hydrophobic residue with a smaller, similar hydrophobic residue; or (v) at least one residue with a non-natural amino acid; or (w) any of the above combinations. A combinatorial approach may be used to determine optimal substitutions to increase immunogenicity.

Example 2: Peptidogenic Proteins of Bovine Pancreatic Trypsin Inhibitor

Bovine pancreatic trypsin inhibitor (BPTI) is an extremely well-characterized small protein, on which there is a substantial body of literature describing its folding, structure, activity, thermodynamic properties, expression properties, and protease specificities (15). Our own lab was the first to express recombinant BPTI and engineer its properties using site-directed mutagenesis (16, 17). Wild type BPTI has three disulfide bonds, cross-linking disulfides 14-38, 30-51, and 5-55; the 14-38 disulfide is on the surface, and the other two disulfides are deeply buried in the hydrophobic core of the protein. Mutations of any one of these disulfides by replacing the two disulfide cysteines with alanine residues destabilizes the BPTI molecule (18). All possible combinations of disulfide bond mutants of BPTI have been made by ourselves and by others, and all are markedly destabilizing. Importantly, where it has been examined, for all combinations of mutants of BPTI that knock out one or two native disulfide bonds, the protein nevertheless maintains a similar three-dimensional structure and trypsin inhibitor activity comparable to wild type BPTI (19-22) Therefore, despite stability differences manifested by Tms ranging from >100° C. to <40° C., the wild type molecule and its disulfide mutants all display similar, if not virtually identical 3D conformational epitopes. For example, at 40° C. the mutant protein would be almost 50% unfolded at body temperature, and at >100° C. (higher than the boiling point of water) the wild type protein is among the most thermostable proteins known.

TABLE 4

Mutants of BPTI that knock out one or more of the native disulfide bonds or core residues while preserving 3D structure

| BPTI variant | Sequence |
|---|---|
| wild type | RPDFC LEPPY TGPCK ARIIR YFYNA KAGLC QTFVY GGCRA KRNNF KSAED CMRTC GGA (SEQ ID NO.: 919) |
| [C14A C38A] | RPDFC LEPPY TGPAK ARIIR YFYNA KAGLC QTFVY GGARA KRNNF KSAED CMRTC GGA (SEQ ID NO.: 920) |
| [C14A, C38A], K15A | RPDFC LEPPY TGPAA ARIIR YFYNA KAGLC QTFVY GGARA KRNNF KSAED CMRTC GGA (SEQ ID NO.: 921) |
| [C14A, C38A], K15A, F22A | RPDFC LEPPY TGPAA ARIIR YAYNA KAGLC QTFVY GGARA KRNNF KSAED CMRTC GGA (SEQ ID NO.: 922) |
| [C14A, C38A], K15A, Y23A | RPDFC LEPPY TGPAA ARIIR YFANA KAGLC QTFVY GGARA KRNNF KSAED CMRTC GGA (SEQ ID NO.: 923) |
| [C14A, C38A], K15A, N43G | RPDFC LEPPY TGPAA ARIIR YFYNA KAGLC QTFVY GGARA KRGNF KSAED CMRTC GGA (SEQ ID NO.: 924) |
| [C14A, C38A], K15A, F45A | RPDFC LEPPY TGPAA ARIIR YFYNA KAGLC QTFVY GGARA KRNNA KSAED CMRTC GGA (SEQ ID NO.: 925) |

For our immunological experiments with BPTI, since we are interested in protease digestion and peptide generation in vivo from the antigen, we will make the BPTI mutants described in Table 4. Mutated residues are underlined, cysteine residues are shown in bold. These consist of wild type BPTI with the surface disulfides 14-38 mutated to alanine, which has been shown to confer increased stability to reducing agents. The BPTI mutants will also be made in the [Lys15→Ala] background. The Lys15-Ala mutation ablates the P1 residue side chain and reduces BPTI's affinity towards trypsin and other proteases by as much as 107-fold, rendering it essentially inactive as a protease inhibitor (23). Additional mutations within the core of the protein (e.g. F22A, Y23A, N43G, F45A) serve to destabilize the protein and alter conformational dynamics to varying degrees while still maintaining a 3D structure comparable to wild type BPTI. This table is intended to be non-limiting with respect to present invention embodiments.

Analogous mutations can be made in the Alzheimer's amyloid precursor protein Kunitz inhibitor (APP-KI), which is a human protease inhibitor homologous to BPTI. APP-KI has a relatively low isoelectric point (pI) and so, unlike BPTI, it should be electrostatically nearly neutral in charge at lysosomal pH. Like BPTI, APP-KI has previously been expressed and characterized in terms of folding, activity, and 3D structure, and it has three disulfide bonds precisely homologous to those found in BPTI.

We will express the mutants both with and without flanking tag sequences. Tags we have used to vary solubility include the calmodulin binding peptide (CBP) tag, which is highly soluble, to the TrpLE tag, which is highly insoluble (24). In a particularly favored construct, however, we use a tripartite tag: AviTag-hexaHis-TEV protease cleavage site. This tag confers intermediate solubility, can by biotinylated using the BirA biotin ligase (25), allows binding to a HisTrap column for purification and/or on-column refolding (Campbell and Anderson, in preparation), and can be cleaved off the antigen if necessary. The antigen can be used to immunize animals either without the tag (i.e., after TEV cleavage) or with the tag intact followed by subtractive depletion of anti-tag antibodies (S. Blackshaw and D. Eichinger, personal communication).

Example 3: Preferred Targets of the Present Invention

As used herein a “Target” is a specifically selected protein disclosed in Table 5 that can be modified to have an improved peptidogenicity as described herein. Column 1 lists the SEQ ID NO. corresponding to the sequence provided in the Sequence Listing. Column 2 lists the “Protein Name” of each Target and Column 3 provides the “UniProt Reference Number” which is a unique “cataloging” number (UniProt Reference Numbers provide a mapping of a proteome to a reference genome assembly, e.g., as produced by the Genome Reference Consortium (GRC)) used in the art that provides publicly known and established descriptions of both the function, expression and sequence information for each Target listed in Column 2. This public information (retrieved from the UniProt database (http://www.uniprot.org) on Aug. 10, 2016) including the sequence information corresponding to each Target, is herein incorporated by reference in its entirety. The Sequence Listing and Table 5 describes the positions of the specific residues in each target protein where mutations can be made to generate the corresponding peptidogenic proteins along with the specific amino acids that can be substituted at each position. In preferred embodiments, multiple substitutions can be made in each target protein at the recited positions in the Sequence Listing and as shown in Table 5. In further preferred embodiments, at least 1, 2, 3, 4, 5, 6, 7, 8, 9, 10 or more of the residues listed in the Sequence Listing and/or Table 5 for each target protein, in any combination, can be changed in the respective starting Target proteins listed in Column 2 using the amino acid specified in the Sequence Listing and/or as described in the last two paragraphs of Example 1. By spreading the mutations over multiple positions and/or target proteins, and by mixing these mutated molecules together, an immunization cocktail can be created.

TABLE 5

| TARGETS | | | |
|---|---|---|---|
| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
| 1 | Hemagglutinin [Cleaved into: Hemagglutinin HA1 chain; Hemagglutinin HA2 chain]/strain A/USA: Phila/1935 H1N1 | A4GCL9 | V7, I20, C21, I22, A26, V33, V36, V43, L49, L50, L58, C59, L61, L67, L69, C72, I74, A75, W77, L78, L79, C84, L87, W93, Y95, I96, V97, Y108, L118, L122, V125, F128, F134, A151, A152, C153, H155, L165, L166, W167, L168, L178, V190, L191, V192, L193, W194, V196, H197, H198, Y209, Y215, V216, V218, V219, Y223, M244, Y246, Y247, L250, L251, I257, F259, A261, L265, I266, A267, Y270, A271, F272, A273, L274, F278, I282, I283, C292, C296, A302, I303, H313, I317, V324, L329, M331, V332, A349, M361, Y366, A388, I389, A440, L452, V459, L462, V466, L470, C481, H486, C488, C492, M493 |
| 2 | Proprotein convertase subtilisin/kexin type 9 (EC 3.4.21.—) | A8T655 | V80, A95, L98, A102, F122, V124, A134, I143 |
| 3 | Plasminogen (EC 3.4.21.7) | B2R7F8 | Y193, W209, C234, W244, C245, F246, C257, I259 |
| 4 | cDNA FLJ60453, highly similar to Proprotein convertase subtilisin/kexin type 9 (EC 3.4.21.—) | B4DEZ9 | V80, L98, A102, F122, V124, A134, I143 |
| 5 | Receptor protein-tyrosine kinase (EC 2.7.10.1) | B4DTR1 | V474, I476, A495, I512, C513, V521, L530, V534, L546, L547, W549, C550, I553, A554, M557, L560, L565, V566, H567, L570, A571, A572, V575, V577, V583, I585, A591, A614, F623, V629, W630, Y632, V634, V636, L639, M640, I655, L659, I670, V675, M679, C682, W683, F693, F700, M703, V711 |
| 6 | Interleukin-4 | D4HNR6 | L31, I34, L38, C48, C70, A72, A73, L76, C89, H100, L107, L110, L114, A118, L133, F136, L140, M144 |
| 7 | Cell wall-binding repeat protein/NAP07 | D5RWT1 | F32, F51, F53, F73, A74, F104, F124, A129, A132, F143, F164, A165, F195, F215, A220, A223, F237 |
| 8 | Insulin, isoform 2 | F8WCM5 | L35, A38, L39 |
| 9 | Fusion glycoprotein F0 | G8EJ09 | L204, I206, I214, S215, I233, V247, M251, L257, I261, M274, I280, V281, Y299, V301, L303, C313, C333, C343, V349, F352, V365, F366, C367, C382, A412, I413, V414, C416, C422, A424, V442, V450 |
| 10 | TcdA | I6YE93 | F2585, A2593, F2604, F2625, A2626, F2656, F2676, A2681, A2684, F2698 |
| 11 | Spike glycoprotein/isolate United Kingdom/H123990006/2012 (HCoV-EMC) | K9N5Q8 | C30, F40, W44, I48, A53, Y58, Y64, I67, L74, Y85, F101, Y105, F112, V117, I120, A123, A124, I132, Y144, V153, L169, V170, L172, C176, A182, Y184, C185, C195, F232, C237, F239, Y243, W253, F254, I256, V263, L265, M278, F279, A282, I290, Y292, Y293, I300, A309, A312, F313, Y314, Y316, L318, V329, A336, C339, L347, C349, Y351, F354, V360, Y361, F366, A368, C383, F404, C407, Y409, L411, L414, L415, L417, V420, F423, C425, A434, C437, Y438, F446, A461, I464, F467, Y469, C478, A482, Y497, C503, I573, Y577, V584, C585, C603, Y606, V616, F617, C620, V631, Y632, Y648, Y649, C650, C654, V655, V657, V659, V661, I662, Y663, A671, L673, V677, C679, L697, L707, V711, C713, V724, C727, L729, L731, L735, C736, A737, V770, I782, F786, I795, V802, C806, V810, C811, C817, L821, Y824, F827, C828, L835, L893, L894, F895, V898, Y909, C912, L923, C925, V934, L935, Y947, W960, A968, F972, Y978, V989, L990, I997, F1001, A1004, A1007, F1012, A1018, V1026, A1030, A1032, L1033, L1036, L1040, F1044, A1046, I1047, A1049, I1054, L1058, A1065, I1067, L1070, I1071, L1075, L1078, A1080, L1086, V1103, C1106, V1107, F1116, C1117, I1123, V1127, A1130, L1134, F1136, Y1141, L1155, C1156, A1166, Y1171, F1172, W1184, Y1192, I1197, V1209, Y1211, L1223, L1260, L1262, M1266, L1276, Y1280, I1281, C1320, C1323, C1327 |
| 12 | Serine/threonine-protein kinase Sgk1 (EC 2.7.11.1) | O00141 | A115, V126, F158, F166, L172, F174, V175, L184, A199, Y202, A203, A204, I206, A207, A209, L210, L223, I228, L230, I236, L238, A265, V278, W280, W281, C282, L283, A285, V286, L287, M290, A324, L327, L328, L331, I349, F355, L363 |
| 13 | AP-4 complex subunit mu-1 | O00189 | V187, L189, V191, L195, I199, V210, I214, L216, M226, I228, L230, F234, V250, L270, V281, M282, Y284, L286, F296, L311, V313, L315, L317, C319, A327, V330, L332, L334, L347, W363, L365, V368, M380, A405, L407, F409, L411, L419, Y449 |
| 14 | Toll-like receptor 4 | O00206 | Y38, C40, L59, L61, L69, F74, F77, L80, L83, L85, C88, I90, I93, A97, Y98, L101, L104, L107, L109, I114, A121, F122, L125, L128, L131, A133, L141, I146, L149, L152, L155, V157, A158, I162, F165, L167, F171, L174, L177, L180, L182, I187, I190, L195, V197, L198, L203, L206, L208, L210, M215, I218, A222, F223, I226, L228, L231, L233, M243, C246, I247, L253, V255, L258, L260, F272, A276, L277, L280, F288, L290, Y296, L297, I300, L303, F304, L307, V310, F313, L315, V318, I320, V323, F326, F330, W332, L335, L337, C340, F342, L348, L350, L353, L356, F358, G363, L372, L375, L378, L380, L385, F387, C390, C391, F396, L401, L404, L406, I412, M414, F418, L421, L424, L427, F429, M437, V442, F443, L446, L449, I450, L452, I454, V461, I466, F467, L470, L473, L476, M478, F483, L488, F492, L495, L498, L501, |

TABLE 5-continued

TARGETS

| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
|---|---|---|---|
| | | | L503, C506, L508, A515, F516, L519, L522, V524, L525, M527, F532, F533, L535, Y540, L543, L546, L549, Y551, I556, L571, L574, L576, F581, F590, L591, I594, L600, M607, V620 |
| 15 | Tumor necrosis factor receptor superfamily member 10A | O00220 | C132 |
| 16 | Agouti-related protein | O00253 | C94, C119 |
| 17 | Tubby-related protein 1 | O00294 | V295, C307, L309, L326, L337, I352, I367, L370, V381, F382, L403, A404, A405, V406, V423, I424, I425, I437, L446, L461, I493, V503, L504, F506, F514, L516, Y518, L522, C523, A524, L525, A527, F528, A529, I530, A531, L532, L539 |
| 18 | Tumor necrosis factor receptor superfamily member 11B | O00300 | C41, C44, C65, C124 |
| 19 | Krev interaction trapped protein 1 | O00522 | A10, V12, A13, V14, I15, Y28, Y33, I35, L36, L37, L54, I68, V72, A108, L110, I112, V113, L135, L152, M156, L157, L160, L164, I174, L292, H293, A296, L304, A323, I325, H326, A328, C329, A336, L340, C346, A362, A363, I370, V371, L374, C396, A407, I424, V434, V444, I447, I463, I465, W487, L491, L508, I522, A527, I528, I530, L531, A535, L539, A546, L551, I552, L554, A555, L557, L558, L559, H571, I584, V585, L590, A594, I601, Y605, L621, F625, L626, C629, I632, V658, V660, V662, L667, H668, L669, L670, F697, I699, V710, A715, V718, L722, L725 |
| 20 | C-C motif chemokine 21 | O00585 | L63, F64, C75, A76, V83 |
| 21 | Lysosomal alpha-mannosidase | O00754 | A241, Y306 |
| 22 | Receptor-type tyrosine-protein phosphatase T | O14522 | F74, M75, V77, A88, L90, L92, H101, F105, L120, V122, V124, V135, A149, L151, A152, I153, Y161, V163, F165, I177, A178, V179, V184, F211, C213, L227, A250, V252, Y265, C267, V268, I269, V277, A281, L305, I307, V325, I358, L362, L403, L405, C417, V424, L449, I458, L460, L462, L464, I502, I504, Y519, I521, F553, Y562, F564, I566, A568, V578 |
| 23 | Tumor necrosis factor receptor superfamily member 10B | O14763 | C81, C139 |
| 24 | Tripeptidyl-peptidase 1 | O14773 | L49, F51, A52, L61, V65, L80, L82, V85, A86, V89, V99, A105, F119, C122, L124, I126, A129, L133, F138, V150, Y157, L159, V167, F169, V170, L173, V200, Y209, A226, C227, A228, F230, L240, F243, V277, Y279, L280, M281, A283, A285, I287, F304, L305, W307, L308, V320, H321, V323, Y336, I337, V340, L344, A347, A348, A349, L355, F356, A363, F378, A380, V385, V388, F397, V404, V426, A448, V452, A453, A454, L455, Y459, V461, V462, V471, A476, V480, F481, I484, L485, L487, I488, V518, H523, C526, F536, V545, L556, L560 |
| 25 | Tumor necrosis factor ligand superfamily member 11 | O14788 | L168, I170, L184, L206, V208, Y214, L216, A218, I220, F222, L238, V240, V242, L283, I289, I291, V293, A310 |
| 26 | Growth/differentiation factor 8 | O14793 | C281, C282, C372, C374 |
| 27 | Ras-related protein M-Ras | O14807 | L11, Y14, L16, V17, V18, V19, V24, L29, F33, V39, I56, A61, I62, L63, V65, L66, A69, M77, M82, F88, L89, I90, V91, Y92, V94, V103, F106, I110, V113, F119, M121, I122, L123, V124, A125, I136, A145, A157, V164, A167, F168, L171, V172 |
| 28 | Tumor necrosis factor receptor superfamily member 13B | O14836 | C89, C100, A101 |
| 29 | Interferon regulatory factor 6 | O14896 | W449 |
| 30 | Natural cytotoxicity triggering receptor 3 | O14931 | A35, L37, C39, A49, F56, H89, A91, I95, V98, I105, Y106, C108, V110, V112, L125 |
| 31 | Peripheral plasma membrane protein CASK | O14936 | F8, C15, V26, C29, V40, V45, F48, L59, L69, I74, L77, L87, M89, V90, F91, L99, C100, I103, Y113, A118, M122, I125, L126, A128, L129, C132, I137, I138, H139, V142, C146, V147, L148, L149, V158, L160, A166, A187, V191, V202, W203, C205, V207, I208, L209, F210, I211, L212, L213, F227, I230, W242, A249, L252, V253, M256, V267, A270, W275, L276, L295, A310, V312 |
| 32 | Cyclin-G-associated kinase (EC 2.7.11.1) | O14976 | L40, V42, A57, L68, L71, I82, L92, I98, I107, L122, L130, C145, V148, L149, I151, F152, C156, A158, V159, M162, H171, L179, L181, I187, L189, F192, I198, I246, L249, L253, L256, F288, I292, M295, V309, L313, A317, I328, F525, V640 |
| 33 | Synapsin-3 | O14994 | L94, L95, V96, I97, W104, F126, C139, V141, I162, L163, V164, V181, V192, L211, F223, V226, V246, V247, V261, F267, V273, V274, A281, I295, A304, Y305, W335, V336, C339, I348, C349, A350, V351, A353, I363, M371, M385, A386, V389 |
| 34 | Spectrin beta chain, non-erythrocytic 2 | 015020 | F63, W66, V67, L71, L81, L85, L91, L92, L94, L95, V119, A122, L123, L126, L133, I141, V142, L152, V153, I156, I157, I162, I165, L182, C186, V198, F201, W205, A210, F211, A213, I214, V215, L228, H234, L237, A240, F241, A244, L253, |

TABLE 5-continued

TARGETS

| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
|---|---|---|---|
| | | | L254, V259, I269, I270, Y272, V273, A274, Y276, Y277, L2225, A2238, V2246, C2248, L2250, L2255, F2257, L2278, V2295, F2296, L2298, F2308, A2310, W2319, V2323, A2326 |
| 35 | Niemann-Pick C1 protein | O15118 | W27, V59, C63, L73, C74, C75, L80, L94, C97, C100, L104, L107, C113, L121, V141, L144, Y146, V148, F152, A153, M156, A159, C160, V163, A172, L173, C177, W189, I190, F194, C227, C243, L408, I410, F431, L435, V443, L444, L446, I450, V462, L464, I467, C479, I481, V484, L485, Y487, F488, L495, A507, H510, H512, C516, C533, V541, L545, V546, L547, A558, L561, I563, F565, V567, A580, W583, F587, L649, L656, A659, L720, L724, V727, F763, A1035, F1100, A1124, M1138, M1228 |
| 36 | Laminin subunit alpha-5 | O15230 | L273 |
| 37 | Phosphomannomutase 2 | O15305 | L8, C9, L10, F11, L17, M28, F31, L32, L35, I41, V43, V44, V52, L56, V60, Y64, V67, F68, L73, A75, I87, L99, C103, M126, L127, V129, I132, F144, F157, L161, I178, F180, V182, C192, L193, V196, F206, F207, I220, C241 |
| 38 | Phosphatidylinositol 3,4,5-trisphosphate 5-phosphatase 2 (EC 3.1.3.86) | O15357 | A31, L34, L35, F44, L45, V46, A55, L58, C59, V60, I71, V81, V87, L98, I99, Y102, L113, V117, I424, V426, F427, I428, W431, I466, V468, F469, L489, I508, V510, A511, V512, L513, V514, A543, V544, V546, F548, F550, F555, F557, C560, H601, F603, F605, L608, Y610, I619, L631, L637, V646, F657, W688, C689, I692, L693, Y707, C709, I713, V721, F722, V727, M1201, L1205, L1217, L1228, L1236, V1241, L1250 |
| 39 | Eukaryotic translation initiation factor 3 subunit H | O15372 | V36, V39, V45, L67, I78 |
| 40 | Neural cell adhesion molecule 2 | O15394 | L32, F40, C42, A44, W53, L78, I80, A83, C93, A95, V107, A132, V134, C136, I173, I176, Y184, C186, V190, I201, V203, V205, A220, A222, F230, C232, W244, L266, V268, I271, Y279, C281, A283, A294, L296, I304, L320, C322, W334, F343, I354, L365, I367, V370, Y378, C380, A382, M393, I418, I420, C422, V424, W434, L460, I462, Y473, C475, A477, Y488, A493, A512, V514, F516, Y530, V532, L556, I567, V569, A570, A571, L611, I613, A621, V628, L653, L656, V664, I666, A668 |
| 41 | Toll-like receptor 3 | O15455 | A35, C37, I53, L56, L58, L63, L66, F71, Y74, L77, L80, V82, I87, L98, L101, V103, L104, L106, L111, F119, L125, L128, L130, I135, F143, L149, L152, L154, L164, L170, L173, L176, L178, I183, L186, L191, I193, F194, L199, L202, L204, I209, C216, F217, L223, L226, L228, V231, L241, C242, L245, I250, L253, L255, L260, F268, L269, L271, L276, L279, L281, L286, V289, F294, L297, L300, F303, L305, I310, L313, L318, L321, V324, L327, L329, F351, L354, L357, L360, M362, F375, L378, L381, L384, L386, L396, F401, L404, L409, H410, L412, L414, I419, I422, A426, F427, L430, L433, L436, L438, L440, I443, L447, W452, L455, I458, I461, L463, L469, L471, F476, V479, L482, L485, L487, V490, L492, V495, F502, L505, L508, L511, L513, I521, M525, L526, L529, L532, L535, L537, L542, L545, W546, F557, L558, L561, L564, L567, L569, F574, F582, L585, L588, I591, L593, L595, L598, L601, F606, L612, L615, L617, I622, V625, A633, F634, L640, M642, F647, I654, F657, Y675, V688 |
| 42 | Fibroblast growth factor 10 | O15520 | L82, L90, I92, L111, I113, V123, A125, L132, A133, M134, C150, L152, Y164, M176, V178, A179, L180, A199, F201 |
| 43 | Leucine-rich repeat transmembrane protein FLRT2 | O43155 | I75, L100, I121, L129, L132, L135, L138, L140, I159, L161, L163, L164, L166, L185, A193, L203, L206, L209, V211, L215, L216, F235, I237, L254, L257, L259, L278, L281, L288, L291, F296, L299, L305, I318, L325 |
| 44 | Kunitz-type protease inhibitor 2 | O43291 | C84, C133, C179 |
| 45 | Desert hedgehog protein | O43323 | A59, V67, A95, M99, C103, V107, L110, A111, V114, L123, V125, W129, L140, H141, A146, L147, I149, Y159, L161, L162, A163, A166, V174, V182, V184, V186, A188, V194 |
| 46 | Glutamate receptor ionotropic, delta-2 | O43424 | V445, V446, F453, V454, F470, V474, L475, L478, A491, L508, V509, A517, I519, I521, L524, V534, V547, L548, L549, L562, L671, Y679, M708, I712, V732, A738, F739, V740, V745, L746, F758, Y770, I772, A773, L774, F784, I788, M797 |
| 47 | Tumor necrosis factor ligand superfamily member 14 | O43557 | A96, L98, L112, A132, L133, V135, Y141, I143, V147, L149, I162, H164, L166, L180, V215, V216, V217, L224, F235 |
| 48 | Carbonic anhydrase 12 (EC 4.2.1.1) | O43570 | W43, I58, L60, Y79, L89, V96, L98, M104, I106, L118, L120, H121, W122, H133, A142, L144, H145, I146, H148, A160, A168, L170, A171, V172, L173, I174, Y183, I186, L190, V193, V202, I207, L210, C230, V234, W236, V238, F239, I245, L250, L251, L253, A256, L257, M270, V285 |
| 49 | Alpha-actinin-4 | O43707 | F56, W59, C60, L64, F78, L82, L84, L87, L88, V112, A115, L116, I119, L126, A131, I134, V135, L143, M145, I146, I149, I150, A154, I155, I158, L169, C173, V185, F188, W192, A197, F198, A200, L201, I202, L215, V221, L224, A227, F228, A231, M240, A243, I246, A256, I257, M258, Y260, V261, F264, Y265, A274, A415, F418, A422, L436, I449, I473, L480, V491, I498, L505, L516, H530, Y533, A537, M544, I563, L577, I587, A594, L605, I619, V626, L637, M679, I719, I743, M815, I880 |

TABLE 5-continued

TARGETS

| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
|---|---|---|---|
| 50 | EGF-like repeat and discoidin I-like domain-containing protein 3 | O43854 | C59, C116, C154, M325, W351, A356, A366, W367, L378, V380, V388, I391, A396, V405, Y408, L410, A411, Y422, A453, I456, I458, I467, L469, L473 |
| 51 | Tolloid-like protein 1 (EC 3.4.24.—) | O43897 | A148, A149, W157, I162, F178, A181, W185, V191, I203, F205, I226, V238, V239, L242, V245, I246, F248, H250, H252, V261, I268, F276, I296, M297, H298, I313, A340 |
| 52 | Peroxisome biogenesis factor 1 | O43933 | V19, V108, I155 |
| 53 | Kalirin (EC 2.7.11.1) | O60229 | L2148 |
| 54 | Cubilin (460 kDa receptor) | O60494 | Y952, I962, I970, L1020, F1024, I1037, Y1068, C1074, Y1076, I1086, L1095, L1107, I1109, F1143, F1154, A1156, C1191, W1193, L1195, A1202, F1203, M1255, F1270, A1272, V1281, L1291, C1306, W1308, V1318, V1368, L1370, F1382 |
| 55 | Gremlin-1 | O60565 | C178 |
| 56 | Toll-like receptor 5 | O60602 | L72, L75, L94, L97, A114, L121, L124, L144, L147, I157, L169, I175, F177, I182, L190, L314, L317, L338, L341, L359, V362, I365, A425, V447, L450, L475, V497, L507, L531, L553, I555 |
| 57 | ATP-binding cassette sub-family C member 9 | O60706 | M702, I703, V704, C709, L714, L715, A717, I718 |
| 58 | Voltage-dependent L-type calcium channel subunit alpha-1F | O60840 | A252, A700, I707, A1015, V1082, A1095, Y1120, A1372, M1389 |
| 59 | Matrix metalloproteinase-20 | O60882 | L45, Y49, L75, L81, L122, I126, V138, A141, V142, A145, L146, A148, W149, V153, L155, A165, I167, I169, F171, A190, F193, F205, W211, L220, F221, V223, A224, A225, F228, A231, L232, L234, A242, L243, M244, Y245, Y250, L258, V263, I266, L269 |
| 60 | Low-density lipoprotein receptor-related protein 5 | O75197 | L35, L36, F37, A38, V43, L62, A65, A67, V68, V77, Y78, W79, V82, A86, I87, L113, L122, Y123, W124, I132, V134, M165, Y166, W167, I176, A179, M181, V190, A212, I219, A242, L250, W252, I260, H261, I284, V286, L309, L311, L312, C321, C323, L344, L345, L346, A347, I355, L357, A375, Y388, W389, A396, I397, L430, Y431, W432, I440, V442, M473, Y474, W475, I484, A487, L489, L517, W519, I530, L545, I568, L588, M589, C605, L615, C616, F617, C627, I1274, C1323 |
| 61 | Core histone macro-H2A.1 | O75367 | A19, F23, V25, M28, I32, H36, V43, A45, V47, Y48, M49, A50, A51, V52, L53, L56, I60, L61, A64, A67, A68, V76, H80, I81, L83, V85, L91, V98, A101, L197, L199, I200, I204, L207, A208, F210, A214, I215, I216, I223, L233, F241, V245, L255, A258, A270, V273, I274, H275, C276, L290, V294, C297, L298, A301, I309, A310, F311, I314, A326, A327, I330, L331, A333, I334, F338, I346, V349, F351, Y362, M366 |
| 62 | Filamin-B | O75369 | F22, C26, L30, I37, L40, L44, L50, I51, L53, L54, V80, V82, A83, L84, F86, L87, I92, I102, I110, L111, L113, V114, L117, I118, I123, L145, W148, I149, I153, F161, W165, A170, L171, A173, L174, V175, A179, C183, A198, A201, M202, A205, L209, V211, V214, I215, I220, V230, M231, Y233, L234, F237, A257, A275, V279, A284, V291, V317, H327, V329, V331, F333, I338, V345, V1043, F1061, I1063, A1068, V1097, Y1099, Y1107, V1109, I1111, I1118, A1125, I1127, V1136, A1138, V1156, A1161, A1170, V1192, Y1194, Y1202, L1204, M1206, Y1208, V1220, I1231, V1243, F1251, V1253, I1270, Y1290, V1292, Y1294, H1302, V1304, V1306, V1320, V1331, A1341, F1349, V1351, A1356, A1385, Y1387, Y1395, V1397, I1399, I1406, V1413, V1424, V1435, V1445, A1450, V1459, V1481, V1493, V1495, Y1497, I1502, V1509, V1511, V1520, V1532, A1534, F1540, I1542, A1544, A1547, I1556, V1578, Y1580, Y1588, I1590, V1592, Y1594, I1599, I1606, A1608, A1614, C1617, F1636, V1638, A1643, V1648, V1652, I1674, A1678, Y1684, I1686, V1688, I1695, V1702, A1704, V1755, V1764, V1784, V1786, H1796, M1798, I1800, I1807, V1824, F1842, I1844, V1878, Y1880, Y1888, I1890, V1892, A1906, I1908, I1964, F1966, H1974, V1976, I1978, V1994, A2002, A2005, F2023, V2025, V2059, Y2061, Y2069, V2071, F2075, V2087, I2089, V2133, H2153, V2155, H2165, V2167, V2169, V2185, V2196, F2214, I2216, V2250, Y2252, A2254, Y2260, V2262, I2264, I2271, V2278, V2280, I2281, A2287, L2290, L2300, I2310, L2312, A2315, I2319, V2323, V2345, H2355, I2357, V2359, F2361, V2373, V2387, L2394, F2405, I2407, A2412, V2440, Y2442, Y2450, I2452, V2454, Y2456, I2462, A2469, A2512, V2515, A2525, V2535, C2537, V2571, V2575, V2585, W2587, I2592, V2599 |
| 63 | Vacuolar protein sorting-associated protein 26A | O75436 | F42, V48, V52, H65, I68, I70, F72, V73, I76, L101, F111, V114, V126, L128, Y130, F131, L132, V134, V151, M166, L174, I176, F178, Y180, Y185, I191, I195, M207, L209, L211, A231, I246, I248, L250, L252, F268, V270, Y272, L274, L276, L278, I292 |
| 64 | Low-density lipoprotein receptor-related protein 6 | O75581 | L23, L24, Y25, A26, L31, V34, V47, L50, A53, A55, V56, F58, V59, I65, Y66, W67, V70, A74, I75, V90, V91, L94, L100, C102, L109, Y110, W111, I119, V121, L128, M152, Y153, W154, I163, A166, M168, I177, L189, L196, Y197, W198, A199, I206, A218, V219, L224, A229, L232, L237, Y238, W239, I247, L248, A249, C250, I271, A273, L296, C297, |

TABLE 5-continued

| TARGETS | | | |
|---|---|---|---|
| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
| | | | L298, M299, C308, C310, L317, L331, L332, L333, A334, L339, I342, L344, A362, Y375, W376, A383, I384, A414, L417, Y418, W419, I427, V429, L453, M460, Y461, W462, I471, A474, A475, L476, V485, A496, I504, W506, M517, I532, W547, I555, L575, M576, C592, L602, C603, L604, C614, L634, L635, F636, I642, I645, A664, A666, I676, Y677, I686, A689, V700, V712, L719, Y720, W721, A722, I729, V731, L755, M762, W764, I773, A776, A777, M778, V787, A793, I798, L805, W807, I815, A829, L832, I845, W847, I855, A858, I869, V876, V881, C893, L903, C904, A906, L936, L937, F938, I944, L959, V967, A969, L979, Y980, W981, I982, I989, A992, Y1027, I1028, Y1029, C1032, I1038, V1040, V1051, L1052, A1061, V1062, M1071, Y1072, F1073, I1083, A1086, A1087, L1088, L1116, F1117, W1118, A1119, I1126, L1157, W1159, I1160, I1167, L1188, C1207, I1217, C1218, L1219, C1313 |
| 65 | Oral-facial-digital syndrome 1 protein | O75665 | M834, H851, V852, A854, A858 |
| 66 | Protein XRP2 | O75695 | V57, F62, I64, C67, C70, I72, I74, F75, V81, I83, C86, C89, I91, F92, L93, V96, V100, F102, C105, C108, C110, L112, A113, C114, F117, V119, C122, L125, V127, L129, C131, I137, I143, F145, F148, W150, Y152, L155, F157, F159, A162, F167, W171, L189, V195, V199, L207, V221, C236, L237, V238, V239, A248, A250, L253, M257, V270, A277, V280, A285, V297, A299, L300, F302, A307, V308, C311, A333, F340, A344 |
| 67 | Gap junction beta-3 protein | O75712 | L25, A39, W44, F51, C60, C64, W77, V84, I92, L135, L149, C164, V167, C176, M191, C198 |
| 68 | Isocitrate dehydrogenase [NADP] cytoplasmic | O75874 | V10, V11, M13, M18, I21, I22, W23, L25, I26, L30, I31, V35, L39, L44, I46, A60, A61, A63, I64, V69, V71, C73, A74, I76, I99, I102, V107, F108, I112, I113, C114, I117, W124, I128, I129, I130, H133, A134, A179, I189, F192, A193, F197, M199, A200, L207, L209, F223, I226, F227, F239, I244, M254, A258, F265, I266, W267, A268, C269, V281, A282, Y285, M290, M291, L295, V296, C297, V303, A305, A307, A308, I330, A331, I333, F334, A335, W336, L340, A344, L352, A353, F355, A356, A358, L359, V362, I367, F371, M372, L376, A377, A378, F397, M398, L401, L405 |
| 69 | Tumor necrosis factor ligand superfamily member 13 | O75888 | L219, L225 |
| 70 | Dysferlin | O75923 | L2, V86 |
| 71 | Multiple PDZ domain protein | O75970 | M129, A130, F138, L140, I165, V167, A176, I188, L189, A190, I191, L196, A205, V216, L218, V219, I220, A221, I258, L260, V279, A290, I302, L303, I305, L310, V318, V329, L331, I333, A334, V378, L380, I405, V407, A415, V416, I422, I428, V431, L436, A444, V455, L457, L459, L703, I728, I730, I738, A739, L745, L751, V754, L759, A767, A774, V779, I781, V783, V1152, L1154, L1162, I1185, I1187, A1196, L1202, I1208, V1209, V1211, L1216, A1219, A1224, V1235, F1237, V1239, I1337, L1353, A1365, V1375, F1376, I1377, A1386, L1398, L1399, I1401, L1406, A1414, A1421, V1425, I1427, I1428, F1429, I1430, A1435, I1630, I1632, I1654, I1656, A1664, A1665, I1677, V1680, L1685, A1693, V1704, L1706, L1708, I1726, L1728, V1749, A1760, I1772, V1788, V1799, V1803, I1890, I1892, A1901, I1916, A1929, I1940, M1942, V1944, I1988, L1990, L1997, I2014, V2016, A2025, I2037, V2040, L2045, A2053, L2057, V2064, L2066, V2068 |
| 72 | Nebulette | O76041 | A961, F975, I981, V996, L1005 |
| 73 | Bestrophin-1 | O76090 | V90, V158, F248 |
| 74 | Serine/threonine-protein kinase 10 (EC 2.7.11.1) | O94804 | A53, A62, A64, I82, I84, A86, C88, I93, V94, L106, I108, M109, V118, I121, M122, L125, L129, I134, V136, V137, C138, M141, L142, A144, L145, L148, H155, L158, A160, V163, L164, M165, L167, I171, L173, F176, V178, A180, A200, A218, I220, L223, L227, I228, M230, V245, L246, I249, F267, F270, A274, L275, A285, L288, F293, V294, L303, L306, V307 |
| 75 | Tumor necrosis factor ligand superfamily member 15 | O95150 | A97, L99, L117, M132, L139, I141, Y147, I149, V153, F155, A168, I177, V179, V180, I181, I212, L220, L226, V228, V230, V236, F245, F246, A248 |
| 76 | Interleukin-18 receptor accessory protein | O95256 | L165, I173, C175, W191, C221, A236, V238, C273, A275, F277, W289, V326, F335, C337, V339, V350, L352 |
| 77 | Bile salt export pump (ATP- binding cassette sub-family B member 11) | O95342 | A452, L453, V454, A464, L467, I468 |
| 78 | Tumor necrosis factor receptor superfamily member 6B | O95407 | C49, C52, C91, C132 |
| 79 | Apolipoprotein M | O95445 | F49, I50, A51, A53, A54, I69, V70, L145, L146 |
| 80 | Gap junction beta-6 protein | O95452 | I25, A39, W44, F51, C60, C64, H73, W77, V84, A92, I140, F154, C169, I171, C180, M195, C202 |
| 81 | Follistatin-related protein 3 | O95633 | V37, W39, A70, V134, C135, C146, L148, L159, C195, C211 |
| 82 | Interleukin-33 | O95760 | A124, L126, I134, V159, L160, L161, M183, V184, L186, L194, A196, V203, A216, F217, F218, V219, C227, F230, C232, I240, L247, A248, F265 |

TABLE 5-continued

TARGETS

| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
|---|---|---|---|
| 83 | EGF-containing fibulin-like extracellular matrix protein 2 | O95967 | C71, C109, C162, C241, C281 |
| 84 | Cytochrome b5 | P00167 | I17, L28, I29, L30, V34, L41, L51, A55, L84 |
| 85 | L-lactate dehydrogenase A chain | P00338 | I23, V25, V26, V28, A34, C35, A36, I39, L40, M41, A45, L48, A49, L50, V51, L58, L91, V92, I93, I94, L109, V110, V114, F117, F119, I120, I121, V124, C131, L133, L134, I135, V136, V140, I142, L143, V146, A147, V158, I159, C163, F170, M174, C185, V189, L190, V198, V200, M204, V206, L218, V230, V234, V256, A257, L259, A260, I263, V273, I277, I283, V287, F288, L289, V291, C293, L295, L316, A320, L323 |
| 86 | NADH-cytochrome b5 reductase 3 | P00387 | L45, L47, F60, F62, L71, L73, I79, L81, V106, L108, V109, I110, M127, L131, F142, L149, F157, V175, M177, I178, A179, I184, M187, L188, V190, I191, I194, C204, L206, L207, F208, I216, L217, L218, L222, F233, Y237, L239, I258, L270, V271, L272, M273, C284, L288 |
| 87 | Cytochrome c oxidase subunit 2 | P00403 | I83, I97, W106, Y108, V142, L144, I150, M152, I154, H161, W163, A164, V165, L168, A174, F184, M207, I209, V210, L211 |
| 88 | Phenylalanine-4-hydroxylase | P00439 | A34, I35, L37, F39, V51, F55, F79, F80, L83, L91, I94, L98, A104, L109, W120, I125, L128, F131, A132, A165, W187, V190, F191, L194, A202, C203, Y206, L213, F219, I224, L227, V230, F233, L234, F240, L255, L258, A259, F260, V262, F263, C265, Y268, I269, I283, C284, L287, L288, H290, V291, L293, F294, F299, A300, F302, I306, A309, L311, A313, I318, L321, A322, I324, F327, V329, L333, I340, A342, Y343, A345, L347, L348, L354, C357, A373, L385, Y386, Y387, A389, A395, V399, F402, A403, I406, F410, I421, L424, I432, A434 |
| 89 | Superoxide dismutase [Cu—Zn] (EC 1.15.1.1) | P00441 | A5, C7, L9, V15, I18, I19, F21, V30, V32, I36, L39, H44, F46, H47, V48, H49, A61, H64, H72, H81, V82, L85, V88, A90, A96, V98, V104, I105, L107, I113, I114, L118, V119, V120, H121, A141, A146, C147, I150 |
| 90 | Coagulation factor VIII | P00451 | L26, A28, L90, L91, I95, I105, L107, V115, L117, A119, A131, V147, Y155, W157, Y177, L191, I192, A194, L196, V197, C198, L217, F218, A219, F221, H251, V253, Y256, V272, W274, V276, I277, I288, F295, I307, A315, L319, C329, M339, A341, V343, V345, I405, A406, A407, Y414, A415, L431, Y442, V445, F447, I467, L472, L480, I482, F484, Y492, I494, L517, Y530, W532, Y552, L566, I567, L570, L571, I572, C573, L594, F595, F598, Y605, M633, I636, V640, V648, W656, I658, V670, F677, L689, V697, M699, M701, L709, C711, M721, A723, L725, I1719, A1720, A1721, V1752, V1753, F1754, H1774, L1775, L1777, L1778, I1782, A1784, I1790, V1792, F1794, Y1802, F1804, V1826, W1836, V1838, M1842, C1851, A1853, Y1856, H1867, L1870, I1871, L1874, L1875, V1876, C1877, V1892, F1895, A1896, L1897, F1899, F1902, F1937, H1938, A1939, I1940, L1948, L1951, M1953, A1954, I1959, W1961, Y1962, L1963, L1964, H1973, I1975, F1977, F1982, L1997, V2005, V2017, C2019, M2029, F2033, V2035, M2046, A2066, A2070, A2080, W2081, I2099, I2100, H2101, A2108, I2117, F2120, I2122, Y2124, Y2134, F2145, I2163, I2164, A2165, L2181, L2185, M2186, C2188, C2193, M2199, I2209, A2220, W2222, A2227, A2237, W2238, L2249, V2251, F2253, V2259, V2262, V2267, M2274, V2276, F2279, I2281, F2302, L2316, L2325, I2327, I2336, A2337, L2338, M2340, V2342, A2347 |
| 91 | Coagulation factor XIII A chain | P00488 | L46, H65, Y70, L75, I76, V77, F83, V85, I87, F89, F100, V102, Y104, V105, I106, V120, A133, V136, V143, L145, I147, V155, F158, Y161, V162, A163, Y182, I183, L184, F185, V194, L196, Y205, V206, I213, F214, W226, I235, C239, V242, M243, L250, V259, M266, V275, L276, A292, W293, I299, Y303, V310, C315, W316, V317, F318, A319, V321, F322, L326, C328, L329, I331, A333, V336, Y339, A342, L349, I353, L355, Y373, H374, C375, W376, A379, M381, F390, A395, V396, C410, A413, A417, I418, H420, H422, A429, V432, F433, A434, V436, L440, I441, Y442, I461, I465, V466, Y482, L493, A498, V519, M521, F523, F534, L536, I538, F540, I550, A552, Y553, L554, A556, I558, Y561, V576, L578, I590, Y595, L605, H606, F607, F608, V609, A611, I613, V619, L620, L628, V642, M647, V649, V651, F653, L661, V664, V666, L668, I684, C696, L706, I707, A708, M710, L715, H717, V718, V724 |
| 92 | Hypoxanthine-guanine phosphoribosyltransferase | P00492 | V35, I37, I42, L49, A50, V53, M57, I62, V63, A64, L65, C66, L68, F74, F75, L78, L79, I82, I93, I100, L125, V130, L131, I132, V133, I137, M143, L146, L149, V150, V160, A161, L163, L164, F181, I183, V188, V189, Y191, A192, F199, L202, V205, C206, V207 |
| 93 | Tyrosine-protein kinase ABLI (EC 2.7.10.2) | P00519 | L88, C100, A102, V111, W127, A137, L141, F149, L150, V151, I163, L165, A179, L198, V199, H202, L213, A217, I242, V268, V270, F283, L284, A287, V289, M290, I293, L298, L301, V304, C305, Y312, I313, I314, L323, L327, V335, V339, L340, M343, A344, I347, A350, M351, L354, I360, H361, L364, A365, A366, C369, V371, V377, V379, F382, L384, F401, A407, L411, V422, W423, F425, V427, L428, L429, Y440, V448, L452, M458, C464, M472, C475, W476, F486, I489, F493 |

TABLE 5-continued

TARGETS

| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
|---|---|---|---|
| 94 | Epidermal growth factor receptor (EC 2.7.10.1) | P00533 | L41, F55, C58, V61, L65, I67, V70, L79, I82, V85, Y88, V89, L90, I91, A92, V96, I99, L101, L104, I106, I107, A118, L119, A120, V121, L132, L135, M137, L140, I143, A147, V148, F150, L156, V159, I167, V168, C199, W200, C223, C236, A237, A238, C240, C260, V300, V301, C326, C337, I340, F345, I351, I356, F359, C362, I365, L369, I371, V374, A375, L392, L395, V398, I401, L405, L406, I407, L417, A419, F420, L423, I426, L438, A439, V440, V441, L443, I445, L448, L450, L453, I456, V461, I463, L469, C470, Y471, A472, I475, L480, C499, C510, C515, W516, C571, C624 |
| 95 | Adenylate kinase isoenzyme 1 | P00568 | L5, I10, F12, V13, V14, C25, I28, I60, L73, L76, M80, F90, L91, I92, Y95, F105, I109, L114, L115, L116, V118, M125, I146, V160, Y164, V173, V186 |
| 96 | Prothrombin (EC 3.4.21.5) | P00734 | Y87, C90, A93, L100, C103, A109, Y116, C129, C157, W168, C169, Y170, C181, I183, A242, C262, V272, W273, C274, Y285, C286, V295, F324, F329, C336, L355, I364, V365, A370, M374, W377, V379, M380, L381, F382, L390, C391, A393, L395, I396, W400, V401, L402, A404, A405, H406, C407, L408, L409, L422, L423, V424, I426, L444, H450, I463, A464, L465, M466, L468, V472, I478, H479, V481, C482, L483, A489, L492, L493, A495, V501, W504, L507, L523, V525, V526, L528, I530, V531, C536, I544, M548, F549, C550, A551, A563, C564, F572, V573, M574, W582, M585, I587, V588, C594, Y600, F602, Y603, H605, V606, F607, L609, W612, I613, V616, I617 |
| 97 | Coagulation factor IX (EC 3.4.21.22) | P00740 | C128, V132, V227, A233, V242, V243, L244, I256, V257, I262, V263, A265, A266, I275, V277, V278, A279, I316, A317, L318, L319, L321, V331, V353, W356, L369, V374, C382, F395, C396, A397, H415, V416, L425, I428, I443, Y444, V447, Y450, V451, I454 |
| 98 | Coagulation factor X (EC 3.4.21.6) | P00742 | C121, C136, I235, V236, C241, C246, A250, L251, L252, I253, C261, I265, L266, I271, L272, A274, A275, C277, V286, V288, V302, I309, H311, I323, A324, V325, L326, L328, V338, A341, C342, A349, L353, G359, V361, F364, L377, M379, L380, V382, C390, L392, M402, C404, A405, H423, V424, F432, V433, I436, A444, I451, Y452, V455, F458, W461, I462 |
| 99 | Complement factor D (EC 3.4.21.46) | P00746 | I26, L27, M40, A41, V43, C51, V54, L55, V61, L62, A64, C67, V78, L80, L115, L116, L117, L118, L120, L126, L133, C148, V150, A151, W153, V169, L171, C179, I189, L193, C195, A196, C204, L212, L218, V221, V222, C229, Y238, V241, I248 |
| 100 | Plasminogen (EC 3.4.21.7) [Cleaved into: Plasmin heavy chain A; Activation peptide; Angiostatin; Plasmin heavy chain A, short form; Plasmin light chain B] | P00747 | A31, C49, C53, C61, A63, F64, C73, M76, Y111, W127, C152, W163, C164, Y165, C176, I178, M186, Y193, W209, H217, Y219, C234, W244, C245, F246, C257, I259, Y283, C296, W299, L319, C324, W334, C335, H336, C347, I349, Y385, C398, W401, H407, H409, L421, C426, W436, C437, F438, C449, L451, Y489, C502, W505, H513, C531, W542, C543, Y544, C555, V557, C577, V581, W594, V596, L598, C607, L611, V617, L618, A620, C623, Y633, V635, I636, L637, V654, I666, A667, L668, L669, L671, V681, I682, A684, C685, C699, I701, W704, L716, A719, L721, V723, C729, L735, L744, C745, A746, H748, L764, V765, C766, Y772, L774, V777, A785, V792, Y793, V794, V796, F799, V800, I803 |
| 101 | Coagulation factor XII (EC 3.4.21.38) | P00748 | C135, V158, C161, C163, C209, A388, A389, A398, L401, L408, A410, A411, L414, V425, L427, L462, A463, L464, L465, L467, V482, C500, A503, W505, C532, C548, A549, L567, V568, C569, L580, I583, V598, V602, I609 |
| 102 | Complement factor B (EC 3.4.21.47) | P00751 | L58, A96, C103, Y121, I127, C145, C158, C165, V177, V187, C205, M223, V230, A231, F234, L235, I242, M269, I271, Y272, L273, V274, L275, I281, F286, A289, C292, L293, I297, V300, Y309, L311, V312, Y314, A315, V322, V324, V335, L339, I342, A358, L359, V362, V383, I384, I385, L386, M387, L391, V401, I405, L409, I411, Y426, V427, F428, V430, I439, A443, H451, F453, V455, M458, L461, V464, F465, M468, V481, W495, A497, I499, V501, C511, M512, A514, V515, V516, F520, V521, L522, A524, A525, C527, F528, V530, V539, V541, I569, V577, A578, L579, I580, L582, C596, C599, A606, L607, L622, I628, A630, L631, F632, V633, V645, I647, C656, A660, A663, V669, V675, V676, F680, L681, C682, C695, L703, I704, V705, F711, I712, V714, V716, V721, A738, F741, H742, I743, L745, V748, L752, L756, L761, L764 |
| 103 | Renin (EC 3.4.23.15) | P00797 | I90, I92, F99, V101, V102, F103, V110, W111, V112, C117, A123, C124, F130, V154, I162, I163, V165, V170, M173, F174, M180, V193, V194, M196, F198, I209, F210, I213, V218, V223, F224, F226, Y227, Y228, I242, I262, V266, W267, I269, M271, V274, L288, A289, V291, I298, I305, L308, M309, V322, V323, C325, L331, I334, F336, L338, Y343, L345, Y350, F352, C362, L364, A365, I366, A380, L381, A383, F385, I386, Y390, F393, I400, F402, A403 |
| 104 | Carbonic anhydrase 2 (EC 4.2.1.1) | P00918 | W16, V31, I33, Y51, I59, A65, F66, V68, F70, A77, V78, L79, Y88, L90, F93, H94, F95, H96, W97, H107, A115, A116, L118, H119, L120, V121, H122, W123, A133, V134, L140, A141, V142, L143, I145, F146, L147, V149, L156, V159, V160, V162, L163, I166, F175, F178, L183, L184, L188, Y190, W191, Y193, L197, L202, L203, C205, V206, W208, I209, V210, L211, I215, V217, V222, F225, L228, F230, M240, L250, I255, A257 |

TABLE 5-continued

| TARGETS | | | |
|---|---|---|---|
| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
| 105 | Argininosuccinate synthase (EC 6.3.4.5) | P00966 | V7, V8, L9, C19, I20, L21, W23, L24, V31, I32, A33, Y34, L35, A51, V64, F68, V69, F72, I73, I77, L89, L93, A94, C97, A99, I105, A106, Y113, C132, A143, F150, Y163, A164, L185, M186, H187, Y190, L195, L206, L223, I225, F227, V235, V238, L250, F251, L254, V257, A258, H261, V263, V269, I281, A286, I289, L290, A293, H294, I297, F317, A318, V321, Y322, C331, I338, V345, V349, V351, V353 |
| 106 | Serine protease inhibitor Kazal-type 1 | P00995 | V46, C47, L60, C61, I71, I73 |
| 107 | Antithrombin-III | P01008 | M49, A75, V80, L83, A86, F90, A91, F94, Y95, L98, I108, F109, L110, L113, I115, A118, F119, A120, M121, A126, C127, L131, L134, M135, V137, F138, F140, I143, I151, H152, F153, F154, F155, A156, L158, L162, A166, A175, L178, F179, V197, A200, F207, I218, V222, I230, I234, A238, L242, V244, L245, V246, L247, V248, I251, F253, W257, F261, F271, A281, M283, M284, V301, L302, L304, F306, I311, M313, V314, L315, I316, L317, V327, L331, L343, L348, V349, V350, M352, I357, L363, L367, L372, L375, L383, I386, A388, L394, V396, A399, H401, A403, L405, V407, A414, A415, A416, A419, V420, V421, I422, A423, F434, A436, F440, L441, V442, F443, I444, V447, I453, F454, M455, V458, A459 |
| 108 | Alpha-1-antitrypsin | P01009 | F47, I50, L54, F57, A58, F59, L61, Y62, L65, I74, F75, F76, V79, I81, A82, A84, F85, A86, M87, L88, I100, L101, L104, F106, I111, I116, F120, L123, L124, L127, L134, L142, F143, L144, F154, V158, L161, Y162, V169, F171, A177, I181, V185, I193, V197, V205, F206, A207, L208, V209, I212, F213, F214, W218, F222, V224, F232, V234, V242, M244, M245, F251, I253, L259, V263, L264, M266, Y268, A272, A274, I275, F276, F277, L278, L284, L287, L291, I295, F299, L300, A308, L310, H311, L312, I317, L323, L327, L330, I332, V335, A340, L342, V345, L351, L353, A356, V357, H358, A360, V361, L362, I364, A371, A372, A374, M375, F376, L377, A379, I380, V388, F390, F394, V395, F396, L397, M398, L407, F408, M409, V412, V413 |
| 109 | Angiotensinogen | P01019 | V44, A103, V106, L109, A110, L113, F115, I117, Y118, V133, L134, A138, V139, F140, L143, A144, L146, L158, L162, V164, L175, V180, L181, A183, L184, A186, V187, L191, V192, L203, L205, V208, V209, V211, F212, L217, L219, F223, L227, Y230, F241, A247, M255, V258, L276, A277, F278, Y281, V282, F284, M288, F291, F300, V310, L313, V331, V334, A340, C341, L342, L343, L344, I345, V356, F361, I377, L379, M381, L384, L392, L395, L396, I404, L405, L409, L411, L414, V424, I428, F430, L432, L456, F460, L461, A463, V464, A469, A471, L472, H473, F474, L475, V478 |
| 110 | Complement C3 | P01024 | M25, I28, I29, L34, M42, L44, A46, H47, V55, V57, V59, L76, V86, F88, I90, V106, V108, A110, F112, V117, V121, L122, V123, Y129, I138, Y139, V145, Y147, I149, F150, V152, V163, V165, I167, V188, L189, W204, I206, A208, Y210, F222, V224, F232, Y243, I245, L251, V253, I255, A257, V265, A269, V271, F273, I275, L284, I293, V300, L302, L319, L324, V326, A328, V330, I346, I348, I355, F364, M368, F370, L372, V374, V376, A384, V387, V389, L400, A407, L409, I422, V424, A443, Y446, Y455, L456, L465, V473, F475, I487, Y490, L493, I494, I521, I526, F529, L531, V532, A533, Y534, Y535, L537, V546, V547, A548, V555, I585, A591, V593, V596, A597, V602, I616, W617, V620, V638, F639, A642, L644, F646, C693, C694, M698, M703, V723, F724, C727, C728, I731, W802, A806, V825, F829, L833, V839, V840, V845, I847, A849, L851, L860, V862, V864, L866, A871, C873, A876, I888, V896, Y898, V899, I900, V901, V910, V912, A914, A915, V916, V925, L929, V931, L947, I962, V971, I980, L982, V987, M990, A994, V995, A997, L1000, L1003, C1010, M1015, I1016, M1018, V1022, I1023, A1024, V1025, Y1027, L1028, A1045, I1049, L1057, A1058, F1059, A1065, F1066, A1067, A1068, F1069, A1073, L1078, A1080, Y1081, V1082, V1083, V1085, F1086, L1088, A1089, V1090, L1100, C1101, A1103, V1104, L1107, V1117, F1118, V1124, H1126, M1129, M1141, A1142, A1145, F1146, V1147, L1148, I1149, L1151, A1154, C1158, V1162, L1165, A1172, L1176, Y1180, L1183, Y1187, V1189, A1190, I1191, A1192, A1195, L1196, A1197, L1202, F1210, W1220, L1227, Y1228, V1230, A1232, Y1235, A1236, L1237, L1238, A1239, L1240, L1241, V1249, V1252, V1253, L1256, Y1266, A1271, F1273, M1274, V1275, F1276, A1278, L1279, A1280, Y1282, L1292, L1294, V1296, L1298, I1311, F1330, V1332, A1334, L1342, V1344, Y1348, A1350, F1361, L1386, I1388, C1389, I1402, L1403, I1405, M1407, M1408, F1411, A1412, L1418, L1421, I1429, L1444, I1446, Y1447, V1451, A1460, F1461, V1463, L1471, A1476, V1477, V1479, A1481, Y1482, Y1483, C1489, Y1493, C1518, A1536, Y1543, V1544, Y1545, L1549, F1558, Y1561, M1563, I1565, F1584, C1590, Y1602, L1603, M1604, W1605, Y1620, L1649, F1652 |
| 111 | Complement C5 | P01031 | V24, I25, A27, F31, V33, A35, I39, V40, I41, F50, A52, I54, I56, V71, L73, L85, I87, V102, V106, M117, L126, Y135, V141, V143, V145, Y146, L148, L161, F163, I183, I190, W199, I201, A203, Y205, F217, V219, I238, F246, I248, I250, A252, V260, A263, V265, I267, F269, I271, M283, L292, F301, V307, L310, L323, I325, V327, V329, Y347, L363, I371, |

TABLE 5-continued

TARGETS

| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
|---|---|---|---|
| | | | V373, V375, V388, L390, A418, V428, L431, F433, V435, A448, A454, Y457, L465, I484, V486, Y499, L502, I503, I526, M534, L540, L541, V542, Y543, Y544, L554, V555, L561, I563, V573, V588, L590, M592, V600, A601, L602, A603, A604, V605, A608, V609, L620, A643, V645, F646, A649, L651, F653, I683, A687, V695, C698, C699, C711, C724, I725, A727, F728, C731, C732, V734, A735, V780, W797, I799, V802, I804, C810, V819, V823, V833, I839, L841, V845, Y846, C856, V888, V896, V900, L901, I910, F912, L914, L927, L944, V968, L977, V979, V984, I987, L988, A1008, A1010, L1012, V1015, F1019, Y1020, V1021, Y1024, L1025, L1049, V1068, W1077, L1078, A1080, F1081, A1082, L1083, V1089, L1104, L1107, I1127, L1142, Y1143, A1146, F1147, V1149, I1150, I1152, A1155, C1159, I1164, A1167, L1168, A1171, L1175, F1186, L1188, A1189, I1190, A1192, Y1193, A1194, F1205, I1208, F1227, W1228, A1245, V1248, A1252, Y1253, A1254, L1255, L1256, L1259, V1267, V1270, I1271, W1273, L1274, F1284, I1291, A1293, I1294, L1297, L1303, L1309, M1311, I1313, V1315, M1328, F1333, V1340, L1346, V1348, A1357, V1359, V1361, V1365, I1402, A1404, A1406, Y1408, H1421, A1422, V1423, M1424, I1426, L1439, L1442, F1450, V1460, L1462, I1467, V1475, F1477, I1479, A1491, F1493, V1495, Y1498, H1499, C1505, V1519, A1545, A1552, I1557, Y1559, A1560, Y1561, V1563, Y1577, A1579, L1581, A1590, I1598, F1600, A1609, Y1617, L1618, I1619, M1620, A1624, Y1637, I1645, C1657, F1660, L1664, F1667 |
| 112 | Complement C5a anaphylatoxin | P01032 | C22, C47, A50, C55 |
| 113 | Cystatin-C | P01034 | V49, A52, A56, L90, V92, L94, G95, C109, C123, F125, I127 |
| 114 | GTPase NRas | P01111 | Y4, L6, V7, V8, V9, A11, V14, L19, L23, V29, V44, I46, C51, L52, L53, I55, L56, A59, M67, M72, F78, L79, C80, V81, F82, A83, I84, F90, I93, L95, Y96, I100, V103, V109, M111, V112, L113, V114, L120, V125, A130, A134, A146, V152, A155, F156, L159, V160, I163, M168 |
| 115 | Platelet-derived growth factor subunit B | P01127 | V127, V153, V170, L172 |
| 116 | Low-density lipoprotein receptor | P01130 | I40, V45, C52, I83, C95, C116, I122, C134, C155, I161, A166, C173, C204, C222, C318, C338, C352, C377, Y400, L401, F402, F403, V409, M412, L414, I423, A431, L432, V436, I441, W443, I451, A480, V481, I488, Y489, W490, V498, V500, A501, M531, Y532, W533, I542, L547, V556, L575, W577, V578, I585, L605, L611, A612, V618, F619, W620, A627, I628, A631, A643, L646, C667, C677, C681, L682, C698 |
| 117 | Transforming growth factor beta-1 | P01137 | L258, C293, C294, V295, F302, C326, L340, A341, L364, I366, C387, C389 |
| 118 | Beta-nerve growth factor | P01138 | C136, V157, V159, V163, C189, A210, A218, A219, I223, I225 |
| 119 | Vasopressin-neurophysin 2-copeptin | P01185 | C44, C52, I57, C58, C59, C65, A72, C75, C92, C98, A99, A100, C104, C105, C110 |
| 120 | Somatotropin | P01241 | F36, A39, A43, L46, L49, A50, Y54, F70, C79, I84, L99, L101, L102, I104, L106, L107, L108, I109, W112, V116, L119, F123, A131, V136, L140, L143, I147, L150, Y186, L189, F192, M196, V199, F202, L203, V206 |
| 121 | Insulin [Cleaved into: Insulin B chain; Insulin A chain] | P01308 | L35, A38, L39, I91, C95, L105, C109 |
| 122 | Insulin-like growth factor II | P01344 | L37, L41, F52, I66, C70, C75, L80, Y83, C84, A85 |
| 123 | Lymphotoxin-alpha | P01374 | A65, L67, I68, L94, L99, V101, Y107, V109, V113, F115, L131, H133, V135, L181, V198, F200, A202 |
| 124 | Tumor necrosis factor | P01375 | A90, V92, A94, A98, L105, V117, L124, V125, V126, L131, Y132, L133, I134, V138, F140, C145, V150, L152, H154, I156, A160, L202, L208, A210, V226, F228, I230 |
| 125 | Interferon gamma | P01579 | Y6, I7, F10, C13, I14, A31, L34, A40, F52, L56, I67, M68, I72, V73, Y76, F77, L79, F80, I89, V93, I96, M100, F104, F105, F115, A132, I133, L136, M140, L158 |
| 126 | Interleukin-1 alpha | P01583 | I135, L136, A163, F166, A170, Y171, A178, V182, I183, Y192, I214, L221, F223, F234, I244, A245, V252, L254, F264 |
| 127 | Interleukin-1 beta | P01584 | C124, L126, L134, V135, L142, A144, V156, F158, M160, V163, V174, A175, L176, L178, L185, C187, M211, F215, V216, F217, L226, F228, I238, F262 |
| 128 | Erythropoietin | P01588 | L39, A46, A49, C56, C60, L62, V68, A87, V90, L94, L97, A100, L118, V122, A125, L129, L132, L136, A141, A145, A162, L168, F169, F175, L176, L180, Y183 |

TABLE 5-continued

| TARGETS | | | |
|---|---|---|---|
| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
| 129 | Interleukin-2 receptor subunit alpha | P01589 | A38, L47, C67, C80, C125, V143, V148, Y150, C168 |
| 130 | T-cell surface glycoprotein CD4 | P01730 | L39, C41, A43, F51, W53, I61, L62, L69, L76, A80, W87, F92, L94, I95, I96, L99, Y107, C109, V111, V118, L120, L121, V122, F123, L134, L139, L141, L143, V153, C155, L169, V171, L174, W182, C184, V186, I199, V201, V219, F221, F223, L238, F254, V261, M274, L282, L284, A287, A292, L297, L299, L308, V312, L314, V315, V316, M317, L326, C328, V330, L340, L342, V358, W368, C370, L372 |
| 131 | Ig epsilon chain C region | P01854 | I131, L133, C135, V137, W149, L178, W185, Y191, C193, V195, I237, C239, V241, V251, V280, L284, Y297, C299, V301, L310, V326, L343, C345, I347, F350, I355, V357, W359, V386, L390, V392, F403, C405, A407, V408, H409, A412, V418, V424 |
| 132 | HLA class I histocompatibility antigen, B-7 alpha chain | P01889 | M29, Y31, Y33, F46, V52, F57, V58, F60, A73, W75, I76, Y83, Y91, A95, L102, L105, L119, M122, C125, V127, Y140, Y142, Y147, I148, L150, L154, W157, A163, A164, A177, L184, C188, V189, L192, Y195, L196, L203, V213, A223, L225, C227, A229, F232, Y233, L239, W241, A269, A270, V271, V272, V273, Y281, C283, V285, H287 |
| 133 | HLA class II histocompatibility antigen, DR alpha chain | P01903 | F47, M48, F49, F57, V59, A77, A81, A84, A86, I88, L130, I131, C132, I134, F137, W146, F173, L176, L179, Y186, C188, V190, H192 |
| 134 | HLA class II histocompatibility antigen, DQ alpha 2 chain | P01906 | H50, F58, V60, I78, A85, M89, L131, I132, C133, V135, I138, W147, I174, L177, L180, Y187, C189, V191, H193 |
| 135 | HLA class II histocompatibility antigen, DQ alpha 1 chain | P01909 | H50, F58, V60, A84, I88, L130, C132, V134, I137, W146, I173, L176, L179, Y186, C188, V190, H192 |
| 136 | HLA class II histocompatibility antigen, DRB1-15 beta chain | P01911 | F36, L37, F46, F47, V53, F55, L56, Y59, V67, F69, F76, W90, L97, A103, C108, V120, V128, L138, L143, L144, V145, C146, V148, F151, W160, M171, L190, V199, Y200, C202, V204 |
| 137 | HLA class II histocompatibility antigen, DRB1-3 chain | P01912 | F36, L37, F46, F47, V53, Y55, L56, Y59, V67, F69, F76, W90, L97, C108, V120, V128, L138, L143, L144, V145, C146, V148, F151, W160, V171, L190, V199, Y200, C202, V204 |
| 138 | HLA class II histocompatibility antigen, DQ beta 1 chain | P01920 | F39, V40, F49, V56, Y58, V59, Y62, A70, F72, Y79, W93, L100, C111, L123, V131, L141, L146, L147, V148, C149, V151, F154, W163, V174, L193, V202, Y203, C205, V207 |
| 139 | Collagen alpha-1(I) chain (Alpha-1 type I collagen) | P02452 | C63 |
| 140 | Collagen alpha-1(II) chain (Alpha-1 type II collagen) [Cleaved into: Collagen alpha-1(II) chain; Chondrocalcin] | P02458 | C57 |
| 141 | Collagen alpha-1 (III) chain | P02461 | C55, C1262, L1265, V1279, I1290, C1294, I1303, V1310, V1326, F1328, A1364, I1368, Y1370, A1377, L1390, L1392, F1400, C1417, F1429, Y1431, L1439, I1441, I1444, A1445, V1458, V1463, F1465 |
| 142 | Collagen alpha-1 (IV) chain [Cleaved into: Arresten] | P02462 | V1448, L1474, Y1475, L1487, Y1521, W1522, L1523, I1545, C1548, A1549, V1550, C1551, A1553, F1583, H1586, C1604, F1613, I1614, C1616, C1622, C1662, V1664, C1665, M1666 |
| 143 | Alpha-crystallin A chain | P02489 | L75, V77, V94, I96, V124, L129, L139, F141 |
| 144 | Apolipoprotein A-I | P02647 | V35, L38, A39, Y42, L46, Y53, F57, L106, V117, L138, Y139, L198 |
| 145 | Apolipoprotein E | P02649 | W44, A47, F51, L55, V58, V65, L69, L70, V74, L78, M86, L89, L96, L100, A109, L111, L115, A117, A118, L122, M126, V129, C130, L133, Y136, L144, L151, V153, L155, A156, L159, L162, L166, L173, L177, Y180, A194, L247, L270, V298 |
| 146 | Fibrinogen alpha chain [Cleaved into: | P02671 | I675, Y692, W708, L714, L724, V726, L728, A738, Y740, V744, Y751, L753, A762, A765, H780, F785, C799, A800, W807, Y809, A815, L817, V841, W843, L853, V856, M858 |

TABLE 5-continued

| TARGETS | | | |
|---|---|---|---|
| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
| | Fibrinopeptide A; Fibrinogen alpha chain] | | |
| 147 | Fibrinogen beta chain [Cleaved into: Fibrinopeptide B; Fibrinogen beta chain] | P02675 | C241, I244, M254, Y255, I257, V268, C270, W279, I282, F292, Y299, C316, Y322, W323, I329, L340, L341, I342, M344, A354, H355, Y356, F359, V361, Y368, V372, A379, A382, L383, A387, H400, F405, C424, W432, W433, Y434, A439, A440, Y447, Y452, V465, V466, W467, M477, M480, M482 |
| 148 | Fibrinogen gamma chain | P02679 | C179, I182, Y193, I195, V206, C208, V219, F220, Y237, W253, I259, I262, Y270, A271, L272, V274, L276, A286, Y288, A289, F291, V293, Y300, L302, F307, A312, A315, F316, F321, H333, F338, F348, C352, A353, W360, W361, M362, H366, A367, H369, L370, Y375, Y380, Y389, I393, I394, W395, M405, M410, I412, I413, L418, H427, A431 |
| 149 | Acetylcholine receptor subunit alpha | P02708 | V153, L154, A167, V177, V201, I203 |
| 150 | Band 3 anion transport protein | P02730 | M435, C479 |
| 151 | Protein AMBP [Cleaved into: Alpha-1-microglobulin | P02760 | C287, A304, C333 |
| 152 | Transthyretin | P02766 | L32, V34, V36, A45, V48, V50, V52, L75, L78, F84, I88, Y89, V91, I93, Y98, W99, A111, A117, I127, A128, A129, L130, L131 |
| 153 | Serum albumin | P02768 | V31, A32, F43, A45, L46, V47, L48, I49, A50, F51, A52, Y54, L55, C58, H63, L66, V70, A74, C77, C86, L93, L98, A102, M111, C114, F126, C148, F151, L163, A167, F173, A175, L178, F181, A182, A188, F189, C192, L202, L209, A215, C224, A225, F235, A239, A241, F247, A250, A253, V255, L258, V259, V265, C270, L274, L275, C277, A285, I295, L299, C302, V317, F333, V334, V339, Y343, F354, A359, V367, L369, L370, L371, L373, Y377, L381, C384, Y394, V397, F401, V405, C416, F427, L431, L432, V439, V442, L447, V448, V450, L454, V457, C461, A473, V480, L481, L484, V486, H488, V497, C500, F512, F531, A535, I537, A552, L553, V554, L556, V557, A563, L568, V571, F575, F578, V579, C582, F592, L607, L609 |
| 154 | Ferritin light chain | P02792 | V13, A15, V17, L20, V21, Y24, A27, Y31, L34, Y37, F38, V48, F51, F52, L55, A56, Y63, L66, L67, M69, W90, A96, M97, A99, A100, M101, L107, L111, L112, L114, L126, L130, F134, M145, L149, L152, F167 |
| 155 | Capsid protein/genotype D subtype adw (isolate United Kingdom/adyw/1979) (HBV-D) | P03147 | F9, L15, L19, F23, F24, A36, Y38, A54, L55, C61, W71, W102, F103, L108, F110, V120, F122, W125, A131, Y132, A137, I139, L140 |
| 156 | Estrogen receptor | P03372 | C185, V187, C188, V199, C202, C205, F209, C227, I229, C237, A239, C240, L242, C245, M250, A307, M315, L319, A322, M342, L345, L349, L354, M357, I358, W360, A361, V364, F367, V376, L378, L379, A382, W383, I389, L391, V392, L402, A405, L408, L410, V418, F425, F435, F445, V446, C447, L448, I452, L453, L454, V458, H474, I475, V478, I482, L486, M490, L507, I510, I514, M517, M522, M528, L540, L544 |
| 157 | Fusion glycoprotein F0/strain A2 | P03420 | F32, C37, A39, V40, A47, L48, V56, I57, I59, V76, I79, L83, A89, V90, L93, L158, V164, L171, V187, L188, L195, I199, L203, C212, I214, V220, F223, L230, I233, F237, V247, M251, L252, L257, L260, I261, M264, I266, M274, I280, V281, I288, S290, I291, L297, A298, Y299, V300, V301, L303, Y306, C313, C322, I332, C333, L334, Y342, C343, V349, F351, F352, V365, F366, C367, I379, L381, C382, C393, I395, I407, L410, A412, I413, V414, C416, C422, A424, V442, M447, V450, V459, I475, Y478, A490, V495 |
| 158 | Hemagglutinin [Cleaved into: Hemagglutinin HA1 chain; Hemagglutinin HA2 chain]/strain A/Bangkok/1/1979 H3N2 | P03441 | A11, L13, C14, L15, A19, V26, V36, L42, V43, I51, C52, I58, C64, L66, I67, L70, L71, C76, F79, L86, F87, V88, F94, C97, Y98, Y100, Y105, A106, L108, V112, A113, L118, F125, A138, C139, F147, F148, L151, L154, L164, Y178, W180, V182, H183, H184, Y195, V202, V204, I230, I232, Y233, I236, V237, I242, L243, I245, L251, I252, A253, F258, I274, C281, I282, I288, V309, L316, A317, A334, W343, Y351, A373, A425, L447, L455, C466, F467, I469, H471, C473, C477, I478, I481, A495 |
| 159 | Hemagglutinin [Cleaved into: Hemagglutinin HA1 chain; Hemagglutinin HA2 chain]/strain | P03446 | I20, C21, I22, V33, V43, L58, C59, L69, C72, L74, I78, L79, Y95, I96, V97, L118, F122, C150, M163, L166, I188, V189, F190, W192, I194, Y207, V216, M242, Y244, L249, V255, I257, L263, I264, A265, C294, L327, A347, Y364, A386, L460, L468, H484, C486, C490 |

TABLE 5-continued

| TARGETS | | | |
|---|---|---|---|
| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
| | A/Duck/Alberta/60/1976 H12N5 | | |
| 160 | Hemagglutinin [Cleaved into: Hemagglutinin HA1 chain; Hemagglutinin HA2 chain]/strain A/Shearwater/Australia/1972 H6N5 | P03448 | A8, I19, I21, V42, L48, L49, F57, C58, L66, L68, C71, I73, W76, I77, L78, C83, L86, W92, Y94, I95, V96, Y107, L117, L120, I121, V127, F133, C151, Y153, L163, L164, W165, I166, I177, I189, L190, Y191, F192, W193, V195, H196, H197, Y208, V215, M217, I243, Y245, I249, L250, L256, V258, L264, I265, A266, Y269, A270, F271, F273, A281, C292, C296, V302, L303, I317, V324, L329, L331, A332, A349, M361, Y366, A388, V389, A440, L452, V459, L462, V466, L470, C481, H486, C488, C492, M493 |
| 161 | Hemagglutinin [Cleaved into: Hemagglutinin HA1 chain; Hemagglutinin HA2 chain]/strain A/Turkey/Ontario/6118/1968 H8N4 | P03456 | I19, C20, I21, V32, V42, Y57, C58, L68, C71, I73, I77, Y78, Y94, I95, V96, L117, F121, C149, I162, L165, I188, I189, F190, L191, W192, I194, Y207, V216, M242, Y244, L249, L255, I257, L263, I264, A265, C295, A348, Y365, A387, L461, L469, H485, C487, C491, A509 |
| 162 | Hemagglutinin [Cleaved into: Hemagglutinin HA1 chain; Hemagglutinin HA2 chain]/strain A/Turkey/Wisconsin/1/1966 H9N2 | P03457 | L10, I21, C22, I23, V34, V44, L51, L59, C60, L68, L70, C73, I75, I79, Y80, Y96, I97, V98, L119, F123, C151, M159, L162, A174, I184, L185, F186, M187, W188, I190, Y203, V212, I238, Y240, L245, L251, I253, L259, I260, A261, C290, H304, L323, A343, Y360, A382, L456, L464, H480, C482, C486 |
| 163 | Neuraminidase (EC 3.2.1.18)/strain A/Memphis/1/1971 H3N2 | P03471 | W87, I94, F97, I106, I114, V116, Y121, V122, C124, F132, A133, L134, L140, L158, L159, C175, A177, C183, L190, V192, C193, V194, A201, A203, F205, Y207, L223, C230, V231, C232, V239, V240, M241, I254, L255, F256, I257, V275, C278, C280, Y281, Y284, V287, C289, I290, C291, V302, V303, I305, Y316, V317, C318, L321, V322, V349, W352, A353, F354, V360, W361, M362, Y374, F377, V379, I397, V398, I409, F410, I418, C421, F422, Y423, V424, L426, V436, W438, I443, V444, V445, F446, I464 |
| 164 | Neuraminidase (EC 3.2.1.18)/strain A/Tern/Australia/G70C/1975 H11N9 | P03472 | L88, I95, A106, V107, V115, V117, Y122, V123, C125, F132, Y133, A134, L135, L159, I160, W162, C177, I178, C185, M192, I194, C195, I196, A203, A205, V206, I207, Y209, A221, L225, C232, V233, C234, C239, V241, V242, F243, I256, Y257, Y258, F259, H276, I277, C280, C282, Y283, I289, C291, C293, V304, I305, I307, Y318, I319, C320, V323, L324, V350, F353, Y355, W362, L363, I369, Y375, M377, L378, V380, A383, I397, V398, F410, M411, Y420, A422, C423, F424, Y425, V426, L428, V438, I445, V446, M448, C449, A464 |
| 165 | Neuraminidase (EC 3.2.1.18)/strain B/Lee/1940 | P03474 | F92, I114, I115, F119, V120, A121, F130, L132, L156, V159, A175, A176, A181, C182, I191, V193, A200, L201, V202, I204, I221, L222, I232, C236, Y237, L238, M239, I240, A245, F253, L254, I256, I265, H273, C277, I287, C289, A290, C291, A298, F302, V303, L305, I314, L323, I333, H354, W364, M377, L379, M400, V401, F411, C424, I425, I427, M429, V430, H431, H439, A441, A442, A444, I445, Y446, L448, L454, L455 |
| 166 | Neuraminidase (EC 3.2.1.18)/strain A/Turkey/Oregon/1971 H7N3 | P03476 | F94, I106, V116, Y121, V122, C124, F132, A133, L134, L158, F161, C176, C184, M191, V193, C194, M195, A202, A204, I206, Y208, L224, C231, C233, V240, A241, V242, V255, Y256, W257, I258, L277, C280, C282, I286, V288, C290, I291, C292, W303, M304, I306, Y316, V317, C318, H322, V348, F351, F353, W360, L361, F373, I375, V378, L396, V397, F409, I410, F417, F421, Y422, V423, L425, V436, I443, V444, F446, I464 |
| 167 | Neuraminidase (EC 3.2.1.18)/strain A/Turkey/Ontario/6118/1968 H8N4 | P03477 | I105, V113, V115, F120, I121, F131, F132, L133, L157, C160, A177, W178, A180, A182, C183, L190, L192, I194, A201, V202, A203, L205, M223, V231, C232, Y238, L240, I241, A250, Y252, I254, I257, I262, H274, F275, C278, C280, Y281, V287, C289, V290, C291, I303, F305, I313, C317, I320, F321, F350, F352, Y354, V358, W359, I360, F372, M374, V375, V382, I394, I395, F407, C422, F423, W424, V425, M427, W438, I444, F446 |
| 168 | Neuraminidase (EC 3.2.1.18)/strain A/Shearwater/Australia/1972 H6N5 | P03478 | I98, I106, V108, F113, V114, F124, F125, L126, L150, V153, W171, A173, A175, C176, M183, I185, V187, A194, Y195, A196, I198, L216, V224, C225, I226, Y231, V233, M234, A243, Y245, I247, V255, H267, I268, C271, C273, Y274, M277, V280, C282, V283, C284, L296, F298, C310, I313, F346, F348, V354, W355, A356, I360, F368, V370, L371, I378, I384, V390, L391, F403, I415, C418, F419, W420, L421, M423, W435, F443 |

TABLE 5-continued

| TARGETS | | | |
|---|---|---|---|
| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
| 169 | NADH-ubiquinone oxidoreductase chain 1 (EC 1.6.5.3) | P03886 | Y43, A50, A52, M53, F56 |
| 170 | Angiogenin (EC 3.1.27.—) | P03950 | F33, C50, I53, M54, C63, I66, F69, I70, H71, I77, A79, I80, L93, V102, C105, C116, Y118, V127, V128, V129, P136, L139 |
| 171 | Coagulation factor XI | P03951 | F30, C46, C50, C56, L57, L58, F59, C76, L78, M120, A130, C136, C140, F148, F149, C165, L167, A220, V225, C226, C230, C236, F238, F239, C255, L257, A274, C283, V289, F301, C317, C321, C327, F329, F330, A337, C346, I366, I388, W401, V403, L405, C416, I420, I421, I426, L427, A429, A430, V444, Y445, V463, I481, A482, L483, L484, L486, V490, C500, C514, V516, W519, A535, I537, C545, Y549, I554, C560, A561, A570, L579, C581, V586, H588, L589, V590, I592, V607, Y608, V611, V612, Y614, I618 |
| 172 | Catalase (EC 1.11.1.6) | P04040 | A76, A79, A81, F85, V87, I91, A97, V99, F100, I109, A110, V111, F113, A117, F132, V134, F136, W143, L145, I152, F153, F154, I155, I159, F164, W183, W186, L193, V196, F200, I205, H209, M212, L222, V230, C232, F234, Y236, A250, L265, F266, A268, W277, F279, I281, M284, A289, F294, L299, V313, L316, V317, L318, V329, I332, A333, I343, L351, L355, V375, V443, Y447, L459, C460, I463, A464, L467, A478, V479, F482, V485, Y489, I493, L496, L497 |
| 173 | RAF proto-oncogene serine/threonine-protein kinase (EC 2.7.11.1) | P04049 | I58, V60, L62, V72, L78, C81, L82, L86, A97, V98, A118, L126, V128, C152, C165, C176, V180, C184, V372, I405, V420, I446, A449, A453, M456, L459, H466, M469, L476, V482, I484, F487, A513, V516, V531, Y534, V537, L538, M542, M581, V585, C588, F599, I606 |
| 174 | Glucosylceramidase (EC 3.2.1.45) | P04062 | V54, C55, C57, F76, L108, F120, A123, M124, A127, A128, A129, I132, A139, L142, L143, L144, Y147, F148, I153, Y155, I157, I158, V160, M162, A163, C165, F167, A175, L183, L199, I200, A203, L213, L214, A215, L224, H245, W248, A249, Y251, F252, F255, L256, Y259, L264, A268, V269, A271, C287, L288, F290, F298, I299, L303, L318, M319, L320, A331, V334, A340, I347, A348, V349, H350, A357, L363, L375, F376, A377, A380, C381, V382, W396, Y402, I406, I407, V414, W417, L422, A423, L424, V437, I441, I442, V443, F450, M455, F456, H458, L459, H461, F462, I466, V473, A485, V486, A487, L488, A495, V496, V497, V498, V499, L500, L509, I511, L519, I528, H529, Y531, W533 |
| 175 | Vitamin K-dependent protein C (EC 3.4.21.69) | P04070 | C105, C131, L212, V227, V228, L229, A240, V241, L242, V248, L249, A251, C254, V263, L265, L280, I300, A301, L302, L303, V339, I363, I365, C373, A388, M406, A408, V417, L419, V434, Y435, V438, I445, I449 |
| 176 | Cystatin-B | P04080 | A20, V23, L27, F54, I55, V57, V65, H66, L67, V69, L82 |
| 177 | Trefoil factor 1 | P04155 | C51, C57, C68, F69 |
| 178 | Major prion protein | P04156 | I139, Y150, Y157, V161, Y163, F175, V176, C179, V180, I182, I184, M205, M206, V209, V210, M213, C214 |
| 179 | Superoxide dismutase [Mn], mitochondrial (EC 1.15.1.1) | P04179 | L38, I42, I46, M47, H50, H54, H55, V59, L62, A72, I82, L88, H98, F101, W102, L105, L117, A120, I121, F131, L135, W147, W149, L150, C164, L170, L179, L180, I182, V184, W185, A188, Y189, Y200, L201, I204, V207, I208, W210, V213, Y217 |
| 180 | Phosphatidylcholine-sterol acyltransferase (EC 2.3.1.43) | P04180 | V49, I50, L51, V52, L60, A62, A117, V133, V149, L152, V163, A165, A166, Y168, L184, V188, M191, V199, F200, L201, I202, L206, C208, L209, H210, L211, L212, F214, L215, F230, I231, A235, I241, M244, A248, I261, F289, I290, F305, F306, L309, L328, V333, V335, C337, L338, Y339, V372, A373, C380, W383, L396, M404, V405, I414, L418 |
| 181 | HLA class II histocompatibility antigen gamma chain | P04233 | C213, V253 |
| 182 | T-cell surface glycoprotein CD3 delta chain | P04234 | V33, V35, C37, Y71 |
| 183 | von Willebrand factor | P04275 | V815, C827, C829, C849, C851, C1272, L1276, L1278, V1279, F1280, L1281, L1282, F1293, L1296, F1299, V1300, M1303, M1304, L1307, V1314, V1316, A1317, V1318, V1319, Y1321, I1329, L1340, A1344, V1347, A1355, V1360, L1361, F1369, A1377, I1380, L1382, L1383, L1384, M1385, A1386, F1397, V1401, L1404, I1410, V1411, I1412, V1414, I1416, A1420, I1425, I1428, F1438, L1440, V1443, L1446, I1453, V1454, L1457, L1497, V1499, A1500, F1501, V1502, L1503, F1514, F1520, M1521, V1524, I1525, M1528, I1535, V1537, V1539, L1540, Y1542, Y1550, I1561, V1565, A1581, L1582, L1585, A1600, V1604, Y1605, M1606, V1607, V1625, V1626, I1628, V1630, I1642, L1657, A1661, V1665, L1666, C1670, L1690, V1692, I1693, L1694, L1695, L1696, F1707, F1713, A1714, F1717, I1718, A1721, V1732, L1733, Y1735, V1743, L1754, V1758, M1761, I1770, A1773, L1774, A1777, L1781, A1795, |

TABLE 5-continued

TARGETS

| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
|---|---|---|---|
| | | | V1796, V1797, I1798, L1799, V1800, V1808, A1812, A1815, V1822, I1825, I1827, L1836, L1839, L1857, V1861, L1871, C2724, L2786, C2804 |
| 184 | Argininosuccinate lyase | P04424 | L34, V39, A44, Y45, L49, I63, L67, V70, I88, H89, A91, L96, A104, L107, V118, L121, M125, C129, L132, L136, W137, L139, I140, M143, V144, A147, F155, L161, W169, I173, L174, A177, L180, L187, V190, I194, L197, L199, L216, L220, F222, A232, F238, V239, A240, F242, L243, W245, A246, C249, M250, L253, M256, A257, L260, F268, F270, V271, L273, L293, I296, V303, L310, L325, A331, V332, V335, M339, L343, A346, V349, I350, L353, M360, A363, M368, L369, L373, A374, Y375, L377, A387, A390, A394, A398, L405, L413, F420, V424, V434, A444, V448 |
| 185 | HLA class II histocompatibility antigen, DP beta 1 chain | P04440 | Y36, A46, F47, F53, L54, Y57, A65, F67, F74, W88, L95, V101, C106, L118, V126, L136, L141, L142, V143, C144, V146, F149, W158, V169, V186, L188, V197, Y198, C200, V202 |
| 186 | Envelope glycoprotein gp160/group M subtype B (isolate HXB2) (HIV-1) | P04578 | A55, V65, A70, M95, V101, M104, I108, W112, V120, C131, I154, I165, L193, H216, A221, A224, I225, G235, C239, V242, I251, L259, L260, V270, I284, I285, V286, L288, V292, I294, C296, M326, C331, I333, W338, L342, I345, A346, L349, I359, I360, F361, H374, F376, C378, F383, C385, L390, F391, L416, C418, I423, I424, V430, A433, M434, I449, L452, L453, L454, I467, F468, W479, L483, Y486, V489, I491, V505, I548, V549, L555, L556, A558, I559, A561, L565, L566, V570, I573, L576, I580, L602, A607, I635, I642, W666, W680, M687, I688, V698 |
| 187 | Receptor tyrosine-protein kinase erbB-2 (EC 2.7.10.1) | P04626 | H42, M45, L46, Y50, C53, V56, L60, L62, L65, F73, L74, I77, V80, Y83, V84, L85, I86, A87, V91, V94, L96, L99, I101, V102, A113, L114, A115, V116, L137, L140, L142, L145, I148, V153, I155, L161, C162, Y163, I172, F173, C204, W205, C227, C240, A241, A242, L304, C331, L345, A355, V356, I361, F364, C367, I370, L374, A375, F376, L397, F400, L403, I406, L410, I412, L422, F425, L428, V430, I431, A440, L443, L445, L448, I450, L453, L455, L461, L465, A466, L467, I468, H469, L474, C475, F476, V477, L494, C504, C520, W521, C540, C576 |
| 188 | High affinity nerve growth factor receptor (EC 2.7.10.1) | P04629 | L103, A110, L117, L122, L138, C215, L249, L251, V254, L258, C265, A267, V282, C300, I301, L346, L348, L361, A363, A376 |
| 189 | Hemagglutinin [Cleaved into: Hemagglutinin HA1 chain; Hemagglutinin HA2 chain]/strain A/Duck/England/1/1956 H11N6 | P04661 | I19, C20, I21, V32, V42, V49, F57, C58, I60, I66, L68, C71, F73, A74, W76, I77, L78, C83, L86, W92, Y94, I95, V96, Y107, L117, F121, V124, F127, F133, A149, C151, F153, M163, V164, L166, I176, V188, L189, I190, V191, W192, I194, H195, H196, Y207, V214, V216, Y221, M242, F244, Y245, I248, V249, I255, F257, F263, L264, A265, Y268, A269, F270, I272, L280, C294, H308, H311, I315, L327, A347, Y364, A386, L460, L468, H484, C486, C490 |
| 190 | Heat shock protein beta-1 | P04792 | V6, F8, L10, V97, L99, V101, A105, V118, I120, V148, L163, V165, A167 |
| 191 | Cytochrome b-245 heavy chain (EC 1.—.—.—) | P04839 | A394, V398, V404, M405, L406, V407, V413, F416, I419, V423, L436, F441, Y442, F454, L458, F473, F520, I532, V534, F535, L546 |
| 192 | Insulin-like growth factor I | P05019 | L58, A61, L62, F73, I91, C95, C100, L105, Y108, C109, A110 |
| 193 | Fructose-bisphosphate aldolase B (EC 4.1.2.13) | P05062 | L16, I19, A20, I23, V24, I30, L31, A32, A33, M40, L44, F59, I62, L63, F64, V66, I70, I74, V77, I78, L79, L84, F94, I97, L98, V104, V105, I107, L109, L131, C135, Y138, V143, F145, W148, A150, L152, L162, A163, I164, A168, A170, L171, A172, Y174, A175, C178, L183, V184, I186, V187, C202, V209, L210, V213, A216, L217, L228, L229, V234, Y244, A250, A252, V254, A256, L257, V261, V265, I268, C269, F270, A280, L282, L284, I287, L298, F300, Y302, A305, L306, A308, A310, A313, W314, F328, M329, A332, A334, A338, L357 |
| 194 | Amyloid beta A4 protein | P05067 | I34, A35, L41, M43, Y72, C73, V85, I94, W97, C117, C133, W150, A154, C158, C174, F179, V182, F184, V185, C186, C291, C316, C337, V375, L442, L453, Y476, A479, V490, L494, Y497, V498, A500, A523, I537, L548, A555, I558, I666, V669, H684, L688, V689 |
| 195 | Arginase-1 (EC 3.5.3.1) | P05089 | I8, I10, I11, A13, F15, V24, V30, L31, L36, L40, V67, V73, A76, L80, A81, V84, A85, V87, L95, V96, L97, H101, L103, A104, I105, I108, H111, H115, L118, V120, I121, W122, V123, A125, I129, L140, V145, L148, L149, L152, I169, A171, I174, V175, Y176, I177, L179, L190, F198, V211, M212, L219, I227, H228, L229, F231, V233, L236, A243, L252, I260, I264, L273, I275, M276, V278, V293, A296, I299, A302, C303, F304 |
| 196 | Aldehyde dehydrogenase, mitochondrial (EC 1.2.1.3) | P05091 | C36, I39, F40, A48, F54, V68, A69, V76, A79, V80, A82, A83, A85, W93, L104, L105, L108, A109, L111, I112, Y118, L119, A120, A121, L122, L125, L139, V142, L143, C145, L146, Y149, A150, A153, V178, C179, L189, L190, M191, A193, L196, A199, L200, A201, V205, V206, V207, M208, V210, L216, A218, L219, Y220, V221, A222, L224, I225, A228, V234, V235, I237, V238, A245, I249, A250, V255, V258, A259, I270, A273, A274, I293, I294, A303, A307, H308, A310, |

TABLE 5-continued

TARGETS

| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
|---|---|---|---|
| | | | L311, F312, F313, C318, C319, C320, A321, F326, V327, F335, A343, I370, Y373, I374, F397, I398, V402, F403, V406, I412, A413, I417, V421, M422, I424, L425, F427, I430, V433, V434, L444, A445, A446, A447, V448, F449, L459, A478, F482, L494, L499, Y502 |
| 197 | Integrin beta-3 | P05106 | C31, C39, C42, L43, C49, A50, W51, C52, C64, L70, C75, V109, I114, L116, L118, F126, I128, V130, V133, V138, I140, Y141, Y142, L143, M144, L146, M150, I157, L160, L164, A165, M168, I177, F179, A181, F182, V183, Y190, Y192, A198, C203, C210, Y216, L220, L222, F229, V233, F249, A251, I252, M253, A255, C258, I262, L271, L272, V273, F274, I291, M313, Y315, M321, L325, L332, I333, F334, A335, V336, Y344, I351, L359, V366, I370, A373, Y374, V381, L383, L392, A398, C400, I406, L409, C412, L415, V421, F423, I425, A427, V429, F440, I442, L451, V453, V455, C461, C474, C497, C499, C512, C521, C547, C562, C584, C593, C601, C624, V641, C661, C681, C689, V691, F693, L705 |
| 198 | Integrin beta-2 | P05107 | C25, V30, C33, C36, I37, C43, W45, C46, C62, L68, C73, L98, V103, L105, L107, A113, F115, V117, F119, I127, L129, Y130, Y131, L132, M133, L135, M139, V146, L149, L153, L154, A156, L157, I166, F168, F171, V172, F179, V180, C191, C198, F204, F217, V221, I226, L237, A239, M240, M241, V243, A244, C246, I250, V255, L258, L259, V260, F261, A262, I278, Y293, Y301, L307, L311, I316, I319, F320, A321, V322, Y330, L333, I337, A341, L345, V352, I356, A359, V367, L369, L378, Y382, C400, V403, I409, F411, V413, V415, A417, F426, I428, A430, V437, V439, V441, C445, C459, C467, C481, C483, C497, C506, C534, C549, C557, A572, C573, C582, C590, C612, A629, C662, V672, Y674, I687, V689 |
| 199 | Interleukin-4 | P05112 | L31, I34, L38, L41, C48, I56, F69, C70, A72, A73, V75, L76, C89, H100, L103, L107, L110, L114, A118, L133, F136, L137, L140, M144 |
| 200 | Interleukin-5 | P05113 | V84, L87, L91 |
| 201 | Plasminogen activator inhibitor 1 | P05121 | V31, A32, A35, F38, V40, V42, F43, V46, A47, V55, V56, F57, Y60, V62, A63, V65, L66, A67, M68, L69, L71, I81, M85, I89, M94, A95, L101, L105, I114, A119, I120, F121, V122, L128, F132, F136, F140, V144, V147, F149, A155, I159, V163, I171, L174, L175, V180, L186, V187, L188, V189, A191, L192, F194, W198, F202, L211, F212, M224, M225, F231, Y244, I246, L247, L249, Y251, L256, M258, F259, I260, A261, A262, L270, L273, L277, A279, I282, W285, L296, V297, L298, F301, V307, L309, L313, L316, M318, M321, F329, L332, L338, V340, A343, L344, V347, I349, V351, A358, A363, V364, I365, V366, A368, M377, F381, L382, F383, V384, V385, H387, V393, L394, F395, M396, V399, M400 |
| 202 | Protein kinase C gamma type | P05129 | L120, V386, A461, I476, W538, L544 |
| 203 | Plasma protease C1 inhibitor | P05155 | L142, A145, F149, L153, Y154, A168, F169, I174, A175, L177, L178, L193, L197, F213, V218, I224, F225, L230, F236, I262, V266, I274, L278, L281, V288, L290, A292, I293, L295, F313, M325, Y330, A333, A342, V344, L347, L353, L355, V356, M370, L374, L386, M409, M413, L430, M441, H443, L447, L449, V454, A456, A457, A458, A459, A461, L478, F479, V480, L481, F488, V490, F491, M492 |
| 204 | Complement factor I (EC 3.4.21.45) | P05156 | C33, V74, A76, C86, F100, V129, I140, A150, V152, A153, C154, A163, C181, L182, V184, C186, L193, A210, C214, C229, C241, C247, L254, C256, C266, I357, C365, I368, I375, L376, A378, A379, L382, I430, A431, L432, I433, A452, C467, L491, M508, C510, A511, L529, V530, C531, V540, W541, V543, V558, V562 |
| 205 | Alkaline phosphatase, tissue-nonspecific isozyme | P05186 | L46, A51, V54, I55, M56, F57, L58, A69, A70, L87, M89, A96, A111, A114, A116, Y117, L118, A123, V128, V130, I150, L151, A154, V161, I163, V164, V169, A172, A179, A182, M192, A196, I204, A205, L208, M209, I215, V217, I218, M219, M226, L252, V253, W256, I269, L275, L278, V283, L286, L287, L289, F290, M295, M312, V315, A316, L320, F327, F328, L329, L330, V331, I336, H340, A345, A348, L349, A352, V353, M355, A358, I359, A362, L372, V374, V375, A377, H379, I395, A412, I413, V459, V461, A468, L471, V480, V483, M484, A485, A487, I490 |
| 206 | Interleukin-6 | P05231 | I53, I57, I60, I64, L67, A86, L92, C111, I115, I116, L119, F122, V124, Y125, L126, Y128, L129, A140, V143, L150, I151, L154, I164, L179, M189, I194, L195, F198, F201, L202, A208 |
| 207 | 60S acidic ribosomal protein P1 | P05386 | A8, C9, A13, L16, I28, I32, F47 |
| 208 | T-cell surface glycoprotein CD4 | P05540 | A222, F224, F226, L239, F255, V262, L283, I285, A293, L298, L300, V311, L313, V314, V315, M316, L326, C328, V330, L340, L342, I358, W368, C370 |
| 209 | Integrin beta-1 | P05556 | C27, A32, C38, I39, C45, C64, I114, L119, L121, L123, F131, L133, I143, L145, Y146, Y147, L148, M149, L151, M155, V162, L169, M173, I182, F184, F187, V188, Y195, I196, C213, Y219, F232, V236, F252, A254, I255, M256, V258, A259, |

TABLE 5-continued

| TARGETS | | | |
|---|---|---|---|
| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
| | | | C261, I265, V270, L273, L274, V275, F276, I293, Y316, L322, L326, I331, I334, F335, A336, V337, Y345, L348, I352, L360, V367, I371, I372, V382, L384, C415, I418, F426, I428, I430, I445, V454, V456, L458 |
| 210 | Gag-Pol polyprotein/group M subtype B (isolate MN) (HIV-1) | P05961 | L8, W16, I19, L21, Y29, V34, A37, L41, L50, L51, C57, I60, L61, L64, L75, L78, V82, A83, L85, Y86, C87, V88, I94, A100, I104, W158, V161, V162, F167, V171, I172, F175, A182, L187, M190, L191, V194, A199, A200, L204, I208, A212, I239, A240, W252, V261, Y265, I269, L273, I276, V277, I285, F296, Y299, V300, F303, Y304, L307, A309, L325, C333, L337, M350, C353, C395, A405, C416, L499, I507, I509, A516, L518, V526, L527, M530, V550, Y553, I556, I558, I560, C561, A565, V569, L570, V571, I578, I579, L583, L584, L591, V603, I624, A626, L627, I630, C631, I640, I643, V653, F654, A655, I656, L667, V668, F670, L673, V683, A691, L693, V699, V701, L702, V704, A707, Y708, F709, V711, L713, F717, A722, F723, I725, I728, Y737, Y739, V741, L742, W746, A751, I752, F753, M757, I760, L761, F764, L780, Y781, V782, L786, H791, I795, L798, H801, L802, L803, F807, F820, W822, M823, Y825, L827, W832, V834, L839, W845, V847, I850, L853, L857, A860, I863, Y864, I867, L872, L876, L888, A892, L896, A897, L903, L918, I919, A920, V922, W930, Y932, I934, L942, A948, A953, V958, L961, A964, V965, I968, I973, V974, F982, L984, I986, W991, W994, W995, A1001, W1003, I1004, W1007, V1016, W1019, I1027, F1033, V1035, A1039, A1048, Y1050, L1062, L1072, A1074, I1075, H1076, L1077, A1078, L1079, V1086, I1088, V1089, A1095, I1099, V1111, I1114, I1115, L1118, V1124, L1126, V1141, V1145, A1161, M1175, A1186, W1214, V1225, I1226, L1227, A1229, V1230, H1231, I1237, F1253, L1254, L1257, A1258, V1279, C1283, L1311, I1314, A1328, V1329, A1332, V1333, I1344, A1349, I1353, A1358, I1361, V1378 |
| 211 | Collagen alpha-2 | P05997 | C64 |
| 212 | T-cell surface glycoprotein CD5 | P06127 | F33, A35, C44, L48, V50, L52, V59, C60, W64, A77, V80, C81, L90, L92, I105, I106, C107, F114, C125, L128, L130, C132, L133, V289, V291, L300, C301, W312, V315, C316, C321, C350, C360, V365 |
| 213 | Insulin receptor | P06213 | L29, C35, I40, L47, L50, C53, V55, I56, L60, M65, L81, M83, I84, L88, L90, V93, L99, L102, F103, L106, V108, I109, A119, L120, I122, M125, L128, L131, L133, L136, V144, I146, L152, I163, L164, C186, C209, W210, C223, C228, C235, C239, C252, A254, F275, W278, C286, V305, L326, I348, A354, L357, C360, I363, L367, I369, I371, L381, L385, I388, I391, Y394, L395, I397, L406, F408, F409, L412, I415, F427, A429, L435, L438, W439, L446, I448, L453, F455, H456, L461, I466, M469, I512, L514, W516, L532, A537, M580, I591, V593, A608, I638, L640, V657, I809, I820, L822, A824, C825, V867, H868, V886, V900, C911, V923, I925, A927, F942, V944 |
| 214 | Tyrosine-protein kinase Lck (EC 2.7.10.2) | P06239 | V66, L88, A100, I111, A137, L141, F151, L152, I153, L165, V167, I183, I193, L205, Y209, L216, L220, V240, L245, L247, V270, V272, L275, F285, A289, L295, L300, L303, A305, V306, V307, I312, I314, I315, L324, L328, L341, L342, M344, A345, I348, A349, M352, I355, I361, H362, L365, A367, A368, I370, V372, C378, I380, A381, F383, A386, A408, A411, F417, V423, W424, F426, I428, L429, L430, I433, V449, L453, C465, L469, M473, C476, W477, F487, L490, V493, L494 |
| 215 | Alpha-galactosidase A (EC 3.2.1.22) | P06280 | W44, H46, C63, I64, L68, F69, M72, A73, M76, W81, Y86, L89, C90, I91, C94, W95, M96, L120, A121, V124, L129, L131, I133, Y134, A135, V137, Y152, A156, F159, V164, L167, F169, L180, Y184, M187, A190, V199, Y200, C202, I219, C223, H225, W226, I232, I239, I242, L243, I253, W262, M267, L268, V269, I270, V281, M284, A285, L286, W287, A288, I289, M290, A291, A292, L294, M296, A307, L311, V316, I319, F337, V339, W340, A348, A350, V351, A352, M353, I354, I367, V369, L372, A377, C378, A381, C382, I384, L403, I407, V413, L414, L415, L417 |
| 216 | HLA class II histocompatibility antigen, DO alpha chain | P06340 | H50, F58, V60, A78, A87, I89, L131, I132, C133, V135, I138, W147, F174, L177, V180, Y187, C189, V191, H193 |
| 217 | Gelsolin | P06396 | F59, I70, W71, V73, L78, V81, L85, F89, A94, Y95, V96, I97, L98, V101, L112, H113, W115, A127, A128, L135, A143, F157, A173, L189, F190, V192, V198, A200, F210, C215, F216, I217, L218, L220, I224, W227, L238, A240, V243, I247, G254, G264, M270, L271, P276, A279, L280, A282, G283, A292, A298, L300, V303, M310, A316, F321, A322, L326, C331, F332, I333, L334, I342, F343, V344, A358, L359, A362, F365, I366, V377, V379, L380, F389, F392, A434, M439, I449, I452, F468, Y474, I475, I476, Y478, Y480, I489, I490, W493, V526, H534, L535, L538, F539, M544, I545, I546, L565, F566, V568, A578, L588, A593, F594, V595, L596, A602, L604, W605, A610, A618, L621, L622, V632, F641, A644, L645, L657, L669, A671, C672, V680, L693, A694, V698, M699, L700, L701, V707, F708, V709, W710, A723, L724, A727, I744, V747, F756 |

TABLE 5-continued

TARGETS

| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
|---|---|---|---|
| 218 | Complement C2 (EC 3.4.21.43) | P06681 | L47, A82, C89, Y107, V113, C144, C151, A160, V173, C191, I462, M573, V697 |
| 219 | Complement C5 | P06684 | A691, C703, C728, A731, C735, C736, A739 |
| 220 | Glycogen phosphorylase, liver form (EC 2.4.1.1) | P06737 | I16, V25, L28, F32, L36, F54, A55, L56, A57, V60, L64, V83, Y84, Y85, L86, L88, F90, L96, M100, I101, L105, A108, C109, I113, L118, L123, L132, L137, L140, A141, A142, C143, F144, L145, M148, A149, L151, L153, A154, A155, Y156, Y158, I160, Y162, V201, F203, V222, A224, V239, M242, L244, W245, A247, A273, I276, L280, L294, Y298, F299, V300, V301, A302, A303, L305, I308, I309, F317, F327, F330, V334, A335, I336, L338, A344, L345, A346, I347, L350, M351, F354, I357, L360, A365, L368, F373, A374, Y375, V380, W388, L392, V393, L396, L397, H400, I403, I404, I407, I415, L418, M429, L431, I432, I440, M442, A443, L445, C446, I447, A452, V453, V456, A457, I459, H460, V464, F469, F472, L475, I487, W492, L493, L494, A501, L503, I504, Y512, V513, L516, L519, L522, H523, F531, L532, V538, L544, F546, L550, M563, F564, V566, I571, Y574, L578, L579, C581, L582, H583, V584, I585, I591, V604, I605, I606, A610, A611, M616, A617, I620, I621, L623, I624, V627, V630, V631, M636, V637, L641, V643, I644, L646, V651, L653, A654, V657, I658, A660, L663, I667, A670, M680, F682, M683, L684, A687, L688, I690, A696, M700, A701, F712, A729, L736, L739, V742, I743, I746, F759, I762, L766, F772, F775, Y778, Y781, V782, C784, V788, Y792, V802, L803, I806, A807, F812, I818, Y821, A822, W826 |
| 221 | Glucose-6-phosphate isomerase | P06744 | A2, L4, F10, L13, W16, L26, F40, I51, V53, Y55, L59, V60, V64, M67, L68, L71, A72, V77, A79, A80, M84, A97, V98, L99, H100, V101, A102, L103, I111, V118, V125, M129, F132, C133, V136, I149, V152, I153, I155, M166, V167, A170, L171, V184, I192, L205, F206, I207, I208, A209, F213, A222, A225, F229, A233, A238, V239, H242, F243, V244, A245, L246, V253, F256, I258, F264, F266, W269, V270, Y274, L276, W277, A279, I280, L282, I284, A285, L286, F293, L296, L297, A300, M303, F307, L312, A316, V318, L319, L320, A321, L322, L323, I325, W326, A337, M338, L339, Y341, L345, F348, F352, V379, Y392, I395, C404, F406, L407, I408, F429, L436, M437, A445, L463, I477, F479, L482, M486, L487, A489, L490, V491, A492, M493, Y494, H496, I498, F499, V500, I503, I504, W505 |
| 222 | Tumor necrosis factor | P06804 | A93, V95, L127, V137, V141, F143, L154, H156, V158, C179, L204, L210, A212, F230, V232 |
| 223 | Beta-hexosaminidase subunit alpha (EC 3.2.1.52) | P06865 | W24, Y37, V60, L61, A64, L90, V94, L95, V96, V97, Y116, L118, I120, C125, L127, V132, W133, A135, L136, L139, F142, I156, I161, H169, L172, L173, L174, L181, I186, L190, V192, M193, L198, V200, F201, H202, W203, H204, L205, V206, F211, F216, L221, Y234, V239, V242, A246, I251, V253, L254, A255, F257, L264, W266, L273, V290, F300, M301, F304, F305, V308, F312, L317, H318, L319, F326, W329, I335, M339, L351, F354, Y355, I356, L359, L360, V363, Y366, V371, V372, W373, V376, I389, V391, V398, Y400, L404, V407, A414, L415, L416, W420, L422, F434, Y435, A457, C458, M459, L469, L473, W474, A477, A479, V480, A481, L484, W485, A496, L500, F503, L507, V519 |
| 224 | Thrombomodulin | P07204 | C369, C388, C390, C413, C439, C464 |
| 225 | Vitamin K-dependent protein S | P07225 | C212, C241, C265, C267 |
| 226 | Prostate-specific antigen | P07288 | I25, V40, V42, V53, L54, V55, V60, L61, A63, A64, C66, I73, L75, F90, V92, L121, L123, L124, L126, L132, A135, V136, C152, A154, F165, V174, L176, C184, C198, A199, L217, C219, L223, I226, L242, Y243, V246 |
| 227 | Cathepsin D (EC 3.4.23.5) [Cleaved into: Cathepsin D light chain; Cathepsin D heavy chain] | P07339 | L71, I83, I85, F92, V94, V95, W104, V105, C117, Y123, L147, V156, F179, F190, F195, I198, L199, M201, V214, F215, L218, F229, A268, W270, V272, L274, V277, V279, L285, A292, V294, M301, V308, L311, A317, I327, I338, L340, L342, L349, Y354, F370, L382, L385, V388, F389, I390, Y394, V396, F397, V404, F406, A407 |
| 228 | Trypsin-1 (EC 3.4.21.4) | P07477 | I24, V39, L41, L52, W57, V58, V59, A61, C64, I69, V71, L73, V80, L81, F87, I88, I108, M109, L110, I111, L113, I119, V123, I126, L128, C139, I141, W144, C160, A163, C171, A173, Y175, F184, C185, V186, V204, C206, L210, V213, V214, V228, Y229, V232, Y235, V236, I239 |
| 229 | Decorin | P07585 | V65, C67, V75, L86, L88, I93, I96, F101, L107, L110, L112, I117, A124, F125, L128, L131, L134, L136, L144, L152, L155, A157, I162, V165, F170, L173, M176, I179, L181, L186, A195, F196, M199, L202, I205, I207, A208, I212, I215, L223, L226, L228, I233, V236, L241, L244, L247, L250, L252, I257, L265, L271, L274, L276, L281, L288, I294, V297, L299, I304, F312, C313, Y324, V327, L329, A352 |
| 230 | Prosaposin | P07602 | C66, V69, V70, A73, I86, L90, C94, V110, I117, L118, V131, C132, C230, C265, C271, V317, C318, L321, V325, I338, M345, C346, C357, V360, I368, L369, V381, C382, V411, C412, L415, V416, L419, I432, L436, C451, F454, L462, L466, M470, V475, C476, A481 |

TABLE 5-continued

| TARGETS | | | |
|---|---|---|---|
| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
| 231 | Beta-hexosaminidase subunit beta (EC 3.2.1.52) | P07686 | A55, W57, L70, C91, L93, L94, A97, V124, L127, V129, I131, A139, Y149, L151, V153, A158, L160, A162, V165, W166, A168, L169, L172, F175, I189, I194, H202, I205, L206, I207, L214, I219, L223, A225, M226, F228, F231, V233, L234, H235, W236, H237, I238, V239, F244, I249, L254, Y266, V271, V274, A278, I283, L286, F289, L296, W298, L305, I322, L333, F336, F337, I340, F344, I349, H350, L351, F358, W361, I367, M371, L383, F386, Y387, I388, V391, L392, I395, I398, I403, V404, W405, V421, V423, Y429, L433, V436, V443, I444, L445, W449, L451, Y463, Y464, A486, C487, L502, W503, A506, A508, V509, L513, W514, A525, L529, H532, M536, I541, A548 |
| 232 | Uromodulin | P07911 | C106, C315, V357, F369, A424 |
| 233 | Proto-oncogene tyrosine-protein kinase receptor Ret (EC 2.7.10.1) | P07949 | Y30, F31, Y36, L40, V42, L50, V53, L68, L72, L80, I86, L95, L97, L109, V121, L123, V125, A143, V145, F147, C166, F174, F185, C197, V223, L229, L239, A241, V242, C243, V245, F258, V260, V262, Y263, A269, Y314, F329, L358, L372 |
| 234 | Fumarate hydratase, mitochondrial | P07954 | V62, A70, V92, I93, A95, F96, I98, L99, A102, A103, A104, V106, A117, A119, I120, A123, A124, V127, L138, V140, V153, V156, I157, A161, I162, V175, V181, F191, A194, M195, H196, I197, A198, A199, A200, V203, L207, L211, L214, L218, A220, F225, I228, I229, I231, V240, L242, L244, F248, Y251, V255, A258, I262, M266, I269, L272, A273, A274, A278, F289, V293, A294, V297, L303, A308, L315, A317, H318, A320, L321, L324, M328, A332, L335, I338, A339, I342, L356, L358, C377, M380, V383, A384, V387, M388, V392, V394, V407, M411, M412, I413, V416, L417, A420, L422, L423, F430, C434, V435, V436, I438, A440, I445, M449, L455, L459, A468, I471, A475, L482, A486, L492, F497 |
| 235 | Gap junction beta-1 protein | P08034 | F51, C60, C64, H73, C168, V170, C179 |
| 236 | Rhodopsin | P08100 | V11, Y26, W35, F103, C110, L112, I179, C185 |
| 237 | Beta-microseminoprotein | P08118 | C38, C57, C60, C62, I67, C84, V97 |
| 238 | Annexin A6 | P08133 | A26, L29, A32, M33, I43, L44, I47, V58, Y62, L70, I71, L74, L85, I86, V87, L89, M90, A98, I101, A104, I105, C114, L115, I116, I118, L119, M127, L130, A133, Y134, L142, I146, I147, M157, L158, V159, L162, V177, V181, L184, A187, F199, I200, I202, L203, L211, V214, F215, Y218, I226, I230, L241, M242, L243, A244, V245, V246, C248, I249, F256, A257, L260, A263, M264, L274, I275, I277, M278, V279, L284, M286, L287, I289, I292, F293, L301, I305, L317, L318, L320, V338, A339, W343, V357, A369, L372, A375, M376, I386, I387, I390, I401, F405, L413, M414, L417, L428, I429, L432, M433, Y439, A441, W44, A447, M448, A457, L458, I461, L462, A463, I470, I473, A476, Y477, L485, L489, I500, L501, A505, A519, A523, V525, A526, I529, L530, I532, F547, M548, I550, L551, L559, V562, F563, F566, V574, I578, A589, F590, A592, I593, V594, V597, L602, F604, A605, L608, M612, L622, I625, M626, I632, L634, L635, I637, F641, L649, I653, A664, L665, L666, L668, C669 |
| 239 | Multidrug resistance protein 1 (EC 3.6.3.44) | P08183 | A58, M75, L107, M111, Y118, V125, A129, F135, C137, A139, A140, I144, I147, F151, F152, A154, I155, M156, I160, L171, L175, V179, I182, I186, A198, V206, L214, I218, A233, A250, A254, V257, A260, V264, A266, F267, Y277, L281, A284, A292, A301, A302, A308, A311, A313, F314, L332, V334, F335, V338, A348, A358, A362, I365, I369, I375, L392, V397, L410, L413, V417, V423, A424, L425, V426, C431, L439, M440, V451, I458, I461, V463, L466, I470, V473, L479, F480, I484, I488, I500, V504, A507, A509, I513, V524, I539, A540, I541, A542, A544, I551, L553, L554, A557, V569, A572, L573, A576, I583, I585, V592, I598, A599, F601, L615, Y622, I700, C717, A718, I735, I736, L754, L758, F759, L762, A780, L784, L788, V792, F793, M796, L797, L818, A822, V825, A828, A834, A841, L857, A897, A900, I901, F904, V907, F916, A935, C956, A961, L976, V977, F983, A1001, A1005, H1007, I1008, V1035, F1037, V1040, F1042, L1053, L1056, V1060, L1066, A1067, L1068, V1069, V1079, L1082, L1083, V1094, I1101, L1104, V1106, L1109, L1113, V1116, F1123, A1128, I1131, I1145, A1148, A1149, A1152, I1154, Y1165, V1169, A1185, I1186, A1187, L1190, L1198, L1199, V1214, A1217, C1227, I1228, I1230, I1237, I1243, V1244, V1245, L1260, Y1267 |
| 240 | Mineralocorticoid receptor | P08235 | C603, V605, V617, C620, C623, F627, A630, C645, I647, A657, C658, C663, M668, L742, A752, L765, L769, L772, M777, W783, A784, L787, F790, L801, W806, L809, F812, L814, L827, A830, L833, F835, C849, I855, F859, L862, L864, F866, Y869, I871, M872, V874, L875, L876, L877, L878, F892, M895, L903, V907, L924, L927, L928, M931, F943, V954, L960, I964 |
| 241 | Beta-glucuronidase (EC 3.2.1.31) | P08236 | W45, F47, L68, V99, W100, Y101, V119, V120, I123, A130, V132, L147, I168, I170, A171, I172, L176, F208, Y211, L214, V218, L220, V244, L258, V260, L262, V282, W288, L303, V305, L307, A309, V324, F336, I338, F345, H346, V348, L373, L376, A378, A380, F381, Y386, Y388, M395, V402, V403, I404, C407, L412, H426, M430, V433, A442, V444, |

TABLE 5-continued

| SEQ ID NO. | Protein Name/Strain | UniProt ID No. | TARGETS: Exemplified Sites of Mutations to Generate Peptidogenic Protein (Each position can be substituted alone or in any combination with any of the other listed amino acid positions.) |
|---|---|---|---|
| | | | M445, W446, V448, A449, A459, L463, M465, V466, V479, V482, A493, V498, I517, L521, F525, I536, I537, Y541, A543, Y561, L565, L566, Y569, L573, V581, L585, I586, F589, F592, V601, I608, F609, A618, A619, L622, Y626 |
| 242 | ATP-dependent 6-phosphofructokinase, muscle type | P08237 | I18, A19, V20, L21, A27, M30, A32, A33, V34, A36, V37, V38, A46, V48, V51, L58, V59, V73, L77, A101, A102, L105, L113, C114, V115, I116, L122, F128, L135, V159, L161, V162, I165, F169, I176, A181, I185, M186, V189, A196, F203, V204, L205, V207, C212, L215, A216, L217, F229, I230, L243, C244, L247, I260, I261, V262, A263, A266, I279, V283, V284, V293, L296, A307, L312, A320, V321, L324, L325, A333, V335, V336, L348, V358, A370, A389, A404, V405, M406, V408, A412, A413, M415, A417, A418, V419, V423, V433, L434, V435, V436, F440, V456, I481, V494, I495, I496, A501, Y502, L506, C519, F522, V523, V524, I525, A527, V533, V540, A542, A545, C550, C553, A560, V567, F568, I569, I570, C577, L580, A581, A584, L586, A587, I595, L605, V609, L612, M616, L624, V625, L626, I640, Y644, A676, M679, A683, M684, M687, I691, A702, V710, L711, V723, L726, W742, L745 |
| 243 | Neutrophil elastase (EC 3.4.21.37) | P08246 | I30, V45, L47, A57, L59, V65, M66, A68, A69, V72, A73, A79, V80, V82, L84, I118, V119, I120, L121, V133, A153, M154, W156, A166, L172, V174, C187, L206, V207, C208, I212, I215, A216, C223, A231, F232, A233, V235, I242 |
| 244 | 72 kDa type IV collagenase (EC 3.4.24.24) | P08253 | A50, L54, C60, L74, M77, L83, I124, L135, V140, A143, F144, A147, F148, W151, L157, A167, I169, I171, F173, F184, A192, F195, F207, L212, W213, V221, V223, Y225, G226, A228, C233, F235, F237, C247, W258, C259, C274, A286, C291, F295, C305, W316, C317, C332, A347, C349, F353, F355, W374, C375, A376, A379, Y381, W387, C390, L397, F398, V400, A401, A402, F405, H407, A408, M409, L411, A419, L420, M421, A422, Y427, L433, I441, L444, I478, A479, I485, F487, F488, I493, W494, A522, V523, Y524, A526, V533, F534, F535, Y543, L556, V568, A570, A571, F572, I582, F583, I606, L617, A619, V620, V621, F631, F632, L640, W657 |
| 245 | Neuraminidase (EC 3.2.1.18)/strain A/Equine/Kentucky/1/1981 | P08326 | I104, V112, V114, F119, V120, F130, F131, L132, L156, V159, A176, W177, A179, A181, C182, M189, V191, V193, A200, V201, A202, V204, L222, C231, I232, Y237, V239, M240, A249, Y251, I253, A256, I261, H273, I274, C277, C279, Y280, V286, C288, V289, C290, L302, I304, C316, I319, F349, F351, V357, W358, A359, I363, F371, I373, I374, I393, I394, L397, F406, L418, C421, F422, W423, V424, M426, W437, I443, M445 |
| 246 | Neprilysin (EC 3.4.24.11) | P08473 | A66, L69, F83, A87, C88, L118, L122, A132, A136, A138, L139, L157, L158, I164, W167, V169, W174, A184, A187, I188, A189, L191, I201, L203, I217, H218, I219, Y231, A244, Y245, F248, M249, V252, A253, I256, M273, V276, L279, I283, A284, A286, M303, L305, A306, I308, L314, I316, W323, F326, I330, M331, I336, V344, V345, V346, A348, Y351, L352, L355, L359, L367, M371, W373, I376, V380, L383, Y387, F394, C411, A412, V415, M419, A422, V423, Y427, V440, I444, I447, V450, F451, L455, A463, A469, A473, A475, L493, Y497, L500, A539, I553, V554, F555, F564, F565, L573, I578, M580, I582, I586, F590, F615, M622, Y626, A634, I649, A650, A658, A661, Y662, L685, F686, F687, L688, F690, A691, V693, C695, A703, I719, L723, F729, C735, M741, V749 |
| 247 | Integrin alpha-IIb | P08514 | L34, Y42, F50, L54, H57, I66, V67, V68, A70, V84, C87, L115, L124, V128, I135, V136, A137, C138, A139, W144, V146, A153, V158, C161, L163, A164, A172, Y174, C198, A200, L212, V213, L214, A216, L225, L226, A227, A229, V231, I234, L243, V247, Y284, V285, V286, A288, W291, A297, V298, I300, L301, F320, A325, V329, L337, L338, V339, A341, A354, V356, V359, Y360, L361, L378, F387, A392, L394, L397, I405, A406, V407, A408, V420, V422, L438, A447, F448, Y463, L466, I467, V468, A470, V476, A477, V478, Y479, A481, V485, I518, V522, L535, A537, L539, L541, V552, A581, I596, L598, L600, C633, L662, L664, A675, A681, V682, A688, A693, V715, V716, M724, M734, V736, F750, L752, I754, A775, Y815, L817, V825, L828, I832, V919, C921, M926, V934, L940, L945, L955, A959, V982, L986 |
| 248 | Apolipoprotein | P08519 | C4145, W4148, C4173, C4184 |
| 249 | Pleckstrin | P08567 | V26, V27, L28, I33, F35, I48, V68, F69, I71, H79, F81, W92, I96, I100, M133, I140, C155, F156, V161, I162, L165, A181, L184, L190, A200, F209, A215, Y217, F219, L251, F266, L268, A273, L275, H276, I290, L292, L314, F315, I317, L327, A329, W338, I342, A345 |
| 250 | Collagen alpha-2 | P08572 | L1492, L1518, Y1519, L1531, Y1565, W1566, L1567, I1587, C1590, V1592, C1593, A1595, F1625, H1628, A1630, C1646, F1655, I1656, C1658, C1665, C1705, V1707, C1708, M1709 |
| 251 | Receptor-type tyrosine-protein phosphatase C (EC 3.1.3.48) | P08575 | C226, F246, A248, V279, I281, L295, V297, V301, I319, L321, F340, C365, I369, I408, W410, F420, L422, L444, L455, L457, A459, A463, M499, V501, L518, V520, F537, F550, A552, F554 |
| 252 | Hepatocyte growth factor receptor | P08581 | A48, I62, F63, L64, A66, I70, Y71, V72, L73, L78, L130, I131, C133, C141, H144, I154, I161, C175, V176, V177, I193, F195, F196, V197, I214, V216, L219, I235, V237, Y245, I259, Y260, F261, L262, I278, I279, F281, L288, Y291, M294, |

TABLE 5-continued

| TARGETS | | | |
|---|---|---|---|
| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
| | | | L296, C298, I299, L300, F314, I316, L317, A319, L329, A330, I341, F343, G344, V345, F346, A347, A354, A361, M362, C363, F365, I367, V370, V383, L386, H388, F389, L424, L429, F430, L439, I442, I452, A453, L455, F462, V465, V467, H476, V477, V486, L503, V504, I505, I510, I513, L515, L518, C520, C529, C541, C561, A573, L581, I583, F588, V603, L622, C624, I638, I640, F652, I659 |
| 253 | Complement factor H | P08603 | C21, A48, Y50, V62, C66, C80, V108, A110, C129, C141, V144, C146, V174, F176, M190, C192, C205, Y227, F233, Y235, A249, C251, C325, V347, Y355, I372, C389, F391, L394, V414, L422, V429, C431, Y467, A473, C494, C505, L532, I551, C553, C569, Y587, L593, F595, V609, C611, L636, V655, Y657, I671, C673, C684, Y709, V715, F717, I731, C733, C744, C753, L761, F771, I777, C792, C870, I876, C915, C926, V942, V955, A971, C973, C984, C1048, Y1067, V1073, V1089, C1109, I1120, V1134, Y1136, C1138, L1144, I1150, C1152, C1167, I1169, M1174, I1179, L1181, L1189, V1197, F1199, C1218, L1223, C1228 |
| 254 | Genome polyprotein [Cleaved into: Protein VP0/genotype IB (isolate HM175) (HHAV) (Human hepatitis A virus (isolate Human/Australia/ HM175/1976)) | P08617 | W91, V106, V107, L110, V117, L121, A127, F129, I131, V135, L147, I148, A150, M151, V152, V202, I207, V209, L213, V227, A229, F231, A306, V326, Y329, F331, L346, A347, C350, W356, L360, L376, C379, V418, A443, I444, I448, Y450, C451, V465, L471, F600, Y628, V644, V702, I722, Y727, L734, C738, L841, F869, L880, I907, I911, F914, L953, L954, I962, V1528, V1533, F1535, V1537, M1548, A1550, L1551, V1553, L1558, L1559, V1560, F1576, F1578, V1604, V1605, L1606, M1607, V1609, I1618, I1623, A1631, A1636, L1638, V1639, L1654, V1676, A1679, W1680, M1690, A1694, L1695, V1696, I1706, L1707, I1709, A1712, L1718, V1719, A1720, L1722, V1723 |
| 255 | 40S ribosomal protein S17 | P08708 | V9, A13, I17, C35, I50, A51, V54, I61 |
| 256 | Coagulation factor VII (EC 3.4.21.21) | P08709 | C141, I213, C219, V228, L229, L230, L242, V248, V249, A251, A252, L264, A266, L268, V285, V288, I289, Y294, I303, A304, L305, L306, V318, L321, L333, V341, W344, A354, V362, C370, M387, F388, C389, A390, H408, A409, H411, L418, I421, V422, V436, Y437, V440, Y443, I444, W446, L447, L450, A463 |
| 257 | Interleukin-6 receptor subunit alpha | P08887 | L45, C47, V50, V58, W60, V86, Y94, C96, V130, C132, L148, L149, V150, C176, L178, Y188, V190, M192, V194, L234, V236, L251, F253, L255, Y257, A259, V270, L273, I279, A282, H288, V290, L292, A294 |
| 258 | Dihydropteridine reductase (EC 1.5.1.34) | P09417 | V13, L14, V15, C26, V27, F30, V37, A38, V40, V67, V71, V80, A82, I83, L84, C85, M107, L121, A122, L131, L132, L134, A153, V157, H158, C161, A176, A177, I178, A179, V180, L181, L208, F212, L227, I228, V230 |
| 259 | Fructose-1,6-bisphosphatase 1 | P09467 | L14, F17, V18, L34, L38, A41, V42, I45, A52, L74, V82, L86, A91, C93, V94, L95, V96, V106, V115, V116, C117, F118, L121, V133, I136, F137, I139, Y140, A153, A162, A163, Y165, A166, L174, V175, L176, A177, V182, C184, F185, F194, A223, V224, Y227, V250, V253, L257, I262, F263, L264, L278, L279, Y280, C282, M285, A286, Y287, V288, M289, A292, A296, V303, L304, I311, A315, V317, I318, L319, V325, F328, V331 |
| 260 | Macrophage colony-stimulating factor 1 | P09603 | C39, I43, L51, L54, F69, V70, L75, C80, A85, V89, M93, L112, L115, L119, C122, C134, L145, V149, V152, F153, L160, F167, C171 |
| 261 | Platelet-derived growth factor receptor beta | P09619 | L52, C54, V60, W62, L85, L90, C100, Y117, I118, F119, V120, I147, C149, V151, L160, C190, V225, I231, L233, C235, V237, L265, L276, I278, Y289, C291, V293, I308 |
| 262 | Pro-cathepsin H [Cleaved into: Cathepsin H mini chain; Cathepsin H (EC 3.4.22.16); Cathepsin H heavy chain; Cathepsin H light chain] | P09668 | V240, V279 |
| 263 | Ubiquitin carboxyl-terminal hydrolase isozyme L1 | P09936 | M12, L13, V16, L17, L20, V22, A23, V42, C47, A48, L49, L50, L51, L52, F53, I67, M82, I86, L95, I96, H97, A98, V99, L114, F117, L118, A130, F133, I139, A142, H143, V146, A147, F160, H161, F162, I163, L164, F165, L172, Y173, L175, M179, L193, L194, A197, A198, C201, V212, V217, A218, L219, C220 |
| 264 | Leukotriene A-4 hydrolase | P09960 | C8, V16, C17, L22, V28, L35, A39, L41, V43, L53, L55, V65, I67, M87, I89, A94, L95, I103, I105, F107, A115, L116, L119, Y131, L132, F133, C136, A138, C141, A143, L145, C147, V153, Y157, A159, V161, V163, L167, A169, L170, A173, F192, I198, C200, Y201, L202, A204, V206, V207, V221, V228, F235, M241, L242, A245, L248, L259, L260, V261, L262, F266, C275, L276, F278, V279, L283, I294, A295, I298, H300, W302, V307, W312, W316, L317, H321, Y324, L325, H328, I329, A343, L344, L350, L366, L370, V382, F388, A389, L390, L391, F392, L394, L397, L398, F404, F407, L408, |

TABLE 5-continued

TARGETS

| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
|---|---|---|---|
| | | | Y411, V412, I420, W425, L429, L440, W448, C469, W476, F487, F503, L504, I518, M521, F527, I535, W539, L540, L542, C543, I544, A551, L554, A555, A559, F567, L571, F572, L575, A585, Y589, H597, L603, V604 |
| 265 | Complement C4-A | P0C0L4 | L24, L25, F26, V31, L37, V39, V41, L43, V52, V56, L76, L87, A94, L110, V111, A112, I130, L132, I149, Y150, V156, Y158, V160, A162, I174, V176, V178, I215, A217, F219, F231, V233, F241, I252, I266, A268, I271, V276, A280, V282, L286, L305, F319, V340, A341, A343, I345, L378, A382, L386, V390, V403, V405, A407, V409, V431, I433, I435, L444, A450, V462, L473, L491, M508, L510, V529, V533, F541, F543, V544, A545, F546, Y547, V560, A564, L633, V646, F647, L652, F654, I687, C703, A720, C735, A739, F833, L835, L837, L855, L863, V865, V867, V889, V897, V901, V913, V914, A915, V927, L931, V945, L948, V978, V980, A994, L995, V1000, A1001, M1015, I1016, L1018, A1019, A1023, A1024, Y1027, L1028, A1045, I1049, I1056, Y1066, A1067, A1068, W1077, L1078, A1080, V1082, L1083, V1085, L1086, A1089, L1107, F1117, L1132, V1139, A1140, L1141, A1143, F1144, V1145, I1147, A1148, L1149, V1168, A1175, L1179, A1192, A1193, A1194, I1195, A1197, A1199, L1200, A1205, L1210, A1213, L1217, W1230, I1262, A1266, Y1267, A1268, L1269, H1271, A1282, A1285, L1289, V1306, I1307, A1308, A1311, L1327, V1329, L1331, L1358, I1366, V1368, L1378, Y1384, L1501, V1512, V1522, L1524, F1538, A1540, L1578, A1617, Y1625, F1627, V1629, F1643, I1647, F1667, V1669, Y1683, L1684, I1685, M1686, Y1701 |
| 266 | Complement C4-B | P0C0L5 | L43, I149, I271, L305, V409, L510, A564, L652, I1366 |
| 267 | Serum amyloid A-1 protein | P0DJI8 | M35, A38, F54, A56, A62, A72, A73, A99, A100 |
| 268 | Serum amyloid A-2 protein | P0DJI9 | A72, A99 |
| 269 | Transcriptional activator GLI3 | P10071 | C548, L563, C578 |
| 270 | HLA class I histocompatibility antigen, Cw-7 alpha chain | P10321 | M29, Y31, A35, F46, V52, F57, V58, F60, A73, W75, V76, Y83, Y91, A95, L102, L105, L119, M122, C125, L127, Y142, Y147, I148, L150, L154, W157, A163, A164, A176, A177, L184, C188, V189, L192, Y195, L196, L203, V213, A223, L225, C227, A229, F232, Y233, L239, W241, A269, A270, V271, V272, V273, Y281, C283, M285, H287 |
| 271 | Hemagglutinin [Cleaved into: Hemagglutinin HA1 chain; Hemagglutinin HA2 chain]/strain B/Bonn/1943 | P10448 | A50, L61, C62, C65, L71, A74, L75, C80, A87, V89, V91, C102, I112, L115, L119, A135, Y143, I145, C151, F161, M164, A165, W166, A167, V168, V180, V182, I193, V195, W196, H199, M206, Y210, F218, I251, V253, I266, Y268, I272, L273, L274, V278, A281, I288, C300, L301, H302, A385, A511 |
| 272 | Lysosomal protective protein (EC 3.4.16.5) | P10619 | L54, H61, L62, H63, Y64, W65, F66, V67, V78, V79, L80, W81, L82, L91, L94, L95, H98, F101, W117, A121, V123, L124, Y125, V132, F134, V149, A156, L157, F160, F164, Y167, L172, F173, L174, Y179, A180, I182, Y183, I184, L187, A188, V189, V191, L202, V204, L208, L218, V219, A222, L236, F248, C256, L260, V263, V267, V297, V298, M327, A337, Y340, L341, V346, L350, W359, C362, V366, Y370, M377, Y381, L382, L384, L385, L393, L394, Y395, M401, F411, V412, W426, V428, V441, I447, A448, F449, L450, I452, A455, H457, V459, A466, A467, M470, F471, F474 |
| 273 | Mast/stem cell growth factor receptor Kit | P10721 | I54, L56, C58, W66, Y95, C97, I107, V109, V111, F118, V134, C136, I170, I172, V175, L184, C186, V188, F200, L202, V213, F229, V231, C233, I235, W246, A273, L275, A280, F288, C290, A292, V325, L333, V335, Y337, A339, W348, Y362, V374, L377, L382, Y390, F392, V394, F405, V407, V409, C428, A430, A431, W440, V473, V474, V489, C491, A493 |
| 274 | 60 kDa heat shock protein, mitochondrial | P10809 | A36, M40, V44, L47, A48, V51, V80, A81, A95, V98, V101, A102, A116, V118, L119, A120, I123, A124, I140, V144, A147, V148, A150, V151, L155, V162, I168, V171, A172, A176, I182, I186, A189, M190, F219, F228, C237, A242, V244, L245, L246, I251, I257, V258, A260, L271, V272, I273, I274, A275, V278, A282, L286, V297, V298, A299, V300, A302, L313, M316, A317, A319, V324, F325, L342, V345, V348, I349, V350, L357, L358, I371, I374, A395, L397, V401, A402, V403, L404, V406, V421, A424, A427, A430, A431, V437, L438, C442, A443, L444, L445, C447, I465, I467, I468, L472, A476, A480, I490, V491, I494, A507, M513, I519, A528, L529, A532, A533, A536, L539 |
| 275 | Thyroid hormone receptor beta | P10828 | C107, V109, A114, C124, C127, F131, C151, I153, C164, F166, C169, M174, V225, A228, H229, L246, A268, F269, I280, V283, F286, A287, L290, F293, L304, C308, C309, I312, L315, A318, L328, A335, V336, V349, F354, A371, L372, L373, A375, L377, L378, M379, I392, F399, A402, F403, L421, V425, L428, I431, A436, F439, M442, C446, L456 |
| 276 | Growth hormone receptor | P10912 | F64, C66, L84, C112, F114, Y125, I127, L129, C140, V143, V147, L160, A169, I171, V173, M188, L194, V217, L220, V228, V230, V249 |
| 277 | 78 kDa glucose-regulated protein | P11021 | V30, V31, I33, L35, C41, V42, V44, I53, Y65, V66, A67, F68, A80, V92, L98, I99, V108, V119, Y127, I128, V130, A141, I145, A147, L150, M153, A157, A159, V165, A168, V169, V170, V172, A174, A183, A187, A191, L193, V195, M196, |

TABLE 5-continued

TARGETS

| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
|---|---|---|---|
| | | | A204, A205, A206, I207, A208, L211, I220, L221, V222, F223, L225, F230, V232, L234, L235, I237, F242, V244, V245, A246, L253, F258, V262, M263, F266, I267, Y270, V278, A284, V285, L288, V292, A295, L299, A305, I307, I309, Y313, F318, L322, F327, L334, F335, M339, V342, V345, L346, I356, I359, V360, L361, V362, I371, V375, F379, A393, V394, A395, A398, A399, V400, A402, L422, I426, I437, F451, V461, I463, V465, Y466, I487, I497, V499, F501, L509, V511, A513, V542, L565, Y568, A569, L572, M594, A597, V598, L605, F616, L623, V627 |
| 278 | Hemagglutinin [Cleaved into: Hemagglutinin HA1 chain; Hemagglutinin HA2 chain]/strain A/Duck/Ireland/113/1983 H5N8 | P11132 | V5, I19, C20, I21, A25, V32, I35, V42, I48, L49, L57, C58, L60, L66, L68, C71, V73, A74, W76, L77, L78, C83, F86, W92, Y94, I95, V96, Y107, L117, L120, L121, F127, I133, A150, C151, Y153, V163, V164, W165, L166, I176, L188, L189, I190, L191, W192, I194, H195, H196, A201, Y207, Y213, V214, V216, L221, M242, F244, F245, I248, L249, I255, F257, F263, I264, A265, Y268, A269, Y270, I272, I280, M281, C290, C294, A300, I301, H308, H311, I315, V322, L327, L329, A330, A349, M361, Y366, A388, I389, A440, L452, V459, L462, V466, L470, C481, H486, C488, C492, M493, A510 |
| 279 | Solute carrier family 2, facilitated glucose transporter member 1 | P11166 | I40, Y44, W65, I297, F298 |
| 280 | Solute carrier family 2, facilitated glucose transporter member 2 | P11168 | L10, A17, Y26, V30, I31, I38, Y42, W97, V101, F104, M128, A131, A139, M142, I154, Y164, C165, L171, V172, M174, Y175, I176, I179, W218, L221, L222, A229, L234, L236, L246, A256, L260, L263, M276, L294, I304, V306, A307, L310, I322, Y325, I329, F330, V360, F369, M373, M376, C379, A380, M383, A403, I404, F407, V408, I418, M422, V423, A424, F427, A435, A439, V465, F466, L473, I495 |
| 281 | Pyruvate dehydrogenase E1 component subunit beta, mitochondrial | P11177 | A38, I39, M43, L47, V53, L55, V60, A61, I82, A93, I95, A96, A100, I107, C108, F110, F113, A119, V123, A127, V140, I142, F144, F162, A163, Y166, V174, V175, A183, L186, I187, A190, V197, V198, V199, L200, Y206, F212, A216, I225, I237, V239, V240, V246, A252, A253, L256, C263, V265, I266, M268, I279, V283, L289, V290, I305, I309, A314, I337, I349, I353 |
| 282 | Integrin alpha-M | P11215 | F27, F34, V46, V47, V48, A50, L63, C66, A84, M87, L89, L102, L103, A104, C105, C123, F124, I151, A152, F153, L154, I155, I161, M169, F172, V173, V176, M177, L180, F187, L189, M190, Y192, F200, F202, F205, V215, A228, I231, V234, L238, I252, L253, V254, V255, I256, V271, I272, A275, V280, I281, V284, I285, V287, A290, F291, L300, I303, A304, F313, V315, F318, A320, L321, L328, I332, F333, L365, L366, V378, I390, M399, L404, I411, L419, V420, L421, A423, V432, A433, M434, F435, V464, V466, L474, V475, L476, I477, A479, V491, V493, C494, L509, F520, L527, V530, V538, A539, I540, A542, A551, V552, Y553, L554, F555, I571, A572, L580, F583, L601, V603, A605, V609, L612, V617, L618, V631, V657, I670, V674, L680, A689, F691, L714, L716, L718, I729, L731, L733, L748, F764, L792, V794, F800, V802, V804, V806, V818, F820, F822, C864, I881, F883, A889, L895, L897, A899, V925, M951, H953, Y955, V957, L965, I967, L969, F971, V973, L977, I982, W983, L1014, V1020, A1025, C1027, C1032, F1037, I1039, F1043, A1045, L1047, L1051, W1055, L1064, I1066, A1070, I1072, V1097 |
| 283 | Glycogen phosphorylase, muscle form (EC 2.4.1.1) | P11217 | V16, V25, L28, L36, F54, A55, A57, V60, L64, I83, Y84, Y85, L86, L88, F90, L96, M100, V101, L105, A108, C109, L118, L123, L132, L137, L140, A141, A142, C143, F144, M148, A149, L151, L153, A154, A155, Y156, Y158, I160, Y162, V201, F203, V222, A224, V238, V239, M242, L244, W245, A247, A273, I276, L280, L294, Y298, F299, V300, V301, A302, A303, L305, I308, I309, F317, F327, F330, V334, I336, L338, L345, A346, I347, L350, M351, L354, L357, M360, A365, V368, C373, A374, Y375, V380, W388, L392, L393, L396, L397, H400, I403, I404, I407, F411, V415, A418, M429, L431, V432, I440, M442, A443, L445, C446, I447, A448, A452, V453, V456, A457, I459, H460, L464, F469, F472, L475, I487, W492, L493, V494, A501, V503, I504, F512, I513, L516, L519, L522, L523, F531, I532, V538, L544, F546, L550, L563, F564, I566, I571, Y574, L578, L579, C581, L582, H583, V584, I585, I591, V604, M605, I606, A610, A611, M616, A617, I620, I621, L623, V624, A626, I627, V630, V631, A636, V637, L641, V643, L646, L653, A654, V657, I658, A660, A661, L663, I667, A670, M680, F682, M683, L684, A687, L688, I690, A696, M700, A701, F712, A729, I736, L739, V742, I743, L746, F759, I762, M765, L766, F772, F775, Y778, Y781, I782, C784, V788, Y792, V802, I803, I806, A807, F812, I818, A819, Y821, A822, W826 |
| 284 | Spike glycoprotein/strain A59 (MHV-A59) (Murine hepatitis virus) | P11224 | I16, V44, L79, V87, Y96, I104, A106, V108, L111, A121, I128, F132, V140, I148, A150, V152, C153, I157, C158, C165, F202, H205, A215, F226, Y240, V241, F244, I245, C246, Y258, Y268, L269, F270, I292, V319, C354, F385, F393, V395, L411, A414, Y416, Y429, A468, C471, V474, C479, C481, A482, A499, A529, I534, I549, F550, A551, L585, F594, F619, A641, L652, C658, V661, C682, C706, C775, C780, C786, V800, L876, Y891, V900, V906, I912, A931, V952, |

TABLE 5-continued

| TARGETS | | | |
|---|---|---|---|
| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
| | | | I956, A980, A994, I998, I1030, A1039, L1046, I1047, A1053, L1054, L1067, A1072, A1075, V1079, I1099, V1103, Y1111, F1112, I1113, H1114 |
| 285 | Acetylcholine receptor subunit beta | P11230 | W141, C151, Y157, C165, V329 |
| 286 | Ras-related protein Ral-A | P11233 | H15, V17, I18, M19, V20, V25, L30, F34, V55, L57, V62, I64, I66, L67, A70, I78, F83, F89, L90, C91, V92, F93, I95, F101, F107, I111, V114, V120, F122, L123, L124, V125, L131, V137, A142, A146, A158, V164, V167, F168, L171, M172, I175, M180 |
| 287 | Medium-chain specific acyl-CoA dehydrogenase, mitochondrial | P11310 | A27, A52, F55, A56, I60, A65, I78, A81, M87, I91, C106, L107, I108, L112, A113, C116, V119, A122, M131, I133, Y145, L146, M149, C156, A157, C159, I172, I185, I192, W200, Y201, F202, L203, L204, A205, A215, A218, F219, F222, I223, V224, I233, C244, I250, F252, V255, V257, L263, V272, A273, A276, V283, V284, A285, A286, A288, V289, L291, A292, A295, A299, A303, M326, V330, A333, M335, A340, A341, A354, A357, A361, A365, L368, A369, A372, V387, A394, Y397 |
| 288 | Fibroblast growth factor receptor 1 | P11362 | L51, L53, C55, V86, V88, C101, F114, V174, F176, C178, I215, M217, V220, Y228, C230, V232, F275, C277, C341, A343, L356 |
| 289 | Glucose-6-phosphate 1-dehydrogenase | P11413 | I33, F34, I35, I36, M37, A39, A44, I48, I52, W53, L55, I67, V68, Y70, A71, F88, F101, Y118, L121, M125, A134, L137, F138, Y139, L140, Y147, V150, I154, C158, I167, I168, I196, Y197, I199, Y202, M207, I230, C232, V233, L235, I255, I256, V259, M260, L264, L265, M267, L268, C269, V271, A272, M273, V284, Y308, Y322, F337, A338, A339, V340, V341, L342, V344, W349, F354, I355, L356, C358, A361, A367, V369, L371, V391, I392, V394, A399, L440, V444, F452, I464, F465, A492 |
| 290 | Dystrophin | P11532 | V25, F29, L40, L50, L51, L54, V77, A80, L81, L84, I99, I111, I114, L140, W143, V144, V156, A168, A171, L172, I173, L196, A199, F200, A203, I228, Y231, I232, L235, Y344, L348, L355, V375, H382, I399, V420, L427, L445, L3053, V3070, Y3073, M3088, L3098, A3109, L3112, L3115, L3119, L3121, A3129, M3145, I3150, C3153, L3154, Y3158, V3175, C3178, L3179, W3181, L3182, L3183, F3199, I3204, L3206, C3207, C3229, L3234, L3238, I3242, I3244, V3263, C3266, W3294, L3295, V3297, L3298 |
| 291 | C-1-tetrahydrofolate synthase, cytoplasmic | P11586 | L20, V24, L38, A39, I40, L41, I53, A60, I63, V81, I85, V94, F97, L98, V114, V124, L135, C152, L155, I156, A168, V169, V170, M181, L185, C195, V206, I211, L212, V213, V214, V222, I227, A231, V233, I234, V256, A261, I268, M278, A281, L283, M284, A291, L393, V394, A396, L397, V405, F406, A407, V480, L497, I502, F518 |
| 292 | Cholesteryl ester transfer protein | P11597 | A26, V29, A36, A51, V72, I103, V106, V108, I188, I200, I207, F267, L313, V328, V329, A336, C350, F367, V376, F380, L426 |
| 293 | B-lymphocyte antigen CD20 | P11836 | F146, L147, L152, I162, I164, C167, Y182, C183 |
| 294 | Amyloid beta A4 protein | P12023 | Y476, A479, V490, Y497, L509, F512, A523, I537, L548, M580, L749, M752 |
| 295 | Collagen alpha-3 | P12111 | C3112, C3158, C3162 |
| 296 | Coagulation factor V | P12259 | V36, A37, A38, V65, Y66, L85, L86, A92, I98, V100, F102, L110, I112, H113, A126, V142, Y150, W152, I154, C167, I171, Y172, L186, I187, L190, I192, C193, L213, L214, F215, A216, F218, V234, V238, I245, V247, I253, W255, H256, L257, L258, F267, I269, H270, F271, L276, L288, V289, A296, M298, W306, I308, H315, M320, I324, I354, A355, A356, Y363, Y391, V394, M395, L431, F435, Y443, Y483, I487, C500, A516, L519, L523, L524, I525, C526, A546, F548, M586, I589, V593, V608, W610, H611, F612, I621, I624, H629, F631, L643, V651, V653, M655, W661, L663, L675, F679, I1584, A1585, A1586, V1618, F1620, I1643, I1648, A1650, I1656, V1658, F1660, Y1668, L1670, H1671, A1672, L1675, Y1677, Y1708, W1710, A1712, A1729, Y1730, L1744, I1745, L1748, I1750, C1751, F1769, V1770, L1771, L1772, F1776, A1807, I1808, L1818, M1820, V1826, L1828, L1830, I1839, H1840, V1841, V1842, F1844, H1845, L1849, L1864, L1872, W1882, L1884, V1888, M1896, F1900, I1902, C1907, L1913, A1937, A1947, W1948, I1963, V1971, F1993, F2032, I2043, L2054, L2056, M2072, A2101, A2111, W2112, A2114, L2123, I2125, I2133, A2135, I2136, C2141, V2150, Y2153, I2155, F2178, I2196, I2201, V2203, I2212, A2213, L2214, L2216, L2218 |
| 297 | Low affinity immunoglobulin gamma Fc region receptor II-a | P12318 | A41, L53, V58, L60, C62, I73, W75, A94, Y102, C104, L117, L120, L124, V125, L126, L131, F133, I139, L141, C143, H144, V154, F156, F157, F172, A177, Y185, C187, I203, V205 |
| 298 | Bone morphogenetic protein 2 | P12643 | F305, C329, A343, M371, C393, C395 |

TABLE 5-continued

| TARGETS | | | |
|---|---|---|---|
| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
| 299 | Bone morphogenetic protein 4 | P12644 | F317, C341, A355, M383, C405, C407 |
| 300 | Angiotensin-converting enzyme | P12821 | A46, F49, A57, A86, W97, A101, Y105, L117, I121, L132, M147, L172, L176, L185, L186, A188, W189, W192, H193, A196, L200, Y204, F207, A214, Y231, L240, Y244, L247, Y251, L254, H255, A256, V258, L262, I271, I277, A279, H280, L282, A287, W290, I293, V297, L306, V308, M312, A319, M322, F323, A326, F329, F330, L333, F342, F366, F372, I374, V388, H389, M392, I395, Y397, Y401, L408, F416, A419, I420, V423, L424, L426, L434, L439, Y453, L454, L455, M457, A458, L459, A463, L465, F467, L470, V471, W474, W492, L495, I502, C503, F513, A515, A517, V521, F531, V532, V535, L536, F538, F540, H541, L544, C557, I559, A565, L569, L573, V584, L585, A596, L599, Y602, F603, V606, A649, F652, Y674, Y700, A704, I717, I720, I721, L732, M747, L770, M774, L783, L784, A786, W787, W790, A794, I798, Y802, Y805, L808, A812, A821, Y829, L838, F842, L845, L848, Y849, L852, H853, A854, V856, A859, L860, I869, I875, A877, H878, L879, L880, A885, W888, I891, V895, A901, M904, A909, M910, M920, F921, A924, F927, F928, L931, F940, L946, V956, F964, F970, I972, L983, A986, H987, M990, I993, Y995, Y999, V1004, A1005, L1006, A1010, F1014, A1017, I1018, V1021, L1022, A1023, L1024, V1026, L1032, L1037, F1051, L1052, M1053, M1055, A1056, L1057, I1060, A1061, I1063, F1065, Y1067, L1068, V1069, W1072, W1090, L1093, L1100, C1101, F1111, A1115, I1119, F1129, V1130, I1133, I1134, F1136, F1138, H1139, A1141, L1142, C1143, H1153, C1155, I1157, A1163, L1167, A1170, M1171, F1175, A1182, M1183, I1186, A1194, A1196, M1197, Y1200, F1201, L1204, L1208 |
| 301 | Cadherin-1 | P12830 | C163, I178, V188, V204, F205, L214, V216, L220, Y228, L230, A234, M246, I248, I250, V252, F262, V271, V284, A301, M316, I326, V328, Y341, L343, V344, V345, A347, A348, A359, A361, I363, V365, L396, L436, L442, L452, V454, V456, A471, V473, V475, Y508, I542, L548, Y561, A563, I565, A567, L581, L583, I600, I612, I650, L652, I665, L667, L669, M670, L681, V683 |
| 302 | Xaa-Pro dipeptidase | P12955 | V18, L22, F23, L30, C31, L34, I45, V46, V47, F71, H72, W73, A74, F75, V77, C82, V85, I86, V88, L95, F96, V97, L136, L144, L145, L176, I180, V185, V194, L195, A205, H206, V209, M210, L222, F226, C243, C245, I267, M272, C273, F275, M277, Y281, F284, A285, I288, F292, V305, Y306, A308, V309, V316, W326, H330, A333, L338, L341, I346, M354, L359, F363, M364, L368, L372, L394, L397, L403, M407, V408, L409, V411, I415, Y416, L422, A425, F443, V449, I451, V455, I475 |
| 303 | Hemagglutinin [Cleaved into: Hemagglutinin HA1 chain; Hemagglutinin HA2 chain]/strain A/Gull/Maryland/704/1977 H13N6 | P13103 | I21, C22, V23, V34, V44, I51, Y59, C60, L70, F75, I79, V80, Y96, L97, L119, L122, F123, I126, F129, I135, C151, F167, I177, V189, L190, V191, L192, I195, Y208, V217, M243, I245, I250, I256, F258, F264, L265, A266, Y271, I273, F282, C295, I302, L328, A348, Y365, A387, L461, L469, H485, C487, C491 |
| 304 | Platelet glycoprotein Ib beta chain | P13224 | V37, C39, L60, L62, L67, A69, L70, W91, C93, L97, L100, L104, L116, C118, L128, L129, L137 |
| 305 | C-C motif chemokine 2 | P13500 | C34, C35, C59, A63, V64, I65, F66, I74, A76, V83 |
| 306 | Cystic fibrosis transmembrane conductance regulator | P13569 | V1240, L1242, L1253, F1257 |
| 307 | Integrin alpha-4 | P13612 | Y44, F52, H59, L67, V69, A71, A74, A87, C91, L106, V142, C144, L160, C165, A196, C198, A200, V212, M213, A215, L225, V227, V245, L251, F260, V268, V269, A272, H275, A281, Y282, I283, F284, L291, F306, V313, L315, L323, L324, V325, A327, V339, V341, A349, A366, F368, L375, I378, V386, A387, I388, A390, A399, I400, Y401, Y403, I418, F430, Y445, A449, V450, A452, A458, V459, L460, L461, V466, F502, M519, L521, F535, V550, A562, A579 |
| 308 | Sodium/potassium-transporting ATPase subunit alpha-3 | P13637 | H34, M36, V41, A58, L94, A98, C101, V125, V130, V161, I162, V175, V176, L180, V181, A191, L193, I195, C201, V203, F234, C239, A244, V247, V248, A264, I278, A289, A310, I312, F313, I317, L326, V332, A338, C346, V354, C364, L371, M376, A379, M381, W408, A410, L411, I414, A415, L417, C418, A421, V432, A445, L446, V457, L480, I482, H483, Y493, L494, L495, V496, M497, I504, L512, Y532, L535, F545, C546, H547, L550, L573, C574, F575, V576, L578, M581, A587, V589, A592, V593, C596, A599, I601, I604, M605, A614, A616, A618, I623, I624, A635, A636, A650, A652, I678, V679, F680, A681, I691, V692, C695, V702, V709, A714, L715, A718, I720, V722, A723, M724, I739, L740, F745, V752, L757, I758, Y768, L770, F783, L792, I800, A809, L812, L834, V835, L839, A843, I847, Y859, I862, L863, |

TABLE 5-continued

| TARGETS | | | |
|---|---|---|---|
| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
| | | | F868, L873, W880, C908, A911, F912, F913, V914, I916, V917, V918, V919, L924, I926, C927, L944, L948, A955, L968, M970, A981, I988, L999, Y1013 |
| 309 | Delta-aminolevulinic acid dehydratase | P13716 | L31, Y33, I35, F36, V37, L50, V53, Y56, L61, L65, V76, L77, I78, F79, V81, A94, A101, A104, I105, L108, L115, V117, C119, V121, C122, L123, H129, C132, L134, L150, A151, V153, A154, Y157, C162, V164, V165, A166, M170, M171, V175, I178, L182, V193, M194, Y196, A198, F200, A211, A212, A234, V238, L249, M250, V251, V261, V264, H268, L273, A274, V275, Y276, H277, V278, F282, V300, A303, M304, F307, A310, A312, I315, I316, Y318, Y319, L323, L324 |
| 310 | Tissue factor (TF) (Coagulation factor III) | P13726 | A41, F51, L55, Y66, V68, I70, C89, L91, I95, A105, V107, V155, V157, V159, L175, F179, L183, Y185, L187, Y188, Y189, F207, I209, V211, F219, V221, A223, V224, I225 |
| 311 | HLA class I histocompatibility antigen, alpha chain E | P13747 | L26, Y28, H30, F43, V49, F54, V55, F57, M66, A70, W72, M73, Y80, A88, A92, F95, L99, L102, L116, W118, M119, C122, L124, F137, Y139, Y144, L145, L147, L151, W154, A160, A161, A174, L181, C185, V186, L189, Y192, L193, L200, V210, A220, L222, C224, A226, F229, Y230, L236, W238, H245, A266, A267, V268, V269, V270, Y278, C280, V282, H284 |
| 312 | HLA class II histocompatibility antigen, DO beta chain | P13765 | F33, V34, F43, V50, F52, V53, F56, L60, V64, F66, F73, W87, L94, A100, C105, V117, V125, L135, L140, L141, H142, C143, V145, F148, W157, V168, L187, V196, Y197, C199, V201, W214 |
| 313 | Electron transfer flavoprotein subunit alpha, mitochondrial | P13804 | L23, V24, I25, I41, A43, A44, V51, C53, L54, V55, C60, V63, A64, L67, C68, V70, V76, A79, L92, L95, I96, I108, C109, A110, L119, V123, A124, A125, I135, F144, V165, F166, V168, V218, V219, L225, F231, L234, L237, A238, A243, A244, A247, A251, V263, V270, Y275, I276, A277, V278, M290, A298, A305, I307, V323 |
| 314 | Glycogen [starch] synthase, muscle (EC 2.4.1.11) | P13807 | V28, L80, Y102, W160, F165, L166, L190, F202, A215, A247, F287, H291, F293, F307, A345, I456, V473, F477, L482, C500, V504, L592 |
| 315 | Endothelin-3 | P14138 | C107, C169 |
| 316 | Macrophage migration inhibitory factor | P14174 | P2, F4, V6, F19, L23, L27, C57, A58, L62, Y76, L79, L80, L83, L84, L88, I90 |
| 317 | Folate receptor beta | P14207 | A34, C51, W54, A58, C59, C60, M86, C90, F94, C99, L100, C103, V126, L128, C129, C133, W136, C140, F176, L182, C183, L186, C203, I204, M206, V219, A220 |
| 318 | Hepatocyte growth factor | P14210 | I39, F42, L50, C70, A71, C74, L80, C84, A86, F87, V88, C96, W98, F99, F101, F112, L118, Y136, C149, W152, L172, C177, C189, F190, C206, Y219, C232, W235, C260, W270, C271, Y272, C283, I285, C288, Y313, W329, C354, W364, C365, F366, C377, I380, C383, V495, M508, V509, L511, C519, L523, V529, L530, A532, C535, Y544, A546, L548, I550, L579, V580, L581, M582, L584, V594, I597, C612, V614, L629, A632, L634, C642, I657, C658, A659, C669, L677, C679, V687, V690, I691, F706, V709, A713, I716 |
| 319 | Perform-1 | P14222 | V61, L249, F442 |
| 320 | D(2) dopamine receptor (Dopamine D2 receptor) | P14416 | V78, F189 |
| 321 | Solute carrier family 2, facilitated glucose transporter member 4 | P14672 | L24, A27, A31, Y40, V44, I45, I52, Y56, W81, V85, A86, F88, I99, M112, A119, M126, A129, L138, I145, Y148, L155, V156, M158, Y159, V160, I163, A187, W202, L205, L206, V210, A213, V218, L220, L230, A240, L244, L247, L260, L278, L288, I290, A291, L294, A305, V306, Y309, I313, F314, V344, H353, L357, M360, C363, A364, M367, A370, A387, I388, F391, V392, I402, I406, V407, A408, F411, A419, A423, V449, F450, L457, I479 |
| 322 | Platelet glycoprotein IX | P14770 | L93 |
| 323 | Interleukin-1 receptor type 1 | P14778 | I39, W57, H75, L81, F83, A86, C96, V97, V98, C104, I107, A111, L140, C142, M145, F148, W160, L181, V183, Y194, C196, A198, I209, I213, F215, V238, L246, C248, V250, W260, L296, I298, I301, F305, F310, C312, F313, A314, L327 |
| 324 | Matrix metalloproteinase-9 | P14780 | A45, L49, L74, L78, C99, I121, I137, A140, F141, A144, F145, W148, L154, A164, I166, I168, L187, A189, H190, A191, F192, A202, F204, W210, V218, P219, F222, A225, C230, F234, G238, C244, W255, C256, C271, A283, C288, F292, C302, W313, C314, A315, C329, C347, F351, F353, W372, C373, A374, F379, W385, C388, L395, F396, V398, A399, A400, F403, H405, A406, L407, L409, A417, L418, M419, Y420, F425, L431, I439, A515, A523, L531, L533, F534, I556, F580, F581, F582, V587, L604, V613, L626, F627, F635, F673, C674, Y679, L702 |
| 325 | Interleukin-2 receptor subunit beta | P14784 | C36, Y38, A42, I44, C46, W48, V61, A63, L88, L98, V101, V104, L106, V108, F124, F127, L130, L132, C148, I150, F167, A169, F206, V208, V210 |

TABLE 5-continued

| TARGETS | | | |
|---|---|---|---|
| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
| 326 | Gamma-aminobutyric acid receptor subunit alpha-1 | P14867 | V416 |
| 327 | Protein C-ets-1 | P14921 | A323, A327, F340, L341, L342, L345, C350, I354, F363, L365, V371, A372, L389, L393, I401, I402, V411, F414, L418, L429, L433 |
| 328 | Junction plakoglobin | P14923 | A140, A162, A163, V166, A174, L179, L185, V186, A188, V189, V190, M193, L209, L212, L219, I222, I228, A230, L231, V232, V242, A246, I247, L250, L253, A260, V264, L270, M273, F284, L285, A286, C291, L292, L295, A296, I306, A308, L315, V316, I318, M319, L327, V334, L335, L338, C341, I348, V349, A351, M354, A356, L357, L361, L368, V369, C372, L373, L376, L379, V382, A383, L389, V392, L393, L396, V397, L400, L408, C410, A411, L415, L418, V429, V435, L438, I439, A441, A445, I451, A455, V456, A458, L459, L462, A472, V476, I485, V486, L488, L489, L497, V498, A500, I502, L504, I505, L508, A509, L510, A513, A516, L518, V523, I524, L527, L530, L531, A534, M556, I559, V560, C563, A566, L567, L570, A571, I580, I586, L588, F589, V590, L592, L593, I600, A604, A605, V607, L608, L611, A612, A618, A620, I621, A623, A626, L630, L633, L634, A642, A645, A646, V648, L649 |
| 329 | Leukemia inhibitory factor | P15018 | L44, I48, L52, L55, A59, L62, Y66, F74, L81, C82, L102, L105, Y106, I108, V109, V110, L112, L116, I119, A130, L133, L137, L144, L147, L148, V151, L152, C153, L155, C156, V164, C185, L187, L188, Y191, I195, L198 |
| 330 | Phosphoglycerate mutase 2 (EC 3.1.3.13) | P15259 | L6, V7, M8, V9, H11, F22, A28, A38, A42, A44, I45, F52, I54, C55, Y56, L60, A63, L67, I70, L71, L87, H91, L95, V112, M126, I136, Y142, L156, I160, A163, W167, I171, I175, A177, V181, L182, I183, A184, A185, H186, L190, I193, V194, L197, I205, L210, I214, I216, V217, Y218, L220, V239 |
| 331 | Interferon gamma receptor 1 | P15260 | V46, W48, F59, V61, V63, C85, I87, L98, V100, V102, A104, A120, I141, I143, I145, Y172, V174, V176, I187, C200, C214, V215, A217, I238 |
| 332 | Arylsulfatase A | P15289 | I23, V24, L25, I26, F27, A28, L31, L36, L49, Y63, V64, A74, A75, L76, L77, L100, V107, A108, L111, Y116, M120, A121, W124, L126, I147, Y149, H151, C156, C161, V177, I179, L181, L182, A189, L194, L197, Y201, A205, L208, M209, A212, F219, F220, L221, Y222, Y223, A224, H226, H227, F238, F247, L251, L254, A257, V258, L261, I265, L275, V276, F278, A280, V310, A314, L315, A331, L337, L340, A341, A344, L358, F375, Y376, V386, F387, A388, V389, Y394, A396, H397, C414, H415, P426, L428, L459, C500 |
| 333 | Beta-1,4-galactosyltransferase 1 | P15291 | V154, V178, A179, I180, I181, I182, F184, L191, W194, L195, L198, H199, V201, L202, L207, Y209, I211, Y212, V213, I214, A225, L227, L228, V230, A235, Y241, F244, V245, F246, L251, I252, Y260, H268, I269, A272, V289, A291, L292, F297, I300, F303, W308, W310, I317, L321, M366, L367, Y376, L386, V392, I394 |
| 334 | V-type proton ATPase subunit B, kidney isoform | P15313 | V47, V52, V53, L54, V57, V66, F68, V80, V83, A88, I89, V90, V92, C106, V117, M121, V125, F126, I147, M163, I164, I168, I171, V173, I177, A178, I183, I185, F186, A188, I196, A197, A198, I200, C201, A204, L206, V207, H217, A222, I223, V224, F225, A226, A227, M228, F238, F242, V251, C252, L253, F254, L255, I266, I267, L271, A272, L273, A276, F278, L279, A280, V287, L288, V289, I290, L291, M294, Y297, A298, A300, L301, V304, A306, A307, M321, L325, I328, Y329, A332, V335, I342, I345, I347, L348, I359, F365, I371, V373, L377, I386, V388, A399, H409, V412, L416, C419, Y420, V426, F448, L449, F452, F456, I457, V467, L471, W475, L478, F481 |
| 335 | Folate receptor alpha | P15328 | C37, L53, C57, W60, A64, C65, C66, W86, M92, C96, F100, C105, L106, C109, V132, L134, C135, C139, W142, C146, C152, W156, F178, F182, L188, C189, I192, Y197, I210, M212, V225, A226, M233 |
| 336 | B-lymphocyte antigen CD19 | P15391 | L36, C38, W52, F83, V87, F94, L96, C97, V113, L188, L196, L198, C200, W214, L225, L228, W240, L246, L248, W281, W283, L284, W290 |
| 337 | Granulocyte-macrophage colony-stimulating factor receptor subunit alpha | P15509 | L47, C60, L62, C81, F94, V96, I128, M134, C136, Y150, L152, C178, F192, V194, C233, W237, F251, Y253, L255, V257, L270, V294, I296, A298, A299 |
| 338 | Membrane cofactor protein | P15529 | C80, A93, M123, F125, L139, C141, A148, V160, V187, I208, C210, V226, V252, I268, C270, C283 |
| 339 | Vascular endothelial growth factor A | P15692 | C52, I61, I72, F73, V78, L80, L92, I106, F122, C213, C225 |
| 340 | Immunoglobulin lambda-like polypeptide 1 | P15814 | W67, C82, V97, L104, V106, L107, V116, A128, A131, L133, C135, L136, M137, F140, Y141, L145, V147, W149, A151, A174, A175, L179, L181, Y192, C194, V196, H198, V203 |
| 341 | Arylsulfatase B | P15848 | L47, V48, F49, L50, L51, A52, L55, V60, L72, V80, Y85, Y86, L98, I105, V122, L128, L132, L133, M142, V143, W146, L148, C155, Y168, L169, Y175, H178, I184, A193, F196, F215, A219, L232, F233, L234, L236, A237, L238, V241, Y255, Y266, A267, M269, V270, M273, V277, V280, L284, V294, F295, I296, F297, L321, V326, V329, F331, V332, I348, |

TABLE 5-continued

| TARGETS | | | |
|---|---|---|---|
| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
| | | | H349, I350, L354, L357, A361, V376, I380, I389, L391, L392, A431, A432, I433, L440, L441, C447, L474, F475, L498, L502, W529 |
| 342 | Beta-galactoside alpha-2,6-sialyltransferase 1 | P15907 | L109, L144, F160, W165, A178, C184, A185, V187, L193, I202, A207, V208, L209, A214, V223, I229, L231, M232, F243, L254, I255, V256, W269, F277, Y281, Y284, F293, I295, L296, M300, L304, L308, M325, L326, I328, I329, I330, M331, M332, C335, V338, I340, Y341, L344, Y369, L378, V379, L382, I390, L392, A396, L398 |
| 343 | Desmoplakin | P15924 | C191, M195, V214, I228, L235, A247, L251, Y255, L258, I275, F312, A343, I347, I364, C367, I368, H371, F381, A385, Y403, L414, L421, V446, L463, C467, V476, C482, W493, V495, V508, L510, I512, A519, I526, M544, L547, C553, I560, A562, L568, V623, V1975, A1977, L1980, C1983, V2004, I2018, A2019, A2021, L2031, A2034, L2048, A2051, A2053, A2054, I2058, V2069, A2072, I2086, A2089, A2092, A2110, M2122, L2124, L2125, A2127, V2134, V2141, F2142, L2143, A2148, F2172, Y2183, L2186, L2201, V2217, L2222, I2250, I2260, A2261, I2263, A2277, A2288, L2292, A2294, A2296, A2297, I2301, V2312, A2315, L2329, A2332, V2336, Y2339, A2353, L2367, L2368, A2370, I2377, H2384, L2386, A2391, F2415, L2424, Y2426, L2429, L2443, L2444, I2619, A2621, I2622, I2631, L2650, L2651, A2653, C2656, I2660, L2671, A2674, V2679, L2688, A2691, A2694, A2709, A2712, F2726, F2729, L2736, V2737, A2750, L2774, I2783, Y2785, A2788, A2805 |
| 344 | Mucin-1 | P15941 | I1049, F1054, L1058, Y1065, Y1066, L1069, F1086, F1094, V1099, F1107, L1134, V1141 |
| 345 | P-selectin | P16109 | W42, W53, C60, L67, V68, A69, L79, Y90, W91, I92, I94, A114, A118, C131, V132, I134, I136, W145, A156, L157, C158, C168, C194, C226, C244, C288, F290, C306 |
| 346 | Integrin beta-4 | P16144 | L1544, V1546, Y1560, V1562, I1577, V1587, F1598, V1600, A1602, I1618 |
| 347 | Toxin A (EC 3.4.22.—) | P16154 | L9, A13, Y23, I26, L27, L30, L36, Y45, L48, L51, I55, F58, M59, L71, L74, I78, V82, L97, H98, F99, V106, A110, Y113, W117, L128, W129, A134, F135, L136, V137, L140, A143, I144, A152, L156, F170, Y171, M175, I178, Y179, F185, I201, I204, I205, H208, L209, I231, I239, L244, F245, I253, Y254, L258, L259, A266, A267, I270, V271, L273, L274, A275, L276, V282, Y283, L284, M288, L289, I314, L316, A318, I319, F334, F345, I349, I358, F359, L362, V367, L370, I372, I374, A375, A385, L386, I387, L394, V398, V402, Y406, L409, L413, A416, F423, F430, L434, F445, L446, I449, L453, F457, A461, L467, A472, Y473, A476, Y477, F480, L483, L497, F500, A526, L561, V580, Y582, I583, I584, C597, F600, I608, I609, I610, Y636, I638, L642, V648, V650, F652, I653, F665, L673, I677, F680, I684, I688, V693, V695, L697, C700, M702, F703, Y713, L717, L718, I721, I725, L729, V732, I737, I739, A741, L756, I764, A769, I770, I780, A791, I806, L857, V867, L871, L885, I886, F888, V900, F902, I903, F920, Y923, I927, L961, F965, I967, V987, V989, L991, A993, L1000, I1003, L1009, A1016, L1050, V1068, A1078, I1084, V1122, Y1125, F1126, L1129, L1152, V1153, I1154, C1169, I1171, A1173, I1204, M1222, L1224, A1227, F1232, L1253, I1256, F1264, I1276, L1279, I1288, I1290, F1299, I1304, F1317, Y1324, L1326, L1328, I1333, I1337, L1339, W1345, I1346, F1347, V1353, L1383, I1390, L1405, I1413, L1415, I1416, I1417, I1419, L1430, L1441, I1448, L1451, I1458, A1473, I1474, I1482, L1493, F1503, F1516, M1517, I1524, I1538, F1540, I1542, V1550, V1552, L1555, L1557, V1561, Y1565, V1569, M1582, F1585, L1586, F1591, L1594, F1608, L1610, V1611, F1621, F1633, F1646, V1653, V1654, V1655, L1671, Y1675, L1678, V1688, L1689, I1690, Y1695, I1701, I1714, I1728, L1730, W1739, F1746, I1768, L1769, F1782, L1790, I1793, F1864, L1872, F1883, F1905, A1906, F1936, F1956, A1961, A1963, A1964, V1965, F1977, F1998, F2006, F2017, F2039, A2040, F2070, F2090, A2095, A2097, A2098, Y2109, Y2110, F2111, F2132, F2151, F2153, I2158, I2161, F2173, A2174, F2204, F2224, A2229, A2231, A2232, Y2244, F2245, F2263, F2265, F2287, A2288, F2318, F2338, A2343, A2345, A2346, I2352, Y2357, F2359, F2380, F2399, F2401, I2406, I2409, F2421, A2422, L2445, F2452, F2472, A2477, V2478, A2479, V2480, Y2492, F2493, F2512, F2514, F2534, A2535, F2565, F2585, A2590, A2593, I2599, F2604, Y2605, F2606, F2625, A2626, F2656, F2676, A2681, A2683, A2684, A2685, I2691, F2697, F2698 |
| 348 | Beta-galactosidase (EC 3.2.1.23) | P16278 | F41, I51, I55, H56, Y57, W65, L69, M72, A75, A79, I80, V84, W86, H89, V104, F107, L108, A111, H112, L116, V118, I119, L120, Y125, I126, A128, W130, M132, L135, A137, L139, L140, L146, L147, Y154, V158, W161, L162, L165, L166, M169, L172, L173, V180, I181, V183, Y189, Y199, L200, L203, F207, V215, F218, L228, L236, Y237, V240, A251, F269, V289, L293, I296, A301, V303, L305, M307, F308, I309, A320, L337, A340, Y347, L350, I353, I354, A387, A388, L392, F406, F415, V416, Y418, C426, L432, V439, A443, V447, L455, I465, A471, L473, L475, V477, V483, I489, L495, L499, L501, W509, I511, A519, L524, A550, F551, I558, I571, F573, V581, W582, I583, L588, Y591, L601, V603, I616, V618, A624, A635, V636, F638 |
| 349 | Histone H1.5 | P16401 | I47, L65, I83, L87, I90, L96 |

TABLE 5-continued

TARGETS

| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
|---|---|---|---|
| 350 | Cytotoxic T-lymphocyte protein 4 | P16410 | V40, A48, A54, F56, C58, Y60, A66, V69, V71, V73, C85, A86, A87, L95, V112, L114, I116, Y127, C129, V131, I149, V151 |
| 351 | Epithelial cell adhesion molecule | P16422 | Y32, C48, C66, V68, A122, I144, H150, L162, L176, F180, L185, I191, L195, V207, I209, A213, Y215 |
| 352 | Histo-blood group ABO system transferase | P16442 | A92, I94, I116, L118, V120, A122, I123, L130, F133, L134, A137, F141, M142, H145, V147, H148, Y149, Y150, V151, F152, M189, M191, I192, F195, C196, F200, V204, Y206, L207, V208, C209, V210, V212, M214, F216, V220, V222, I224, L225, L228, F229, L232, A254, I256, Y264, Y265, L266, G268, F269, F270, V274, V277, L280, C284, M288, V290, A298, H305, L306, L310, V318, L319, Y323, L324, W325, L336, L339, F341 |
| 353 | Thyrotropin receptor | P16473 | C41, L57, L59, L64, I67, F72, I78, I81, V83, L89, L92, F97, V103, I106, I108, L114, A121, L122, L125, L128, L131, I133, L144, V147, F154, L156, I158, M164, I167, L175, L180, L182, L184, F189, V192, A196, F197, V205, L207, L213, A220, L231, V233, L252 |
| 354 | Interleukin-7 receptor subunit alpha | P16871 | L55, C57, I73, Y92, I107, V109, L123, V127, F146, V148, V160, V167, A168, I203, V205 |
| 355 | Fumarylacetoacetase | P16930 | L17, V21, F22, I32, V34, A35, I36, I40, L41, L43, I46, F50, L55, F62, L67, F70, M71, A77, A81, L85, L89, L96, L102, A106, L196, M198, L200, M202, A203, F204, F205, V206, A221, M228, V229, L230, M231, W234, A236, V259, V263, V264, A268, L269, L287, F295, I297, V301, L303, C315, W324, M326, L327, L330, L345, L346, A347, I351, M362, L375, V390, I392, C396, I403, F405, C408, V412 |
| 356 | Alpha-N-acetylgalactosaminidase (EC 3.2.1.49) | P17050 | W30, A32, C49, I50, L54, F55, M58, A59, M62, W67, Y72, L75, I77, C80, W81, L91, I102, L105, A106, V109, L116, I118, Y119, A120, M122, V138, A142, F145, V150, L153, L155, Y169, M172, A184, F185, C187, L205, C209, L211, W212, I218, V225, I228, L229, L239, V242, W248, M253, L254, L255, I256, A268, M270, A271, L272, W273, V275, L276, A277, A278, L280, M282, I296, L297, M302, I305, I324, V326, Y327, A337, L338, V339, F340, F341, L355, I365, A368, F386, I390, M397, L400 |
| 357 | Aspartate aminotransferase, cytoplasmic | P17174 | V34, L36, L51, V53, V54, V57, F80, A84, A88, A95, V104, A112, L113, I115, A117, L120, A121, V134, V136, H144, F148, F174, L178, A181, I186, V187, V188, L189, A193, H194, I209, A210, M213, F221, F222, A238, A240, I241, F244, F251, C253, A254, F257, F261, V268, L271, M288, V292, A304, I306, V307, A308, W320, V324, M327, A328, L338, L342, I354, M360, F361, L374, I380, L382, I388, V390, L393, L398, V401, A402, A408 |
| 358 | HLA class I histocompatibility antigen, alpha chain G | P17693 | M29, Y31, A34, A35, F46, A48, V52, F57, V58, F60, M69, A73, W75, V76, Y83, A95, L102, L105, L119, W121, M122, C125, L127, Y140, Y142, Y147, L148, L150, L154, W157, A163, A164, V176, A177, L184, C188, V189, L192, Y195, L196, L203, V213, A223, L225, C227, A229, F232, Y233, L239, W241, A269, A270, V271, V272, V273, Y281, C283, V285, H287 |
| 359 | Neuronal acetylcholine receptor subunit beta-2 | P17787 | V56, L60, L83, W87, L119, A135, V137, I143, W145, A149, F173, I183, L185 |
| 360 | ATP-dependent 6-phosphofructokinase, liver type | P17858 | I18, V20, L21, A27, M30, A32, A33, V34, A36, V37, A46, V48, I51, L58, V59, V73, I77, A101, A102, L105, L113, C114, V115, I116, L122, F128, L135, A159, L161, V162, I165, F169, I176, A181, I185, M186, I189, A196, F203, V204, L205, V207, C212, L215, A216, L217, F229, I230, M243, C244, L247, I260, I261, I262, A263, A266, V279, V283, V284, V293, L296, A307, L312, A320, V321, L324, L325, A333, V335, V336, L348, V358, A370, A389, A403, I404, L405, V407, A411, A412, M414, A416, A417, V418, V422, V432, Y433, V434, V435, F439, V455, I480, L493, V494, V495, A500, Y501, L505, A510, C518, M521, C522, V523, I524, A526, V532, L539, A544, M549, C552, A559, V566, F567, I568, V569, C576, L579, A580, I585, A586, V594, L604, V608, M611, M615, L623, V624, L625, L639, Y643, L678, A682, M683, L686, L690, A701, V709, I710, V722, L725, W741, L744 |
| 361 | Ganglioside GM2 activator | P17900 | L80, C106, C136, C183 |
| 362 | Complement receptor type 1 | P17927 | C43, A52, L69, I84, C86, C99, I121, I127, Y129, A143, C145, V152, I164, C166, V191, Y193, I213, C215, C238, F256, V262, V278, C280, C493, I534, I571, I577, C595, V641, C665, C688, F706, V712, V728, C730, C943, I984, C986, C1004, I1021, I1027, A1043, C1045, A1052, I1064, C1066, V1091, Y1093, C1095, I1113, C1115, C1138, F1156, V1162, V1178, C1180, C1396, I1437, V1480, C1498, V1544, C1568, C1591, F1609, I1615, V1631, C1633 |
| 363 | Vascular endothelial growth factor receptor 1 | P17948 | F135, M148, L154, I156, C158, V160, V167, L169, F192, I194, A197, L205, C207, A209, Y220 |

TABLE 5-continued

| TARGETS | | | |
|---|---|---|---|
| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
| 364 | TFIIH basal transcription factor complex helicase XPD subunit (EC 3.6.4.12) | P18074 | L40, M42, L53, A54, M57, A58, L70, Y72, C73, I80, V83, I84, L87, L102, L107, A108, L109, L115, A139, L170, L177, C190, Y192, L194, A195, A202, Y209, V231, V232, A236, I239, C243, L251, L256, C259, L263, A298, V309, C375, L382, A404, L406, C437, A443, I444, I455, I456, L461, L471, F473, M493, I494, Y520, A537, F539, I561, Y584, A594, L596, L597, V599, A617, I619, M620, F621, V623, A635, A656, A660, V664, A667, M677, V678, F684, W696, A704 |
| 365 | Toxin B (EC 3.4.22.—) | P18177 | L9, A13, Y24, I27, L28, L31, M37, Y46, L49, I52, Y59, L72, F75, L79, V83, L98, H99, F100, I107, Y114, W118, V129, F130, A135, F136, L137, I138, L141, V145, A149, F171, F172, M176, I179, F186, I202, I205, V206, L210, I232, V240, F246, L254, Y255, L259, V260, W263, A267, A268, I271, L272, I274, A276, L277, M283, Y284, L285, M289, L290, L317, A319, I320, F335, F346, L350, I359, F360, L363, A368, L371, V373, I375, A376, L387, I388, C395, I399, I403, Y407, L410, L414, A417, F431, I435, M447, L450, L454, F458, V462, L468, A473, Y474, A476, A477, Y478, L481, F484, L498, F501, A527, L562, I578, Y580, I581, V582, A594, C595, F598, A599, V606, L607, F608, A618, Y634, I640, I646, L648, F650, F663, L671, I675, A678, A682, I686, I691, I693, L695, M700, F701, Y711, L715, L716, V719, I723, M727, I730, I735, V737, A739, L754, I762, I778, V789, F1866, F1888, F1908, A1909, F1938, H1956, F1958, F1979, F1999, F2019, F2039, A2040, F2069, F2090, A2095, F2305, A2306, F2335, F2355, A2360 |
| 366 | Vinculin | P18206 | F4, H5, I9, L13, A17, I20, L70, M74, A77, V81, C85, A91, A92, L95, A104, I109, L116, L124, A129, V131, I134, C138, L145, A148, Y160, L164, M171, I175, L182, L191, V192, V198, L201, L205, A208, M209, V213, I223, A226, M237, I241, I244, V247, L248, A269, I273, A280, W283, A298, I299, I302, A306, I321, V335, A353, L360, L363, V367, I384, I388, A391, I408, A411, A415, A419, I431, I438, L445, V466, L470, L473, A480, A500, A518, C545, V548, L551, L576, L580, L609, A613, F626, F633, A644, A679, L683, F695, L734, A760, I763, V766, V783, A786, L790, V828, V831, A909, M956, I966, A970, L973, A977, I987, I988, A990, A991, M994, A995, M998, M1001, L1015, C1018, A1019, I1022, A1023, A1025, V1029, A1033, A1037, C1040, L1049, V1052, C1053, I1056, L1063, A1071, A1087, L1091, A1095, L1098, M1099, V1102, V1106, A1109, A1112 |
| 367 | Interleukin-1 receptor antagonist protein | P18510 | F38, I40, V56, A57, V73, A80, L81, F82, L83, C91, L92, C94, L103, F123, F125, F136, C147, A149, V156, L158, F171 |
| 368 | Cytidine deaminase/strain 168 | P19079 | L6, A10, A13, A28, A29, L30, L31, A54, A58, L59, A62, L73, A74, V75, A76, A77, C89, I93, V101, V103, V104, V117 |
| 369 | Erythropoietin receptor | P19235 | A39, L41, L42, L50, C52, F53, L60, C62, F63, W64, F79, Y81, L83, F105, C107, L120, L122, V124, I139, V142, V143, L144, L145, V152, V162, L164, W166, I178, Y180, V182, V184, L207, F218, A219, V220, A222, M224 |
| 370 | Lymphocyte function-associated antigen 3 | P19256 | F43, V54, W56, V63, A64, L90, I92, L95, Y103, F116, L118, L121, L129, C131, V140, M156, M163, C166 |
| 371 | Vascular cell adhesion protein 1 | P19320 | A37, V43, L45, C47, L80, M82, V85, Y93, C95, A97, I108, F115, I133, V135, C137, V139, V142, F145, I150, L152, L178, L193, C195, A197, L199, A325, V331, L333, C335, L368, L370, V373, Y381, C383, V385, I396, F403, V421, V423, C425, V427, V430, L433, I438, L440, L466, L481, C483, A485, L487 |
| 372 | Tumor necrosis factor receptor superfamily member 1A | P19438 | C59, C62, C72 |
| 373 | Hemagglutinin [Cleaved into: Hemagglutinin HA1 chain; Hemagglutinin HA2 chain]/strain A/Budgerigar/Hokkaido/1/1977 H4N6 | P19694 | I25, C26, M27, V38, V48, L54, V55, L63, C64, L70, C76, I78, I79, A82, L83, C88, L91, V98, F99, I100, V106, C109, Y110, F112, Y117, L120, L124, A125, F130, F137, A150, C151, F159, F160, L163, L166, Y191, W193, V195, H196, H197, Y208, V215, V217, I243, F245, Y246, I249, V250, L255, I256, F258, L264, I265, A266, Y271, I288, C295, H296, V302, V323, L330, A331, A348, W357, Y365, A387, A439, L461, L469, C480, F481, I483, H485, C487, C491, I492, I495, A509 |
| 374 | Nuclear factor NF-kappa-B p105 subunit | P19838 | F57, L69, V84, A93, V95, I96, V97, L99, V100, H109, A110, H111, L113, I122, C123, A127, V133, V134, L139, L153, M157, A160, C161, L170, L175, I196, A199, A200, V212, L214, F216, A218, A238, I239, A247, L250, V262, I268, L270, L271, I282, F284, I311, V312, F313, V329, V331, L333, F347, Y349, Y350, M808, L819, Y820, L823, L835, A836, F848, L858, M859, L872, A875, L876, A884, I888 |
| 375 | C-X-C motif chemokine 3 | P19876 | C45, I52, C69, V74, A76, L78, C85, L86, V93, I96, L101 |
| 376 | Complement receptor type 2 | P20023 | I47, I58, L63, C65, V96, Y108, V114, V130, C132 |

TABLE 5-continued

| TARGETS | | | |
|---|---|---|---|
| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
| 377 | HLA class II histocompatibility antigen, DP alpha 1 chain | P20036 | M54, F55, F63, V65, F83, A87, A92, I94, L136, I137, C138, I140, F143, W152, F179, L182, V185, Y192, C194, V196, H198 |
| 378 | Myeloid cell surface antigen CD33 | P20138 | V82 |
| 379 | Kallikrein-2 (EC 3.4.21.35) | P20151 | I25, C31, V40, A41, V53, L54, V55, V60, L61, A63, A64, C66, V73, L75, V90, V92, L121, L123, L124, L126, I132, V135, V136, C152, A154, F165, C173, V174, L176, C184, C198, A199, L217, C219, L223, I226, A241, V242, Y243, V246, I253 |
| 380 | B-cell receptor CD22 | P20273 | W24, W35, C39, V40, I42, C44, L53, L76, F94, L95, C102, L117, L119, W128, M129, L134, V136, I145, C161, C167, Y170, I172, W176, V198, L204, F206, W210, C219, L229, L236, V238, V255, C265, W279, L294, L296, Y307, C309, L325, V327, Y329, V349, C353, A357, W366, Y394, C396, L413, V415, V422, I426, I432, V438, L440, C442, V451, W456, L470, I472, V475, W477, C484, A486, C491, L499, V501, Y503, A504, V508, V510, L527, C529, V539, W543, L556, I561, Y569, C571, I577, V589, Y591, L596, V598, V606, L614, C616, A620, Y627, W629, F630, L644, L646, Y657, C659, V677, Y678, Y679, I684 |
| 381 | Integrin alpha-L | P20701 | F45, I57, V58, L70, C73, L109, A110, C111, C119, C129, Y130, V155, L157, V158, F159, L160, F161, L167, I175, F178, M179, V182, M183, L186, Y191, F193, A194, A195, V196, F198, F206, F208, Y211, A236, I237, V240, V244, V258, L259, I260, I261, I262, I273, A276, I279, Y282, I283, I284, I286, F290, L299, F302, A303, F310, F317, L320, L323, F324, L327, V364, V365, A367, A370, A374, F377, L378, L404, L411, L420, A421, V433, L434, L435, V467, L477, L478, L479, I480, A482, V494, L510, F521, L528, I531, V539, A540, V541, A543, A550, Y552, I553, F554, L561, I569, I578, F581, A597, A600, A603, M607, I608 |
| 382 | Integrin alpha-X | P20702 | F30, F37, V49, V50, V51, A53, L66, C69, A87, M90, L92, L105, L106, A107, C108, C126, F127, I152, V153, F154, L155, I156, M170, F173, V174, V177, F188, L190, M191, F193, F201, F203, F206, L216, A229, A231, I232, V235, L239, I253, L254, I255, V256, I257, V272, I273, A276, I282, A285, I286, V288, A291, F292, L301, I304, A305, F314, V316, F319, L322, L329, I333, F334, A352, V366, L367, A369, A379, I391, M400, L405, A412, L420, V421, L422, A424, A433, V434, I435, F436, V465, V467, L475, V476, L477, I478, A480, V492, V494, C495, L510, F521, L528, V531, V539, V540, I541, A543, A552, V553, Y554, L555, F556, I572, A573, L581, F584, L602, A603, V604, A606, V610, L613, V618, L619, I632, V650, I658, L671, V675, L681, A690, F692, L700, F715, L717, L719, I730, L732, L734, L749, L765, L793, V795, L801, A803, V805, V807, I819, F821, H823, C863, A880, F882, A888, L894, L896, A898, V924, A951, H953, Y955, V957, L965, V967, I969, F971, V973, L977, V982, W983, I1014, L1020, A1025, C1027, C1032, F1037, V1039, L1043, F1045, L1047, L1051, W1055, I1059, V1064, V1066, A1070, I1072, L1097 |
| 383 | B-cell lymphoma 3 protein | P20749 | L139, V143, V151, F158, L176, H177, A179, V180, V188, L191, A208, H210, A212, C213, C220, L221, A223, L224, A245, L246, H247, A249, V250, V258, L260, L261, L280, I281, A283, V284, M291, V292, L294, L295, A312, L313, A316, V325, L328, V354 |
| 384 | Calpain-3 (EC 3.4.22.54) | P20807 | L138, L145, L189, F200, A210, L212, Y216, A218, F239, A335, V363, F404, F658, A662, I668, L673, L677, V681, C697, M700, M704, L712, F717, L720, I724, F731, I742, M747, A750, V751, A754, Y763, I777, F779, F782, I783, C785, F786, L815 |
| 385 | Collagen alpha-1 | P20849 | L59, V65, A86, F113, L114, F117, M119, W128, I130, W131, I133, I144, I146, V153, F155, F169, I183, M184, I185, V187, A192, L194, A218, V219, V231, L235, M238, I240 |
| 386 | Nebulin | P20929 | A6617, F6631, I6637 |
| 387 | N(4)-(beta-N-acetylglucosaminyl)-L-asparaginase (EC 3.5.1.26) | P20933 | I91, L105, I108, A111, I112, V114, A115, V118, A132, A136, A243, A253, A254, A256, L263, A272, V273, A285, C286, I290, I293, F300, A303, V304, C306, C317 |
| 388 | Filamin-A | P21333 | F49, C53, L57, I64, L67, L71, L77, I78, L80, L81, V107, V109, A110, L111, F113, L114, I129, I137, L138, L140, I141, L144, I145, I150, L172, I176, L180, I185, F188, W192, A197, L198, A200, L201, V202, A206, C210, A225, A228, M229, A232, L236, I238, V241, I242, I247, V257, M258, Y260, L261, F264, A284, A302, V306, A311, V318, V344, H354, V356, V358, F360, I365, V372, V495, A501, V505, A510, V519, F540, Y542, Y550, V552, I554, I561, V568, A595, F597, V598, V599, V633, Y635, Y643, A644, V647, I654, A661, V675, V697, H743, A745, V747, V761, V1070, F1088, I1090, A1095, V1124, Y1126, Y1134, I1136, I1138, I1145, A1152, V1154, V1163, C1165, F1181, V1183, A1188, I1197, I1219, Y1221, Y1229, V1231, I1233, Y1235, L1247, V1258, V1270, F1278, V1280, V1297, Y1317, V1319, Y1321, |

TABLE 5-continued

TARGETS

| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
|---|---|---|---|
| | | | H1329, V1331, V1333, V1347, V1358, F1376, V1378, A1383, V1412, Y1414, Y1422, L1424, V1426, V1433, V1440, V1451, V1463, V1473, A1478, V1487, V1509, I1521, V1523, Y1525, V1530, V1537, V1539, V1548, V1560, A1562, F1568, I1570, A1572, A1575, I1584, V1606, Y1608, Y1616, I1618, I1620, Y1622, I1627, V1634, A1636, A1642, C1645, I1672, V1674, A1679, V1684, V1688, I1710, A1714, Y1720, I1722, V1724, V1731, V1738, A1740, F1791, I1795, I1799, V1808, V1828, V1830, H1840, M1842, I1844, I1851, L1856, F1858, V1860, V1868, A1870, L1875, F1886, V1888, I1902, V1922, Y1924, Y1932, I1934, V1936, V1943, F1948, A1950, V1952, V1987, I2009, F2011, H2019, V2021, V2023, I2039, A2047, V2050, L2057, F2068, I2070, A2075, L2080, L2082, I2084, V2104, Y2106, Y2114, I2116, I2118, F2120, V2125, V2132, V2134, A2176, V2178, Y2198, I2200, H2210, V2212, V2214, V2230, A2238, V2241, A2257, F2259, I2261, A2268, I2273, V2275, V2295, Y2297, V2299, Y2305, V2307, V2309, F2311, I2316, V2323, V2325, A2326, A2332, L2335, L2345, V2355, L2357, A2360, I2364, V2368, V2390, Y2400, I2402, V2404, F2406, I2418, V2432, L2439, F2450, V2452, A2457, V2485, Y2487, A2491, Y2495, I2497, I2499, Y2501, I2507, A2514, A2557, V2560, A2570, V2580, C2582, V2616, Y2618, L2620, L2628, V2630, W2632, I2637, V2644 |
| 389 | Neurofibromin | P21359 | I1592, I1605, F1606, Y1607, V1609, F1613, L1623, V1642, A1670, Y1680, L1715, I1719, A1743, I1755, A1761, V1762, V1772, A1785, I1788, F1799, L1801, I1803, F1812, C1817, I1820, I1824 |
| 390 | Phosphatidylcholine translocator ABCB4 | P21439 | A64, M81, L109, M113, Y120, V127, A131, F137, A141, A142, I146, I149, F153, F154, A156, I157, L158, I162, L173, L177, I181, I184, I188, A200, V208, L216, I220, A235, A252, A256, A259, A262, V266, A268, F269, Y279, L283, A286, A294, I303, A304, A310, A313, A315, F316, M334, V336, F337, I340, A350, A360, A364, I367, I371, I377, L394, V399, L412, L415, V419, V425, A426, L427, V428, C433, L441, I442, I453, I460, F463, V465, L468, I472, V475, L481, F482, I486, I490, I502, V506, A509, A511, I515, V526, I541, A542, I543, A544, A546, I553, L555, L556, A559, V571, A574, L575, A578, I585, I587, V594, I600, A601, F603, L617, Y624, V700, C717, A718, I735, I736, I753, I757, F758, L761, A779, L783, L787, A791, F792, M795, L796, L817, A821, V824, A827, A833, A840, L856, A896, A899, I900, I903, V906, F915, A934, C955, A960, L975, V976, F982, A1000, A1004, H1006, L1007, I1034, F1036, V1039, F1041, L1052, L1055, V1059, L1065, A1066, L1067, V1068, V1078, V1079, L1081, L1082, V1093, A1107, L1110, V1112, L1115, L1119, V1122, F1129, A1134, I1137, I1151, A1154, A1155, A1158, I1160, Y1171, V1175, A1191, I1192, A1193, L1196, L1204, L1205, V1220, A1223, C1233, I1234, I1236, I1243, I1249, V1250, V1251, L1266, Y1273 |
| 391 | Tumor necrosis factor alpha-induced protein 3 | P21580 | L10, A18, I21, I37, H38, H39, F40, M43, H44, L48, F51, I64, A67, L68, L77, L83, A94, L104, M105, H106, A107, Y111, M112, W113, V115, L122, A125, L126, F138, A175, H195, I196, F197, V198, L199, C200, I202, L203, I207, I208, V209, V229, I232, Y233, L234, I248, V249, L250, V258, L260, V261, A272, V273, V288, H289, F290, L291, L302, L307, V314, I325, A327, A328, L330, I339, L341, Y345, V349, C404, C624, C779 |
| 392 | Kit ligand (Mast cell growth factor) | P21583 | V40, L43, L55, I70, M73, V74, L77, L81, I100, I101, L104, I107, V108, F140, F141, F144 |
| 393 | Ephrin type-A receptor 1 | P21709 | L81, A92, V95, H96, V97, L99, F101, V103, F122, L124, V148, L181, L183, A184, F185, A190, V192, L194, V197, V199 |
| 394 | Fibroblast growth factor 7 | P21781 | L69, C71, L77, I79, V85, M98, I100, V108, I110, L119, A120, M121, C137, F139, Y151, V165, A166, L167, A186, F188 |
| 395 | Fibroblast growth factor receptor 2 | P21802 | M162, V169, V175, F177, C179, A181, F198, L216, M218, V221, Y229, C231, V233, Y244, L246, F276, C278, W290, I324, C342, A344, A355, L357 |
| 396 | Ryanodine receptor 1 | P21817 | L13, V19, V20, L21, C23, A25, L34, C35, L36, A37, A38, I63, C64, F66, L68, L77, L100, Y102, A105, I106, L108, H110, L117, A131, V134, L136, C145, W147, M149, V162, I168, L170, L179, V190, A192, W199, M201, V213, L219, L221, H223, C229, L230, I232, V244, Y246, V251, A255, L258, W259, L261, L273, L279, V281, H283, V284, Y289, L290, A291, V299, V300, A306, F313, F315, I338, C345, V347, L356, A375, L387, L389, A399, A400, M402, I403, Y410, F413, L435, V440, L444, L447, I448, F451, L470, L476, F477, M482, V486, C489, I490, L493, F502, A506, I517, V518, L521, L524, L528, W685, A686, V706, C745, I754, V779, V780, A874, F909, V984, A988, H992, L1038, V1042, A1093, V1101, W1103, A1104, L1114, A1120, V1122, F1123, V1148, C1150, I1152, I1159, F1161, I1181, V1190, A1449, W1451, V1452, L1465, V1471, V1473, M1475, I1515, M1526, F1528, A1550, F2754, A2759, Y2761, H2763, A2767, L2813, A2815, M2816, L2862, M2874, L2878, A2879, A2923, L2926, L2927, L2930 |
| 397 | Receptor tyrosine-protein kinase erbB-3 (EC 2.7.10.1) | P21860 | L52, Y53, C56, V58, V59, L63, I65, L77, I80, V83, V87, L88, V89, A90, F94, L97, L99, L102, V104, V105, A116, I117, F118, V119, L121, A130, L131, L134, L136, L139, I142, V147, I149, L155, M158, I161, I166, V167, C190, C194, W195, |

TABLE 5-continued

| TARGETS | | | |
|---|---|---|---|
| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
| | | | C231, A232, A245, C255, C259, V295, V296, C331, V343, I348, F351, C354, I357, L361, F363, I376, L384, F387, V390, I393, L397, I399, F409, V411, F412, L415, I418, F428, L430, I432, V438, L441, F443, L446, I449, I454, I456, L462, C463, H465, V473, L474, C493, C504, C509, W510, C529, C533, C552 |
| 398 | Succinate dehydrogenase [ubiquinone] iron-sulfur subunit, mitochondrial (EC 1.3.5.1) | P21912 | F42, I44, V63, V72, A75, L76, I79, L87, C101, M103, L111, A112, I127, F146, L183, A190, C191, Y199, Y206, A210, V211, L212, A215, L234, L240, A262, I263, I266 |
| 399 | Tenascin-X | P22105 | C435, C466, L3669, L3671, A3679, F3683, L3685, A3716, L3718, L3729, L3731, A3859, L3861, Y3873, V3875, V3877, L3898, A3909, V3911, A3947, L3949, Y3961, L3963, L3977, L3986, Y3995, A3997, L3999, A4001 |
| 400 | Cadherin-3 | P22223 | V116, L131, I141, V157, F158, L167, L169, L173, L183, A187, I201, I203, V224, V237, A254, M269, I279, V281, Y294, L296, I298, A300, A312, A314, V316, I318, L349, L390, L396, L406, V408, V410, A425, I427, V429, Y462, V495, L501, Y514, V516, V518, A520, L534, L536, I553, L565, V602, L604, V617, L619, L621, I633, A635 |
| 401 | Interleukin-10 | P22301 | L41, L44, A47, V51, F55, L66, L70, A82, L83, M86, Y90, V94, A98, V109, L112, L116, C126, L130, V139, A157, M158, F161, F164, I165, I168 |
| 402 | C-C motif chemokine 1 | P22362 | I47, L62, F64, A74, V81 |
| 403 | Ectonucleotide pyrophosphatase/phosphodi-esterase family member 1 | P22413 | C164, C166, C170, A392, I507, I632, F638, L826 |
| 404 | Potassium voltage-gated channel subfamily A member 5 | P22460 | I124, I126, L138, L146, F165, F172, I175, Y179, V191, F196, I200, Y203, I260, V445, A451, V452, A455, A470, A474, C500 |
| 405 | Protein-glutamine gamma-glutamyltransferase K (EC 2.3.2.13) | P22735 | V709, I711, L721, V724, F726, L728, I744 |
| 406 | Carbonic anhydrase 4 (EC 4.2.1.1) | P22748 | Y25, I54, I56, Y75, W81, V83, V90, M92, L94, I100, Y109, A111, L114, L116, W118, H128, M137, M139, H140, I141, H143, A164, L166, A167, F168, L169, V170, F180, L187, I190, Y217, C229, V233, V237, F238, I242, L244, F252, L256, M266 |
| 407 | Peptidyl-prolyl cis-trans isomerase B | P23284 | V42, V44, V46, Y47, F48, L50, I52, V60, I61, F62, L64, F65, V69, V73, F76, A78, L79, A80, F86, Y88, F93, V96, I97, M101, I102, I118, F123, L130, H132, W137, V138, M140, F152, F153, I154, V167, V168, F169, V172, V178, V179, V182, L194, V197, I198, I199, I205 |
| 408 | Glycine receptor subunit alpha-1 | P23415 | V65, V67, C69, I71, I73, Y86, V88, I90, L92, W96, L101, L111, L146, I148, V154, I160, L162, L164, C166, L170, F173, C180, M182, L184, L194, F196, C237, I238, A240, F242, L244 |
| 409 | Receptor-type tyrosine-protein phosphatase delta | P23468 | A41, F43, C45, W57, F69, V81, L82, I84, L87, Y96, C98, A100, L113, V115, A143, M145, C147, A148, A149, W159, L192, I194, Y205, C207, A209, A221, L223, I255, C257, A259, V267, W269, V294, C302, A304, A315, I317, I339, L341, I356, V373, V380, F391, V393, V394, A395, I434, V436, V453, V463, I479, V490, V492, A494, I532, L534, Y547, L549, I564, L575, F583, L585, A586, A587, I626, V628, I647, A651, L674, I685, V687, A689, L937, L956, L981, V992, V994, A996 |
| 410 | Tumor necrosis factor ligand superfamily member 4 | P23510 | V64, F66, M86, V93, I95, C97, Y101, I103, L105, V113, I115, L117, V135, V149, L151, L170, L172 |
| 411 | Brain-derived neurotrophic factor | P23560 | C141, A150, V164, V166, V170, C196, A217, I226, I231, I233 |
| 412 | Follicle-stimulating hormone receptor | P23945 | F30, C32, V37, A48, L51, F53, L58, I61, F66, F69, L72, I75, I77, L83, I86, V90, F91, L94, L97, I100, I102, A105, L108, L109, A115, F116, L119, L122, L125, I127, I132, L135, V138, I141, V147, L149, I151, I157, I160, F165, L168, V173, L175, L177, I182, A189, F190, L195, L198, L200, L206, V213, L223, I225, I230, L238, L241, L244, A246, L261, A267 |
| 413 | Sodium-dependent noradrenaline transporter | P23975 | L95, L109, A145, I156, L238, F272, L284, I291, A305, I309, L319, V325, Y367, V379, L386, V387, F388, I389, L390, Y391, A394, A405, I428, F459, I466, L469, L472, A477, L486, I490, F495, F540, I549, A554, W556, V569 |

TABLE 5-continued

| TARGETS | | | |
|---|---|---|---|
| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
| 414 | Protein kinase C eta type (EC 2.7.11.13) | P24723 | V360, M370, L371, A372, V383, V390, I406, L407, A410, F415, L416, L429, F430, F431, V432, L441, A456, Y459, A460, A461, I463, I464, A466, L467, L470, I475, Y477, V485, L487, C493, L495, F498, W537, M540, L543, L544, M547, A581, I584, L585, F588, I608, F613, F614, V641, F644, F671, F674 |
| 415 | Deoxyribonuclease-1 (EC 3.1.21.1) | P24855 | I25, A26, A27, F28, I30, F33, M38, V44, I47, V48, I50, L51, Y54, I56, A57, L58, V59, V62, A69, V70, L73, L77, Y102, L103, F104, V105, V111, F131, I137, V138, F140, V147, F150, A151, I152, V153, L155, A157, A162, I166, L169, V172, V176, V185, M186, L187, M188, F191, A193, I206, L208, I218, C231, A232, I236, V237, V238, A239, L243, A246, F257, A268, I271, V277, V279, L281 |
| 416 | C-X-C chemokine receptor type 1 | P25024 | L37, C110, C187, V190 |
| 417 | C-X-C chemokine receptor type 2 | P25025 | L155 |
| 418 | Adenomatous polyposis coli protein | P25054 | L137, L204, I224, C344, L356, A383, A386, L387, I391, V406, L407, L410, I413, Y416, C417, C420, I446, V450, L453, A465, M466, L469, L472, A474, I475, A476, L478, L479, V481, L497, A501, A504, L505, L508, L519, C520, C525, M526, L529, L540, I544, A545, V547, L548, L551, L563, V569, L572, M573, C575, A576, V588, L589, A591, L592, L595, I606, A612, L613, L616, I631, I638, L639, V642, I646, L656, C661, L665, I676, A680, C681, L684, L687, A703, L707, I718, A725, L729 |
| 419 | Myelin protein P0 | P25189 | L48, C50, F64, W66, F80, F95, I112, I114, F125, C127, L144 |
| 420 | Tumor necrosis factor receptor superfamily member 6 | P25445 | C63, C73, C85, C119 |
| 421 | Integrin beta-7 | P26010 | C54, I55, C61, W63, C64, L86, L123, A124, V128, V130, L132, V142, F144, V152, L154, Y155, Y156, L157, M158, L160, M164, I191, F193, F196, V197, F204, V205, C216, F229, F242, V246, V251, A264, I265, L266, A268, A269, C271, I275, L283, L284, V285, F286, Y327, L337, A340, I345, A347, V348, Y356, A367, V378, A385, L395, Y408, C428, V431, V437, F439, V441, L443, A445, L455, L457, A459, L466, V468, L470 |
| 422 | Hemagglutinin [Cleaved into: Hemagglutinin HA1 chain; Hemagglutinin HA2 chain]/strain A/Mallard/Astrakhan/263/1982 H14N5 (Influenza A virus (strain A/Mallard/Gurjev/263/1982 H14N5)) | P26136 | I29, C30, L31, A35, V42, V52, L58, V59, L67, C68, L74, C80, L82, I83, A86, L87, C92, L95, V102, F103, I104, V110, C113, Y114, F116, Y121, L124, L128, A129, L134, F141, A154, C155, F163, F164, L167, L170, I181, Y195, W197, V199, H200, H201, Y212, V219, V221, I247, I249, Y250, L253, V254, I260, F262, L268, I269, A270, Y275, I292, C299, L300, I306, V327, L334, A335, A352, W361, Y369, A391, A443, L465, L473, C484, F485, I487, H489, C491, C495, I496, I499, A513 |
| 423 | Hepatocyte growth factor-like protein | P26927 | C157, C169, Y199, W215, C240, W250, C251, Y252, C263, L265, C391, W394, H400, L414, C419, C431, C443, V484, W494, V496, L498, L511, I517, L518, A520, V536, L538, V555, L569, V570, L571, L572, V584, C602, I604, A605, L624, C632, M645, C646, L665, A666, C667, L675, I678, I679, V697, I704 |
| 424 | Serum paraoxonase/arylesterase 1 | P27169 | L28, I48, A63, F64, I65, I85, M88, L129, L130, V131, V132, V141, L143, F144, L153, I159, L167, I170, F178, Y179, G180, V205, F220, A223, I226, V235, I237, A238, I245, V247, L267, V268, L280, V282, C284, H285, V304, I307, A322, L328, V333, A334, L341, L342, I343, A350, L351, C353 |
| 425 | Dipeptidyl peptidase 4 (EC 3.4.14.5) | P27487 | Y43, Y68, L69, A81, L90, I114, L116, A130, Y132, I134, L142, L164, A165, V167, I172, V174, I198, W201, V202, Y203, V207, A213, L223, A224, Y225, A226, F228, I236, Y238, Y241, A259, A261, F268, V270, V271, I287, M293, Y299, L300, C301, V303, I311, L313, W315, V324, M325, I327, C328, C339, L340, I346, W353, V354, F371, H383, I384, C385, I389, V404, L415, Y416, Y417, I418, L431, I434, V442, L445, C447, C454, Y468, L470, C472, L482, L500, V507, L514, L519, M528, L530, L542, L543, L544, V546, A548, C551, A555, L567, A568, I573, I574, V575, A576, F578, M591, A593, I594, L598, V603, I607, A609, A610, F613, V619, I624, A625, I626, Y631, Y634, V635, M638, V639, L640, C649, I651, A652, V653, A654, V656, W659, Y661, Y662, V665, Y666, Y670, M671, Y683, V688, A692, F695, Y700, L701, L702, I703, H704, V711, I719, L723, V724, V726, F730, Y735, H740, I742, I751, M755, F758, I759, C762, F763 |

TABLE 5-continued

| TARGETS | | | |
|---|---|---|---|
| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
| 426 | Genome polyprotein [Cleaved into: Capsid protein C/strain Brazil/97-11/1997 (DENV-1) | P27909 | L29, M48, M126, V128, C148, C167, C180, C182, V189, Y191, A251, A255, M281, C283, V301, V303, V304, L305, C310, V311, M314, A315, L321, I323, L325, V330, L339, C340, I341, A360, C385, L394, C396, A397, F399, L405, V410, L415, Y417, V419, V421, I444, I453, L455, L461, L463, C465, L471, V477, L478, L479, M481, V488, F493, L517, V518, L544, H562, L563, C565, L567, M569, L572, C582, F586, V592, V600, V602, V604, Y606, C613, I615, I632, V638, I647, I658, V660, W671, I963, I993, L1396, L1398, I1497, Y1498, I1500, V1513, V1515, F1516, V1520, F1521, H1522, M1524, L1533, M1534, V1547, L1551, I1552, Y1554, W1558, F1560, V1570, V1572, I1573, A1574, V1575, V1584, F1591, A1600, I1601, I1614, V1615, V1622, L1624, Y1625, V1630, Y1636, V1637, A1643, L1680, I1683, V1684, A1687, L1695, I1696, L1697, A1698, V1703, A1704, M1707, A1708, L1711, V1733, L1735, M1736, H1738, F1741, Y1754, M1756, I1757, I1758, M1759, A1762, I1770, A1771, A1772, I1776, A1785, A1786, A1787, I1788, F1789, M1790, I1827, V1835, W1836, F1837, V1838, I1847, A1848, C1850, L1851, I1859, L1861, F1866, W1878, Y1880, V1881, V1882, A1891, V1898, I1899, V1917, V1925, A1928, A1930, A1931, I1937, Y1948, V1949, L1955, A1962, A1967, L1970, L1971, I1974, L1984, F2009, V2010, L2012, L2018, W2021, L2022, V2026, A2027, W2038, C2039, V2048, I2057, L2067, A2074, F2086, F2089, A2090, W2506, Y2521, I2526, V2529, L2538, A2547, V2548, A2553, L2555, F2558, V2559, V2564, V2570, I2571, L2573, C2575, C2584, A2585, V2590, V2593, Y2596, V2625, C2633, L2636, L2637, C2638, I2649, L2655, V2657, L2658, V2661, W2664, L2665, C2671, I2672, I2674, L2675, Y2678, V2682, L2686, M2689, M2696, L2697, H2708, M2710, Y2711, W2712, V2713, I2720, V2724, M2730, L2731, I2769, I2776, V2817, L2820, W2824, I2865, M2866, A2870, L2873, V2904, A2914, A2917, F2923, C2939, C2942, V2943, Y2944, M2969, L2971, A2973, L2976, A2980, F2983, M2984, W2989, F2990, V2999, L3007, Y3009, L3011, I3014, I3017, M3022, I3034, A3057, I3060, Y3065, V3069, V3070, V3072, V3081, V3084, I3085, L3101, F3104, M3107, V3109, L3111, I3112, M3115, L3126, V3135, L3139, L3147, M3150, A3151, I3152, V3158, V3159, F3166, A3169, L3170, A3172, L3173, M3176, V3198, F3200, F3205, I3216, V3217, V3218, C3220, V3227, A3230, A3236, A3244, A3251, W3254, L3256, F3259, H3260, L3264, A3267, A3268, A3270, I3271, A3274, V3275, V3277, H3290, L3302, W3305, V3308, W3309, W3315, V3328, L3331, A3352, I3355, I3359, L3365, L3372, M3375, M3378 |
| 427 | Interleukin-1 receptor type 2 | P27930 | V46, L48, W69, A92, L93, L95, A98, C108, I121, L150, W169, L192, V194, Y205, C207, I220, I224, C258, V260, L262, A276, I281, V328 |
| 428 | Genome polyprotein [Cleaved into: Core protein p21/genotype 1a (isolate H) (HCV) | P27958 | V194, V203, C207, C226, C229, V230, C238, W239, V240, L258, I262, L265, A269, C272, L275, C281, L286, F291, W353, V355, A426, L427, W437, F442, C459, F465, C486, C494, A499, V502, C503, V506, C508, F509, F537, L539, W549, C552, W554, C564, A566, C569, C581, C585, F586, A592, Y594, C597, I603, C607, M608, V609, Y611, V629, M631, A642, A643, C644, C652, L665, V674, A684, I690, L692, V699, Y701, V720, L724, L725, L754, C922, V949, L964, A1004, I1061, L1070, A1071, C1073, I1074, V1077, C1078, W1079, V1081, A1085, V1097, L1108, V1109, L1120, L1130, L1132, I1140, V1142, I1158, L1161, L1169, C1171, A1176, V1177, L1179, F1180, A1190, A1192, V1193, F1195, I1196, V1198, L1201, L1228, V1251, L1252, V1253, L1254, M1268, I1291, Y1293, Y1296, A1301, I1312, I1314, C1315, C1318, I1326, I1329, V1332, A1336, L1343, V1344, V1345, L1346, A1347, I1362, I1373, F1375, I1380, V1384, I1385, L1391, I1392, F1393, C1394, C1400, L1403, L1407, I1412, V1432, V1433, V1434, V1435, L1440, F1444, F1448, V1451, I1452, F1470, A1481, Y1499, L1517, C1518, C1520, Y1521, A1526, Y1528, L1539, Y1542, L1555, F1557, W1558, V1561, L1565, I1568, F1572, L1586, V1587, A1588, A1591, C1594, A1599, L1611, H1619, L1624, L1625, L1628, I1641, I1645, V2128, L2441, L2450, L2451, V2457, Y2458, A2465, Y2484, V2487, V2491, A2493, A2494, A2495, V2498, A2500, A2508, C2509, Y2523, A2525, V2528, A2532, A2535, I2539, L2546, L2547, I2558, C2566, A2577, L2579, V2581, L2585, V2587, V2589, C2590, A2594, L2595, V2598, V2599, L2602, A2605, V2606, Y2611, V2621, L2624, A2627, M2635, L2637, Y2639, V2648, I2653, I2659, Y2660, C2662, C2663, A2669, A2672, I2673, L2676, L2680, Y2681, L2686, C2694, C2699, A2701, V2704, L2705, C2709, L2713, A2719, A2721, A2722, C2723, A2726, L2728, M2733, L2734, V2735, L2740, V2741, V2742, I2743, C2744, A2754, L2756, F2759, A2762, M2763, Y2766, A2768, I2783, V2790, A2793, Y2802, L2804, L2812, A2813, A2815, A2816, L2829, I2832, I2833, A2836, L2839, W2840, A2841, I2844, L2845, M2846, H2848, F2849, F2850, L2859, A2862, C2865, I2867, A2870, C2871, Y2872, I2874, L2877, L2879, I2882, I2883, L2886, A2891, F2892, V2905, A2906, C2908, L2909, L2912, V2914, A2919, W2920, A2924, V2927, L2931, L2932, A2938, A2939, C2941, L2945, F2946, A2949, A2961, A2962, F2971, A2973, Y2975, I2980 |

TABLE 5-continued

| TARGETS | | | |
|---|---|---|---|
| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
| 429 | Proteasome subunit beta type-8 (EC 3.4.25.1) | P28062 | L76, A77, F78, F80, V84, I85, A86, A87, V88, A92, A94, V106, I107, L113, L114, M117, C124, L131, C135, L137, I146, V148, A150, A151, L155, M159, M169, M172, I173, C174, L183, V186, A207, M211, A224, L227, A231, I232, A233, A235, V245, V246, M248, Y249, H250, M251 |
| 430 | HLA class II histocompatibility antigen, DM beta chain | P28068 | L51, M61, A73, L90, C97, V117, V119, M132, L133, A134, C135, V137, F140, W149, C192, V194 |
| 431 | Gamma-aminobutyric acid receptor subunit beta-3 | P28472 | V63, M65, I67, I69, Y82, L84, M86, W92, L97, I141, V149, A159, L165, C175, L177, I179, I189, A199, L233, L235, F237 |
| 432 | Mitogen-activated protein kinase 1 | P28482 | A9, V14, F19, V21, Y25, I31, A35, Y36, M38, C40, A42, V49, V51, A52, I53, I56, C65, L69, I72, I74, L75, I83, I84, I86, I89, I95, M98, V101, Y102, I103, V104, L112, L115, L116, L121, H125, I126, C127, F129, L130, I133, L134, L137, I140, H141, A143, V145, L146, H147, L150, L155, L156, L157, L163, I165, F168, L170, A171, L184, A189, W192, Y193, A195, I198, M199, L200, Y205, I209, I211, W212, V214, C216, I217, L218, A219, M221, L222, I227, F228, L234, L237, I240, L241, L244, L252, I255, A260, L264, L267, F279, A286, L287, L289, L290, M293, L294, A307, L308, L313, F329, M333, L335, L338, L343, I347 |
| 433 | Granulins (Proepithelin) (PEPI) [Cleaved into: Acrogranin (Glycoprotein of 88 Kda) (GP88) (Glycoprotein 88) (Progranulin); Paragranulin; Granulin-1 (Granulin G); Granulin-2 (Granulin F); Granulin-3 (Granulin B); Granulin-4 (Granulin A); Granulin-5 (Granulin C); Granulin-6 (Granulin D); Granulin-7 (Granulin E)] | P28799 | C133, C157, C215, C239, C290, C314, C372, C396 |
| 434 | ADP-ribosyl cyclase/cyclic ADP-ribose hydrolase 1 (EC 3.2.2.6) | P28907 | F59, V63, C67, Y70, M77, V85, F89, A92, F93, I101, Y106, L109, M110, C119, I122, L123, L124, A132, F135, L145, L149, L150, L153, A154, W159, C160, V187, F188, V192, A197, A199, A200, V204, V206, M207, L208, I215, F216, F222, V225, V227, L230, V235, L238, A240, V242, L253, I259, L262, I266 |
| 435 | Tumor necrosis factor receptor superfamily member 8 | P28908 | C44, C45, C48, C58, C65, C69, Y74, C81, A83, C84, V85, C87, L92, V93, C98, V105, C106, C108, F113, C114, C122, A123, C125, C131, I136, V137, C233, C240, C244, Y249, L250, C256, C259, V260, C262, L267, V268, C273, W275, C281, C283, C289, C297, A298, C300, C306, V311 |
| 436 | Gap junction beta-2 protein | P29033 | W44, F51, C60, C64, H73, C169, A171, C180 |
| 437 | Neuroendocrine convertase 1 | P29120 | C319, A393, V411, A511, L525 |
| 438 | Amyloid beta A4 protein | P29216 | C49, C53 |
| 439 | Ephrin type-A receptor 3 (EC 2.7.10.1) | P29320 | L33, Y68, V70, L82, V87, A92, I95, Y96, V97, L99, F101, L103, V112, F120, L122, I146, M155, V171, F179, Y180, L181, A182, F183, A188, V190, A191, L192, V195, V197, A436 |
| 440 | Ephrin type-B receptor 2 (EC 2.7.10.1) | P29323 | W43, V61, W72, L73, I78, A83, I86, V88, M90, F92, V94, V103, F111, L113, I141, V150, I159, F166, V169, F174, Y175, L176, A177, F178, L187, V190, V192, A435 |
| 441 | Collagen alpha-5 | P29400 | I1464, L1490, Y1491, L1503, Y1537, W1538, L1539, I1561, C1564, A1565, V1566, C1567, A1569, F1599, H1602, C1620, F1629, I1630, C1632, C1638, C1678, V1680, C1681, M1682 |
| 442 | Interleukin-12 subunit alpha | P29459 | V48, M51, A55, I105, C123, L131, M141, M159, I163, C196, L199, I209 |
| 443 | Interleukin-12 subunit beta | P29460 | V30, V32, V33, V46, I58, W60, V79, A85, C90, L102, L104, I116, A133, F140, C142, W144, V191, C193, I208, V210, V212, A214, Y220, Y223, I229, I233, V252, V254, L271, F273, C274, V275, V277, A304, I306, V308, A310 |

TABLE 5-continued

| TARGETS | | | |
|---|---|---|---|
| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
| 444 | Protein PML | P29590 | C57, C66, L73, H74, L76, C129, C140, C148 |
| 445 | Non-receptor tyrosine-protein kinase TYK2 (EC 2.7.10.2) | P29597 | L28, V30, A53, V56, I60, A61, V64, L73, L76, A81, L91, L101, F103, F109, Y151, L152, F153, F160, A165, L184, M186, A187, L191, H193, C214, I215, F219, Y259, L260, L263, A267, V277, L280, L283, V316, V318, I324, C378, F380, V393, I395, C402, L403, L405, L407, A413, F416, V417, L419, V420, Y423, L426, V438, H452, Y471, L472, L483, L485, V487, I507, V526, L529, I563, V639, L641, L644, F655, A659, V676, C677, I684, M685, V686, L695, L699, V714, A715, L718, A719, A721, L722, L725, V735, I740, L742, I755, L757, V762, V773, I776, A780, W798, F800, A802, L804, L805, I807, C838, L841, L844, C848, F859, I862, L866, L913, V927, V929, A934, W944, I948, L951, H958, I959, I960, C966, L974, L976, V977, L986, L990, L1000, L1001, F1003, A1004, I1007, C1008, M1011, L1014, I1020, H1021, L1024, A1025, A1026, V1029, L1031, V1037, I1039, F1042, L1044, A1045, A1069, C1072, F1078, V1084, F1087, V1089, L1091, Y1092, L1094, L1124, L1127, L1128, L1134, C1140, V1144, M1148, C1151, W1152, L1165, L1169 |
| 446 | CD40 ligand | P29965 | A124, V126, L138, V153, L161, V163, Y169, I171, A173, V175, F177, F189, A191, L193, L231, A235, V237, V239, V241, F256, L258 |
| 447 | Peroxiredoxin-5, mitochondrial (EC 1.11.1.15) | P30044 | V67, V76, L78, F82, V88, L89, F90, V92, F96, C100, H104, L105, F108, A112, L115, A117, V123, A124, C125, L126, V128, A131, W137, A140, A143, L150, A151, F157, L178, F181, M183, V184, V185, V190, A207, I210 |
| 448 | T-cell differentiation antigen CD6 | P30203 | V58, V60, A78, A79, A81, V82, C83, A126, A151, V153, A171, V174, M176, V185, C186, A195, V197, V198, C199, A255, A257, V278, V280, F282, V289, C290, A299, V301, L302, C303, C308, M326, Y328, L337, A355, V358, C360 |
| 449 | Lens fiber major intrinsic protein | P30301 | A12, A15, A19, Y23, V24, L28, L32, V44, A45, F48, A51, V67, A70, V71, A74, A86, Y89, A97, A101, V112, L116, V127, A130, V142, I145, F146, A161, V164, L168, H172, A181, M183, A186, A190, A192, V203, Y204, I209 |
| 450 | HLA class I histocompatibility antigen, B-8 alpha chain | P30460 | M29, Y31, A35, F46, V52, F57, V58, F60, A73, W75, I76, Y83, F91, L102, L105, L119, M122, C125, V127, Y140, Y142, Y147, I148, L150, L154, W157, A163, A164, V176, A177, L184, C188, V189, L192, Y195, L196, L203, V213, A223, L225, C227, A229, F232, Y233, L239, W241, A269, A270, V271, V272, V273, Y281, C283, V285, H287 |
| 451 | Tyrosine-protein kinase receptor UFO (EC 2.7.10.1) | P30530 | L54, C56, L58, V98, L102, C117, V119, V133, C160, W173, F203, C205, A207, A219, I221 |
| 452 | Type-1 angiotensin II receptor | P30556 | I27, C101 |
| 453 | Fibroblast growth factor 9 | P31371 | L66, C68, L74, I76, I94, L95, V105, I107, L116, M118, C134, F136, Y148, V164, A165, L166, F184, F187, V197, L200 |
| 454 | Cytokine receptor common subunit gamma | P31785 | C62, V64, M70, C72, W74, L85, L87, C102, L106, C115, L117, L124, F128, V129, V130, L132, L146, L148, V152, L162, L165, L170, L172, W174, L183, H185, V187, F221, V223, F227, A234 |
| 455 | Low affinity immunoglobulin gamma Fc region receptor II-b | P31994 | A50, L62, V67, L69, W84, A103, Y111, C113, L126, L129, L133, V134, L135, L140, F142, I148, L150, C152, L160, V163, F165, F166, F181, A186, Y194, C196, I212, V214 |
| 456 | Low affinity immunoglobulin gamma Fc region receptor II-c | P31995 | A50, L62, V67, L69, W84, A103, Y111, C113, L126, L129, L133, V134, L135, L140, F142, I148, L150, C152, L160, V163, F165, F166, F181, A186, Y194, C196, I212, V214 |
| 457 | Carcinoembryonic antigen-related cell adhesion molecule 8 | P31997 | L36, A45, V51, L52, L53, V55, Y65, W67, I79, I80, A105, L107, M109, V112, Y120, L122, V124, F138 |
| 458 | Neuronal acetylcholine receptor subunit alpha-3 | P32297 | A139, L140, A153, I187, L189 |
| 459 | 4-hydroxyphenylpyruvate dioxygenase (EC 1.13.11.27) | P32754 | V22, F24, A29, A33, M40, F42, V61, I62, I67, V68, F69, L71, I96, F98, C103, V107, A110, V131, A134, L136, H144, L146, V147, C176, I184, V185, Y200, V217, L224, V228, V229, A230, I236, M238, I240, I252, I267, A268, L269, I274, A277, I278, L281, Y296, L317, I322, Y331, L332, L333, I335, L346, F347, L348, V350, I351, F368 |
| 460 | T-lymphocyte activation antigen CD80 | P33681 | A46, L48, C50, I64, W66, V73, L74, L99, I101, I103, Y114, C116, V118, I160, C162, W175, V200, L204, F214, C216, I218 |
| 461 | Surface antigen S/isolate Human/India/Ind3/1967 (VARV) (Smallpox virus) | P33795 | F36, A66, L83, I210, V238 |

TABLE 5-continued

| TARGETS | | | |
|---|---|---|---|
| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
| 462 | N-acetylgalactosamine-6-sulfatase (EC 3.1.6.4) | P34059 | I33, L34, L35, L36, L37, M38, M41, L46, M62, F69, F72, Y73, A75, A84, A85, L86, L87, L91, F97, A104, I113, I117, L123, L124, L128, I137, V138, W141, L143, H154, W159, H166, V180, Y190, A203, Y209, A213, F216, I217, F226, F227, L228, Y229, W230, A231, V232, A234, Y240, A241, Y254, A257, V258, I261, I265, I268, L272, V283, F284, F285, A291, I294, C308, F314, M318, A322, L323, A324, W325, I342, F346, L350, L368, Y384, M391, A392, A393, A400, H401, V427, I441, F442, A464, I468, L486 |
| 463 | Neurotrophin-4 | P34130 | V118, V120, A179, I193 |
| 464 | Catenin alpha-1 | P35221 | A128, L141, L150, V157, I161, L164, L173, L187, A191, L198, M207, A208, L221, L229, L243, I244, L248, V252, I255, A258, A259, F285, L305, I312, A316, M319, I333, A339, V340, L344, L347, L348, M371, L378, L382, A385, V386, H389, V390, L395, L401, L404, A407, A408, V416, F423, A427, L430, V433, A434, A437, C438, V450, M452, L457, A459, L460, V464, A468, L471, A480, W491, V497, L498, A501, V502, F511, L512, V514, I519, C526, A529, L530, L538, A542, I545, A549, V552, V556, V572, L573, L579, V583, F587, A594, F611, A614, V618, I622, I625, F691, L698, I712, A716, M719, M723, M726, V742, A745, A746, I749, A752, M756, L759, I763, L776, L780, I783, L790, C793, A815, L818, I819, A821, A822, L825, M826, A828, V829, V833, A839, A896, A902 |
| 465 | Catenin beta-1 | P35222 | A149, I153, L160, V168, A171, A172, V175, I188, M194, V195, A197, I198, V199, M202, C213, A215, L218, L221, L228, I231, I237, A239, L240, V241, V251, L252, A255, I256, L259, L262, L263, A269, V273, L279, M282, L285, F293, L294, A295, C300, L301, L304, A305, I315, A317, L324, V325, I327, M328, L336, L337, V343, L344, L347, C350, I357, V358, A360, M363, A365, L366, L368, L370, L377, V378, C381, L382, L385, L388, A391, A392, M398, L401, L402, L405, V406, L408, L409, V417, C419, A420, A421, I423, L424, L427, V438, I444, L447, V448, V451, A454, I460, A464, I465, A467, L468, L471, A481, A484, V485, L491, V494, V495, L497, L498, L506, I507, A509, V511, L513, I514, L517, A518, L519, A522, A525, L527, A532, I533, L536, L539, L540, A543, V564, M566, I569, V570, C573, A576, L577, L580, A581, V584, I590, I596, L598, F599, V600, L602, L603, I610, V613, A614, A615, V617, L618, L621, A622, A627, A628, A630, I631, A633, A636, L640, L643, L644, V651, A652, A655, A656, V658, L659, L781 |
| 466 | Interleukin-13 | P35225 | L43, L46, I47, L50, C62, V67, M76, Y77, A79, A80, L81, L84, I93, L100, C104, V125, F128, V129, L132, L136 |
| 467 | Thrombospondin-2 | P35442 | I600, C619, A639, C707, C715, C720, C756, C779, C815, C838, C876, A882, C912, C932, C948, F959, V965, L967, L988, I998, A999, V1000, F1005, F1010, V1016, Y1024, A1025, F1027, V1028, F1029, Y1031, F1037, Y1038, V1039, M1041, A1057, L1065, V1067, V1068, L1078, A1081, L1082, W1083, V1092, L1114, H1116, I1123, V1125, Y1145, L1150, L1152, F1153, V1154, F1155, V1160, F1162, L1165, Y1167, C1169 |
| 468 | D(3) dopamine receptor (Dopamine D3 receptor) | P35462 | C103 |
| 469 | Alpha-L-iduronidase (EC 3.2.1.76) | P35475 | V32, V34, W47, F52, A61, V65, L72, L74, A75, Y76, V77, A79, V88, W92, L93, L94, L96, V97, L114, Y117, L120, L121, F130, L132, M133, A136, F140, F143, V149, W152, L155, V156, L159, A160, Y163, V172, W175, F177, W180, F198, Y201, Y202, A204, C205, L209, L216, L218, F225, L237, L238, Y258, I259, L261, I272, V279, I283, A300, A314, V316, Y318, A319, A320, M321, V322, V323, V325, I326, A327, H329, L333, A340, L346, A351, L353, F360, L365, A367, V371, L381, L382, V386, L387, A389, L393, A394, L396, L401, V418, L421, A422, A436, A437, V438, L439, I440, Y441, A442, A448, V456, L460, V472, L476, C481, F501, M504, A507, L530, L535, L537, V538, H539, V540, C541, V551, L564, V565, L566, V573, C577, L578, Y581, I583, L604, V614, Y618, V620, A622 |
| 470 | Fibrillin-1 [Cleaved into: Asprosin] | P35555 | C67, C80, C100, C134, C145, C853, C875, A882, I911, C1526, C1534, C1562, C1564, A1569, I1607, L1613, L1616, C2061, C2083, C2084, C2085, I2110, C2111, C2137, C2164, C2190, C2363, C2364, C2365, W2371, C2378 |
| 471 | Myosin-9 | P35579 | V34, A44, A54, V56, L58, M86, L89, A95, V97, L98, L101, Y105, L109, I110, Y111, Y113, F117, C118, V119, V120, I121, I129, I134, V135, Y138, M146, H149, I150, Y151, I153, A157, M161, I170, L171, C172, A178, V187, I188, Y190, L191, A192, V194, A195, A214, I217, L218, A220, F221, A224, F235, F238, I239, I241, F243, V250, A252, Y257, L258, A264, F274, I276, F277, Y278, Y279, L280, L288, L292, L293, F302, L303, I310, F319, A325, M326, M329, L339, L340, V342, I343, V346, L347, L349, I352, F354, A363, A370, A371, V374, L377, L378, F385, I389, L390, A410, F412, A413, I414, A416, L417, A418, A420, Y422, M425, F426, L429, V430, I433, L437, I448, I450, L451, F456, F464, L467, C468, Y471, L479, F480, Y492, I497, F504, L508, C511, I512, L514, I515, I524, L525, L527, L528, F542, V546, F556, F568, C569, I570, I571, H572, V577, Y579, A581, W584, M589, I596, A597, L600, F607, V608, W612, V646, Y650, L654, L657, M658, L661, F668, V669, C671, I672, I673, V688, L689, L692, V697, I701, I703, F708, F714, F717, Y721, I729, A739, C740, M743, I744, V761, F762, F763, V767, L771, I783, F786, M809, M871 |

TABLE 5-continued

TARGETS

| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
|---|---|---|---|
| 472 | Alpha-actinin-2 | P35609 | F44, C48, L70, L75, L76, V100, L114, A119, I122, V123, I134, I138, A142, I143, I146, L157, C161, I173, W180, L184, L186, C187, A188, L189, I190, L203, I209, I212, A215, M216, A219, A231, V235, A244, I245, M246, Y248, V249, F252, Y253, A262, L289, A290, I297, L304, A315, M316, L348, L378, A381, L389, A403, F406, A410, H413, A417, L424, V437, H444, I461, A465, L468, V479, I486, L493, L504, M507, H518, F521, A525, M532, A535, I551, L565, I575, V582, I593, L607, V614, L625, A646, I649, I667, L678, H683, L695, V707, M717, I720, L727, I731, M798, A839, Y844, I845, L850, A859, I863, A878 |
| 473 | Metalloproteinase inhibitor 3 | P35625 | I40, I42, A44, V46, L60, I64, V79, I82, L104, M113 |
| 474 | Copper-transporting ATPase 2 (EC 3.6.3.54) | P35670 | V145, L147, V149, I161, V165, A183, I185, Y187, L197, V201, F206, C271, I279, V285, A297, V299, L311, I315, I363, I365, I377, I381, V401, L413, I417, C490, L492, I494, V503, I506, L510, V516, V519, L520, A528, I530, Y532, I542, A543, I546, A553, I566, L568, I570, I582, L586, A595, A604, V606, F608, I618, I619, I622, A629, V820, C1079, V1106 |
| 475 | Myosin-11 | P35749 | V38, A48, V58, V60, L62, M90, L93, A99, V101, L102, L105, Y109, L113, I114, Y115, Y117, F121, C122, V123, V124, V125, I133, I138, V139, Y142, M150, H153, I154, Y155, I157, A158, A161, M165, I174, L175, C176, A182, V191, I192, Y194, L195, A196, V198, A199, A221, I224, L225, A227, F228, A231, F242, F245, I246, I248, F250, V257, A259, Y264, L265, A271, F281, I283, F284, Y285, Y286, M287, M295, L299, L300, F309, L310, I317, F326, A332, M333, M336, I346, L347, V349, V350, V353, L354, L356, I359, F361, A370, A377, A378, V381, C382, L384, M385, F392, I396, L397, A417, F419, A420, V421, A423, L424, A425, A427, Y429, L432, F433, I436, L437, V440, L444, L455, I457, L458, F463, F471, L474, C475, Y478, L486, F487, Y499, I504, F511, L515, C518, I519, L521, I522, V531, L532, L534, L535, F549, L553, F563, F575, I577, I578, H579, V584, Y586, A588, W591, M596, V603, L607, F614, V615, W619, V653, Y657, L661, L664, M665, L668, F675, V676, C678, I679, I680, A692, V695, L696, L699, V704, I708, I710, F715, F721, F724, Y728, I736, A746, C747, M750, I751, I768, F769, F770, V774, L778, F806, W832, L885 |
| 476 | Glutaredoxin-1 | P35754 | V6, I10, V15, V16, V17, F18, I19, C26, A29, I32, L33, I48, I57, L61, V73, F74, I75, L86, L95, L99, A104 |
| 477 | Vascular endothelial growth factor receptor 2 | P35968 | V136, I148, C150, L161, C162, A163, F185, I187, I192, A195, V198, C200, A202, I223, L244, C246, A248, V254, L292, I294, V297, Y305, C307, A309, V322 |
| 478 | Tyrosine-protein kinase BTK (EC 2.7.10.2) | P35991 | V219, A221, L233, L235, Y241, A254, I264, A291, V427, I429, I432, F442, M449, L457, V458, Y461, V463, C464, I470, I472, I473, L482, L486, L498, C502, V505, C506, A508, M509, L512, H519, L522, A523, A524, C527, V529, V535, V537, F540, V568, I580, W581, F583, V585, L586, M587, W588, I590, I610, A622, I629, M630, C633, W634, F644, L647, I651 |
| 479 | Chitinase-3-like protein 1 | P36222 | L24, V25, C26, Y27, Y28, C41, L46, L50, C51, I54, I55, Y56, F58, A59, L76, Y77, L80, L90, L93, L94, V96, F101, F106, I109, A110, F119, I120, V123, L127, F132, L135, L137, A138, W139, F150, L153, I154, M157, F161, L172, L173, L174, A176, A177, L178, A180, I185, I191, I194, L198, F200, I201, I203, H218, H219, L222, A240, V241, M244, L254, V255, M256, I258, F265, V274, A276, A295, Y297, I299, V316, Y318, A319, W325, V326, Y328, V334, V338, L341, A349, M350, V351, A353, L354, F359, F370, L372, A375, I376 |
| 480 | Phosphoglucomutase-1 | P36871 | L22, V26, Y35, A36, F39, I40, I43, I44, A55, L57, V58, V59, A70, I71, I74, A75, I77, A78, A79, I83, L86, I88, L94, A98, V99, I103, I106, I112, I113, L114, A116, F127, I129, I147, C160, L163, V165, F184, V186, V192, Y195, L199, L208, L212, L218, I220, I222, A224, V228, Y232, V233, I236, L237, L241, F257, A269, L272, M276, F283, A285, A286, F287, M295, I296, L297, V304, V310, A311, V312, I313, I320, F323, F331, A332, M335, L341, A345, F362, L371, L373, C374, I386, L392, W393, A394, V395, L396, A397, W398, L399, I401, V409, I412, L413, F424, V433, A438, M441, L445, M449, F454, V468, L490, L492, F494, I500, V501, F502, I514, L516, Y517, I518, I528, L536, L539, A543, L549 |
| 481 | Receptor-type tyrosine-protein kinase FLT3 (EC 2.7.10.1) | P36888 | L143, L182, C231, A233, L268, I270, C272, A274, C330, F369, F418, A420, A443 |
| 482 | Bone morphogenetic protein receptor type-1A | P36894 | A428, I437, V450, V473, V496, L499, W504, A509, L515, L521, M524, V530 |
| 483 | Activin receptor type-1B (EC 2.7.11.30) | P36896 | A401, Y410, H423, V446, M469, M472, W477, A482, L488, L494, L497, V503 |
| 484 | TGF-beta receptor type-1 | P36897 | A399, F408, H421, V444, M467, I470, W475, A480, L486, L492, L495, I501 |
| 485 | Guanine nucleotide-binding protein-like 1 | P36915 | I363, C365, V366, F368, L376, I377, L380 |

TABLE 5-continued

| TARGETS | | | |
|---|---|---|---|
| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
| 486 | Tumor necrosis factor receptor superfamily member 3 | P36941 | C80 |
| 487 | Pigment epithelium-derived factor | P36955 | L54, A55, A57, F61, L65, Y66, V78, L80, V85, A86, A88, L89, L92, A96, I104, L108, Y122, L125, V129, V143, F144, F154, L158, V184, M188, I205, L207, L208, V210, A211, F213, F231, M244, C261, A264, I274, I275, L293, I298, A310, V314, L317, V325, L329, L337, I346, L353, H358, A360, F362, Y388, L390, F394, I395, F396, V397, L398, L407, F408, I409, I412 |
| 488 | Serine/threonine-protein kinase receptor R3 | P37023 | L405, V418, V441, L464, M467, W472, L483, L489, I492 |
| 489 | TGF-beta receptor type-2 | P37173 | C51, C61, C84, V85, A86, V87, V100, C121, F133, C136, C138, I147 |
| 490 | Electron transfer flavoprotein subunit beta | P38117 | V6, L7, V8, V13, A45, V46, A49, V61, I62, A63, V64, I75, A78, L79, A83, I87, H88, V89, V91, A105, V107, L108, L111, A112, L119, V120, A139, A150, L160, V162, A179, V180, V181, A183, A201 |
| 491 | 40S ribosomal protein S19 | P39019 | V6, F14, L18, A19, F53, A57, A58, A61, L64, V99, A100, V103, L104, V113, L131, A135 |
| 492 | 60S ribosomal protein L3 | P39023 | A45, F46, L47, I56, V76, I78, V79, M84, V87, I89, V105, C114, M153, I160, V162, A164, H165, M168, A178, V185, L194, A197, V207, I217, V219, I220, V222, V231, I284, I314, F320, F330, V331, M332, L333, L345, L347, I368, M382 |
| 493 | Collagen alpha-1 | P39060 | M1454, V1461, I1467, V1469, L1581, L1583, V1584, A1585, L1586, A1600, C1604, A1608, A1619, F1620, L1621, L1628, I1631, V1632, I1642, W1654, L1657, V1679, W1685, V1690, W1691, H1692, C1706, W1709, A1720, L1723, L1728, L1729, C1736, I1741, V1742, L1743, C1744, I1745 |
| 494 | Glial cell line-derived neurotrophic factor | P39905 | V127, F190, A205 |
| 495 | Thrombopoietin | P40225 | L33, L56, V60, L62, A81, I84, L85, V88, L91, V95, A98, L111, L114, V118, I148, F149, F152, L156 |
| 496 | Thrombopoietin receptor | P40238 | L30, L31, C40, F41, F45, L48, C50, F51, W52, L65, Y67, C77, C93, F95, V101, L103, F104, L107, L109, V111, V127, V130, L132, A134, I139, A141, L150, I152, W154, F164, L165, Y167, L234, L246, Y252, W269, W272, L396, I401, L406, L408, W410, A418, Y423, Y427, W435, V437, L438, A444, L449, L451, Y457, A463, Y470, W474, W477 |
| 497 | B-cell antigen receptor complex-associated protein beta chain | P40259 | V61, M63, C65, W76, A105, L107, I109, Y120, C122 |
| 498 | Alcohol dehydrogenase class 4 mu/sigma chain (EC 1.1.1.1) | P40394 | A24, A25, V26, L27, F34, I39, V41, V49, I51, I53, A55, I58, H64, V65, V76, I77, V78, H80, A82, V96, V102, I103, L105, L107, C116, C124, L135, A136, F142, C144, V149, H151, F152, F158, V163, V164, V169, A170, I172, A176, V181, C182, L183, I184, F188, Y192, A194, A195, C207, V208, V209, F210, L212, L217, V219, I220, C223, I231, I232, I234, A244, I253, V265, L266, V274, F278, A290, L291, C294, V302, V303, F331, V340, L343, V344, L354, L357, F364, I367, F371, V383, L384 |
| 499 | Leptin | P41159 | I35, I38, L72, M75, L79, Y82, I85, I97, L101, L104, L108, A112, A146, L150, L154, M157 |
| 500 | Extracellular calcium-sensing receptor | P41180 | A46, V115, I135, F320, A321 |
| 501 | Aquaporin-2 | P41181 | I112, L116, A127, C181, M183, A186, A190, A192 |
| 502 | Glycine--tRNA ligase (EC 3.6.1.17) | P41250 | M124, L128, F133, A137, L157, I161, W165, F169, L189, V203, A214, L218, L222, M239, L254, L280, A301, I304, F305, F308, A323, A324, A349, I351, F354, V368, A369, L373, A380, A387, L392, A395, I401, V405, L406, F409, I410, I413, Y416, L417, V420, L427, F429, W445, A447, I458, V459, C461, C466, L469, L480, A482, A503, I504, V515, I521, I542, L551, V574, I575, F579, L581, I584, M585, Y586, V588, F589, F593, F605, F607, V611, A612, C616, V618, L619, F627, L634, L638, V643, Y658, V666, A667, F668, V670, I672, A684, L686, I695, A697, L702, I705, V706, V719 |
| 503 | T-lymphocyte activation antigen CD86 | P42081 | A36, L38, C40, L53, V54, V55, L95, L97, L100, C110, I111, I112 |
| 504 | Glutamate receptor 1 | P42261 | I25, I27, L30, F31, A41, F42, L46, L55, M70, F74, V82, A84, I85, F86, V94, L97, C101, V106, F108, I109, F113, F121, V122, L123, L125, L129, A132, L133, I136, I137, F145, V146, Y147, V161, A165, I177, L192, V200, V201, V202, C204, L209, L213, I216, I217, Y228, I229, L230, A231, L233, F235, F243, A248, V250, F253, V256, I266, W270, V281, A291, L292, V297, V299, M300, A303, F304, L307, A320, I337, A340, L341, L349, V353, L366, V368, Y409, I410, V411, Y419, V420, L422, F429, Y435, Y438, C439, V440, L442, A443, A444, I446, A447, L456, A466, M477, V478, L481, |

TABLE 5-continued

| TARGETS | | | |
|---|---|---|---|
| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
| | | | A486, V488, A489, V490, A491, L493, I495, I503, F509, L512, I514, I516, M517, I518, I647, L653, A654, Y661, F672, F673, M684, Y687, M688, V695, V697, M704, V707, Y714, A715, Y716, L717, L718, Y725, Y746, I748, A749, V760, A763, V764, L765, L767, L772, L773, L776, W780, W781 |
| 505 | Glutamate receptor 3 | P42263 | I34, I36, L39, F40, A50, F51, V55, F69, L71, V86, F90, V98, A100, I101, F102, M110, L113, C117, F124, V125, F129, F137, V138, I139, M141, L145, A148, I149, L152, L153, F161, V162, Y163, I177, A181, V193, M209, Y217, L218, I219, C221, I226, L230, V233, V234, Y245, M246, L247, A248, L250, F252, V260, A265, I267, F270, V273, V280, F283, W287, A298, A301, L303, A308, L309, A313, I314, V316, I317, A320, F321, L324, A337, I354, A357, L358, M366, I370, I383, V385, I425, V426, V427, Y435, V436, Y438, L445, Y451, Y454, C455, V456, L458, A459, Y460, I462, A463, L472, A482, M493, V494, L497, A502, I504, A505, V506, A507, L509, I511, I519, F525, L528, I530, I532, M533, I534, I665, L671, Y679, F690, F691, M702, Y705, M706, V713, V722, V725, F732, A733, F734, L735, L736, Y743, Y764, V766, A767, V778, A781, V782, L783, L785, L790, L791, L794, W798, W799 |
| 506 | Phosphatidylinositol 4,5-bisphosphate 3-kinase catalytic subunit alpha isoform | P42336 | M16, L21, V22, C24, L25, L26, M30, I31, V32, C36, L42, I45, L49, A53, L61, I69, F70, V71, V73, F82, F83, L89, L92, L94, F95, L99, V101, I117, A120, I121, V125, F128, V136, F139, I143, L144, C147, A150, A163, Y165, I181, I190, V192, V193, I194, L209, I211, V220, I221, A222, A224, L239, L244, L252, V254, C255, C257, Y260, F261, L262, L267, Y270, Y272, I273, C276, L285, L293, L327, I330, L334, I336, I338, A341, I354, Y355, V356, I360, Y361, V376, L387, Y389, I393, L396, A399, A400, L402, C403, L404, I406, C407, V409, C420, L422, A423, L429, F430, L443, L445, L452, L456, V461, L473, L475, V484, I492, A496, L531, I534, L540, L551, C558, V559, I564, L565, L568, L569, L570, V580, A581, M583, V587, I593, A598, M599, L601, L602, V611, F614, A615, V616, C618, L619, L628, Y631, L632, L635, V636, V638, L639, L648, L649, V650, L653, L654, A657, L658, I663, H665, F667, F668, W669, L671, V680, F684, L686, L687, L688, Y691, C692, A694, C695, Y698, L699, L702, V706, A708, M709, L712, L715, I718, L719, L735, M739, F744, A747, L748, F751, L755, L761, L764, C769, I771, L779, L781, W783, I788, M789, L792, L793, I799, F801, L807, L812, L814, I816, I817, M820, W824, L831, M833, L834, L839, L847, I857, I860, L877, H878, L881, A893, L896, F897, C901, A902, Y904, C905, V906, A907, F909, I910, L911, I913, I921, M922, V923, L929, F930, H931, F934, F937, L938, F954, F960, L961, I962, V963, I964, C971, F977, F980, C984, A987, Y988, A990, I991, A995, F998, I999, L1001, F1002, M1004, M1005, M1010, L1013, F1016, I1019, Y1021, I1022, L1026, A1035, F1039, M1043, W1051 |
| 507 | Protein AF-9 | P42568 | V7, L11, L13, H15, A17, V34, V36, F47, V48, V51, V52, F53, Y71, I82, L83, I85, V87, F89, Y102, L104, F131, L135, I522, I526, I530, V555, L558 |
| 508 | Dipeptidyl aminopeptidase-like protein 6 | P42658 | V131, V133, F156, V165, A201, L202, V220, L242, A245, I255, F256, I257, I262, W291, L292, Y293, A303, A314, I318, L328, L356, H357, V358, L361, L368, M370, Y382, I383, V394, A395, V396, W398, I407, C411, A413, W429, F447, H462, I463, V487, I500, F502, L514, A517, V520, L528, C536, F550, C554, V564, H565, L606, M608, I610, L624, L625, M649, V650, A655, V656, V657, L672, V676, M689, V692, M695, V706, A707, V708, Y716, L717, I721, F733, C735, A738, I742, F745, A749, A751, L757, Y767, V772, V776, L785, I786, I787, H788, I795, F797, H799, L807, I839, F843 |
| 509 | Leukemia inhibitory factor receptor | P42702 | V81, I112, L134, L153, V170, V176, L211, H216, V218, I220, V254, F269, C270, C271, V277, A280, I299, V314, F316, I327, A329, I349, C351, W353, L371, F397, Y406, F408, L410, A412, I427, V431, L451, F459, C466, I468, V494, I509 |
| 510 | Wiskott-Aldrich syndrome protein | P42768 | F258, L267, L270, F271, L281, I290, F293, I294, V303, L326, I438, L470 |
| 511 | Growth/differentiation factor 5 | P43026 | C400, F409, C433, A447, I476, C498, C500 |
| 512 | Platelet-activating factor acetylhydrolase IB subunit alpha | P43034 | V111, M123, V124, A126, I132, L146, V153, L165, A166, C168, I174, L176, W177, M188, V195, V198, I207, V208, A210, I216, W219, V237, V240, I249, A250, C252, V258, V260, L272, V279, C281, L311, L312, I320, L334, V341, I353, L354, C356, A357, L362, W365, Y367, V383, V396, V404, V406 |
| 513 | Cathepsin K (EC 3.4.22.38) | P43235 | I44, L48, Y126, V130, C136, C139, W140, A141, A147, L148, L159, L162, L167, V168, V171, A185, F186, V189, I195, Y201, M211, A219, C221, I227, L235, A238, V239, V242, V245, V247, A248, I249, A251, F256, F258, Y264, Y265, L274, H276, A277, V278, L279, A280, V281, Y283, W292, I294, W302, I308, M310, A311, A317, C318, I320, A321, L323, A324 |
| 514 | Hemagglutinin [Cleaved into: Hemagglutinin HA1 | P43258 | A11, L13, C14, L15, A19, V26, V36, L42, V43, I51, C52, I58, C64, L66, I67, L70, L71, C76, F79, L86, F87, V88, F94, C97, Y98, Y100, Y105, A106, L108, V112, A113, L118, F125, A138, C139, F147, F148, L151, L154, L164, Y178, W180, |

TABLE 5-continued

| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
|---|---|---|---|
| | TARGETS | | |
| | chain; Hemagglutinin HA2 chain]/strain A/Duck/Hong Kong/64/1976 H3 | | V182, H183, H184, Y195, V202, V204, I230, I232, Y233, I236, V237, V242, L243, I245, L251, I252, A253, F258, I274, C281, I282, I288, V309, L316, A317, A334, W343, Y351, A373, A425, L447, L455, C466, F467, I469, H471, C473, C477, I478, I481, A495 |
| 515 | Hemagglutinin [Cleaved into: Hemagglutinin HA1 chain; Hemagglutinin HA2 chain]/strain A/Duck/Hong Kong/231/1977 H3 | P43259 | A11, L13, C14, L15, A19, V26, V36, L42, V43, I51, C52, I58, C64, L66, I67, L70, L71, C76, F79, L86, F87, V88, Y94, C97, Y98, Y100, Y105, A106, L108, V112, A113, L118, F125, A138, C139, F147, F148, L151, L154, L164, Y178, W180, I182, H183, H184, Y195, V202, V204, I230, I232, Y233, I236, V237, V242, L243, I245, L251, I252, A253, F258, I274, C281, I282, I288, V309, L316, A317, A334, W343, Y351, A373, A425, L447, L455, C466, F467, I469, H471, C473, C477, I478, I481, A495 |
| 516 | Hemagglutinin [Cleaved into: Hemagglutinin HA1 chain; Hemagglutinin HA2 chain]/strain A/Goose/Hong Kong/10/1976 H3 | P43260 | A11, L13, C14, L15, A19, V26, V36, L42, V43, I51, C52, I58, C64, L66, I67, L70, L71, C76, F79, L86, F87, V88, F94, C97, Y98, Y100, Y105, A106, L108, V112, A113, L118, F125, A138, C139, F147, F148, L151, L154, L164, Y178, W180, V182, H183, H184, Y195, V202, V204, I230, I232, Y233, I236, V237, V242, L243, I245, L251, I252, A253, F258, I274, C281, I282, I288, V309, L316, A317, A334, W343, Y351, A373, A425, L447, L455, C466, F467, I469, H471, C473, C477, I478, I481, A495 |
| 517 | Neuronal acetylcholine receptor subunit alpha-4 | P43681 | A141, H142, A155, V165, I189, L191 |
| 518 | 2-C-methyl-D-erythritol 2,4-cyclodiphosphate synthase/strain ATCC 51907/DSM 11121/KW20/Rd | P44815 | H11, L19, I20, I21, V26, F32, I33, A34, V40, A41, L42, H43, A44, L45, A48, I49, L50, A52, A53, I58, L77, L78, A81, V85, I92, V95, I97, I99, M106, I110, M113, A115, I117, A118, L121, I125, V128, A132, I147, A148, C149, A151, A153, L154, L155, I156 |
| 519 | Aspartoacylase (EC 3.5.1.15) | P45381 | I11, V14, A15, I16, F17, V31, I41, A57, L69, F73, A93, I96, F100, I111, I112, F113, M122, C124, L126, L128, L136, I137, M139, F140, I143, V154, L156, I170, V175, I177, V179, M195, M198, A202, L203, F205, I206, F209, I220, V222, I225, A241, L247, V281, V283, A294, F295, A296, I308 |
| 520 | Short/branched chain specific acyl-CoA dehydrogenase, mitochondrial | P45954 | A72, I76, M83, V93, L97, M103, I105, V107, V122, L123, V124, I125, L128, A129, A133, V135, A136, C139, I146, L149, I150, L163, L166, C175, A181, A192, L201, I208, A211, A214, L216, F217, L218, V219, M220, A221, I232, F235, L236, V237, L244, C261, L263, V268, V270, L276, A286, I295, I297, A298, A299, M301, L302, L304, A305, C308, I316, L332, L343, A346, A353, A354, A367, A370, A374, A378, C385, V400, A407 |
| 521 | Chemokine XC receptor 1 | P46094 | A26, W27, V28, F29, A30, L32, A33, V36, L37, C39, L40, F42, L46, V47 |
| 522 | Large proline-rich protein BAG6 | P46379 | V19, V21, A35, V39, F42, I46, V50, L59, L72, V77, I82, L84 |
| 523 | Vesicle-fusing ATPase (EC 3.6.4.6) | P46459 | V23, I74, F121, V514, A551, A554, L623, L627, L677 |
| 524 | Neurogenic locus notch homolog protein 1 | P46531 | C423, C438, C449, C456, C461, C487, C525, C942, C1056, C1180, C1454, C1467, C1496, C1509, L1515, C1536, L1574, V1575, V1576, V1577, V1578, L1585, F1592, L1596, L1600, I1616, V1676, L1678, I1680, C1685, A1696, V1699, A1700, L1703, A1705 |
| 525 | 40S ribosomal protein S10 | P46783 | L15, F16, M21, A23, V45, A48, M49, L79 |
| 526 | E3 ubiquitin-protein ligase NEDD4 (EC 6.3.2.—) | P46934 | G451, Y463, L499, L529, L563, Y785, F858, F948, M964, I979, L988, A990, L992, F996, A1008, W1011, F1012, I1015, M1019, F1027, F1054, F1056, I1057, V1060, A1061, M1063, A1064, V1065, L1071, F1075, Y1080, M1083, L1084, M1093, L1104, F1119, I1121, V1143, Y1151, V1155, M1168, F1171, F1175, L1178, I1179, I1184, F1187, L1192, M1196, C1197, W1207, V1223, I1224, F1227, W1228, A1230, V1231, L1242, L1243, V1246, F1257, L1260, F1269, V1271, L1290, L1292, L1301, L1305, I1309 |
| 527 | 3-hydroxyanthranilate 3,4-dioxygenase (EC 1.13.11.6) | P46952 | L32, I48, L64, V66, L85, V89, V100, V104, L116, Y119, L194, V211, A213, L230, L248, L255, A272 |
| 528 | F-actin-capping protein subunit beta | P47756 | A9, L25, L39, L60, V119, Y120, A129, V131, L133, I134, H152, V154, V156, A165, Y167, L169, V173, M174, V217, M220, I224 |
| 529 | Tumor necrosis factor ligand superfamily member 6 | P48023 | A147, L149, L160, L181, I183, Y189, V191, V195, F197, L207, H209, V211, L257, V259, F276, L278 |

TABLE 5-continued

TARGETS

| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
|---|---|---|---|
| 530 | Stromal cell-derived factor 1 | P48061 | I59, A61, I72, I79 |
| 531 | Glycine receptor subunit beta | P48167 | V80, V82, V84, I86, Y101, V103, I105, W111, L116, L128, L163, I165, V171, I179, L181, C183, L187, F190, C197, M199, L201, L211, F213, C255, V256, V258, F260, L262, V273, I280, V281, F288, L309, A328, L329, L333, C336, V350, M353, A370, A470 |
| 532 | Transcription factor SOX-9 | P48436 | V114, A116, L123, L135, L139, F154 |
| 533 | G protein-activated inward rectifier potassium channel 4 | P48544 | W108, A139, L168, A206, V207, I208, L217, V221, I234, A236, L238, L252, I257, L274, M289, V301, V303, L305, A318, Y322, F351, A368 |
| 534 | T-complex protein 1 subunit epsilon | P48643 | A33, A41, M48, A75, I77, I87, M91, V109, V110, A113, L116, L123, I133, A140, A144, A169, L173, A186, A189, A192, V204, I229, M239, A246, I248, A249, I250, L251, F255, I289, I292, A297, L299, A300, I301, C302, A310, L314, L319, A321, I330, I333, A356, V359, V373, I374, I385, F386, I387, L402, A405, V408, I409, L412, V419, A424, A425, I427, A430, V433, A437, F451, A452, A454, A461, V477, L510, A520, I527 |
| 535 | Protein ERGIC-53 | P49257 | V64, I80, V82, A83, V93, W94, A99, V106, V108, F110, V112, A120, L123, A124, W126, Y127, A128, V137, F138, V147, F150, F151, I165, I167, I168, I174, F194, V201, A203, I205, L212, V214, I216, A231, F244, I246, A248, H257, V259, F262, F265 |
| 536 | Alpha-aminoadipic semialdehyde dehydrogenase | P49419 | L33, L42, Y55, C70, I77, A78, V80, V92, A95, A98, W102, V114, I117, L121, I125, L128, L131, V132, L134, M136, V147, Y150, V151, I153, C154, A157, I179, L187, V188, I190, I191, V198, A199, V200, Y201, A206, I207, A208, M209, I210, C211, V214, C215, L216, W217, L225, I226, V228, A229, V230, I234, L238, A246, I247, L250, C252, I257, A260, M261, A262, V267, L269, L270, V286, L294, A302, I303, I304, A305, V314, A318, A321, A326, A333, L336, F337, I338, V346, L350, Y369, L372, F381, A384, V385, A388, Y408, V409, I413, V414, A424, A430, I432, L433, V435, F436, F438, V444, L455, I459, F460, W470, Y516 |
| 537 | Alanine--tRNA ligase, cytoplasmic (EC 6.1.1.7) | P49588 | I10, F14, F17, F18, A42, A44, M46, F49, A69, A70, C75, I76, F97, L101, W104, C115, M117, A118, L121, L122, Y134, V135, F138, C152, W156, C184, C187, I190, H191, A200, L212, W215, L217, F219, I220, I238, M242, L244, L247, V248, Y258, F263, Y266, I270, A288, A294, Y295, V297, L298, A299, H301, A302, I305, V307, A308, L309, L324, I327, L328, A331, V332, A335, L339, F346, A347, L349, V350, V353, L357, F361, I375 |
| 538 | Prolactin-releasing peptide receptor | P49683 | A44 |
| 539 | Cartilage oligomeric matrix protein | P49747 | C287, C292, C328, C351, C387, C410, C448, C484, C504, F531, L539, L570, A571, V572, F577, F582, H587, V588, Y596, A597, I600, F601, F609, Y610, V611, M613, A629, A631, I635, L637, A639, V640, L650, A653, L654, W655, V664, W684, L686, H688, Y694, I695, V697, M717, L722, V724, F725, C726, I732, W734, A735, L737, C741 |
| 540 | Presenilin-1 | P49768 | V89, C92, M93, V96, A136, I213, L226, A231, A234, L235, A246, V261, A285, V379, L381, F386, Y389, V391, L392, V393, A396, C410, I414, I439, M457 |
| 541 | Bis(5'-adenosyl)-triphosphatase (EC 3.6.1.29) | P49789 | F23, A24, V36, L37, V38, C39, L58, V65, V69, H94, V99, A139, L142 |
| 542 | Presenilin-2 | P49810 | V95, C98, M99, V102, I219, L232, A237, A240, L241, A252, V267, A291, L362, F367, Y370, L373, V374, A377, C391, I395, I420 |
| 543 | Glycine amidinotransferase, mitochondrial (EC 2.1.4.1) | P50440 | V66, W72, V78, I79, V80, A83, A86, C87, V88, V95, A97, Y107, F115, A123, I127, M130, C131, L134, L163, Y164, A166, M167, I171, L172, I173, V174, I179, I180, A182, M184, A185, W186, A195, Y196, I200, Y203, M218, L222, I229, V245, C252, F253, A255, A256, I259, A261, I265, F266, A267, V272, M281, I294, I304, F308, I310, I311, V316, L317, F330, M353, M360, V362, L363, M364, L365, V370, M371, V372, I379, F383, V393, I395, A398, L401, F405, H406, W408, C410, V412 |
| 544 | Serpin H1 | P50454 | L102, V107, A109, A203, V226, M271, L324 |
| 545 | Dynamin-2 (EC 3.6.5.5) | P50570 | V13, L16, F20, L29, I34, A35, V36, V37, A42, V47, L48, F51, V52, F56, L57, L69, L71, L73, I74, A81, F83, F91, V97, I120, L122, V124, V129, L132, L134, I135, L137, I140, I152, I156, I160, I164, I171, L172, A173, V174, A177, A186, A190, V193, I201, V203, I204, L207, A216, I232, V234, F259, Y265, A269, L277, L281, L285, I289, L293, L300, L304, L305, F336, F340, F370, L374, L384, I388, I392, A408, F409, V413, V417, C424, C427, V428, V431, L435, V439, C442, L452, I459, V460, I475, I479, L526, I528, Y541, F543, L545, L550, W552, I572, F586, A587, I588, F589, I603, L605, C607, V613, W616, F620, V625, V664, M675, I679, M683, I691, L695, L699, L729, A732 |

TABLE 5-continued

| TARGETS | | | |
|---|---|---|---|
| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
| 546 | Palmitoyl-protein thioesterase 1 | P50897 | V36, V88, V95, L99, L105, F120, A123, V124, H143, F147, C160, I163, V181, A183, Y195, F201, L202, A203, I205, Y215, L222, V228, F230, L258, L263, L269, L283 |
| 547 | Sodium/potassium-transporting ATPase subunit alpha-2 | P50993 | H42, L44, L49, A66, L102, A106, C109, V133, V138, V169, I170, V183, V184, L188, V189, A199, L201, I203, C209, V211, C241, F242, C247, A252, I255, V256, A272, I286, A297, A318, I320, F321, I325, L334, V340, A346, C354, V362, C372, L379, M384, A387, M389, W416, A418, L419, I422, A423, L425, C426, A429, V440, A453, L454, V465, L488, I490, H491, H500, V501, L502, V503, M504, I511, L519, Y539, L542, F552, C553, L557, L580, C581, F582, V583, L585, M588, A594, V596, A599, V600, C603, A606, I608, I611, M612, A621, A623, A625, I630, I631, A642, A643, A657, A659, I685, V686, F687, A688, I698, V699, C702, V709, V716, A721, L722, A725, I727, I729, A730, M731, I746, L747, F752, V759, L764, I765, Y775, L777, F790, L799, I807, A816, L819, L841, V842, L846, A850, I854, Y866, I869, L870, F875, L880, W887, C915, A918, F919, F920, A921, I923, V924, V925, V926, L931, I933, C934, L951, L955, A962, L975, M977, A988, I995, L1006, Y1020 |
| 548 | Ras-related protein Rab-7a | P51149 | L9, V11, I12, I13, L14, V19, L24, M25, Y28, V52, V57, M59, I61, A65, Y78, C83, C84, V85, L86, V87, F88, V90, L99, F106, F120, V121, V122, L123, V134, A139, C143, A156, V162, A165, F166, I169, A170, A173 |
| 549 | Ras-related protein Rab-27A | P51159 | L13, Y27, L96 |
| 550 | Transcription activator BRG1 (EC 3.6.4.—) | P51532 | M1462, I1465, V1466, V1469, I1501, F1507, I1510, I1514, L1525, V1529, C1533, A1536, L1553, F1557, V1560 |
| 551 | Galactokinase (EC 2.7.1.6) | P51570 | A16, V32, A34, L53, V64, V73, A107, V110, V113, A120, A127, V128, V130, V133, L139, A143, V147, A148, F152, L153, A167, C170, A173, V211, I222, C243, V246, L255, L263, A266, A278, H280, V281, A291, A292, A294, Y318, C322, L328, V329, A332, C351, L356 |
| 552 | Methyl-CpG-binding protein 2 | P51608 | L124, F132, L138, F142 |
| 553 | Fatty aldehyde dehydrogenase (EC 1.2.1.3) | P51648 | V8, L27, A29, L30, M33, V34, I41, I45, L49, V56, V61, V64, I68, M71, L75, V104, V105, L106, I107, F115, L117, I119, L122, I123, A125, I126, A127, A128, A131, V132, I133, I134, L150, L151, L159, Y160, L173, F182, V193, A196, A197, C214, I216, V225, C226, I229, Y234, C237, I247, L248, C249, I257, I261, I282, F288, I291, L294, I313, A314, V317, L318, V327, M328, I332, I336, L337, I339, A348, L359, A360, L361, Y362, V363, F364, M374, V388, Y410, F419 |
| 554 | C-C chemokine receptor type 5 | P51681 | Y187 |
| 555 | N-sulphoglucosamine sulphohydrolase (EC 3.10.1.1) | P51688 | A25, L26, L27, L28, L29, A30, L58, F60, A63, F64, V67, A75, L77, L81, M88, L107, L111, I120, I121, V126, V131, Y132, I152, I155, V159, F162, F171, F172, L173, Y174, V175, A176, F177, F193, C194, I207, A232, L236, Y240, V250, V253, L257, L267, I276, F278, L285, V296, A311, V313, L318, I322, L323, L348, A351, M376, V379, L386, F408, L411, L438, L464 |
| 556 | Arylsulfatase E | P51690 | M61, L163, L292 |
| 557 | Amyloid-like protein 1 | P51693 | F395, A398, V409, L413, L467, L477 |
| 558 | Potassium voltage-gated channel subfamily KQT member 1 | P51787 | W379, W392, I394, I396 |
| 559 | Chloride channel protein ClC-Ka | P51800 | V547, L558, A559, V567, Y579, V582, V594, L599, L618, L635, L641, A644, F648, V658, V668, M673, A676 |
| 560 | Ribosomal protein S6 kinase alpha-3 | P51812 | V85, A93, A98, I121, F129, V131, I146, L155, F165, V170, Y173, L174, A175, L177, A178, A180, L181, L184, L187, I189, I190, Y191, L194, I199, L201, H206, I207, L209, F212, A225, A236, H245, A249, W251, W252, F254, V256, L257, M258, M261, F268, I280, L281, L285, F290, A295, L298, L299, L302, A308, V318, I321, F327, L335, A347, C439, V450, I453, I464, I466, L467, Y470, I476, V491, V492, L501, L502, I505, L506, A516, L520, I523, V527, L530, V535, V536, H537, L540, I545, I557, I559, F562, M576, I601, L604, V606, L607, L608, Y609, M611, L612, F618, A619, I629, W645, A652, L655, V656, M659, L660, A670, V673, W678, V699, A702 |
| 561 | Cytoplasmic tyrosine-protein kinase BMX (EC 2.7.10.2) | P51813 | V442, V444, A461, L467, L472, V478, C479, V488, L497, L513, M516, C517, V520, C521, M524, L527, L537, A538, A539, C542, V544, V550, V552, V561, A580, V595, W596, F598, I600, L601, M602, V605, F606, V621, A637, M645, C648, F659, I666 |

TABLE 5-continued

TARGETS

| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
|---|---|---|---|
| 562 | Spermine synthase | P52788 | L9, F11, L13, L26, F30, A36, L48, A49, Y51, A59, L61, I63, V69, L71, L73, I89, V93, Y134, I150, I152, I161, I163, I181, V194, L195, I196, L197, I204, L205, I208, V216, M218, V219, C229, V259, L260, Y263, V273, I274, I298, L299, M303, V305, L306, F313, V348, Y358, V360 |
| 563 | Ephrin-A5 | P52803 | V34, W36, I50, V52, L58, V60, Y77, L79, C102, F118, F130, Y138, I139, L154, V156, V158 |
| 564 | Biliverdin reductase A | P53004 | V11, V12, V13, V14, V16, F42, A62, V70, A71, Y72, I73, H80, I84, F87, L88, V94, L95, V96, M100, A107, L110, H122, L136, L150, A166, F167, I170, L173, W175, L176, M201, V203, L205, L213, W215, F231, F258, I278, C281, L282, A285, I288 |
| 565 | Collagen alpha-4 | P53420 | L1468, L1494, Y1495, L1507, Y1541, W1542, L1543, V1563, C1566, A1567, V1568, C1569, A1571, F1601, H1604, C1622, F1631, L1632, C1634, C1641, C1683, V1685, C1686, V1687 |
| 566 | Dipeptidyl peptidase 1 (EC 3.4.14.1) | P53634 | C30, L35, W39, F41, V66, L68, A74, F84, I86, I87, F92, I94, F102, A103, F105, H127, W134, C136, F137, Y259, A262, M264, M266, A269, I271, L283, V288, Y294, Y304, L305, I306, A307, A311, L316, V317, Y347, Y352, M360, L364, M370, A371, V372, F374, F380, V407, L408, L409, V410, W423, V425, F439, I441, I450, A454, A456, A457 |
| 567 | DNA polymerase subunit gamma-1 (EC 2.7.7.7) | P54098 | F139, A143, A153, L157, W175, Y178, A194, L195, V196, F197, C202, A212, V213, A214, I215, A219, W220, C224, A242, L244, A253, L265, V266, V267, A276, I278, Y282, M289, M297, H298, A300, I301, L304, V359, M393, A397, V400, V406, F407, V422, A425, M427, L428, V432, Y434, L435, V437, W441, A448, L463, A467, F610, I798, W801, A804, I808, A839, L841, A847, V870, L874, A876, V878, A880, V887, A889, V891, I898, A899, A900, L902, A908, A915, A936, A982, A1045, L1061, C1077, I1079, A1082, W1099, V1100, V1101, A1105, V1106, Y1108, H1110, L1111, L1113, V1114, A1115, M1116, L1119, C1130, Y1139, L1140, V1141, A1149, A1150, A1152, L1153, C1162, M1163, A1165, L1168, A1178, A1182, V1183, C1197, A1217, L1218 |
| 568 | Tyrosine--tRNA ligase, cytoplasmic (EC 6.1.1.1) | P54577 | I14, L27, L36, I38, Y39, F53, M56, I59, F62, C67, V69, I71, F73, H77, A78, A85, V94, Y96, Y97, V100, I101, M104, L105, Y129, L136, A171, L172, A181, F183, I191, F192, A195, L199, V208, H209, L210, M211, I232, L234, V241, L245, V260, L261, I264, V267, I277, Y289, L295, F299, V304, L309, V313, L317, L321, I324, L336, A339, A340, I370, V372, I375, I392, V394, V402, V403, L406, L415, V420, V421, V422, L423, L440, L441, C442, A443, L455, V469, L491, F495, I497, A503, F510, I517, C519, I527 |
| 569 | Ephrin type-A receptor 4 (EC 2.7.10.1) | P54764 | I67, V72, L84, I89, A94, V97, Y98, I99, I101, F103, L105, V114, F122, L124, I148, V157, V173, F181, Y182, L183, A184, F185, A190, I192, A193, L194, V195, V197, V199, C204, A212, F214, M245, C247, C273, C276, C325, V344, L346, V398, I400, Y409, F411, I413, A415, V419, V434, A440, V447, V457, L459, V476, I500, Y509, F511, V513, A515, A519 |
| 570 | Alpha-N-acetylglucosaminidase (EC 3.2.1.50) | P54802 | V32, L35, V36, L67, V75, V77, V83, A84, A85, A86, L89, Y92, C99, Y132, I154, M157, A158, I162, L164, A165, A167, I174, V178, A181, I189, A197, F198, A200, L230, M233, F236, V241, L242, F245, V253, F271, L281, I291, F295, L296, Y309, L327, V334, M338, A345, F354, A368, L378, L379, V380, V390, F397, F402, I403, W404, C405, M406, L407, L420, A430, A444, V453, V454, L457, V475, F478, A479, A490, A493, V501, L517, V518, V536, F537, A539, W540, L550, F556, L560, L561, L563, A567, V568, L571, V572, Y575, L584, L591, V597, L598, A599, L602, L603, L606, V609, L610, F616, L618, L622, A625, A635, Y638, L646, L648, W649, A659, L666, V667, Y670, Y671, W675, F678, L679, L682, V701, V709, V724, A727, Y734 |
| 571 | Galactocerebrosidase | P54803 | L83, L95, L98, F437, V576, V607 |
| 572 | Adenylate kinase 2, mitochondrial | P54819 | I16, A18, V19, L20, L21, A26, A32, L35, F39, V41, L64, V80, L82, I83, F96, L97, L98, F101, A108, L111, M115, L122, V125, I126, F128, L134, L135, I139, L143, H145, A182, L183, L187, L197, Y200, Y201, I210, A212, I223, F227 |
| 573 | Allograft inflammatory factor 1 | P55008 | L24, L47, F50, Y54, F57, L59, I65, L70, M73, L74, L86, I90, F101, Y103, F106, L107, A116, L118 |
| 574 | Transitional endoplasmic reticulum ATPase | P55072 | L26, V28, V38, V39, L41, M46, V57, L59, A67, V68, C69, V71, I82, M84, V88, L92, V94, I100, I102, C105, I114, V116, I119, Y134, L135, F139, L153, V154, V161, F163, V165, V166, C174, V176, A177, V181, C184, A214, I216, V220, I241, L242, L243, Y244, I254, A255, A257, V258, A259, I269, I274, L286, A289, F290, A293, A299, I300, I301, F302, I303, L306, I309, A310, I324, V325, L328, L329, M332, L335, V341, I342, V343, M344, A345, A346, I353, L357, F363, V367, I369, L381, V399, A400, H406, V407, L411, L414, C415, A418, A419, A422, A439, V447, F452, A455, L489, V493, V514, L515, F516, L527, A528, A530, I531, A532, F539, I540, I542, L547, L548, V559, F563, A566, C572, V573, L574, F575, F576, I582, V600, I601, M608, I619, I620, A622, L639, I645, L657, A676, L687, I690, A694, I731, H735, A739, V747, I752, L762 |
| 575 | Fibroblast growth factor 8 | P55075 | L74, V83, V85, A93, A95, A102, I126, C127, M128, I135, C145, F147, A158, M169, A170, F171, V190, F192 |

TABLE 5-continued

| TARGETS | | | |
|---|---|---|---|
| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
| 576 | Laminin subunit beta-2 | P55268 | C519 |
| 577 | Cadherin-8 | P55286 | V70, F109, I118, A120, L124, L134, A138, I154, I155, V157, V176, V189, A223, I224, I225, V242, I244, A246, L262, V264, A300, F324, L353, V355, A357, V378, I380 |
| 578 | Cadherin-15 | P55291 | L138 |
| 579 | FAD-linked sulfhydryl oxidase ALR (EC 1.8.3.2) | P55789 | A114, A115, A146, L153, F166, L170, C171 |
| 580 | Eukaryotic translation initiation factor 6 | P56537 | F7, I13, A17, Y23, C24, L25, V26, A27, F34, F38, V49, I53, I59, V64, L70, L71, V72, I84, V97, L104, V107, A115, L116, V117, L129, L133, V142, V148, V153, L160, V161, L173, L177, V179, V186, I193, A194, M197, V198, C203, A204, F205, C206, V218, F222 |
| 581 | Ubiquitin-associated and SH3 domain-containing protein A | P57075 | L28, A38, A41, L42, A53, L57 |
| 582 | Ras-related protein Rab-25 | P57735 | V15, V16, L17, I18, V23, L28, L29, V47, A60, V61, A63, I65, A69, Y74, A76, Y81, Y82, A85, A88, L89, L90, V91, F92, L94, V103, L110, V120, M121, L122, V123, V135, A140, A144, A156, L157, V162, A165, F166, V169, L170, I173 |
| 583 | Anthrax toxin receptor 2 | P58335 | F43, L45, Y46, F47, V48, L49, V55, I62, V66, L69, A70, L80, F82, I83, V84, F85, I91, I102, L109, I120, L124, A127, I131, I142, I143, I144, A145, L146, A159, A163, V173, Y174, C175, V176, V178, L186, I189, L206, I209, I213 |
| 584 | Spike glycoprotein/SARS-CoV (Severe acute respiratory syndrome coronavirus) | P59594 | V328, V337, I345, A350, L374, V382, A384, F387, V388, V389, I397, A398, I405, A406, Y410, L412, C419, V420, L421, A422, F483, V496, V497, V498, L499, V510 |
| 585 | CD81 antigen | P60033 | Y127, L131, A134, V147, H151, C156, V169, L174, C190, I194 |
| 586 | Phosphatidylinositol 3,4,5-trisphosphate 3-phosphatase and dual-specificity protein phosphatase PTEN (EC 3.1.3.16) | P60484 | L25, I33, A34, M35, A39, I50, V53, F56, L57, I67, Y68, L70, I101, F104, C105, L108, A120, A121, I122, H123, A126, V133, M134, I135, C136, A137, L139, A148, A151, Y155, Y174, V175, Y180, L193, F195, M198, F200, F206, V217, F241, V249, V255, F257, H259, M270, F271, F273, V275, F279, V317, L325, A328, F341, V343 |
| 587 | Interleukin-2 | P60568 | L34, L37, L38, L41, I44, L45, I48, M59, F62, F64, M66, L73, H75, L76, C78, L79, L83, L86, V89, L90, F98, L105, I106, I109, I112, V113, F123, I134, V135, F137, L138, W141, F144, C145, I148 |
| 588 | Proteasome subunit alpha type-6 (EC 3.4.25.1) | P60900 | A31, V40, A41, V42, C47, A48, V49, I50, V51, C78, V79, V91, A94, Y96, A99, L114, C115, I118, A119, C136, M138, I139, L140, I141, V151, C154, A165, A167, A168, V195, A198, I199, C201, L202, V217, V219, V220 |
| 589 | Cell division control protein 42 homolog | P60953 | I4, C6, V7, V8, V9, A13, V14, C18, L19, L20, F28, V36, F37, V42, V44, I46, Y51, L53, L55, A59, L70, Y72, V77, F78, L79, V80, C81, F82, V84, V85, F90, V93, W97, V98, I101, C105, F110, L111, L112, V113, I117, L129, I137, A142, L145, A146, L149, V155, C157, A159, L165, V168, F169, A172, I173, A175, A176 |
| 590 | Pterin-4-alpha-carbinolamine dehydratase | P61457 | L17, W25, A33, I34, F40, A46, F49, V53, A57, V73, I75, L77, L85, L92, A93, I96, V99 |
| 591 | Lysozyme C (EC 3.2.1.17) | P61626 | C24, L26, A27, L30, M35, L43, A44, W46, M47, C48, L49, A50, I74, F75, I77, C83, C95, C99, L102, I107, A108, A110, V111, C113, A114, V117, V118, I124, W127, C134, V139, C146 |
| 592 | Beta-2-microglobulin [Cleaved into: Beta-2-microglobulin form pI 5.3] | P61769 | V29, Y30, L43, C45, V47, F50, H51, L59, L60, F82, L84, Y86, F90, Y98, A99, C100, V102, H104, W115 |
| 593 | Transforming growth factor beta-2 | P61812 | C317, C318, L319, F326, C350, L388, I390, C413 |
| 594 | Epididymal secretory protein E1 | P61916 | V37, C42, C47, Y55, V59, F61, I101, Y109, L124, W128, L130, L138, F139, C140, W141 |
| 595 | Ras-related protein R-Ras2 | P62070 | Y15, L17, V18, V19, V20, V25, L30, F34, V40, C55, I57, A62, L64, I66, L67, A70, M78, M83, F89, L90, L91, V92, F93, V95, F101, I104, F107, I111, V114, F120, M122, I123, L124, I125, L131, V137, L145, A146, A156, A158, V164, A167, F168, L171, V172 |
| 596 | 40S ribosomal protein S7 | P62081 | L27, L30, L36, L40, L43, I51, A59, I61, V64, F72, L79, V93, I95, L130, L133, V134, V156, F173, V176, Y177, V185 |

TABLE 5-continued

| TARGETS | | | |
|---|---|---|---|
| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
| 597 | Actin, aortic smooth muscle | P62736 | A9, L10, V11, C12, C19, A21, A31, V32, F33, I36, V37, Y55, A60, L67, I73, M84, I87, W88, F92, L106, L107, A110, L112, M121, I124, M125, F126, F129, V131, A133, M134, V136, A140, V141, L142, L144, I153, V154, L155, V161, H163, V165, I167, L173, A176, M178, L180, L182, A183, L187, L191, I194, L195, A206, I210, V211, I214, C219, V221, A222, I250, I252, F257, C259, L263, F264, I276, I284, C287, I289, I291, L295, Y296, A297, V300, L301, Y308, I311, M315, I319, W342, I347, F354, W358, I359, I371, V372, C376 |
| 598 | 40S ribosomal protein S26 | P62854 | A78 |
| 599 | 60S ribosomal protein L11 | P62913 | L22, A36, L40, V70, V74, I82, L87, F105 |
| 600 | Guanine nucleotide-binding protein G | P63092 | L43, L44, L45, L46, I56, M60, I95, L99, A102, I103, I106, L113, I131, F146, A150, L153, V159, C162, C174, A175, F178, I182, I185, F219, M221, V224, A243, I244, F246, V247, V248, Y253, F273, L282, V287, I288, L289, L291, L296, L297, V301, A337, I341, F345, A351, I372, C379, I383, H387 |
| 601 | Inward rectifier potassium channel 2 | P63252 | V161, L245, I250, I267, L298, A362, F374 |
| 602 | Casein kinase II subunit beta | P67870 | F21, C23, V25, I30, L36, L39, A49, I53, A75, A76, L79, Y80, I83, H84, Y87, I88, I94, M97, F106, C114, M119, L120, V133, C137, F159, F163, L167 |
| 603 | Actin, alpha cardiac muscle 1 | P68032 | A9, L10, V11, C12, V19, A21, A31, V32, F33, I36, V37, Y55, A60, L67, I73, M84, I87, W88, F92, L106, L107, A110, L112, M121, I124, M125, F126, F129, V131, A133, M134, V136, A140, V141, L142, L144, I153, V154, L155, V161, H163, V165, I167, L173, A176, M178, L180, L182, A183, L187, L191, I194, L195, A206, I210, V211, I214, C219, V221, A222, I250, I252, F257, C259, L263, F264, I276, I284, C287, I289, I291, L295, Y296, A297, V300, L301, Y308, I311, M315, I319, W342, I347, F354, W358, I359, I371, V372, C376 |
| 604 | Ubiquitin-conjugating enzyme E2 L3 (EC 2.3.2.23) | P68036 | A3, L7, I14, F22, W35, I39, Y46, A50, F51, I53, I55, F70, H76, I79, V104, I105, L108, L111, V112, L125, F136, A140 |
| 605 | Actin, alpha skeletal muscle | P68133 | A9, L10, V11, C12, V19, A21, A31, V32, F33, I36, V37, Y55, A60, L67, I73, M84, I87, W88, F92, L106, L107, A110, L112, M121, I124, M125, F126, F129, V131, A133, M134, V136, A140, V141, L142, L144, I153, V154, L155, V161, H163, V165, I167, L173, A176, M178, L180, L182, A183, L187, L191, I194, L195, A206, I210, V211, I214, C219, V221, A222, I250, I252, F257, C259, L263, F264, I276, I284, C287, I289, I291, L295, Y296, A297, V300, M301, Y308, I311, M315, I319, W342, I347, F354, W358, I359, I371, V372, C376 |
| 606 | Hemoglobin subunit beta | P68871 | L4, V12, L15, V24, A28, L29, L32, L33, L49, V55, V61, L69, F72, L79, L82, F86, C94, L111, V114, L115, F119, V127, A130, Y131, V134, V135, A139, A141, A143 |
| 607 | Hemoglobin subunit alpha | P69905 | V11, A13, A14, W15, V18, A22, Y25, A27, A29, L30, M33, F34, V56, A64, A66, A70, V71, V74, M77, L81, A89, C105, L106, V108, L110, L114, A124, L126, F129, L130, V136 |
| 608 | Tyrosine-protein phosphatase non-receptor type substrate 1 | P78324 | A51, L53, C55, I66, W68, I106, I111, C121, V122, F168, C170, F175, W184, A213, V215, L217, V226, C228, V230, L246, I250, V271, C273, V275, F278, L285, W287, C331, V333 |
| 609 | Retinal-specific ATP-binding cassette transporter | P78363 | F1968, L1970, L1971, F1982 |
| 610 | Oxidized low-density lipoprotein receptor 1 | P78380 | C155, C172, L179, L180, I182, I191, I195, F202, W203, M204, L206, C243, A244, I246, V251, A260, I263 |
| 611 | Protein jagged-1 | P78504 | F35, L37, C71, F75, L79, Y132, L134, V136, A138, I161, A177, F179, I183, V185, C196, C200, C229, C262, C265, C293, C324, C333, C522, C560, C664 |
| 612 | Reelin (EC 3.4.21.—) | P78509 | C674, C700, C1772, C1794, C2485, C2507 |
| 613 | ETS-related transcription factor Elf-3 | P78545 | V72, W75, I76, C95, L102, L110, F114, L121, I279, F303, F305, V311, A312, L329, M333, L342, F354 |
| 614 | C-C motif chemokine 7 | P80098 | C34, C35, C59, A63, V64, I65, F66, I74, A76, V83, F86 |
| 615 | Protein crumbs homolog 1 | P82279 | C107, C221, C336, C1332 |
| 616 | Mothers against decapentaplegic homolog 3 | P84022 | V12, L15, A34, V35, L38, V39, L42, A54, I55, I65, I67, V77, Y88, C89, C109, A112, V120, C121, V122, H126, Y127, V130, C233, I235, Y237, V244, A250, M255, V257, L271, V283, I290, V294, L296, V303, A305, C307, I313, V315, C320, I334, I342, F343, F348, V363, C370, I372, M374, F376, W380, C394, I396, L398, L400, L407 |
| 617 | Disabled homolog 2 | P98082 | I124, A155, V168 |

TABLE 5-continued

| TARGETS | | | |
|---|---|---|---|
| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
| 618 | Basement membrane-specific heparan sulfate proteoglycan core protein | P98160 | A4204, F4206, F4214, F4219, I4230, L4232, V4234, L4242, L4243, L4244, F4259, I4260, L4262, L4264, L4269, V4270, Y4273, L4275, A4280, V4296, A4298, I4307, V4332, I4334, C4355, V4356, L4359, L4376 |
| 619 | Polycystin-1 | P98161 | A290, I294, W305, F307, H323, Y325, V333, A335, L337, V352 |
| 620 | Nuclear factor NF-kappa-B p100 subunit | Q00653 | L65, V80, A89, I91, V93, V96, H105, A106, H107, I119, C120, A131, L136, M150, L174, A178, V190, L192, F194, A196, I217, L228, V246, L248, L249, V260, F262, I287, V288, F289, V305, L307, L309, F323, Y325, Y326, H493, I496, I504, I511, V520, L531, H532, A534, V543, L546, A551, A563, M564, H565, A567, L578, H605, A607, V608, L619, A637, H639, A641, V650, L653, A675, L687, V742, L778, L782, L794, A795, L817, L818, L831, A834, L835 |
| 621 | Beta-1,4 N-acetylgalactosaminyltransferase 1 (EC 2.4.1.92) | Q00973 | I281, I299, V308, V309, I310, A311, V325, M330, L342, A343, V347, Y351, F361, V382, F426, C429, V449 |
| 622 | Ankyrin-2 | Q01484 | F35, A39, V47, L65, A67, H69, L70, A71, A72, V80, L83, A100, L101, H102, A104, V112, V113, L116, L134, Y135, A137, A138, V145, V146, L149, A168, V169, A170, A178, L182, H197, A199, A200, A208, L212, V226, L237, H238, A240, A241, V248, A249, L252, L270, H271, V272, A273, M281, V282, L285, L303, H304, C305, A306, A307, V314, V315, L318, L336, H337, M338, A339, A340, C347, V348, L351, V371, A372, V380, L384, L468, H469, A471, A472, V480, L501, H502, I503, A504, V513, L516, L534, H535, I536, A538, V545, A546, L549, L567, H568, V569, A570, A571, A579, L582, V602, A603, V611, L615, M839, V970, V974, I991, I993, V1004, C1006, V1009, A1027, I1031, V1033, V1077, V1079, I1081, A1085, F1147, F1151, A1152, V1153, V1154, I1164, V1179, A1181, A1187, V1194, L1196, V1220, L1222, I1233, M1235, I1237, L1260, L1261, V1289, A1297, W1300, L1301, I1302, C1304, A1314, V1317, A1328, F1330, V1332, A1334, A1342, L1344, C1346, F1347, C1348, L1389, F1403, L1413, V1415, L1428, F1430, L1503, L3573, I3576, A3577, L3587, A3588, I3601, L3616, L3617, W3620, A3628, L3633, L3637, I3645, M3649 |
| 623 | Collagen alpha-3 | Q01955 | F1448, L1474, F1475, L1487, Y1521, W1522, L1523, I1545, C1548, V1550, C1551, F1583, F1586, C1604, F1613, L1614, C1616, C1622, C1662, V1664, C1665, M1666 |
| 624 | Inositol polyphosphate 5-phosphatase OCRL-1 (EC 3.1.3.36) | Q01968 | C28, L30, L32, A33, L41, I42, I43, I56, I58, F62, C64, C82, I84, V86, F96, I98, C104, F107, L108, V111, A114, F242, F243, V244, W247, V249, L258, W261, L262, I271, Y272, C273, I274, F276, L279, A285, W297, V301, M322, M323, L324, L325, I326, F327, A328, V358, A359, V360, F362, F364, F369, C370, I371, V372, L376, I393, F399, I411, V417, W419, L420, L423, Y425, V435, L447, L453, Y479, A496, W497, C498, I501, L502, L519, V527, A529, F531, I533, V535, F572, F574, V577, I589, F599, W614, A617, L624, I632, L634, V636, V638, V643, L657, L659, L661, L669, C679, F680, L684, L687, C688, I738, L741, V742, L745, A749, L755, L765, I768, L772, V787, A788, A790, L791, F794, L795, V802, I803, C811, L812, V824, I825, L828, V835, F836, L839, F842, L843, L846, V855, I860, A861, F864, L868, F890, L891 |
| 625 | Tumor necrosis factor receptor superfamily member 17 | Q02223 | C24, C37, C41 |
| 626 | Pro-neuregulin-1, membrane-bound isoform | Q02297 | C196, C221 |
| 627 | Collagen alpha-1 | Q02388 | C2876, C2925 |
| 628 | Desmoglein-1 | Q02413 | C58, I70, A71, I73, V83, Y85, F100, I109, I111, V115, F123, I125, C127, A129, L143, V145, V147, L179, I218, L225, L235, V237, C255, I257, I259, I290, A305, L331, V333, L337, L347, I349, V351, I372, V374, V376, V394, A409, Y423, L433, L442, Y460, I464, I479, I481 |
| 629 | Desmocollin-2 | Q02487 | L185, L195, V201, F209, I211, I231, I233, I252, I304, L311, Y319, L321, I323, V325, C341, I343, V376, F404, L417, V419, L433, I435, V437, V458, V460, A495, I506, W517, L533, Y545, I547, A551, L563, I565, I584, C585, A633, L635, V648, I650, V652, L664, V666 |
| 630 | Aminoacylase-1 | Q03154 | Y19, L20, A34, F38, A42, V52, V60, V62, L63, H80, V83, A98, M114, L122, M141, F158 |
| 631 | Trefoil factor 2 | Q03403 | C31, C52, C58, C69, F70, L73, C81, C101, C118, F119 |
| 632 | Mevalonate kinase | Q03426 | V8, A10, V14, H20, A21, V27, L29, V31, L33, L39, L41, V49, L51, L91, V109, A111, F112, L113, L115, Y116, L117, I119, C120, L129, L143, A147, A148, V151, C152, L153, A154, A155, A156, L157, L158, I185, A189, A206, V207, A213, L214, L233, L234, V250, I268, C275, M282, L305, V310, L315, L318, L331, C339, V353, L360, A374, V377, I379 |

TABLE 5-continued

TARGETS

| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
|---|---|---|---|
| 633 | Complement factor H-related protein 1 | Q03591 | Y53, I70, C87, V110, I127, C129, I249, C251, C266, A296, C317 |
| 634 | 1,4-alpha-glucan-branching enzyme (EC 2.4.1.18) | Q04446 | L31, L38, F45, I59, F69, C88, A92, A95, V98, L100, V136, L142, V144, V145, I146, I157, A161, V164, L197, I199, Y200, H203, V204, I206, Y216, F219, V223, L224, I227, L230, Y232, C234, I235, L237, M238, I240, M241, H243, F249, I253, F256, F257, A258, A259, L269, L272, V273, A276, I281, V283, L284, L285, V287, V288, H289, A292, L300, F303, Y310, F311, H319, I334, L335, F337, L338, L339, I342, W345, L346, Y349, F351, F354, F356, V359, M362, L363, Y364, A389, L390, Y392, L393, M394, L395, A396, L399, V400, I410, A411, M417, A419, L420, I439, W443, L446, W455, M457, I460, L464, I474, A475, Y476, A477, H480, L490, A491, M503, I513, I517, L519, H520, M522, I523, L525, I526, H528, L530, Y535, L536, F538, M539, F543, L549, F551, A563, L580, F583, M587, L590, W596, L597, I613, I614, A615, F616, L621, L622, F623, I624, F625, V638, F646, L650, A654, L683, V685, I687, V691, A692, L693, I694, L695, V698 |
| 635 | Glutamate carboxypeptidase 2 (EC 3.4.17.21) | Q04609 | F61, I70, L74, F77, L83, A84, A93, V108, L110, Y113, V115, L117, I128, I130, V158, F161, A163, F164, L174, V175, Y176, V177, A180, L188, C196, I200, V201, I202, A203, V214, A217, V225, I226, L227, Y228, Y234, A236, V253, I258, L259, A264, L268, A274, V287, V294, I297, A302, L305, L306, M309, A313, W319, V329, V342, M344, I346, I355, V358, L362, V372, I373, L374, H377, V382, F383, I386, A393, V394, H396, I398, V399, F402, L405, I416, L417, F418, A419, W421, A423, F426, L428, L429, A435, L442, V447, A448, Y449, I450, A452, I456, Y460, L462, V464, C466, L469, M470, V474, L477, W93, W497, L515, F521, V523, F524, F525, I530, A531, A535, Y537, Y549, L551, H553, V555, L561, V562, F565, F570, H573, V576, A577, V579, M583, V584, L587, A588, C597, Y600, A601, V603, L604, Y607, A608, I611, V627, L632, V636, F639, A643, F646, L661, M664, L668, M669, L671, F675, L679, F686, Y687, H689, I691, Y692, A693, F705, I708, L712, V728, I732, Y733, A735, A736, V739, A742, A743, L746 |
| 636 | Copper-transporting ATPase 1 (EC 3.6.3.54) | Q04656 | V10, I12, V14, M17, C22, V23, I26, I30, A48, I50, Y52, L62, I66, L173, M175, V177, I189, I193, A211, I213, Y215, V222, M225, I229, F234, F281, I283, V292, I295, L299, A317, V319, L331, I335, I381, I383, M386, C391, V392, I395, I399, V419, Y421, L431, I435, C490, I492, V503, I506, L510, I516, L520, A528, V530, Y532, I542, I546, L566, L568, V570, I582, L586, C595, A604, I606, Y608, I618, I619, I622, A629, V837 |
| 637 | Neurogenic locus notch homolog protein 2 | Q04721 | C315, C491, C642, C1184, C1443, C1455, C1484, L1490, C1509, C1522, W1529, L1547, I1549, V1551, L1558, F1565, L1573, V1623, L1625, I1627, C1632, F1640, A1646, A1647, L1649, L1650, A1651 |
| 638 | Activin receptor type-1 (EC 2.7.11.30) | Q04771 | V402, L411, V424, V447, L470, L473, W478, L489, L495, I498 |
| 639 | Acetylcholine receptor subunit epsilon | Q04844 | V49, I51, L53, V55, I61, V74, I76, I78, W80, V105, W106, V111, L112, A123, V128, V130, V136, W138, A142, C148, V150, W159, F166, V176, F178, V230 |
| 640 | Focal adhesion kinase 1 | Q05397 | V39, H58, V64, I67, I68, V72, C82, L87, L124, Y128, F137, F146, F147, Y148, A160, A168, L171, C173, L174, L188, Y194, L203, F207, A217, F228, L241, F243, F244, L247, F258, L272, A273, I274, I280, A294, I302, L316, L318, A323, V329, A331, A337, M340, A341, L343, I344, C348, A369, I373, V436, V451, A452, I453, C459, F468, A472, M475, I483, V489, I490, V495, I497, I498, M499, C502, L507, L511, I524, Y526, A527, L530, A533, L534, L537, I547, A548, A549, V552, L553, V554, V560, L562, F565, L567, A579, M589, A590, V605, M607, F608, C611, M612, I615, V631, I635, L651, L654, M655, C658, W659, F669, L672, L676, V928, L931, V932, M938, I942, Y950, V957, L961, L964, V968, I983, L990, L997, A1004, M1020, A1024, L1027, A1028, A1031, L1034, I1038, A1041 |
| 641 | External core antigen/genotype F2 (isolate Brazil/w4B) (HBV-F) | Q05495 | Y35, F38, L44, L45, F53, A63, H81, L84, A87, A98, V118, L129, L130, F132, H133, V144, L148 |
| 642 | Glutamate receptor ionotropic, NMDA 1 | Q05586 | A71, V107, Y109, A111, Y158, I163, A236, L269, A279, A284, I301, V309, I314, I400, V401, F408, V409, C436, C454, C455, F458, C459, I460, L462, L463, L466, V479, M501, M502, L505, A510, M512, I513, V514, A515, L517, L538, I540, L541, V542, L672, Y681, A682, V689, F693, M702, Y703, M706, A717, V721, L726, A728, F729, I730, W731, V735, L736, F738, L746, F758, I760, M762, V772, I776 |
| 643 | Tyrosine-protein phosphatase non-receptor type 11 (EC 3.1.3.48) | Q06124 | W6, F7, H8, A16, L19, L20, F29, L30, A31, L43, V45, I54, I56, Y63, L65, F71, A72, L74, A75, L77, V78, Y81, L88, I96, L98, L102, A122, L125, L126, F135, L136, V137, F147, V148, L149, V151, I172, L190, L193, V194, V209, L210, L212, L216, I221, A223, I226, V230, L233, F247, L254, I282, L283, F285, V290, Y304, A307, I309, I310, Y327, I328, A329, C333, V338, F341, W342, M344, V345, V352, I353, V354, M355, C367, Y370, W371, Y380, M383, V385, L401, L403, |

TABLE 5-continued

TARGETS

| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
|---|---|---|---|
| | | | V419, Y422, H423, F424, W427, V439, F442, L443, V446, I453, V459, V460, V461, H462, C463, A465, I467, G468, F473, I474, V475, I476, I478, L479, I480, I482, I483, V488, I492, V494, I498, V501, M508, V509, Y515, F517, I518, Y519, A521, V522, I526 |
| 644 | Tyrosine-protein kinase BTK (EC 2.7.10.2) | Q06187 | L31, V427, I429, I432, F442, A446, M449, M450, L452, L457, V458, V463, C464, I470, I472, I473, L482, L486, L498, M501, C502, V505, C506, A508, M509, L512, H519, L522, A523, A524, C527, V529, V535, V537, F540, L542, V568, I580, W581, F583, V585, L586, M587, W588, I590, Y591, Y598, I610, L616, A622, V626, M630, C633, W634, F644, L647, I651 |
| 645 | Acetylcholine receptor subunit delta | Q07001 | V52, V54, L56, L58, I79, W83, V108, W109, L115, V131, V133, V139, W141, A145, C151, I153, W162, F169, I179, L181, I253, V330 |
| 646 | Early activation antigen CD69 | Q07108 | Y97, A109, C113, L120, A121, I123, L132, W142, V143, L145, C173, V174, L176, I193, C194 |
| 647 | Neuraminidase (EC 3.2.1.18)/strain A/Duck/Ukraine/1/1963 H3N8 | Q07599 | M83, A92, F95, I104, I112, V114, I115, F119, V120, F130, F131, L132, L156, V159, A174, A176, W177, A179, A181, C182, M189, V191, V193, A200, V201, A202, I204, V214, L222, C231, I232, C236, Y237, W238, V239, M240, A249, Y251, I253, A256, I261, H273, I274, C277, C279, Y280, V286, C288, V289, C290, L302, I304, L315, C316, A317, I319, V346, F349, F351, V357, W358, M359, I363, F371, I373, L374, I376, V393, V394, L397, F406, L418, C421, F422, W423, V424, M426, W437, I443, V444, M445 |
| 648 | Prolow-density lipoprotein receptor-related protein 1 | Q07954 | F859, C861, C879, C895, F900, C902, I908, C914, C920, C936, C943, C955, C961, F982, C984, C1002, F1020, C1022, C1040, F1067, C1069, C1088, F1110, C1112, C1131, C1152, V1158, L1160, C1172, C2679, C2696, C2715, F2739, C2741, C2759, C2781, V2786, V2788, L2793, C2794, C2800, A2804, C2812, C2818, C2837, F2863, C2865, C2884, C2912, C2930, F3379, C3381, C3399, C3453, F3458, C3460, I3467, C3473, C3479, C3494, F3499, C3501, I3508, C3514, C3520, C3536, C3543, V3549, C3555, C3561, C3575, F3580, C3582, I3588, C3594, C3600, C3613, C3620, C3632, F3659, C3661, C3679, C3703, C3749, C3767 |
| 649 | Hemagglutinin [Cleaved into: Hemagglutinin HA1 chain; Hemagglutinin HA2 chain]/strain A/China: Nanchang/11/1996 H1N1 | Q07FI5 | V7, I20, C21, I22, A26, V33, V36, V43, L49, L50, L58, C59, L61, L67, L69, C72, V74, A75, W77, I78, L79, C84, L87, W93, Y95, I96, V97, Y108, L118, L122, V125, F128, F134, A150, C152, H154, L164, L165, W166, L167, L173, L177, V189, L190, V191, L192, W193, V195, H196, H197, Y208, Y214, V215, V217, V218, I243, Y245, Y246, L249, L250, I256, F258, A260, L264, I265, A266, Y269, A270, F271, A272, L273, F277, I281, I282, C291, C295, A301, I302, H312, I316, V323, L328, M330, V331, A348, M360, Y365, A387, I388, A439, L451, V458, L461, V465, L469, C480, H485, C487, C491, M492 |
| 650 | Hepatocyte growth factor | Q08048 | F43, C71, A72, C75, C85, A87, F88, V89, C97, W99, L119, W153, C178, C190, F191, C207, C233, W236, C261, C272, C284 |
| 651 | Interleukin-10 receptor subunit beta | Q08334 | L38, A54, L57, C74, F76, L87, V89, A91, V108, L127, M145, V156, V189, V191, L195, V208 |
| 652 | Epithelial discoidin domain-containing receptor 1 | Q08345 | M37, A72, W73, L87, V89, V97, V100, I141, M159, A161, V164, F166, L178, V180, L182, L191, Y194, A196, V208, L210, L231, F241, Y255, V256, W258, V268, M270, F274, F280, M283, V285, C287, A295, V301, C303, F305, V336, L338, A343, L346, C348, F350, L357, L358, F359 |
| 653 | Tyrosine-protein kinase ITK/TSK (EC 2.7.10.2) | Q08881 | I358, V388, I390, I393, A397, F403, A407, L418, V419, V424, C432, V434, L443, L447, L459, M462, C463, V466, C467, M470, L473, H480, L483, A484, A485, C488, V490, I496, V498, F501, V522, V541, W542, F544, V546, L547, M548, W549, V551, V567, I571, A583, I590, M591, C594, W595, F605, L608, L612 |
| 654 | ATP-binding cassette sub-family C member 8 | Q09428 | I701, I703, L708, M710, I711, V712, C717, L722, L723 |
| 655 | Potassium voltage-gated channel subfamily A member 1 | Q09470 | A347 |
| 656 | Neuraminidase (EC 3.2.1.18)/strain A/Chicken/Victoria/1/1985 H7N7 | Q0A2R1 | L86, V93, A104, I105, I113, V115, Y120, V121, C123, M130, Y131, A132, L133, L157, I158, C175, V176, C183, M190, I192, C193, V194, A201, A203, V205, Y207, A219, L223, C230, V231, C232, A238, V239, V240, M241, V254, M255, Y256, F257, I275, C278, C280, Y281, I287, C289, V290, C291, A298, I302, I303, I305, Y316, V317, C318, V321, L322, V349, F352, F354, W361, L362, F374, M376, L377, I379, A382, I396, V397, F409, I410, Y420, F424, Y425, V426, L428, V439, L446, I447, A448, L449, A465, I467 |

TABLE 5-continued

| TARGETS | | | |
|---|---|---|---|
| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
| 657 | Hemagglutinin [Cleaved into: Hemagglutinin HA1 chain; Hemagglutinin HA2 chain]/strain A/Duck/Germany/1949 H10N7 | Q0A448 | A26, V50, L58, C59, M60, Y65, L68, C71, V74, M76, I78, C83, W91, L94, I95, I101, C104, L115, I119, I125, M128, I138, C147, Y156, L159, L162, Y178, H186, L187, I188, I189, W190, I192, H193, Y205, I212, V214, I240, F242, V247, I253, F255, H257, L261, I262, A263, V267, L270, I277, C287, C291, F292, A345, Y362, A384, L458, L466, H482, C484, C488, A506 |
| 658 | Endogenous retrovirus group K member 13-1 Env polyprotein | Q0ED31 | A54, H65, A69, M94, M99, V100, M103, L110, W111, L115, V119, V154, I165, Y193, C220, V226, I227, L228, C230, C241, V244, I253, L261, I272, I286, I287, V288, H289, L290, V294, I296, C298, I327, A330, C332, I334, W339, L343, V346, L350, I359, I360, F361, H374, C378, F382, F383, Y384, C385, L390, F391, L410, C412, I414, I417, I418, A427, M428, I437, I443, I446, L447, L448, F462, W473, L477, Y480, V483, I485, V499, I542, L549, A552, I553, A555, L559, L560, V564, I567, L570, V574 |
| 659 | Carcinoembryonic antigen-related cell adhesion molecule 8 | Q0Z7S6 | L36, A45, V51, L52, L53, V55, Y65, W67, I79, I80, A105, L107, M109, V112, Y120, L122, V124, F138 |
| 660 | Spike glycoprotein/isolate N5 (HCoV-HKU1) | Q0ZME7 | F67, F103, V106, V125, I137, V138, A150, C151, C156, V162, L198, H201, F209, A211, Y212, A214, F222, Y236, V237, M238, C242, Y256, Y266, L267, L268, A279, C282, L333, C352, F383, V388, F391, A392, L409, C423, Y427, Y458, A477, I588, F589, L624, F633, A680, C719, C743, V765, I943, A1025, A1070, A1084, L1085, L1098, A1103, A1106, F1143, I1144 |
| 661 | NS3 protease | Q0ZNA6 | C16, V33, V35, V36, L44, A45, C47, V48, V51, C52, W53, V55, A59, L64, I71, L82, V83, W85, L94, L104, L106, V107, V113, I114, V116, V132, L135, L143, L144, C145, A150, V151, I153, F154, A164, A166, V167, F169, V170, V172, M175 |
| 662 | Calcium-activated potassium channel subunit alpha-1 | Q12791 | F815, L907, M922, C923, C943, A946, F955, L1026, A1037, I1060, A1104 |
| 663 | Potassium voltage-gated channel subfamily H member 2 | Q12809 | I30, A32, C44, F48, C49, L51, C52, A57, V59, C64, C66, A78, I82, A83, I96, A97, F98, C105, V110, V112, L127, A763, A778, I782, I787, I804, F805, V822, A824, L830, V841 |
| 664 | Glutamate receptor ionotropic, NMDA 2A | Q12879 | M112, I116, A136, M162, F170, F177, V187, V191, V203, V217, L248, L260, V292, L307, I408, V409, F416, V417, V419, C436, V440, C455, C456, F459, C460, I461, I463, L464, L467, L479, W493, M496, I497, V500, A505, V506, M507, A508, V509, L512, V522, V529, V535, M536, V537, V662, L665, F670, F682, I694, M701, M705, A716, A727, F728, I729, A732, A733, V734, L735, Y761, I763, A764, L765, I775, A778, L779, F782, M788, L791, V807 |
| 665 | Unconventional myosin-Ie | Q12965 | A1058, F1072, I1078, F1100 |
| 666 | Glutamate receptor ionotropic, kainate 2 | Q13002 | L36, F38, I41, A56, F57, A60, V61, I64, L71, I83, A91, A95, L99, V103, A104, A105, I106, F107, A115, V118, C122, V127, H129, I130, V147, L149, F153, L156, A159, I160, L163, V164, V172, V174, V175, L185, L188, A191, L197, L204, A211, L215, M218, V226, I227, F228, A235, A236, I238, L239, A242, M247, Y254, I255, F256, L259, L261, L264, M276, F279, L282, W296, M316, A320, A321, L322, M323, A326, V327, V329, V330, A333, M340, L345, W353, F359, I363, A366, I375, F387, L389, V391, I392, W405, L433, I434, V435, Y443, V444, F446, L453, F459, Y462, C463, I464, L466, L467, L470, I480, A490, M501, V502, L505, A510, L512, A513, V514, A515, L517, A518, I527, F533, L536, I538, I540, L541, Y542, L674, A675, I680, Y682, A684, M691, F694, M705, M709, V716, V718, V728, Y733, A734, F735, L736, M737, I742, L752, Y764, V766, I778, A781, I782, L785, L791, M794, W799 |
| 667 | T-lymphoma invasion and metastasis-inducing protein 1 | Q13009 | M40, A441, L446, V454, V467, L469, L474, F476, V497, I501, V502, V514, F515, C516, L517, A524, F527, L535, W538, I542, H543, A545, C546, A547, A551, L563, M616, C623, Y624, L639, M651, F662, A664, V666, A667, A668, I848, Y858, L873, A884, I895, I898, A903, L906, L920, V924 |
| 668 | Secretory phospholipase A2 receptor | Q13018 | F182, C204, C219 |
| 669 | Platelet-activating factor acetylhydrolase | Q13093 | I56, C67, M71, F80, L81, Y84, Y85, W97, I98, Y103, L111, L116, M117, L124, F125, A132, Y144, L146, V147, V148, H151, F156, I165, A168, F172, I173, A175, H179, A184, A186, Y189, V222, A226, C229, A232, L233, I239, I267, A268, V269, I270, A277, V279, I280, L283, F289, C291, I293, A294, A297, M299, V306, I310, L314, F315, F316, I317, I328, M331, C334, I344, F354, F357, A380, A387, L389, A390, F391, L392, F402, I422 |

TABLE 5-continued

| TARGETS | | | |
|---|---|---|---|
| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
| 670 | S-methyl-5'-thioadenosine phosphorylase (EC 2.4.2.28) | Q13126 | I12, I14, I15, L26, L45, C55, V56, L57, L58, A76, I78, A80, L81, H88, V89, I90, V91, C95, L98, I107, V108, I109, I110, A132, L152, A156, M169, V170, F186, A191, V193, V199, V202, L204, A205, I210, C211, Y212, A213, I215, A216, M217, A218, L250, I255, I258 |
| 671 | Glutamate receptor ionotropic, NMDA 2B | Q13224 | I35, I37, A38, V39, I40, V65, I81, I85, V97, V98, F99, A100, I108, A109, I111, L112, I115, A117, I123, L124, I126, A135, F146, A154, V156, M157, I160, M161, F169, I171, V172, F176, F182, I186, I190, V202, L205, I216, L220, L223, I228, L229, L230, Y231, C232, A237, I240, F241, A244, L249, W256, I257, V258, L261, V262, A263, L277, I278, V280, V293, I299, I300, A303, A304, M307, L308, I329, L335, L339, V342, V363, I364, I365, L367, V376, I408, V409, F416, V417, V419, C436, I440, C456, C457, F460, C461, I462, I464, L465, I468, L480, W494, M497, I498, V501, A506, Y507, M508, A509, V510, L513, V523, I530, V536, M537, V538, V663, L666, F671, F683, I695, M702, M706, A717, A728, F729, I730, A733, A734, V735, L736, Y762, I764, A765, I766, V776, A779, I780, L783, M789, L792, V808 |
| 672 | Chitotriosidase-1 (EC 3.2.1.14) | Q13231 | L24, V25, C26, Y27, F28, A32, A39, F41, L46, L50, C51, L54, I55, Y56, A57, F58, A59, M61, Y77, F80, L90, L93, L94, A95, I96, F101, F106, M109, V110, F119, V120, A123, L127, F132, L135, L137, W139, F155, L158, V159, L162, F166, L178, L179, L180, A182, A183, V184, A186, V191, V197, I200, A201, L204, F206, V207, L209, A211, H224, L228, V243, A246, V247, W250, L260, I261, L262, M264, F271, V281, A283, A302, Y304, V306, V322, Y324, I325, W331, V332, F334, F340, V344, L347, A355, M356, V357, A359, L360, F365, Y375, L377, I378, L381, C420 |
| 673 | Noggin | Q13253 | L66, V173, C184, V202, L203 |
| 674 | Butyrophilin subfamily 1 member A1 | Q13410 | A40, A46, L48, C50, A58, L63, W65, A73, V74, Y91, L109, I111, V114, Y122, C124, F126, L136, V137, L139, I208, V364, V379, F452, F460 |
| 675 | Mesothelin | Q13421 | I311, L315, I316, L323, C326, V327, L332 |
| 676 | Alpha-1-syntrophin | Q13424 | L13, V31, L33, L40, V42, V88, V90, I112, I114, A122, A123, L129, A134, I135, V138, L143, A151, V162, V163, L164, V166, M215, L236, I238, A241, L247, L249, A251, A257, I264 |
| 677 | Interleukin-18 receptor 1 | Q13478 | I28, V31, L38, H40, W56, V82, L83, F85, V88, Y96, F98, W107, L109, F136, C140, L154, A175, C185, H187, L189, C237, A239, L241, A278, L282, I284, C298, V300, L313 |
| 678 | Myotubularin | Q13496 | I185, L321, Y329, I350, L385, L388, L393, F438, A455, F475, L479, I539 |
| 679 | Sequestosome-1 | Q13501 | A8, L10, L47, V51, F55, A65, F77, A86, I97, I99, L394, M401, L413, L417, A427, I431 |
| 680 | Polycystin-2 | Q13563 | L736, L745, L770 |
| 681 | Myotubularin-related protein 2 | Q13614 | A88, V91, L105, V107, L112, F114, A127, L129, V131, I132, L151, I158, L161, F163, A164, I175, L179, F184, A194, W225, I227, C237, Y240, L244, V245, V246, I250, L255, V258, I267, V269, L270, A279, I281, C284, Y302, L303, A305, I306, I316, I318, F319, A321, A327, I353, L363, L366, Y371, W388, I392, I395, L396, A399, I402, A403, V406, V413, V414, V415, H416, A425, L427, L430, A431, M432, L433, M434, L435, Y439, I442, F445, V447, L448, V449, W453, F456, H458, F460, H466, A472, F480, L481, F483, I484, C486, V487, M490, A497, F498, F504, L505, I508, L509, F517, F520, L521, L533, L540, W541, I544, F551, L564, W576, Y579, Y580, I581 |
| 682 | Cullin-4B | Q13620 | L220, A223, V224, A226, L240, A243, V244, L256, L260, C264, L286, I289, M300, I303, I306, F307, L310, V315, I324, M327, F332, I336, I337, V342, I347, I350, L351, I354, L368, L371, L372, M374, L375, L378, Y381, F385, F389, Y397, V410, Y413, L414, V417, L421, L428, L440, V444, L448, L449, I456, L457, L461, L464, L465, L473, L476, L479, F480, L490, W494, I498, I505, V506, M515, V516, L519, L520, V526, I529, I532, C533, F534, F540, A543, M544, A547, F548, F551, I552, A560, L562, I563, A564, V567, L571, L587, I590, I593, F594, I597, V602, F603, F606, Y607, L611, A612, M629, L633, L645, M648, F708, F711, A734, L743, V745, F748, V752, I767, L778, L782, L785, A786, F808, I823, I850, A853, I854, M858, L869, V873, L886, I890, L893, M899, Y909 |
| 683 | Interleukin-10 receptor subunit alpha | Q13651 | A36, F39, H41, L43, V59, A60, L83, A98, V100, A102, F118, V123, L125, V130, Y157, F161, Y167, I169, V203, V205, V209 |
| 684 | Voltage-dependent L-type calcium channel subunit alpha-1S | Q13698 | A603, V610, V1010, A1023, A1312, L1329 |
| 685 | Laminin subunit gamma-2 | Q13753 | C550, C570 |
| 686 | Ectonucleotide pyrophosphatase/phosphodi-esterase family member 2 | Q13822 | C59, C76, C80, F90, C94, C118, C120, C124, C130, C131, W144, L166, I167, F169, V171, F174, Y178, M186, I189, L192, M202, Y206, Y222, H226, I228, V229, M233, F242, W254, L260, A264, I280, I286, I289, L295, V303, Y304, F306, M325, L329, V336, L339, M340, L343, C351, V352, I355, F356, V357, H360, M362, V365, C367, F372, L373, L390, |

TABLE 5-continued

TARGETS

| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
|---|---|---|---|
| | | | I393, I409, L412, Y424, I444, H445, L446, L447, V454, F477, M484, F488, V489, F495, V501, F504, I507, L509, Y510, M513, C514, L517, L534, M544, A603, V604, Y610, L613, F618, Y622, M628, W631, Y634, C652, V653, V659, A669, L681, F682, A692, A696, F697, V699, M702, V703, M705, A708, V712, W713, F716, V719, L720, V721, A725, V731, V733, I738, F739, V757, I762, V764, Y768, Y769, I771, I772, I795, L796, V816, M820, H823, A825, V827, I830, L833, L836, F838, I849, L850, L852 |
| 687 | Plakophilin-1 | Q13835 | A250, L254, A266, I269, C273, A279, V283, L292, V293, V303, A306, A307, A308, A310, L311, L314, V315, L338, I346, L350, L354, L367, A371, L372, L375, A376, V379, I380, V402, F403, A406, C409, L410, L434, M444, L450, I451, L454, M455, V458, V472, C475, M476, V478, L479, L482, L486, L543, A548, I549, Y552, L555, A567, C568, A569, A571, L572, L575, M582, M586, I590, L597, I600, V611, A616, L618, L619, M622, L628, M632, V636, F637, I657, A661, V665, L668, A670, A700, A704 |
| 688 | Bone morphogenetic protein receptor type-2 | Q13873 | L492 |
| 689 | Voltage-dependent L-type calcium channel subunit alpha-1C | Q13936 | I702, V1131, A1453, M1470 |
| 690 | Coactosin-like protein | Q14019 | C10, A12, A13, Y14, V17, W26, V27, F29, I36, F48, C52, L58, F59, A60, F61, V62, F64, A77, L78, I79, W81, I82, V101, V104, V105, I114, L120, I125, L129 |
| 691 | Heterogeneous nuclear ribonucleoprotein D0 | Q14103 | M99, I101, L104, L113, F117, L130, V143, V154, H160, I167, I184, V186, I198, F202, C226, I228, F230, V236, I239, H245, V247, I254 |
| 692 | Lysosome membrane protein 2 | Q14108 | V42, L43, F64, F66, F67, V69, I75, Y89, F102, I109, A111, I133, L136, I138, V140, V143, I156, L160, L167, V173, L177, I184, I188, L201, Y213, I228, C245, F256, F269, F273, C274, V287, A292, F293, Y295, A299, I301, L302, V323, V326, M337, F342, F349, V350, I353, I369, I376, L377, A379, I387, V389, F395, V396, F406, V408, M409, V415, A422 |
| 693 | Low-density lipoprotein receptor-related protein 8 | Q14114 | F52, C54, C72, C93, H97, I99, C111, C134, V142, C154, A158, F172, C174, L180, C192, F211, C213, A220, C234, C285, C340, I350, C351, C362, C374, L424, F426, I435, L437, I446, A454, A503, Y512, L570, V601, I634, A635, I651, C700 |
| 694 | Dihydropyrimidinase | Q14117 | L7, L8, I9, V14, V15, A23, V25, V27, V32, L35, A54, V59, L60, I64, H67, H69, M70, M75, I80, F83, A89, A90, L91, M97, I98, I99, F101, A102, L110, I111, A113, W117, A121, V125, C126, C127, Y129, L131, H132, V133, A134, V135, V142, M146, L149, V150, V155, F158, M160, M162, A163, Y168, V170, L175, A178, F179, C182, I185, A187, I188, A189, V191, H192, A193, H217, A229, A233, I234, I236, A237, L244, Y245, I246, V247, H248, V249, M250, A254, A255, I258, A261, V268, I273, A274, A275, L277, Y284, A292, A293, H295, V296, M297, L301, L311, M312, L314, L315, L320, C328, F330, F342, I345, V349, V352, M356, V358, I359, W360, V364, F374, V375, V377, A382, A383, I385, F386, I395, A401, I403, V404, I405, W406, I414, V423, F428, C433, V439, I441, V447, F462, I463, A469, I472, Y473, I476 |
| 695 | Desmoglein-2 | Q14126 | L58, L64, I85, Y87, I101, F102, L111, V113, L117, F125, L127, A131, L145, I147, I181, V210, I220, L227, L237, V239, A241, A256, V258, I260, I293, V295, A308, V334, L336, V340, V352, I375, V377, F413, A415, Y428, W437, I438, I447, Y465, V467, I469, A471, V485, I487, V515, W544, V554, L556, I568, F570, I572, L586, L588 |
| 696 | Cytoplasmic dynein 1 heavy chain 1 | Q14204 | L2837, V2838, M2953, L2956, I2993, L3115, V3352, V3472, L3645, I3669, V3780, V3790, I3811, L3856, L3947, V4031, L4158, L4331, F4482, L4514 |
| 697 | Filamin-C | Q14315 | F42, C46, L50, L57, L60, L64, L70, I71, L73, L74, V100, V102, A103, L104, F106, L107, I122, I130, L131, L133, I134, L137, I138, I143, L165, I169, V173, F181, W185, A190, L191, A193, L194, V195, A199, C203, A218, A221, M222, A225, L229, V231, V234, I235, I240, V250, M251, Y253, L254, A278, A296, V300, A305, V312, V338, H348, V350, V352, F354, I359, V366, A590, F592, V593, V594, C626, V628, Y630, Y638, V640, V642, A656, C665, A688, I692, A697, C728, I740, I741, I742, V756, V758, V1065, F1083, I1085, A1090, V1119, Y1121, Y1129, I1131, I1133, I1140, A1147, I1149, V1158, A1160, V1178, A1183, I1192, I1214, Y1216, Y1224, I1226, I1228, Y1230, V1242, V1253, V1265, F1273, V1275, V1292, Y1312, V1314, Y1316, H1324, V1326, V1328, V1342, V1353, F1371, V1373, A1378, V1407, Y1409, Y1417, V1419, I1421, I1428, V1435, V1437, V1446, V1457, V1467, A1472, V1481, V1503, V1515, V1517, Y1519, V1524, I1531, V1533, V1542, I1554, A1556, F1562, I1564, A1566, A1569, I1578, V1600, Y1602, Y1610, I1612, I1614, Y1616, I1621, I1628, A1630, A1636, C1639, I1666, V1668, A1673, V1678, V1682, I1704, A1708, Y1714, I1716, I1718, I1725, V1732, A1734, V1793, V1802, I1822, V1824, H1834, M1836, I1838, I1845, V1862, F1880, I1882, V1916, Y1918, Y1926, I1928, V1930, F1932, I1937, A1944, I1946, I2003, F2005, H2013, V2015, V2017, V2033, A2041, |

TABLE 5-continued

TARGETS

| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
|---|---|---|---|
| | | | V2044, V2064, V2098, Y2100, Y2108, I2110, I2112, F2114, V2126, V2128, V2254, Y2274, V2276, H2286, V2288, V2290, V2306, V2317, F2335, I2337, V2371, Y2373, V2375, Y2381, V2383, I2385, I2392, V2399, V2401, A2402, A2408, L2411, L2421, V2431, L2433, A2436, I2440, V2444, I2466, H2476, I2478, V2480, F2482, I2494, V2508, L2515, F2526, V2528, A2533, V2561, Y2563, A2567, Y2571, I2573, I2575, Y2577, I2583, A2590, A2635, V2638, A2648, V2658, C2660, A2663, V2694, Y2696, V2698, L2706, V2708, W2710, V2715, V2722 |
| 698 | UDP-glucose 4-epimerase (EC 5.1.3.2) | Q14376 | V5, L6, V7, H17, V19, L20, L22, V30, V31, I32, L49, V52, V60, A72, L73, L76, F82, A84, V85, I86, H87, Y104, L115, I118, M119, V124, L127, V128, F129, A133, V135, Y136, L144, H148, I164, I168, W178, A180, V181, L182, L183, A191, I197, M209, V212, V225, I242, H243, V244, L247, A248, H251, A253, A254, L255, L258, Y267, L269, M280, V281, A283, M284, A309, L313, A314, L318, W320, M329, C330 |
| 699 | Semaphorin-3A | Q14563 | I110, L308, V373, I451, V475, L476, L494, L529 |
| 700 | Inositol 1,4,5-trisphosphate receptor type 2 | Q14571 | L9, I11, V15, A19, I27, C37, V38, V39, Y66, V115, L123, H125, L132, A146, F161, I176, L193, V209, W218, L242, H244, C253, L264, A280, W282, I284, H307, A315, A316, L354, F367, H391, V398, I417, F429, A448, L452, L476, V483, I514, V518, C556, H562 |
| 701 | Inositol 1,4,5-trisphosphate receptor type 3 | Q14573 | L8, I10, V14, A18, I26, C36, V37, V38, Y65, V116, L124, H126, L133, A147, L162, V177, L194, V210, W219, L243, H245, C254, L265, A281, W283, V285, H308, A316, A317, L354, F367, H391, I398, L417, F429, A448, L452, L476, V483, I514, V518, C556, H562 |
| 702 | ATP-sensitive inward rectifier potassium channel 11 | Q14654 | L149, L233, L255, L287 |
| 703 | Metabotropic glutamate receptor 4 | Q14833 | L83, L86, A328, V341, L353, A363 |
| 704 | Transmembrane glycoprotein NMB | Q14956 | L274, I279, W283, F285, V293, V299, Y303, F309, A317 |
| 705 | Importin subunit beta-1 | Q14974 | I6, L7, A21, L25, L40, L44, A53, A56, A57, L59, I61, L65, W80, V91, V95, A109, C112, V113, A114, I116, A117, L129, L133, V137, L151, A153, I157, I161, L166, I173, A176, I177, I178, V190, A194, A197, L198, L202, F209, I218, M219, V221, V222, V233, A236, A237, L241, I244, M245, M252, L260, A267, M268, V275, A276, I280, F282, W283, V286, C287, A300, A301, A315, A318, L319, L322, V323, L326, L330, C345, A347, A348, C351, L352, L355, A356, I363, V367, A385, A386, V387, A389, C392, I393, L394, L402, V406, L413, V424, A428, A429, V432, I435, C436, L439, A442, A443, L452, C455, L456, L460, A467, V470, C471, A473, F474, L477, A478, A481, L499, F503, I506, V507, L510, L524, A528, Y529, L532, M533, I535, V536, A540, C543, A546, V547, I554, L558, V561, L562, L584, C585, L588, V591, L592, V595, A600, I603, V607, M608, L611, M614, F615, V624, A628, L629, A631, V632, L635, V636, L639, F643, M647, F650, L658, V666, C667, A670, V671, L673, V674, L677, C678, L681, M693, L696, V709, I713, L714, V716, F717, I720, A721, F728, V735, L736, L739, A742, L758, C765, L766, A768, Y769, I772, V773, L776, V787, V790, V794, I797, L798, F800, I801, I804, V814, V815, A816, A818, A819, L821, I822, L825, A828, V833, V837, I843, L846, L847, A858, L861, A862, A865 |
| 706 | Arf-GAP with coiled-coil, ANK repeat and PH domain-containing protein 1 | Q15027 | V411, C421, C423, A431, V437, L439, C443, H447, L472, M473, I481, I484, I510, L575, M588, A591, A593, A614, A622, C623, L626, A647, L655, A656, F659, A680, I688, L691, L713 |
| 707 | Lysine--tRNA ligase (EC 6.1.1.6) | Q15046 | I84, L105, F108, V128, I132, Y145, L147, L154, V156, A158, L176, I182, V184, I198, I199, L232, V240, I250, I254, L258, F263, I266, I274, I298, H304, V308, V315, Y316, I318, C338, F340, L350, M357, V358, M361, V362, V385, F387, F391, I394, M396, V397, L400, F414, L423, C427, L443, L444, L447, V448, L452, C456, F461, I462, H465, L472, A473, F486, L488, F489, V490, M491, C496, A498, L502, L511, F533, C534, A545, W547, M549, I551, V554, A555, M556, F557, V567 |
| 708 | Advanced glycosylation end product-specific receptor | Q15109 | L36, W51, L53, W72, A76, L84, L86, V89, F97, C99, A101, V115, V117, L133, V141, C144, W157, L192, C208, F210, L214, V238, L257, W271, C301 |
| 709 | Programmed cell death protein 1 | Q15116 | A50, F52, C54, F56, L65, W67, A80, A81, F106, M108, V110, A113, Y121, C123, A125, A140, L142, V144 |
| 710 | Plectin | Q15149 | F185, W188, V189, L193, A196, L203, L207, L213, I214, L216, L217, V240, A243, L244, L247, L254, I262, A263, L271, L273, I274, I277, I278, I283, I286, L301, W304, V309, C317, F320, W324, L329, F330, A332, I333, I334, L341, V347, |

TABLE 5-continued

| TARGETS | | | |
|---|---|---|---|
| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
| | | | L353, L356, A359, F360, A363, V369, L372, L373, V378, I388, I389, Y391, V392, L395, Y396, Y421, V425, L428, M432, I451, L483, V503, L510, L521, C545, L549, A552, L556, V575, L579, A582, L589, V593, L596, V611, L618, L662, L665, W668, V669, V688, I702, F705, A712, Y727, L731, L734, L741, L752, L755, F758, V759, A762, L769, L798, A826, V830, L837, M844, L847, C850, I851, H854, F864, A871, L875, L918, L921, A925, L931, L946, C950, V988, V991, C992, F993, V995, A1002, V1006, L1009, A4418, I4420, I4431, A4434, L4448, L4449, A4453, C4454, I4458, I4459, V4469, A4472, I4486, A4489, A4492, A4507, A4508, A4510, A4520, F4524, L4525, A4548, L4562, A4567, L4572, A4586, L4600, A4603 |
| 711 | Nectin-1 | Q15223 | L49, C51, V65, W67, V78, A79, Y93, I109, L111, Y122, C124, F126, L138, V142, L168, A170, C172, L213, A219, L224, C226, I227, V228, L239, V243, L267, C269, L300, F302, Y314, C316, A318 |
| 712 | Receptor-type tyrosine-protein phosphatase kappa | Q15262 | Y77, M78, V80, A91, L93, L95, H104, F108, L123, I125, V127, I138, A152, L154, A155, V156, Y164, V166, F168, A170, I180, A181, I182, F214, C216, L230, A253, F255, Y268, C270, V271, V280, A284, L308, I310, L312, V328, I361, L365, I406, V408, C420, I427, V454, V463, L465, M467, L469, I507, L509, Y524, I526, F558, Y567, F569, I571, A573 |
| 713 | Receptor tyrosine-protein kinase erbB-4 (EC 2.7.10.1) | Q15303 | Y53, C56, V58, V59, L63, I65, I68, L77, V80, V83, V87, L88, V89, A90, F94, L97, L99, L102, I104, I105, A116, A118, I119, L131, L134, L136, L139, I142, V147, V149, A158, I166, V167, C197, C234, A235, A248, C258, V298, C334, I337, V348, I353, F356, C359, I362, L366, F368, L389, F392, V395, I398, L402, I404, F414, V416, F417, L420, I423, L434, I436, I442, L445, F447, L450, I453, I458, I460, L466, C467, L477, C496, C507, C512, W513, C532, V748, I750, A769, A773, M775, L780, V786, C787, V795, L804, V808, L820, L821, W823, C824, I827, A828, M831, L834, H841, L844, A845, A846, V849, V851, V857, I859, L864, A888, C891, V903, W904, Y906, V908, I910, L913, M914, I929, L933, L939, V949, M953, C956, W957, F967, L970, F974, M977, L985 |
| 714 | Sonic hedgehog protein | Q15465 | A58, A94, M98, C102, L106, L109, A110, V113, L122, V124, W128, L139, H140, A145, V146, I148, M160, L161, A162, A165, V173, I181, C183, V185, A187, A193 |
| 715 | Transforming growth factor-beta-induced protein ig-h3 | Q15582 | V505, M506, L509, F515, L518, A521, I522, L531, V539, F540, A541, A546, L565, H572, I573, L589, L597, V599, V606, V608, V624, V625, H626, V627, I628, L632 |
| 716 | Myosin light chain kinase, smooth muscle | Q15746 | M1536, I1688, L1714 |
| 717 | Neuronal acetylcholine receptor subunit alpha-2 | Q15822 | A163, H164, A177, I211, L213, V286, I314, V349 |
| 718 | Serine/threonine-protein kinase STK11 (EC 2.7.11.1) | Q15831 | V77, L80, M127, V128, M139, L140, A153, F157, I161, L164, L167, I172, V173, H174, I177, L182, L190, I192, C210, V236, W239, A241, V243, L245, F255, I267, L285, L286, M289, I303 |
| 719 | Syntaxin-binding protein 2 | Q15833 | L6, V10, I14, V18, I19, V22, V30, L31, I32, M33, I40, L41, I50, I57, I61, A73, I74, Y75, L77, V84, L87, F91, Y99, A102, I104, F105, F106, L114, L118, L123, L135, A136, F137, V144, F145, L147, A149, L169, L172, A173, I176, A177, L179, C180, A188, I189, L201, A202, V205, L209, L230, L231, I232, M233, A236, A237, V240, L243, L247, F249, M252, A253, L291, V299, V303, L326, H346, H348, L349, A350, C353, V361, L364, C365, L371, L388, I389, V392, L393, L394, I404, V406, L407, L408, L409, Y410, I411, L412, L422, L425, I426, A429, L437, I438, L441, L444, V448, M466, I479, V482, M483, A486, L534, I535, V536, Y537, V538, M539, V542, M544, M547, A549, A550, V553, V563, L564, I565, H569, L571, F576, L577, L580, L583 |
| 720 | Adiponectin | Q15848 | A6, L13, P25, V27, L29, G34, G38, I74, P76, I97, A114, F115, V117, F132, F150, L157, Y158, F160, A161, Y162, V166, V171, V173, L175, L183, V201, L202, L203, L205, V211, L213, F234, F237, L238 |
| 721 | NT-3 growth factor receptor (EC 2.7.10.1) | Q16288 | I71, L134, L157, L182, A298, V301 |
| 722 | Solute carrier family 15 member 2 | Q16348 | I653, V660 |
| 723 | Acid-sensing ion channel 2 | Q16515 | F99, L117, Y190, L217, I219, L221, I248, I257, I402, L428, I432 |
| 724 | Interleukin-17A | Q16552 | C94, C99, V121 |
| 725 | Calcium/calmodulin-dependent protein kinase type IV | Q16566 | C63, L74, V117, L126, F127, Y136, A141, A142, A144, V145, L149, A151, L165, L170, L181, I183, A209, V222, W225, V227, I229, I233, L234, C236, F241, I254, W266, L271, A273, L276, V277, L280, A294, W299, L317, F320 |
| 726 | Laminin subunit alpha-3 | Q16787 | L272 |

TABLE 5-continued

TARGETS

| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
|---|---|---|---|
| 727 | Receptor-type tyrosine-protein phosphatase O | Q16827 | L920, F923, M930, F938, F942, L945, A957, Y974, V979, Y992, A995, I998, Y1007, I1008, A1009, F1021, W1022, M1024, V1025, I1032, I1033, V1034, M1035, L1036, C1047, Y1050, V1065, F1081, I1083, V1092, H1094, Y1097, W1100, I1114, F1117, V1118, V1121, M1132, I1133, I1134, H1135, C1136, V1140, F1146, I1147, A1148, L1149, L1152, V1162, I1164, L1165, V1168, M1171, M1178, V1179, Y1185, F1187, I1188, C1191, V1192 |
| 728 | Toxin B (EC 2.4.1.—)/strain 630 (*Clostridium difficile*) | Q189K3 | L562, I578, Y580, I581, V582, A594, F598, A599, V606, L607, F608, A618, L648, F650, F663, L671, I675, I686, I693, L695, M700, F701, Y711, L715, L716, V719, I723, M727, I735, V737, A739, I762, I778 |
| 729 | Toxin A (EC 2.4.1.—)/strain 630 (*Clostridium difficile*) | Q189K5 | L9, A13, Y23, I26, L30, L48, L51, I55, F58, L71, L74, I78, V82, L97, H98, F99, V106, Y113, W117, L128, W129, A134, F135, L136, A152, F170, Y171, M175, I178, I204, I205, L209, I231, I239, L244, Y254, L258, A266, A267, V271, A275, L276, V282, L284, M288, L289, I314, L316, A318, I319, F334, F345, I349, I358, F359, V367, L370, I372, I374, A375, A385, L386, I387, L394, V398, Y406, L409, L413, A416, F430, L434, L446, I449, F457, A461, L467, A472, Y473, A476, Y477, F480, L483, L497, A526 |
| 730 | Protein Dok-7 | Q18PE1 | V7 |
| 731 | Spike glycoprotein | Q1HLC5 | Y60, M70, L78, F83, F91, F96, A97, V99, F114, A116, I117, I119, F123, V130, V131, L147, I149, V151, C152, M156, C157, H161, I163, L200, H203, F204, F211, A213, F224, Y238, V239, L240, L242, C244, Y252, Y262, L264, C278, A520 |
| 732 | Lipoprotein, Lp | Q1HP67 | W1640, C1665, C1676 |
| 733 | Endogenous retrovirus group K member 113 Env polyprotein | Q1PHM6 | A54, F92, M94, M99, M103, I107, V119, V126, M145, L156, A220, I221, C235, V266, I281, L284, V288, I321, C326, I328, L337, V340, V341, I353, Y378, C379, F385, C417, I422, I423, V429, A432, M433, L452, L453, I469, F470, W481, L485, V491, I493, V507, I550, V551, L557, L558, A560, I561, A563, M567, L568, V572, I575, L578, V582, I637, I644 |
| 734 | CTLA-4 protein | Q28090 | A52, V67, V71, C101, V110, C127, V129, I147 |
| 735 | Hemagglutinin [Cleaved into: Hemagglutinin HA1 chain; Hemagglutinin HA2 chain]/strain A/New Zealand: South Canterbury/35/2000 H1N1 | Q289M7 | V7, I20, C21, I22, A26, V33, V36, V43, L49, L50, L58, C59, L61, L67, L69, C72, V74, A75, W77, I78, L79, C84, L87, W93, Y95, I96, V97, Y108, L118, L122, V125, F128, F134, A150, C152, H154, L164, L165, L167, L173, L177, V189, L190, V191, L192, W193, V195, H196, H197, Y208, Y214, V215, V217, V218, I243, Y245, Y246, L249, L250, I256, F258, A260, L264, I265, A266, Y269, A270, F271, A272, L273, F277, I281, I282, C291, C295, A301, I302, H312, M330, V331, A348, Y365, A387, I388, L461, L469, H485, C487, C491 |
| 736 | HLA class II histocompatibility antigen, DRB1-16 beta chain | Q29974 | F36, L37, F46, F47, V53, F55, L56, Y59, V67, F69, Y76, W90, L97, A103, C108, V120, V128, L138, L143, L144, V145, C146, V148, F151, W160, M171, L190, V199, Y200, C202, V204 |
| 737 | MHC class I polypeptide-related sequence B | Q29980 | L28, L32, V34, F45, L51, F56, L57, Y59, A66, A73, L96, L100, L113, C119, F133, F140, L141, L145, A158, A162, V165, L191, Y194, V223, C225, A227, F230, W239, V268, I272, C282 |
| 738 | MHC class I polypeptide-related sequence A | Q29983 | L28, V34, V49, L51, F56, C59, C64, A73, L96, L100, L113, C119, F133, F140, L141, A162, V165, L191, I221, V223, C225, A227, F230, W239, V268, I272, C282 |
| 739 | Kinesin-like protein KIF7 | Q2M1P5 | V18, A19, L20, V47, L49, V70, Y71, V75, A88, V90, F91, A92, M104, I119, V120, A123, V143, Y145, L146, V148, F153, L156, V192, V220, F221, V223, L225, F248, F250, V251, A281, L282, V285, I286, A288, I306, I309, L310, L314, A318, M322, I323, A324, C325, V326, L340, A343 |
| 740 | Endogenous retrovirus group K member 24 Env polyprotein | Q2N0S5 | A54, A69, M94, M99, V100, M103, L121, L124, L128, L145, C148, M152, F167, L192, A203, C217, A218, A223, I224, L225, C238, V241, L258, V269, F287, V291, I293, F314, A316, I324, C329, V331, L340, V343, V344, L347, I357, F381, C383, F389, L413, C415, I420, I421, I427, A430, M431, Y432, A433, I446, L449, I450, L451, F465, W476, L480, V486, I488, V502, I545, V546, L552, L553, A555, I556, A558, L562, L563, V567, I570, L573, V577, I632, I639 |
| 741 | Endogenous retrovirus group K member 8 Env polyprotein | Q2N0S6 | W44, F52, C53, A54, W68, A69, F92, M94, W95, M99, V100, M103, L110, C118, V119, L121, L124, C125, L128, C130, L145, C148, F150, M152, Y164, F167, L192, C195, I200, A203, C204, C217, A218, A223, I224, L225, C227, C238, V241, I250, L258, V269, V285, F287, V291, I293, C295, F314, A316, I324, C329, V331, W336, L340, V343, V344, L347, I357, F359, H372, C376, F381, Y382, C383, L388, F389, L413, C415, I417, I420, I421, I427, A430, M431, Y432, A433, C442, I446, L449, L451, F465, W476, L480, Y483, V486, I488, A494, V502, I545, V546, L552, L553, A555, I556, A558, L562, L563, V567, I570, L573, V577, I632, I639 |
| 742 | HLA class II histocompatibility antigen, DR beta 5 chain | Q30154 | F36, L37, F46, F47, V53, F55, L56, L67, F69, Y76, W90, L97, A103, C108, V120, V128, L138, L143, L144, V145, C146, V148, F151, W160, V171, L190, V199, Y200, C202, V204 |

TABLE 5-continued

TARGETS

| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
|---|---|---|---|
| 743 | Hereditary hemochromatosis protein | Q30201 | L30, Y32, A49, V53, F58, V59, Y61, L87, L91, I105, L118, L122, C124, H145, L146, A162, A176, L183, C187, L191, L223, C225, A227, Y230, W239, I268, V272, C282, V284 |
| 744 | Genome polyprotein [Cleaved into: Protein C/strain Mr 766 (ZIKV) | Q32ZE1 | I291, C293, V311, V313, V314, L315, C320, V321, V323, M324, A325, V331, I333, L335, V340, Y349, C350, Y351, A370, V381, C395, L403, V404, C406, A407, F409, M415, I420, L425, Y427, I429, M430, L431, V433, V455, A464, L466, L472, L474, C476, L482, Y488, Y489, L490, M492, H496, W497, V499, F504, H512, L528, V529, V541, L555, H574, L575, C577, L579, M581, L584, C594, F598, V612, V614, V616, Y618, C625, I627, M631, A632, L644, I645, I651, M660, L662, L664, I673, V674, I675, I811, V978, I1008, V1536, M1539, H1545, M1547, V1570, L1574, V1575, Y1577, W1581, V1593, L1595, A1597, V1598, I1613, A1623, V1624, I1637, I1645, L1647, Y1648, V1653, V1660, L1703, I1706, V1707, A1710, V1718, I1719, L1720, A1721, V1726, A1727, M1730, L1734, V1756, L1758, M1759, H1761, F1764, Y1777, L1779, I1781, M1782, A1785, I1793, A1794, A1795, I1799, A1808, A1809, A1810, I1811, F1812, M1813, V1850, V1858, W1859, F1860, V1861, I1870, A1871, C1873, L1874, A1877, I1882, L1884, F1889, W1901, F1903, V1904, I1905, A1914, V1921, I1922, V1938, V1946, A1949, A1951, A1952, I1958, Y1969, M1970, A1976, A1983, A1988, L1991, L1992, I1995, L1997, A2003, L2005, F2030, V2031, L2033, L2039, W2042, L2043, A2044, V2047, A2048, W2059, C2060, I2069, V2078, L2088, A2095, F2107, F2110, A2111, W2528, Y2543, I2548, V2551, A2556, A2559, L2560, A2570, V2571, A2576, I2578, L2581, L2587, V2593, V2594, L2596, C2598, A2607, A2608, V2613, V2616, Y2619, V2648, C2656, L2659, L2660, C2661, V2672, L2678, V2680, L2681, V2684, W2687, L2688, F2695, C2696, I2697, V2699, L2700, C2701, Y2703, M2707, M2711, L2714, L2722, V2725, H2733, M2735, Y2736, W2737, V2738, I2745, V2749, L2755, L2756, I2794, I2801, V2842, L2845, W2849, V2880, V2890, M2891, L2898, I2929, A2939, A2942, F2948, C2964, C2967, V2968, Y2969, M2994, L2996, A2998, L3001, A3005, F3008, L3009, W3014, M3015, V3024, L3032, Y3034, L3036, M3039, A3042, M3047, I3059, A3082, V3085, Y3090, V3094, V3095, V3097, V3107, I3110, I3111, V3123, A3126, L3127, F3130, L3133, V3134, V3135, L3137, I3138, M3141, M3149, L3152, V3161, L3165, L3173, M3176, A3177, V3178, V3184, V3185, F3192, A3195, L3196, F3198, L3199, M3202, V3224, F3226, F3231, I3242, V3243, V3244, C3246, I3253, A3256, A3262, A3270, A3273, A3277, W3280, L3282, F3285, H3286, L3290, M3293, A3294, A3296, I3297, A3300, V3301, V3303, H3316, L3328, W3331, V3334, W3335, H3341, I3354, L3357, A3378, I3381, V3385, I3391, M3399, L3402 |
| 745 | N-acetylglucosamine-1-phosphotransferase subunits alpha/beta (EC 2.7.8.17) | Q3T906 | L139, L154, F161, V191, A228, L230, L243, L251, A267, L269, L271, A300 |
| 746 | Integrin beta-2-like protein | Q3UV74 | V127, L129, Y130, F131, L132, M133, V146, L149, L153, L154, L157, I166, F168, I171, F176, F189, L193, L209, A211, V212, V213, V215, A216, I222, L231, V232, L233, Y265, L279, I291, F292, V293, V294, Y302, I309, V324, I328 |
| 747 | Tyrosine-protein kinase (EC 2.7.10.2) | Q3ZC95 | F10, L11, F30, L31, L32, L37, I61, C63, V64, V67, F98, F102, V104, Y112, V113, F114, W124, L128, A384, V427, I429, I432, F442, A446, M450, L457, V463, C464, I470, I473, L482, L486, L498, L499, C502, V505, C506, A508, M509, L512, H519, L522, A523, A524, C527, V529, V535, V537, Y545, V561, V568, I580, W581, F583, V585, L586, M587, I590, Y591, I610, L616, A622, V626, I629, M630, C633, W634, F644, L647, I651, V654 |
| 748 | Envelope glycoprotein gp160 | Q3ZLH8 | A54, H65, A69, V94, V100, M103, V119, I150, L189, C214, A220, I221, C224, C235, V238, I247, L255, I266, I280, I281, V282, L284, V288, I290, A293, I321, C326, V328, W333, L337, V340, A341, I342, L344, I352, I353, F354, H367, C371, F376, C378, L383, F384, L407, C409, I411, I414, I415, V421, A424, M425, I440, L444, L445, F462, W473, L477, V483, I485, V499, I542, V543, L549, L550, A552, I553, A555, L559, L560, V564, I567, L570, V574, I629, I636 |
| 749 | Cytotoxin L | Q46342 | L9, V13, Y24, I27, L31, Y46, L49, I52, Y59, L72, F75, L79, V83, L98, H99, F100, Y114, W118, V129, A135, L137, I138, L141, I145, A149, F171, M176, I179, F186, I206, L210, L254, L259, V260, A267, A268, I274, L277, V283, Y284, L285, I289, L290, L317, A319, I320, F335, F346, I359, F360, L363, V368, L371, V373, I375, A376, A386, L387, I388, C395, V399, I403, Y407, L410, F431, I450, L454, F458, L468, V473, Y474, A477, Y478, L481, F501, A527 |
| 750 | Envelope glycoprotein | Q49DS8 | I13, V15, L17, V21, I23, I53, C58, I60, L69, V72, A74, L76, I84, V85, H99, F108, C110, L115, F116, I127, L129, C131, I136, I137, V143, A146, M147, I162, L165, L166, L167, F181, W192, L196, V202, I204 |
| 751 | Cell adhesion molecule-related/down-regulated by oncogenes | Q4KMG0 | V737, V739, W741, F754, V756, V782, Y791, F793, V795, A797, V815, I832, I843, L845, F862, I864, I891, Y900, I902, M904, C906 |
| 752 | Cordon-bleu protein-like 1 | Q53SF7 | V187, I189, L207, L210, I214, C215, L227, L228, L251, A253 |

TABLE 5-continued

TARGETS

| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
|---|---|---|---|
| 753 | Receptor protein-tyrosine kinase (EC 2.7.10.1) | Q59FL8 | I611, V613, I615, A634, M637, V640, V645, C646, I651, L659, I660, L669, V673, L685, L686, W688, C689, I692, A693, L699, V705, H706, L709, A710, A711, V714, V716, V722, I724, F727, A753, V768, Y771, V773, V775, L778, I794, L798, L804, V814, M818, C821, W822, F832, L835, F839, M842, L850 |
| 754 | Integrin beta | Q59H50 | C81, C88, C91, C107, L113 |
| 755 | Filaggrin-2 | Q5D862 | L33 |
| 756 | Guanine nucleotide-binding protein G | Q5JWF2 | L686, L687, L688, L689, I699, M703, I738, L742, A745, I746, I749, L756, I774, F789, A793, L796, V802, C805, C817, A818, F821, I825, I828, F862, M864, V867, A886, I887, F889, V890, V891, Y896, F916, L925, V930, I931, L932, L934, L939, L940, V944, A980, I984, F988, A994, I1015, C1022, I1026, H1030 |
| 757 | MAGUK p55 subfamily member 7 | Q5T2T1 | A73, L96, L108, V164, A173, L185, V188, I201, I212, F214 |
| 758 | Dyslexia-associated protein KIAA0319 | Q5VV43 | L354, A356, W372, L393, L395, Y403, F405, V407, V409, V422, V424, A629, L644, W660, A679, V681, L684, F691, L693, V695, V709 |
| 759 | Disabled homolog 2-interacting protein | Q5VWQ8 | L653 |
| 760 | Renalase (EC 1.6.3.5) | Q5VYX0 | L5, I6, A9, L15, C16, A17, A31, V32, W33, A56, L58, L80, V106, A107, I111, I114, I115, I135, W142, V144, F154, I157, V158, L159, V163, I166, I173, L185, Y194, A195, L198, F199, I221, V224, V243, V262, V266, F311, L312, A313, C314, F319, I328, A331, V334 |
| 761 | Hemagglutinin [Cleaved into: Hemagglutinin HA1 chain; Hemagglutinin HA2 chain]/strain A/Singapore/1/1957 H2N2 | Q67333 | I7, I18, C19, I20, Y22, A24, V31, I34, V41, I47, L48, L56, C57, L59, L65, L67, C70, I72, A73, W75, L76, L77, C82, L85, W91, Y93, I94, M95, Y106, L116, L119, L120, V123, F126, L132, A148, C149, V151, M161, V162, W163, L164, A174, M186, L187, I188, I189, W190, V192, H193, H194, Y205, Y211, V212, V214, L219, L236, M240, F242, L246, L247, I253, F255, L261, I262, A263, Y266, F268, I270, I278, M279, C288, C292, A298, I299, H306, H309, I313, V320, L325, L327, A328, L331, A345, M357, Y362, A384, F385, A436, L448, H451, V455, L458, V462, L466, C477, H482, C484, C488, M489 |
| 762 | Envelope glycoprotein gp160 | Q69994 | A52, H63, A67, M92, M97, V98, M101, W109, V117, V124, I172, Y239, C240, A246, I247, C250, C261, V264, I273, L281, L282, V292, I306, I307, I308, L310, V314, I316, C318, I346, C351, I353, W358, L362, I365, V366, A367, L369, I378, V379, F380, H393, F395, F402, C404, L409, F410, L430, C432, I434, I437, I438, V444, A447, M448, I463, L466, L467, L468, I483, F484, W495, L499, V505, I507, V521, I565, V566, L572, L573, A575, I576, A578, L582, L583, V587, I590, L593, V597, I652, I659 |
| 763 | Hemagglutinin/A/Viet Nam/1203/2004(H5N1) | Q6DQ33 | F8, I19, C20, I21, A25, V32, I35, V42, I48, L49, L57, C58, L60, L66, L68, C71, V73, A74, W76, L77, L78, C83, F86, W92, Y94, I95, V96, A99, C106, Y107, L117, L120, L121, I124, F127, I133, A150, C151, Y153, V163, V164, W165, L166, I167, I176, L188, L189, V190, L191, W192, I194, H195, H196, A201, Y207, Y213, I214, V216, L221, M242, F244, F245, I248, L249, I255, F257, F263, I264, A265, Y268, A269, Y270, I272, I280, M281, C290, C294, A300, I301, H308, H311, I315, V322, L327, L329, A330, A351, M363, Y368, A390, I391, A442, L454, V461, L464, V468, L472, C483, H488, C490, C494, M495, A512 |
| 764 | Tau-tubulin kinase 2 (EC 2.7.11.1) | Q6IQ55 | V17, V23, Y36, A38, V47, L49, V51, V67, L68, L71, C78, V92, V93, L101, L119, L121, I125, L126, I129, I132, H139, F147, C159, M161, L209, L212, F213, Y214, M215, L216, F219, W226, V235, F255, F258, I262, L276, V279, F280, I284 |
| 765 | Growth/differentiation factor 6 | Q6KF10 | F363, C387, A401, I430, C452, C454 |
| 766 | Iodotyrosine deiodinase 1 | Q6PHW0 | I116, A123, I149, I181, A188, I190, L191, I192, L193, I194, F195 |
| 767 | Spike glycoprotein/HCoV-NL63 | Q6Q1S2 | I485, F487, A489, A491, L509, W541, C577, F579, L581, A583, L596, V598 |
| 768 | Nucleoprotein/strain A/Equine/Santiago/1/1985H3N8 | Q6TXC0 | V33, I36, F39, M43, L56, I57, I63, M66, V67, L68, A70, I96, I116, I119, W120, M136, M137, W139, A153, L154, M163, M189, V190, L193, I194, I197, I201, Y219, C223, L226, F230, A234, M238, M239, V242, L256, L259, A263, I265, L266, C275, L276, A278, Y281, F291, Y296, L307, I312, L315, L328, V329, W330, M331, A332, C333, H334, A336, A337, L341, I347, V352, V363, M371, L381, A387, A427, A428, I444, Y487 |

TABLE 5-continued

TARGETS

| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
|---|---|---|---|
| 769 | Hemagglutinin/ A/Netherlands/219/2003 (H7N7) | Q6VMK1 | V58, I66, C67, L76, C79, L81, L82, I85, C91, A99, L101, I102, I103, C112, L123, L127, I133, I145, C154, Y162, M165, L168, Y184, A192, L193, I194, I195, W196, I198, H199, Y211, I218, V220, I246, F248, L253, V259, F261, F263, A266, F267, I268, A269, P270, A273, F275, L276, I283, C293, C297, Y298, A353, Y370, A392, L466, L474, H490, C492, C496, A514 |
| 770 | Neuraminidase (EC 3.2.1.18)/strain A/Budgerigar/Hokkaido/1/1977 H4N6 | Q6XV28 | L87, V94, A105, I106, I114, V116, Y121, L122, C124, M131, F132, A133, L134, A145, L158, I159, W161, C176, I177, C184, M191, I193, C194, M195, A202, A204, V205, V206, Y208, A220, L224, C231, V232, C233, V240, V241, M242, I255, I256, Y257, F258, I276, C279, C281, Y282, V285, I288, C290, I291, C292, A299, V303, I304, I306, Y317, L318, C319, V322, L323, V350, F353, A354, F355, W362, L363, Y375, M377, L378, V380, A383, I397, I398, A409, F410, I411, F420, F424, Y425, V426, L428, V438, I445, V446, A447, L448, A464, I466 |
| 771 | Tubulin alpha-1A chain | Q71U36 | C4, I5, I7, H8, V9, V14, I16, C20, W21, L23, Y24, C25, H28, I30, F52, F53, V62, A65, V66, F67, V68, L70, V74, I75, V78, L86, I93, A99, A100, Y103, A104, I115, V118, L119, I122, L125, F135, L136, V137, F138, H139, L153, M154, L157, L167, F169, Y172, A174, Y185, I188, L189, L195, C200, A201, F202, M203, V204, A208, I209, I212, C213, L227, L230, I231, I234, V235, I238, A240, L242, V250, L252, F255, L259, V260, I265, H266, F267, L269, A270, A273, V288, I291, C295, M302, V303, C305, Y312, M313, C315, C316, L317, L318, Y319, V323, V328, A331, I335, V344, I355, V363, A369, A374, V375, C376, M377, L378, A383, I384, A387, W388, L391, F395, Y399, Y408, F418, A421, M425, L428, Y432 |
| 772 | Endogenous retrovirus group K member 9 Env polyprotein | Q75760 | A54, A69, M94, M99, V100, M103, I107, V119, L121, V126, I151, C154, A171, L190, A221, I222, C225, C236, L256, L257, V267, I281, I282, V283, L285, V289, I291, C293, F312, I322, A325, C327, I329, W334, L338, I341, V342, I343, L345, I354, V355, F356, H369, F371, C373, F378, C380, L385, F386, L407, C409, I411, I414, I415, V421, A424, M425, I440, L443, L444, L445, I458, F459, W470, L474, Y477, V480, I482, V496, I539, V540, L546, L547, A549, I550, A552, M556, L557, V561, I564, L567, V571, I626, I633 |
| 773 | Rho-related GTP-binding protein RhoU | Q7L0Q8 | V50, C52, V53, L54, V55, V60, L65, V66, Y74, A82, V90, V92, V97, L99, L101, A105, Y118, I123, F124, L125, L126, C127, F128, V130, F136, V139, W143, V144, I147, C151, I156, I157, L158, V159, L175, V183, A188, L190, C191, A192, I195, C203, L211, V214, F215, A217, A218, I219 |
| 774 | Ribonucleoside-diphosphate reductase subunit M2 B (EC 1.17.4.1) | Q7LG56 | L34, I52, A66, W78, F88, I89, I92, L93, A94, F95, F96, F111, V115, V117, A120, F123, Y124, H134, M137, L141, I142, Y145, I146, A158, I159, Y164, A169, W171, V187, V188, A189, A191, A192, V196, F197, F198, A203, A204, I205, L208, L213, M214, L217, I224, F234, A235, C236, M238, F239, V251, I254, I255, A258, V259, F265, L266, A269, L270, V272, L274, I275, M282, I286, A290, L294, F303 |
| 775 | Ankyrin repeat and sterile alpha motif domain-containing protein 1B | Q7Z6G8 | V815, W818, L819, L831, F836, M842, M847, L852, I857, I866, A869, I870, V889, L893, F905, I933, I939, A1064, F1065, A1084, C1085, I1105, L1107, V1109, V1114, I1130, I1133, F1146, A1147, Y1148, I1149, C1160, V1162, F1163, A1171, I1174, L1178, A1181 |
| 776 | E3 ubiquitin-protein ligase HUWE1 (EC 6.3.2.—) | Q7Z6Z7 | A1335, A1338, A1348, L1352, F4001, V4019, V4021, V4026, F4027, L4034, M4042, W4065, Y4066, I4069, M4073, L4080, I4093, F4107, F4109, V4110, I4113, V4114, A4115, A4117, L4124, C4126, F4128, F4132, Y4133, I4136, M4146, F4174, V4207, V4210, C4211, M4215, F4226, F4230, I4234, L4238, I4239, I4241, L4247, I4251, I4278, F4281, A4284, L4285, A4294, V4300, F4311, F4323, I4325, C4341, L4345, L4347, Y4350, L4356, L4360, A4363, I4364 |
| 777 | Hemagglutinin [Cleaved into: Hemagglutinin HA1 chain; Hemagglutinin HA2 chain]/strain A/Equine/Kentucky/1/1981 | Q82559 | A26, L28, C29, L30, A34, V41, V51, L57, V58, I66, C67, V73, C79, L81, I82, M85, L86, C91, F94, L101, F102, I103, F109, C112, Y113, Y115, Y120, A121, L123, V127, A128, L133, F140, A153, C154, F162, F163, L166, L169, L179, Y193, W195, I197, H198, H199, Y210, V217, V219, I245, I247, Y248, I251, V252, I257, L258, I260, L266, V267, A268, F273, I289, C296, I297, I303, I324, L331, A332, A349, W358, Y366, A388, A440, L462, L470, C481, F482, I484, H486, C488, C492, I493, I496, A510 |
| 778 | Fusion glycoprotein F0 | Q84850 | I233, F237, V247, M251, L257, I261, M274, V281, F342, V349, C382, A412, V414, C416, C422, A424, V450 |
| 779 | Regulating synaptic membrane exocytosis protein 1 | Q86UR5 | V600, L602, A614, L616, L618, A633, I635, A644, L650, V656, W659, L664, V672, I676, V685, I687, V689, L746, V748, L750, L759, V761, V763, A766, V782, M784, V818, F823, L828, I830, V832, L846, I849, L853 |
| 780 | Fermitin family homolog 3 | Q86UX7 | L73, L74, I358, V378, F380, L404, I422, V426, L437, C439, A446, W448, M449, A450, C452, L454, A455 |
| 781 | Transmembrane protease serine 6 (EC 3.4.21.—) | Q8IU80 | I504 |

TABLE 5-continued

TARGETS

| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
|---|---|---|---|
| 782 | Sodium channel subunit beta-4 | Q8IWT1 | L51, C53, L64, W68, L79, I80, V84, I101, I114, I116, L118, L121, C131, V133, L149 |
| 783 | Interferon lambda-3 | Q8IZI9 | L27, L45, A59, L65, L75, L82, L85, A93, L94, A96, L98, L102, L126, C136, A161, C169, V174, L181 |
| 784 | Interferon lambda-2 | Q8IZJ0 | L31, L49, A63, L69, L89, A100, L106, C140 |
| 785 | Abl interactor 1 | Q8IZP0 | V451, A453, L465, I473, V475, I476, C488, F495 |
| 786 | Kin of IRRE-like protein 3 | Q8IZU9 | I438, C440, I442, A452, W453, L483, I485, I488, Y497, C499, A501, L514 |
| 787 | Envelope glycoprotein gp160 | Q8J581 | C50, A51, H62, A66, M91, M96, V97, M100, I104, L107, V116, L143, I210, Y212, C213, A219, I220, C223, C234, V237, I246, L254, I265, I267, I279, I280, V281, L283, V287, I289, C291, I320, A323, C325, V327, W332, L336, V339, A340, L343, I351, I352, H366, F375, C377, F383, L408, C410, I412, I415, I416, A422, A425, M426, I441, L444, L445, L446, F460, W471, L475, Y478, V481, I483, V497, I540, V541, L547, L548, A550, I551, A553, L557, L558, V562, I565, L568, V572, I627, I634 |
| 788 | Endogenous retrovirus group K member 21 Env polyprotein | Q8JDI3 | A54, H65, A69, F92, M94, M99, V100, M103, I107, L110, V126, I145, M152, V173, I175, L189, F206, I211, Y213, C214, A220, I221, C235, V238, I247, L255, V266, I280, I281, V282, L284, V288, I290, I321, C326, V328, L337, V340, V341, L344, I352, F354, H367, F369, C371, F376, C378, F384, L405, C407, I409, I412, I413, V419, A422, M423, I438, L441, I442, L443, F457, M464, W468, L472, Y475, V478, I480, V494, I537, V538, L544, L545, A547, I548, A550, L554, L555, V559, I562, L565, V569, I624, I631 |
| 789 | Neuroligin-4, X-linked | Q8N0W4 | I55, V70, Y73, V76, Y78, F88, V109, C110, L132, C146, L147, L149, I151, V153, V168, M169, V170, I172, H173, L190, A191, V196, I197, V198, I199, I201, Y203, I207, F210, L211, A218, L224, I228, A230, L231, W233, I234, V238, V248, I250, F251, A257, C259, V260, L262, L263, A276, I277, I278, A288, I299, L300, A301, V304, C306, V315, L318, L326, I338, I349, Y365, I367, M368, L369, V380, V390, V399, F402, V403, L416, I420, L440, L443, V450, A457, H460, Y470, A471, F472, A488, V493, Y495, V496, F497, F508, L519, V523, M524, Y526, W527, F530, A531, A558, L570, I572, A584, F589, I603 |
| 790 | Jouberin | Q8N157 | V1057, A1058, I1072, I1078, V1080, F1101 |
| 791 | Gamma-aminobutyric acid receptor subunit gamma-1 | Q8N1C3 | I436 |
| 792 | TGF-beta-activated kinase 1 and MAP3K7-binding protein 3 | Q8N5C8 | L13, L16, V27, V28, M32, C42 |
| 793 | Inactive dipeptidyl peptidase 10 | Q8N608 | L69, V94, V95, L117, V139, A142, A155, V158, L180, A183, L192, I193, Y194, I195, I200, L230, Y231, L235, A241, L251, A252, L254, I256, I266, Y280, L294, Y295, V296, V297, L299, L306, Y320, I321, V324, V333, V334, W336, L337, I345, C349, F385, V388, H400, V401, A402, V425, I438, F440, L452, C475, F489, L490, C493, L503, L545, L547, L549, A562, L563, L564, L565, V576, L588, V594, I595, V596, A597, L609, I615, V622, V631, I647, Y655, A657, F668, C670, A675, L680, A684, A686, F687, L692, V711, I721, H723, V730, F732, H734, L742, I773, F777, L781 |
| 794 | Proprotein convertase subtilisin/kexin type 9 (EC 3.4.21.—) | Q8NBP7 | V80, L82, A95, L98, A102, F122, V124, L130, A134, V140, I143, F150, I161, V180, V182, Y183, L184, L185, H193, I196, H229, L230, A231, V233, V234, A242, A245, M247, L250, V252, I271, L283, V284, V285, L286, L287, C301, L304, V309, V310, L311, V312, A314, A315, A322, A328, A330, V333, I334, V336, A338, V346, V359, L361, F362, A363, I368, A371, A388, A389, A390, H391, V392, A393, I395, A396, A397, M399, L400, A409, L411, L415, I424, F429, V441, A442, A473, A475, L484, C486, F489, C509, A511, V520, A522, I523, A524, C526, C527, A542, C588, A594, I596, H597, A598, C600, C601, A603, L606, V622, A625, L632, C654, V656, V672, A674, A676, C678, C679 |
| 795 | Cytoplasmic dynein 2 heavy chain 1 | Q8NCM8 | L1352, F1356, F1368, C1411, L1419, L1438, M1476, V1484, V1496, L1511, L1515, W1626, C1640, M1644, Y1655, C1671, L1675, A1678, V1699, A1736, V1750, L1751, A1753, V1754, A1764, F1788, V1815, A1826, V1872, A1901, L1943, A1962, V1975, V1976, I1977, V1978, W1989, L1992, A1995, M2008, I2053, V2069, F2094, A2105, I2113, C2182, L2200, F2208, F2254, F2275, W2278, L2279, L2301, A2304, L2354, V2355, L2374, A2376, V2395, V2403, L2427, V2474, V2476, V2480, L2524, I2526, A2531, F2548, F2572, L2634, I2640, F2646, L2651, L2653, A2654, V2668, A2701, V2708, L2712, F2722, L2751, H2777, L2780, C2803, V2805, M2808, I2819, C2862, Y2872, F2875, A3208, A3209, A3317, V3318, L3324, V3332, V3353, I3360, A3383, V3390, L3403, A3496, L3509, A3522, F3571, A3572, F3575, W3648, Y3651, C3657, A3694, L3724, L3740, A3754, M3755, A3771, W3776, L3777, A3811, L3822, A3861, |

TABLE 5-continued

TARGETS

| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
|---|---|---|---|
| | | | A3868, F3870, H3871, A3872, C3874, Y3927, I3931, L3944, L4021, L4040, V4090, Y4140, L4141, L4144, I4151, A4202, I4217, C4225, C4248, A4301 |
| 796 | Semaphorin-6D | Q8NFY4 | L150, A179, Y199, I211, Y252, A256, V269, F292, L297, A407, V417, L465, C521 |
| 797 | Protein CASC5 | Q8NG31 | F2149, Y2151, I2154, L2156, I2158, L2197, I2202, V2233, C2236, L2239, I2243, L2265, L2267, F2269, F2278, I2280, L2282, I2309, Y2322, V2326, V2327, I2330 |
| 798 | Envelope glycoprotein | Q8Q7Z9 | M23, I24, I30, L69, A100, I101, C115, V118, V131, L135, L136, V146, I160, I161, V162, L164, V168, I170, C172, A192, F193, I196, M202, H206 |
| 799 | CTLA4 | Q8TDA6 | A54, C58, Y60, V69, V71, V73, C85, L95, V112, I116, C129, V131, I149 |
| 800 | 2-amino-3-carboxymuconate-6-semialdehyde decarboxylase (EC 4.1.1.45) | Q8TDX5 | I5, H6, H8, I9, L10, L17, A37, L39, C53, M63, A72, L73, M79, F80, Y82, L92, C93, L96, L100, F111, L114, L117, M119, A125, M129, C132, V141, I143, V147, L152, L157, V160, Y161, A163, A164, C169, L171, F172, V173, A202, I203, M206, I207, V211, V220, C221, F222, A223, F229, F262, L274, L277, V286, I287, I305, M308, L319, A321, A324, F327 |
| 801 | Partitioning defective 3 homolog B | Q8TEW8 | I12, L434, I499, L509, I527, I533, L550, V553, L558, A566, I584 |
| 802 | Protein Shroom3 | Q8TF72 | A30, L32, A63, L70, V76, I79, A91, L102, L104, V106 |
| 803 | Intelectin-1 | Q8WWA0 | C41, C48, L58, C70, L81, V82, A83, V85, C94, W100, A129, Y139, L147, I149, H151, V152, W161, L167, L176, L183, I186, Y187, W200, V236, F238, V240, F241, A246, A247, A249, L250, C251, M254, H264, C265, F272, C280, F283, F286, I303, A306, A307, L309, L310, F311, Y312 |
| 804 | Palladin | Q8WX93 | F1020, C1022, V1024, I1032, W1034, C1058, L1060, Y1073, I1075, A1077, L1090, C1152, M1154, C1156, V1158, L1193, I1195, V1198, Y1206, C1208, A1210, L1253, C1255, W1267, I1291, L1293, I1295, A1298, Y1306, V1308, A1310 |
| 805 | Relaxin receptor 2 | Q8WXD0 | C52, L59 |
| 806 | Nesprin-2 | Q8WXH0 | A191, V203, W210, A215, F216, A218, I219, I220, L242, A245, F246, A249, V264, I274, M275, Y277, V278, A279, F281, L282 |
| 807 | Mucin-16 | Q8WXI7 | L14325, F14327, I14329, L14332, I14353, L14357, L14360, V14389, C14393, A14399, I14407, F14411, L14421, V14431 |
| 808 | Hemagglutinin [Cleaved into: Hemagglutinin HA1 chain; Hemagglutinin HA2 chain]/strain A/Hong Kong/1/1968 H3N2 | Q91MA7 | A27, L29, C30, L31, A35, V42, V52, L58, V59, I67, C68, I74, C80, L82, I83, A85, L86, L87, C92, F95, L102, F103, V104, F110, C113, Y114, Y116, Y121, A122, L124, V128, A129, L134, F141, A154, C155, F163, F164, L167, L170, Y177, L180, L193, Y194, I195, W196, V198, H199, H200, Y211, V218, V220, I246, I248, Y249, I252, V253, V258, L259, I261, L267, I268, A269, F274, I290, C297, I298, I304, V325, L332, A333, A350, W359, Y367, A389, A441, L463, L471, C482, F483, I485, H487, C489, C493, I494, I497, A511 |
| 809 | Alpha-N-acetylneuraminide alpha-2,8-sialyltransferase (EC 2.4.99.8) | Q92185 | W68, F78, C85, C86, F92, M105, Y107, I117, C138, A139, V140, V141, I146, L147, C152, I156, F161, V162, C165, L167, V178, L184, V185, I191, I192, L199, F206, Y213, A222, F223, L233, V235, Y236, L239, A244, F262, W263, A270, L273, A282, A283, L284, L286, C287, V290, Y293, W296, F298, I307, Y311, Y312, L316, F321, A323, M324, L334, L340, C347 |
| 810 | Nicastrin | Q92542 | C50, L53, L54, C62, I73, V85, M95, V96, L98, F103, M108, L111, L121, A122, V123, W164, L171, F176, F178, I180, F181, L182, L183, V191, I192, L212, C213, A214, M215, L217, C230, C248, L251, V256, W257, M259, V275, V276, V277, A278, A279, L282, F288, A292, A295, A298, V299, A300, F302, V303, L306, A307, A308, A309, A311, L312, A315, V325, M326, F327, V328, F329, F330, F335, Y337, I338, M347, V354, F362, L365, V368, L376, M378, V394, L397, L401, F430, V439, L441, A442, L471, A484, L487, A488, V490, A491, V493, L494, L498, Y499, L501, A502, V511, A513, V518, L521, L522, F525, A529, F534, L538, H553, I555, V566, V567, A570, L571, V605, C620, A628, A630, A634, A658, I660 |
| 811 | Protein NDRG1 | Q92597 | Y73, C92, A119, I145, W183, H214, L284 |
| 812 | Nectin-2 | Q92692 | L52, C54, V68, W70, A83, F85, L103, L127, Y138, F142, L156, V180, A181, C183, V236, C238, V240, L255, V257, V263, W272, L314, C329, V331 |
| 813 | Ryanodine receptor 2 | Q92736 | L14, V20, V21, L22, C24, A26, L35, C36, L37, A38, A39, I64, C65, F67, L69, L78, L113, Y115, A118, I119, L121, H123, L130, C131, A144, V147, L149, C158, W160, I162, V175, L181, L183, L192, V203, A205, A206, W212, V214, L228, L234, L236, H238, C244, L245, V247, V260, Y262, V267, A271, L274, W275, L277, I289, F295, L297, H299, V300, |

TABLE 5-continued

| TARGETS | | | |
|---|---|---|---|
| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
| | | | Y305, L306, L315, L316, A322, F329, F331, I354, C361, I363, L372, A391, I403, L405, A416, V418, I419, F426, F429, L447, V452, L456, L459, I460, F463, L482, L488, F489, M494, V498, C501, I502, L505, F514, A518, I529, L530, L533, L536, A539, L540, W697, A698, V718, C757, I766, V791, V792, A886, F921, V996, A1000, H1004, L1050, V1054, V1115, W1117, L1128, A1134, A1136, F1137, V1162, C1164, V1166, M1173, F1175, F1195, V1204, V1443, W1445, I1446, L1459, V1465, V1467, L1469, I1507, L1518, F1520, A1542, F2720, A2725, H2727, H2729, L2779, M2782, M2828, M2840, M2844, A2845, A2889, I2892, L2893, L2896 |
| 814 | Serine protease HTRA1 (EC 3.4.21.—) | Q92743 | C53, C76, L132, L150, V175, I179, A182, V183, V184, H185, I186, L188, F207, I208, I215, V216, A219, V221, V222, V228, V230, A240, A249, I251, A252, I254, I256, V279, V280, A281, I282, V297, I317, A321, I323, L332, V333, V339, I340, I342, F353, A354, I355, I360, F363, I383, A395, L398, A412, I414, A423, L428, V433, I434, I437, V448, I452, L458, M460, V462, I471, V473 |
| 815 | Secreted frizzled-related protein 3 | Q92765 | A63 |
| 816 | Ras-responsive element-binding protein 1 | Q92766 | C701, C792, C805, C1514 |
| 817 | Disks large homolog 3 | Q92796 | I132, L134, L141, A146, V154, I160, I162, A170, A171, V179, V183, L184, V186, V191, A199, A202, L203, A206, V210, L212, V214, V227, L229, L236, I240, I255, I257, A265, A266, L278, V281, L286, A294, L298, V305, L307, V309, A310, I387, L389, I409, F410, V411, A420, L426, I432, V435, A448, A451, V459, I461, A463 |
| 818 | X-linked retinitis pigmentosa GTPase regulator | Q92834 | A13, V14, H46, A48, V49, V50, L56, M58, F59, L67, V81, V89, A92, H98, L100, V101, V108, A110, L119, I133, A153, A154, L155, L161, M163, W164, I172, H201, A203, F204, V205, L211, V213, F214, L222, L228, H254, V256, V257, V263, F266, L274, L280, I289, H306, A308, L309, L315, M316, F319, C343, H360, M361, V362, V363, A365 |
| 819 | Ectodysplasin-A (Ectodermal dysplasia protein) | Q92838 | L90, V251, L253, V262, L271, L293, V295, Y301, I303, V307, V309, Y311, I312, F314, A318, Y320, V322, I336, C346, I360, V362, I369, I371, M373, F380, A382 |
| 820 | Canalicular multispecific organic anion transporter 1 | Q92887 | A668, V669, L680, A683, M684, I1330, V1332, V1333, L1343, L1347, F1348 |
| 821 | Tumor necrosis factor receptor superfamily member 14 | Q92956 | C53, C54, C57 |
| 822 | Lipoma-preferred partner | Q93052 | C444, L451, C476, I483, A494, F500, C524 |
| 823 | Homogentisate 1,2-dioxygenase (EC 1.13.11.5) | Q93099 | L61, Y62, W97, F112, V113, L119, C120, L131, A132, I133, I135, F136, L137, C138, C146, F147, F154, L155, I156, V157, L163, I165, F169, M172, V174, I179, C180, V181, I182, M186, F188, I190, Y199, I200, L201, V203, F208, L221, F227, V239, V245, I246, L253, A256, F263, V265, A267, W268, Y277, V300, L301, A303, A313, F315, I317, F342, L345, A397, F398, F400, Y423 |
| 824 | Interleukin-22 receptor subunit alpha-2 | Q969J5 | F41, L45, F61, V62, C118, L120, Y131, V135, F152, V176, L178, L183, V205, A241, I243 |
| 825 | SH3 domain-containing kinase-binding protein 1 | Q96B97 | A4, V6, L18, I20, I26, W37, F48, V53, C103, V105, L117, L119, I125, V127, L140, F147, I152, C272, V274, L286, I288, V294, W307, F318, V323 |
| 826 | Interleukin-17 receptor A | Q96F46 | L48, V93, A94, I96, W98, A112, L114, F129, L135, F144, F149, V150, V151, Y157, V159, V161, H163, V182, M190, C196, L217, V219, F221, Y230, I232, L234, V281, I283, F287 |
| 827 | Leucine-rich repeat and immunoglobulin-like domain-containing nogo receptor-interacting protein 1 | Q96FE5 | V55, C57, L76, L78, I83, L86, F91, L97, L100, L102, V107, A114, F115, L118, L121, L124, L131, V138, L142, L145, L148, I150, L158, F163, L166, L169, L172, V174, L179, A186, F187, L190, L193, L196, L198, C201, A210, L211, L214, L217, L220, L222, I230, L241, L244, I246, W249, L252, C259, L260, L265, L268, I270, A282, L286, L289, I299, L310, L313, L318, L323, A330, F331, L334, L340, V342, L347, L350, V354, L361, L364, L366, L371, L377, V380, F381, L387, F389, C396, V402, F407, A424, F444, C446, W458, L482, V484, A487, Y495, C497, A499, A510, L512 |
| 828 | PDZ and LIM domain protein 5 | Q96HC4 | L8, W14, L28, I30, A39, V49, V50, I53, A58, M61, A66, I70, L77, M79, L81, C420, I427, L432, C446, M453, F458, V459, C467 |
| 829 | E3 ubiquitin-protein ligase Itchy homolog | Q96J02 | L20, I22, V24, V43, V45, V47, V71, V73, L79, F81, V83, L95, I102, L106, L113, L122, L135, I137, L139, L328, L440, F456, F496, F535, C539, I550, V552, F558, I565, L573, V579, I580, V592, W596, F597, L600, L611, F638, F640, I641, |

TABLE 5-continued

| TARGETS | | | |
|---|---|---|---|
| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
| | | | F644, I645, A646, M647, A648, Y664, I667, L677, F705, A742, F757, F761, I764, L765, L770, F773, L778, L782, W793, I809, F812, F815, V816, M825, L827, L828, V831, F842, F854, C855, I856, C871, L875, L877, L886, L890, A893, I894 |
| 830 | Serine/threonine-protein kinase WNK4 (EC 2.7.11.1) | Q96J92 | L210 |
| 831 | Roundabout homolog 3 | Q96MS0 | C143, I572, L574, I591, V616, F627, V629, A631 |
| 832 | NACHT, LRR and PYD domains-containing protein 3 | Q96P20 | L10, L14, F25, L29, L54, A55, M58, A67, W68, A69, M70, A71, I74, F75, A87 |
| 833 | Interleukin-17F | Q96PD4 | C102, C107, V129 |
| 834 | SLIT and NTRK-like protein 1 | Q96PX8 | Y61, L63, L65, L70, L73, F78, L87, M89, L94, A101, F102, L105, V108, L111, I113, I118, F121, L129, L132, L135, A137, L142, A149, F150, L153, L156, L159, L161, I166, V173, F174, L182, L184, L189, V197, L198, I201, I207, L208, L209, W214, C216, L220, L223, A234, V239, C241, L247, L252, I387, I390, F395, L401, L404, L406, I411, F419, L422, L425, L428, M430, L435, L438, F443, L446, L449, L452, V454, I459, I462, F467, M470, L473, L476, L478, L483, V490, F491, L496, L499, L501, F506, V514, L515, I524, L526, W531, I537, F540, L556, F569 |
| 835 | Membrane-associated guanylate kinase, WW and PDZ domain-containing protein 1 | Q96QZ7 | F318, Y377, L475, L496, I498, A507, M513, V518, I519, V520, V522, V527, L528, V535, V548, L550, L552, C553, I646, I686, V689, V694, V702, V715, L717, V719, I842, L844, I865, I867, A876, L888, I889, V891, V896, V904, A911, V917, L919, V921, V999, I1001, I1038, A1047, L1053, V1062, I1075, V1086, L1088, V1153, L1166, L1176, A1187, M1193, I1199, I1202, A1215, L1218, V1226, L1228, L1230 |
| 836 | Envelope glycoprotein gp160 | Q993A8 | A13, M38, V44, M47, I51, V63, V70, I97, L136, A167, I168, C182, V185, I194, L202, L203, V213, I227, I228, V229, L231, V235, I237, C239, M269, C274, I276, W281, L285, I288, A289, L292, I302, I303, F304, H317, F319, C321, F326, C328, L333, F334, L359, C361, I366, I367, V373, A376, M377, I392, L395, L396, L397, I410, F411, M418, W422, L426, V432, I434, V448, I491, V492, L498, L499, A501, I502, A504, L508, L509, V513, I516, L519, I523, I578, I585 |
| 837 | Neurogenic locus notch homolog protein 4 | Q99466 | C472, C510, C548, C586, C965, L1638, H1639, A1641, A1642, A1650, L1671, H1672, A1674, V1675, A1679, V1682, C1683, L1686, L1705, M1706, L1707, A1708, A1709, L1716, L1720, A1737, L1738, H1739, A1741, A1742, A1749, A1750, L1753, L1771, F1772, L1773, A1774, A1775, V1782, A1783, L1786, V1806, A1807, L1815 |
| 838 | Protein deglycase DJ-1 | Q99497 | A6, L7, V8, I9, L10, A11, A14, V25, M26, V33, A36, L58, A61, Y67, V69, V70, V71, L72, A79, L82, V88, L92, I102, A103, A104, I105, A111, L112, L113, H115, I117, V123, M133, M134, I152, L153, F164, A165, I168, V169 |
| 839 | Histone H2B type 1-N | Q99877 | V42, V45, L46, A59, M63, V67, I70, F71, I74, A75, A78, A82, I90, I95, A98, V99, L103, A108, A111, A118 |
| 840 | Myocilin (Myocilin 55 kDa subunit) (Trabecular meshwork-induced glucocorticoid response protein) [Cleaved into: Myocilin, N-terminal fragment (Myocilin 20 kDa N-terminal fragment); Myocilin, C-terminal fragment (Myocilin 35 kDa N-terminal fragment)] | Q99972 | V269, W270, W286, I288, V298, Y301, F307, H316, L318, A327, V329, L334, F336, V344, I345, Y347, L349, I360, A363, L381, V383, L388, V390, I391, I401, L403, L406, L411, V426, A429, F430, I431, I432, L436, V449, M476, L486, W489, M494 |
| 841 | Semaphorin-3C | Q99985 | L305, L449, L472, I473, I491, L526 |
| 842 | Sclerostin | Q9BQB4 | C80, L146, C165 |
| 843 | Programmed cell death protein 10 | Q9BUL8 | L22, A41, A46, A51, L81, F100, L103, A107, L110, L114, I117, F127, I134, L141, V145, V148, L160, F167, F174, V190, F191, A194, L197, I198, I204, L205, F208 |
| 844 | Brother of CDO | Q9BWV1 | V622, V624, W626, F639, V641, I668, Y677, F679, V681, A683, V701, I718, I729, L731, F748, I750, I777, Y786, I788, M790, C792 |
| 845 | Complement C1q tumor necrosis factor-related protein 5 | Q9BXJ0 | A108, L123, F125, F143, C145, Y151, F153, V155, V159, L164, L168, L199, V205, V207, F227 |

TABLE 5-continued

TARGETS

| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
|---|---|---|---|
| 846 | Periaxin | Q9BXM0 | V44, A53 |
| 847 | Complement factor H-related protein 5 | Q9BXR6 | Y53, I70, C87, V110, I127, C129 |
| 848 | Disintegrin and metalloproteinase domain-containing protein 33 | Q9BZ11 | L212, L214, Y215, I216, V217, A218, L237, V240, V244, L247, L248, I253, W263, L279, F282, L283, A298, L300, L301, V328, A339, A340, M343, A344, I347, L351, M373, L405, C433, C444, C457, C462, C488, C495 |
| 849 | NACHT, LRR and PYD domains-containing protein 1 | Q9C000 | L13, L21, F24, L28, V53, A54, L57, A66, A70, W74, L82, V136, F365, F801, A824, V825, L828, L842, L844, C847, L849, C854, L870, L872, L877, A882, C886, L899, C904, C910, C911, L918, L927, L929, V939, L942, C943, L946, L953, L956, L958, M967, L971, L974, I983, L1379, V1382, L1389, I1390, V1393, V1396, V1399, L1400, L1403, L1408, V1416, M1426, L1429, L1444, A1447, L1448, L1459 |
| 850 | MCG4778 | Q9D1H1 | L75, F77, I79, L82, I88, I103, L107, L110, V140, C144, A150, I158, F162, L172, V182 |
| 851 | Amyloid beta A4 precursor protein-binding family B member 2 | Q9DBR4 | V594, L611, A614, V630, M632, V639, V641, C654, V656, L659, F661, M662, V664, F671, A672, F673, I674, C684, V686, F687, C689, A693, V696, V700, A703, N738 |
| 852 | Sperm-egg fusion protein Juno | Q9EQF4 | M28, C47, W50, C55, C86, A93, C95, F96, C99, L103, V120, V123, L125, C126, C130, W133, C137, F169, F173, L179, C180, I183, F188, C200, L201, V216 |
| 853 | Fibroblast growth factor 23 | Q9GZV9 | H41, L42, L53, I55, A72, L73, I85, L94, C95, M96, C113, F115, V126, L135, V136, F157 |
| 854 | ADP-ribosylation factor-like protein 6 | Q9H0F7 | V20, L21, C22, L23, I33, I34, F58, M70, A89, I90, F92, V93, I94, V104, L109, L112, I118, I125, L126, F127, F128, A129, V143, L149, C160 |
| 855 | Magnesium transporter protein 1 | Q9H0U3 | L44, I54, M56, L64, V65, Y72, V74, I75, V76, M77, F78, C90, A93, F97, L100, A101, I114, F116, V119, V127, F128, F139, A163, I166, I170 |
| 856 | ATP-binding cassette sub-family G member 8 | Q9H221 | L195, L234, L264, A422, A546, A548, A549 |
| 857 | ATP-binding cassette sub-family G member 5 | Q9H222 | V72, I81, M82, C83, I84, L85, L95, L96, L139, L142, V144, L148, Y150, A155, V168, M172, I185, A204, M214, L215, F216, L235, A239, I244, V245, I249, I263, A264, F273, M280, F284, F298, Y301, Y329, L371, V375, A415, L423, F426, V427, M435, A438, F442, V448, Y458, M463, M464, A466, Y467, V471, A478, F482, C486, Y487, L490, L492, A505, L506, A508, H510, L511, L518, L521, V530, V534, C571, I574, L575, V576, F580, C613, A616, L627, F642 |
| 858 | Cadherin-23 | Q9H251 | I42, L55, F78, V87, L89, V103, F105, V107, V118, I120, V122, V154, V187, V189, V205, A207, L222, I224 |
| 859 | DnaJ homolog subfamily C member 5 | Q9H3Z4 | L16, Y17, L20, I31, A53, I60, A63, L67, I75, V95 |
| 860 | SPARC-related modular calcium-binding protein 1 | Q9H4F8 | I416 |
| 861 | Anthrax toxin receptor 1 | Q9H6X2 | L45, Y46, F47, I48, L49, V55, I62, Y63, F65, V66, L69, L78, M80, F82, I83, V84, F85, L109, L113, M120, F124, A127, I131, I145, I146, A147, L148, F159, A165, V175, C177, V178, V180, L188, I191, A192, L208 |
| 862 | Pleckstrin homology domain-containing family A member 1 | Q9HB21 | L14, F30, L32, F39, F81, V82, M83, L92, W103, V106, L107, C198, L215, I220, I235, C246, L257, F258, I260, V269, V284 |
| 863 | Transient receptor potential cation channel subfamily V member 4 | Q9HBA0 | L487 |
| 864 | Interleukin-21 | Q9HBE4 | L35, V39, L42, A56, C64, A68, F69, C71, F72, L77, I89, L96, F129, L130, F133, L136, L137, I141 |
| 865 | E3 ubiquitin-protein ligase SMURF1 | Q9HCE7 | I15, L17, V19, A22, L25, L33, A38, I40, V42, L68, I76, I78, V80, I86, F94, I133, V135, F324 |
| 866 | Roundabout homolog 2 | Q9HCK4 | C110, A435, L437, W451, L473, L478, Y486, C488, A490, A501, L503, V538, L540, I557, V582, F593, V595, A597, V637, V652, V654, I665, Y668, V670, L699, I710, V712 |
| 867 | Golgi-associated PDZ and coiled-coil motif-containing protein | Q9HD26 | L291, I313, I315, A324, L330, A335, I336, A338, V339, L344, A352, L356, I363, F365, V367 |

TABLE 5-continued

| TARGETS | | | |
|---|---|---|---|
| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
| 868 | Neurexin-3-beta | Q9HDB5 | I96, L113, V115, F117, I125, L126, V127, I129, L139, L141, I143, I148, V150, F152, I159, I161, V168, V176, A185, L187, V189, V194, L204, F207, I213, I215, F224, L228, L231, Y233, V238, L239, V255, V261 |
| 869 | Neuraminidase (EC 3.2.1.18)/strain A/Brevig Mission/1/1918 H1N1 (Influenza A virus (strain A/South Carolina/1/1918 H1N1)) | Q9IGQ6 | L85, I106, V114, V116, F121, I122, F132, F133, L134, L158, C161, A178, W179, A181, A183, C184, L191, I193, I195, A202, V203, A204, L206, L224, A232, C233, V234, F239, I241, M242, A251, Y253, I255, I258, V263, H275, Y276, C279, C281, Y282, V288, C290, V291, C292, V304, F306, L310, C318, V321, F322, F349, F351, Y353, V357, W358, I359, F371, M373, I374, F387, I393, V394, F406, V407, M418, C421, F422, W423, V424, L426, W437, I443, F445 |
| 870 | Spike glycoprotein | Q9J3E7 | L79, V87, F92, F100, I104, A106, V108, F123, I126, V127, I128, F132, V139, V140, I141, I148, V152, C153, C158, C165, A201, F202, F206, F213, A215, F226, I232, V241, L242, F244, C246, Y258, V260, A482, Y891, V900, V906, A994, A1053, L1067, I1113 |
| 871 | Interleukin-23 subunit alpha | Q9NPF7 | C33, L40, A44, L82, C89, L90, I93, H94, L97, Y100, F109, L124, L128, L131, L150, L169, V173, A176, V179, F180 |
| 872 | SLAM family member 7 | Q9NQ25 | F39, I51, W53, L90, L95, L122, V124, Y125, L128, W164, L180, C195 |
| 873 | Serine protease inhibitor Kazal-type 5 | Q9NQ38 | C30, F33, C44, C63, C66, C161, L173, C194, C197, C225, L237, C258, C261, C297, L309, C330, C333, C367, L379, C400, C403, C437, L449, C470, C473, C496, L508, C529, C532, C567, L579, C600, M602, C603, C632, L644, V653, C665, M667, C668, C707, L719, C740, C743, C774, L786, C807, C810, C849, L861, C882, C885, C916, L928, C949, C952, C1014, Y1021, L1027, C1028, I1040 |
| 874 | Ubiquitin carboxyl-terminal hydrolase CYLD (EC 3.4.19.12) | Q9NQC7 | V131, V133, V146, V165, L167, C193, V195, F196, V236, L238, V249, L255, V265, V267, C286, I295, A476, I488, A502, L504, A531, I594, L603, L607, F608, C609, L610, F611, A612, Y633, L640, V645, V654, I659, L662, L666, F685, L689, I693, L700, I717, I730, F745, L752, I754, M756, L775, I777, L780, C788, C802, F816, A863, V864, L865, C866, A874, F875, V876, L886, F888, V906, C909, V912, A935, C945, Y947 |
| 875 | Potassium voltage-gated channel subfamily H member 7 | Q9NS40 | I30, A32, C44, F48, C49, M51, V59, C64, C66, I82, A83, V96, Y98, I112, I127, A766, A781, L785, I790, I807, F808, V825, A827, L833, V844 |
| 876 | Septin-11 | Q9NVA2 | F42, I44, L45, C46, V47, L57, M58, V92, L94, L96, V99, Y114, I117, I121, F125, L129, A149, C150, L151, I154, M169, L172, V176, I178, I179, I181, I182, A183, F196, I200, M228, F234, V237, A252, V262, F270, L273, M276, L285, H293, Y294 |
| 877 | Alpha-parvin | Q9NVD7 | L268, V272, H275, L276, V283, L286, F290, L296, V297, L299, M300, V308, V327, A330, M334, L339, I349, L358, V360, L361, L364 |
| 878 | Sodium channel subunit beta-3 | Q9NY72 | L43, C45, V60, W62, V103, I105, V107, Y118, C120, V122 |
| 879 | Endoplasmic reticulum aminopeptidase 1 (EC 3.4.11.—) | Q9NZ08 | F47, Y57, Y63, L65, I67, L71, F76, V82, I84, A86, I93, I94, L95, A105, L107, L115, L123, I131, A132, L133, L139, L140, V141, Y145, V147, V148, I149, Y151, Y163, L177, A178, F182, A186, A187, A190, F191, C193, F194, A201, F203, I205, I207, F236, M242, Y245, L246, V247, A248, F249, I250, I251, V267, V269, A271, A279, Y281, A282, L283, A285, A286, L289, L290, Y293, F297, L308, A309, A310, I311, F314, A318, M319, W322, L324, Y327, A331, L332, L333, I347, V351, A352, L355, A356, H357, W359, F360, L363, M366, W369, L372, W373, L374, F378, A379, F381, M382, V387, L394, V396, F405, A407, M408, A412, V419, V423, M432, V436, A442, C443, I444, L445, L448, F457, I461, L465, L478, W479, M482, V517, M520, M521, W524, F530, L532, I533, I535, V542, M544, Y549, W563, V565, L567, L582, F600, M604, Y607, Y608, I609, V610, L620, L624, V631, A637, L639, I640, A643, L646, I654, A657, L658, L660, Y663, L664, V673, L680, M687, V695, F699, F702, L703, L731, L732, A735, C743, A747, V767, A770, V771, A776, W782, L785, I801, A804, L805, C806, L814, L817, L818, I827, F832, I835, L836, I839, A849, W850, L853, L860, F864, I871, M874, V875, F882, V891, F895, L898, L905, I915, I929, L933 |
| 880 | Interleukin-1 receptor accessory protein-like 1 | Q9NZN1 | L66, V347 |
| 881 | Programmed cell death 1 ligand 1 | Q9NZQ7 | V21, M36, I38, C40, L53, V55, W57, M59, I64, I65, F67, Y81, L92, A97, A98, L99, I101, V104, Y112, C114, I116, I126, V128, A132, Y134, L153, C155, A157, A163, W167, V193, L197, F207, C209, F211, L214, L224, I226 |

TABLE 5-continued

| TARGETS | | | |
|---|---|---|---|
| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
| 882 | Potassium voltage-gated channel subfamily D member 2 | Q9NZV8 | L66, F84 |
| 883 | Signal-regulatory protein gamma | Q9P1W8 | A49, L51, C53, V64, W66, I104, I109, C119, V120, F166, C168, F173, W182, A211, V213, L215, V224, C226, V228, L244, A247, I248, V269, C271, V273, F276, L283, W285, C329, V331 |
| 884 | Spastin (EC 3.6.4.3) | Q9UBP0 | V116, A123, A130, A145 |
| 885 | Glyoxylate reductase/hydroxypyruvate reductase (EC 1.1.1.79) | Q9UBQ7 | V9, V11, L23, A24, A26, V49, A50, A52, L55, L56, C57, V63, L68, V77, I78, I93, A112, A115, L118, L119, C123, V156, I158, A167, I168, A169, L172, L181, A192, L205, A206, F211, I212, V213, V214, C226, F230, F231, A238, V239, F240, I241, V248, L254, A257, A264, A266, L268, V270, L282, A309, A310, L313 |
| 886 | Beta-1,4-galactosyltransferase 7 | Q9UBV7 | L95, A96, V97, L98, V99, F111, V112, M115, L119, I128, V130, L131, A142, L144, I145, V147, I159, A160, H162, L166, L167, L173, Y175, H184, V185, A186, L190, V200, I203, L204, L205, L206, Y211, M217, F231, I235, L242, L258, A262, A305, L310, I312, C324 |
| 887 | Fibulin-5 | Q9UBX5 | C166, C286 |
| 888 | 5'-AMP-activated protein kinase subunit gamma-2 | Q9UGJ0 | M265, C270, I273, V289, A292, L296, A304, L306, L318, I320, F323, I324, I326, L327, L341, I346, A368, L370, A373, V374, L377, L385, V387, L399, H401, I404, L405, L408, F420, L425, I430, I445, A448, L449, I457, L460, V462, Y473, V478, A482, L490, V494, L498, C511, L517, I520, V529, L532, V533, V534, V535, I545, L547, I550, L551, A553, L554 |
| 889 | Deleted in malignant brain tumors 1 protein | Q9UGM3 | A1896, V1899, I1901, V1910, C1911, A1920, V1922, V1923, C1924, A1981, V1983 |
| 890 | Interleukin-20 receptor subunit alpha | Q9UHF4 | M50, L54, L82, C95, L97, A110, V112, I151, V153, M172, L179, Y181, V183, V185, V216, V218 |
| 891 | Doublecortin domain-containing protein 2 | Q9UHG0 | I141, L143, I144, I158, V169, V173, L187, V195, Y207, V208, A209, V210, Y220 |
| 892 | DNA polymerase subunit gamma-2, mitochondrial (EC 2.7.7.7) | Q9UHN1 | L69, C73, F78, L79, L106, L110, W114, V118, V125, A130, L185, A189, L190, Y193, L197, Y206, L208, A209, C214, A237, L239, V240, W241, F242, W255, W262, W263, F266, F273, L289, F293, W295, I303, L303, L311, L322, V335, L336, V338, L342, M346, L347, A348, Y349, V371, L372, L374, L378, A379, V383, A384, L385, V387, L395, C399, L402, L406, L407, L418, I437, L438, V441, V443, I453, L471 |
| 893 | C-type lectin domain family 2 member D | Q9UHP7 | C86, F87, C103, A108, L110, A111, V113, L122, H131, W132, I133, L135, F155, C163, A164, L166, I183, C184 |
| 894 | Apolipoprotein | Q9UIR5 | W35, C60, C71 |
| 895 | Gap junction delta-2 protein | Q9UKL4 | C62 |
| 896 | Endoplasmic reticulum mannosyl-oligosaccharide 1,2-alpha-mannosidase (EC 3.2.1.113) | Q9UKM7 | V253, F257, A260, Y264, A268, L274, L287, L289, L291, I292, A294, L295, M298, A310, V314, L318, F320, V326, L328, I335, L336, L339, L340, A342, F351, A355, F358, L362, A365, I372, V377, I379, V395, I401, L403, F405, L408, F417, V421, V424, I428, L438, V439, I443, L458, A462, Y466, Y468, L470, I474, Y487, A490, I491, V494, L498, F509, V510, L513, M522, C527, L529, L533, A534, H545, L548, A549, L552, M553, C556, M559, L567, V572, V585, L596, V601, L604, F605, L607, Y616, I623, L624, I641, V644, M656, F660, L661, L665, Y667, L668, L670, L671, V685, F686, A690, H691, L693 |
| 897 | Disintegrin and metalloproteinase domain-containing protein 28 | Q9UKQ2 | C423, C434, C452, C453, C485 |
| 898 | Frizzled-4 | Q9ULV1 | I50, C53, A75, L79, L94, F97, L98, C99, V101, Y102, V103, C117, C121, V124, C128, L132, F135, L143 |
| 899 | Heat shock factor protein 4 | Q9ULV5 | L21, L24, L27, V28, I37, F46, V48, F54, V58, L59, F71, L75, F101, F106, L114, V117 |
| 900 | Neurogenic locus notch homolog protein 3 | Q9UM47 | C194, C428, C466, C504, C617, C884, C921, C1405, C1417, F1437, C1446, C1451, F1456, C1475, A1476, L1513, V1514, L1515, V1517, L1524, F1531, L1535, L1539, V1582, L1584, I1586, A1604, A1607, A1608, L1611, A1613 |
| 901 | Unconventional myosin-VI | Q9UM54 | A9, I31, A43, C63, L65, A71, L73, L74, I77, I86, V90, I93, L94, I95, A96, I103, I112, V127, F128, A129, I130, A131, A134, M138, V140, I147, I148, V149, A155, V164, Y167, L168, A185, L188, L189, A191, F192, A195, F206, F209, I212, F214, V220, I235, Y245, H246, I247, F248, Y249, L251, C252, L265, F271, Y273, L274, Y281, F282, I318, M320, M324, I327, L337, V340, V341, A342, V344, L345, L347, I350, L372, C375, A376, L378, L379, L381, L386, L390, A416, A419, A422, L423, A424, V427, Y428, L431, F432, V435, V436, V439, I452, V454, L455, F471, Y475, C476, L480, F483, |

TABLE 5-continued

| TARGETS | | | |
|---|---|---|---|
| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
| | | | F484, I488, L489, Y496, C514, I515, L517, I518, I525, I528, L529, F543, V547, F577, I578, I579, V586, Y588, F593, L605, I609, I617, L651, L654, L655, L658, F665, I666, C668, I669, I685, L689, M694, V697, L698, M701, Y705, A709, L714, Y718, Y721, L729, F734, C735, A737, L738, F739, L753, V756, F757, F758, F763, A764, I769, L777, L780, V784, I1171, F1180, A1204, H1205, F1206, A1212, M1215, L1226, V1227, M1235, L1245, F1258, W1262, L1271, A1274, I1275, A1280, A1285, L1289 |
| 902 | Rho GTPase-activating protein 26 | Q9UNA1 | A761, A763, L775, F783, V786, L795, I806 |
| 903 | Tumor necrosis factor ligand superfamily member 18 | Q9UNG2 | A82, F84, C100, V101, L109, I111, Y117, I119, V123, A124, V137, L139, Y140, I155, V158, L164, I170, L172, V180, W187, I189 |
| 904 | Protein unc-13 homolog A | Q9UPW8 | L1494, L1500 |
| 905 | Neuraminidase (EC 3.2.1.18)/strain A/Hong Kong/156/1997 H5N1 genotype Gs/Gd | Q9W7Y7 | I87, V95, V97, F102, I103, F113, F114, L115, L139, C142, A159, W160, A162, A164, C165, L172, I174, I176, A183, V184, A185, L187, L205, A213, C214, V215, F220, V222, M223, A232, Y234, I236, I239, V244, H256, Y257, C260, C262, Y263, A266, I269, C271, V272, C273, V285, F287, C299, V302, F303, F330, F332, Y334, V338, W339, I340, F352, M354, I355, F368, I374, I375, F387, I388, M399, C402, F403, W404, V405, L407, W418, I424, F426 |
| 906 | Hemagglutinin [Cleaved into: Hemagglutinin HA1 chain; Hemagglutinin HA2 chain]/strain A/Brevig Mission/1/1918 H1N1 (Influenza A virus (strain A/South Carolina/1/1918 H1N1)) | Q9WFX3 | V7, I20, C21, I22, A26, V33, V36, V43, L49, L50, L58, C59, L61, L67, L69, C72, I74, A75, W77, L78, L79, C84, L87, W93, Y95, I96, V97, C107, Y108, L118, L122, V125, F128, F134, A151, A152, C153, Y155, A158, L165, L166, W167, L168, Y175, L178, V190, L191, V192, L193, W194, V196, H197, H198, Y209, Y215, V216, V218, Y223, A233, M244, Y246, Y247, L250, L251, I257, F259, A261, L265, I266, A267, Y270, A271, F272, A273, L274, I282, I283, C292, C296, A302, I303, H313, I317, V324, L329, M331, A332, A349, M361, Y366, A388, I389, A440, L452, V459, L462, V466, L470, C481, H486, C488, C492, M493 |
| 907 | Genome polyprotein [Cleaved into: Core protein p21/genotype 1b (isolate Con1) (HCV) | Q9WMX2 | L754, V1061, L1070, A1071, C1073, V1074, V1077, C1078, W1079, V1081, A1085, I1097, L1108, V1109, L1120, L1130, L1132, I1140, V1142, V1158, L1161, L1169, C1171, A1176, V1177, I1179, F1180, A1190, A1192, V1193, F1195, V1196, V1198, M1201, Y1244, V1251, V1253, L1254, A1259, A1260, M1268, I1291, Y1293, Y1296, A1301, I1312, I1314, C1315, C1318, I1326, L1327, I1329, V1332, A1336, A1341, L1343, V1344, V1345, L1346, A1347, I1373, F1375, I1380, I1385, L1391, I1392, F1393, C1394, C1400, L1403, L1407, V1432, V1434, V1435, A1436, L1440, F1444, F1448, V1451, I1452, F1470, A1481, Y1499, L1517, C1518, C1520, Y1521, A1526, Y1528, L1539, Y1542, L1555, W1558, V1561, I1568, F1572, L1586, V1587, A1588, A1591, C1594, W1608, L1611, H1619, L1624, L1625, L1628, I1641, I1645, M2025, C2029, I2035, C2052, F2060, I2062, C2070, Y2090, V2091, V2093, V2102, M2105, F2122, V2128, F2147, L2160, L2440, L2449, L2450, V2456, Y2457, A2458, A2464, Y2483, V2486, M2490, A2492, A2494, V2497, A2499, A2507, C2508, Y2522, A2524, V2527, A2534, I2538, L2545, L2546, I2557, C2565, A2576, L2578, V2580, L2584, V2586, V2588, C2589, A2593, L2594, V2597, V2598, L2601, A2604, V2605, Y2610, V2620, L2623, A2626, M2634, F2636, Y2638, V2647, I2652, I2658, Y2659, C2661, C2662, A2665, A2668, A2671, I2672, L2675, L2679, Y2680, L2685, C2693, C2698, A2700, V2703, L2704, C2708, L2712, C2714, A2718, A2719, A2720, A2721, C2722, A2725, L2727, M2732, L2733, V2734, L2739, V2740, V2741, I2742, C2743, A2753, L2755, F2758, A2761, M2762, Y2765, A2767, I2782, V2789, A2792, Y2801, L2803, L2811, A2812, A2814, A2815, L2828, I2831, I2832, A2835, L2838, W2839, A2840, I2843, L2844, M2845, H2847, F2848, F2849, L2858, A2861, C2864, I2866, A2869, C2870, Y2871, I2873, L2876, L2878, I2881, I2882, L2885, A2890, F2891, V2904, A2905, C2907, L2908, L2911, V2913, V2918, W2919, A2923, V2926, L2930, L2931, A2937, A2938, C2940, L2944, F2945, A2948, A2960, A2961, F2970, A2972, Y2974, I2979 |
| 908 | Tumor necrosis factor ligand superfamily member 13B | Q9Y275 | L112, C146, L147, L149, V166, A177, L178, I185, V187, F193, F194, I195, Y196, V199, Y201, M208, H210, I212, L224, L226, M236, C245, A248, L253, L259, L261, A262, I263, A268, V276, F278, F279, A281, L282 |
| 909 | Cofilin-2 | Q9Y281 | V11, V14, M18, A35, V36, L37, F38, I47, I48, I55, V57, Y68, F71, V72, L75, C80, Y82, A83, L84, Y85, A87, V100, F101, W104, A109, Y117, I124, F128, V137, L149, L161 |
| 910 | Ragulator complex protein LAMTOR2 | Q9Y2Q5 | L11, L23, L24, L25, A42, A46, V81, A82, I83, L89, L90, L91, C92, M93, L104, A108 |

TABLE 5-continued

| TARGETS | | | |
|---|---|---|---|
| SEQ ID NO. | Protein Name/Strain | UniProt ID No. | Exemplified Sites of Mutations to Generate Peptidogenic Protein (Each position can be substituted alone or in any combination with any of the other listed amino acid positions.) |
| 911 | Kinesin-like protein KIF3A | Q9Y496 | V15, V17, V18, V19, I46, V48, V76, I85, V88, I96, A98, M110, I122, F127, I130, Y149, L150, I152, V157, L160, M195, H216, F224, I226, I235, L246, L248, V249, A252, L267, V283, I284, L302, L310, M318, C319, A320, I322, A325, L336, A339, A342, I345 |
| 912 | Neurexin-3 | Q9Y4C0 | F337, L576, L582, L585, F711, I824, F875, F896, L909, L949, L988, Y993, V1022, I1101, L1118, V1120, F1122, I1130, L1131, V1132, I1134, L1144, L1146, I1148, I1153, V1155, F1157, I1164, I1166, V1173, V1181, A1190, L1192, V1194, V1199, L1209, F1212, I1218, I1220, F1229, L1233, L1236, Y1238, V1243, L1244, V1260, V1266 |
| 913 | Dystrobrevin alpha | Q9Y4J8 | C258, L266, C270 |
| 914 | Kallikrein-4 (EC 3.4.21.—) | Q9Y5K2 | I31, A46, A47, L48, V59, L60, V66, L67, A69, C72, I79, L81, L83, A99, A114, L117, M118, L119, I132, I135, C148, V150, W153, V168, C178, C192, A193, L211, C213, L217, L220, V236, Y237, L240 |
| 915 | CD2-associated protein | Q9Y5K6 | Y4, V6, L18, I20, I26, L38, F49, V54, C113, V115, L127, L129, I135, F157, V162, C274, L288, F290, I296, F320, A325 |
| 916 | Brefeldin A-inhibited guanine nucleotide-exchange protein 2 | Q9Y6D5 | F654, A679, Y711, F722, A739, A769, I776, I822 |
| 917 | Cadherin-10 | Q9Y6N8 | L63, F102, I111, A113, I117, L127, A131, V147, I148, I150, V169, V182, I217, I218, V235, I237, A239, V255, I257, A293, F317, L346, V348, A350, V371, I373 |
| 918 | Tumor necrosis factor receptor superfamily member 11A | Q9Y6Q6 | C47, C50, A113, C114, C133 |

Example 4: Assays Measuring Alterations in Conformational Dynamics

Alterations in conformational dynamics can be measured by standard methods known in the art. In preferred embodiments, alterations in conformational dynamics can be shown by measuring changes in melting temperatures, in urea-induced equilibrium unfolding studies, and/or Gibbs free energy as compared to the starting protein.

Changes in melting temperature can be shown by the following protocol. For example, a peptidogenic protein (0.20 mg/ml) and a starting protein (as a control) is heated from 10° C. to 72° C. in a 0.1 cm quartz cuvette with a heating rate of 1 degree×min−1 controlled by a Jasco programmable Peltier element. The dichroic activity at 209 nm and the photomultiplier tube voltage (PMTV) are continuously monitored in parallel every 0.5° C. All the thermal scans are corrected for the solvent contribution at the different temperatures. Melting temperature (Tm) values are calculated by taking the first derivative of the ellipticity at 209 nm with respect to temperature. All denaturation experiments are performed in triplicate (see Lori et al., PLoS One, 5; 8(6):e64824 (2013)).

A change in urea-induced equilibrium unfolding can be shown by the following protocol. A peptidogenic protein (final concentration 40 ug/ml) and a starting protein (as a control) is incubated at 10° C. in increasing concentrations of urea (0-8 M) in 25 mM Tris/HCl, pH 7.5, in the presence of 0.2 M NaCl and 2 mM DTT (for non-disulfide containing proteins). After 10 min, equilibrium is reached and the intrinsic fluorescence emission, absorbance at 287 nm, and/or far-UV CD spectra (0.5-cm cuvette) are recorded in parallel at 10° C. To test the reversibility of the unfolding, a peptidogenic protein is unfolded at 10° C. in 7.0 M urea at 0.4 mg/ml protein concentration in 25 mM Tris/HCl, pH 7.5, in the presence of 2 mM DTT and 0.2 M NaCl. After 10 mM, refolding is started by 10-fold dilution of the unfolding mixture at 10° C. into solutions of the same buffer used for unfolding containing decreasing urea concentrations. The final protein concentration is 40 ug/ml. After an incubation period of 15 min to 24 h, the intrinsic fluorescence emission, absorbance at 287 nm, and/or the CD spectra are recorded as a function of urea concentration at 10° C. (see Lori et al., PLoS One, 5; 8(6):e64824 (2013)).

Alterations in Gibbs free energy can be shown by the following protocol. In order to measure Gibbs free energy, differential scanning calorimetry (DSC) experiments are performed on a VP-DSC (Microcal Inc., Northampton, Mass.) instrument at a scan rate of 1.5 deg/minute. Where possible, temperature-induced unfolding of a peptidogenic protein is checked for reversibility by comparing first and second DSC scans. It is understood that reversibility of folding and unfolding is not a requirement for the peptidogenic proteins described herein. The partial molar heat capacity of the protein, Cp,pr(T), is obtained from the experimentally measured apparent heat capacity difference between the sample (containing protein solution) and reference (containing corresponding buffer solution) cells, ΔC_p^app (T). Protein concentration is measured spectrophotometrically using a known molar extinction coefficient. Analysis of the heat capacity profiles according to a two-state model is done using non-linear regression routine NLREG and in-house written scripts. The standard thermodynamic functions under reference conditions are calculated as:

$$\Delta H_{cal}(T) = \Delta H(T_m) + \Delta C_p(T - T_m)$$

$$\Delta S(T) = \Delta S(T_m) + \Delta C_p \ln(T/T_m) = \frac{\Delta Hcal(Tm)}{Tm} + \Delta Cp\ln(T/Tm)$$

$$\Delta G(T) = (T_m - T)(\Delta H_{cal}(T_m)/T_m - \Delta C_p) - T\Delta C_p \ln(T/T_m)$$

Where ΔH(T), ΔS(T), and ΔG(T) are the enthalpy, entropy and Gibbs energy functions of a peptidogenic protein, respectively, ΔHcal is the enthalpy of unfolding at the transition temperature Tm, and ΔCp is the heat capacity of unfolding (see Loladze et al., J. Mol. Biol. 320, 343-357 (2002)).

Example 5: Assays Measuring Peptidogenicity

One of the intracellular conditions that may participate in processing of the peptidogenic proteins as described herein is proteolysis. The influence of the differential stability of the peptidogenic proteins on proteolysis can be determined using one of several in vitro or ex vivo assays.

(a) Cathepsin L Proteolysis

In one embodiment, examination of the behavior of the peptidogenic proteins toward proteolysis is measured by subjecting them to the action of cathepsin L, one of the enzymes known to be critical in protein antigen processing (Hsieh, C. S., deRoos, P., Honey, K., Beers, C., and Rudensky, A. Y. (2002) *J. Immunol.* 168, 2618-2625). Susceptibility of the peptidogenic proteins to proteolysis is assessed using lysosomal cathepsin L. The peptidogenic proteins (0.5 ug/ul) are incubated with various amounts (e.g., 1.5 munits) of enzyme in 50 mM sodium acetate buffer, pH 4.5, for various lengths of time at 37° C. Digestion is stopped using 0.1% TEA, and proteolysis is monitored by reversed-phase HPLC on C18 reverse phase columns (Vydac, Hesperia, CA). Elution of the proteolytic products is carried out with a linear gradient of acetonitrile/water containing 0.1% TEA.

(b) Proteolysis Using Alpha-Chymotrypsin and Carboxypeptidase Y

In another embodiment, examination of the behavior of the peptidogenic proteins toward proteolysis is measured by subjecting them to the action of alpha-chymotrypsin and carboxypeptidase Y. Alpha-chymotrypsin is an endopeptidase which cleaves at the carboxyl terminus of aromatic amino acids; carboxypeptidase Y is an exopeptidase which removes amino acids sequentially from the carboxyl terminus. Proteolytic digestion with these enzymes is specific for unstable conformations, hence, the conformational stability of the peptidogenic proteins determines their resistance/susceptibility to proteolytic digestion. The peptidogenic proteins at 1 mg/ml in 0.5 ml of 20 mM HEPES-buffered saline, pH 7.5, are incubated at 37° C. with 100 ug of alpha-chymotrypsin from bovine pancreas and carboxypeptidase Y from yeast. Each incubation is terminated at various time-points and the digested samples are stored at −20° C. until analyzed. Samples are analyzed by sodium dodecyl sulfate-polyacrylamide gel electrophoresis (SDS-PAGE), through a 15% acrylamide gel and under reducing conditions, then stained with Coomassie Brilliant Blue for visualization.

(c) Proteolysis Using Lysosomal Extracts

In another embodiment, examination of the behavior of the peptidogenic proteins toward proteolysis is measured by subjecting them to the action of lysosomal extracts of bone marrow-derived dendritic cells. The peptidogenic proteins are incubated at various concentrations in the presence of equal amounts of proteins from crude lysosomal extracts from bone marrow-derived dendritic cells. The mixtures are incubated in 0.1 M sodium citrate buffer, 0.5% Triton X-100, and 2 mM dithiothreitol at pH 4.5. Each incubation is terminated at various time-points and the digested samples are stored at −20° C. until analyzed. Samples are analyzed by SDS-PAGE. The experiments are repeated with and without prior adsorption of peptidogenic proteins onto an adjuvant such as aluminum hydroxide. Bone marrow-derived dendritic cells are purified with use of anti-CD11c microbeads from bone marrow cultured in granulocyte macrophage-colony stimulating factor. See, for example, Delamarre et al., FIG. 4.

(d) Proteolysis after Internalization by Bone Marrow-Derived Dendritic Cells

In another embodiment, examination of the behavior of the peptidogenic proteins toward proteolysis is measured by labeling them with FITC per the manufacturer's protocol, incubating bone marrow-derived dendritic cells with the FITC-proteins, and measuring the percentage of FITC+, CD11c+ cells over time. Bone marrow-derived dendritic cells are loaded with 0.5 mg/ml of the FITC-labeled peptidogenic proteins for 1 hour, are washed, and then are cultured at 37° C. for various amounts of time. FACS is then used to determine the percentage of FITC+, CD11c+ cells at each time point subtracted to the percentage of FITC+, CD11c+ cells at time 0 h. This represents the percentage of proteolysis of the peptidogenic proteins. The experiments are repeated with and without prior adsorption of FITC-labeled peptidogenic proteins onto an adjuvant such as aluminum hydroxide.

Example 6: Antibody Production and Sequencing

Ig-seq of antibody repertoires may follow previously described protocols (10, 29) with minor modifications. B cells can be isolated from the serum, spleen, or other tissues of hyperimmunized rabbits. In order to reduce the complexity of the sequencing library, this population can be sorted to enrich for $CD19^{+}CD3^{-}CD27^{+}CD38^{int}$ memory B cells or B cells that recognize the target antigen (5, 30, 31). These cells are then lysed and mRNA is isolated using standard methods, and reverse transcribed to cDNA using 5' RACE with 3' primers specific for the IgH or IgL constant region (9, 32). The cDNA library is then amplified with primers containing the required paired-end adapter sequences and optional barcodes to enable quantification of template and error correction by averaging multiple reads (8, 9).

Complete determination of antibody sequences requires identifying native VH-VL pairs. As each VH and VL sequence is encoded by a separate mRNA, clonal sequencing may be performed by isolating single B cells in sub-nanoliter volume wells (5) or microemulsion (9) prior to mRNA isolation, reverse transcription, and overlap extension or linkage PCR. As an alternative, endogenous VH-VL pairs can be identified through partial cross-linking of purified Fabs prior to LC-MS/MS. Under the appropriate conditions, this will result in a fraction of the Fab heavy and light chains forming interchain crosslinks, and the resulting peptide masses will be used to determine native pairing.

In order to identify the antibodies raised in response to a mixture of peptidogenic proteins, sequence information can be combined with data from high-resolution mass spectrometry. Protein A-purified IgGs can be digested with papain to release the two Fabs from the Fc domain. These can then be immunoaffinity purified on a custom column prepared using the peptidogenic protein immobilized on a solid support, the eluted Fabs proteolytically digested, and the peptide products subjected to mass spectrometry. The resulting peptide masses can be compared with the complete antibody sequencing data to identify the CDR sequences that recognize the antigen. Pairing of IgG VH and VL sequences can be accomplished through chemical cross-linking of the immunoaffinity purified Fabs prior to the proteolytic digest; Young et al have demonstrated the feasibility of this approach (33).

Example 7: Immunization Using a Mixture of Peptidogenic Proteins

Methods of raising antibodies in mammals are well known in the art. In one example, polyclonal antiserum against peptidogenic proteins is raised by immunization of pathogen free rabbits with a total of 500 μg of a mixture of peptidogenic proteins over a period of two months. For example, the peptidogenic proteins can be dissolved in PBS and emulsified with an equal volume of Freund's adjuvant. After the final booster, the serum of the rabbits can be separated to determine the titer of the polyclonal antiserum. To obtain monoclonal antibodies, 4-6 week old Balb/c mice can be immunized with a peptidogenic protein (for example 4 times with 2 week intervals with 10-100 μg/injection dissolved in Freunds complete adjuvant for the first injection, and Freund's incomplete adjuvant for subsequent immunizations). Splenocytes are isolated and fused with a fusion cell line such as Sp2/0 myeloma cells, followed by limiting dilution. Growing clones are screened using for example an enzyme-linked immunosorbant assay (ELISA). 96 cells plates are coated with peptidogenic proteins or with a control protein. The culture supernatant is added, followed by washing and addition of a labeled anti-mouse antibody for detection. After limited dilution cloning of the peptidogenic protein-specific antibody producing hybridomas stable hybridomas are obtained. From each cell, supernatant is collected and by affinity chromatography using protein A sepharose columns monoclonal antibodies can be purified.

Example 8: Another Example of Immunization Using a Mixture of Peptidogenic Proteins In an additional animal model, groups of 5 mice (C57BL/6J; Jackson Labs) can be subcutaneously immunized with 5 μg of endotoxin-free peptidogenic proteins emulsified in alum, which is the adjuvant most commonly used in human vaccines. Three weeks later, mice are bled and the presence of peptidogenic protein-specific antibodies can be determined by titering the seras by ELISA (direct binding of antibodies in sera to wild type BPTI or APP-KI coated, directly or indirectly (via a biotinylated tag and streptavidin), on the wells). To confirm that the peptidogenic proteins have a similar conformation as the starting protein, competitive inhibition assays are performed in which titrated amounts of starting protein and peptidogenic proteins are pre-incubated with the seras prior to adding to the starting protein coated plates. This provides additional evidence, with an immunological probe, that the 3D structure of the peptidogenic proteins has not been compromised by the engineered mutations.

To determine whether the peptidogenic proteins result in better secondary antibody responses, groups of mice can be immunized as described above, and 6 weeks after the primary immunization they can be immunized a second time. One week post-secondary immunization, mice are bled and antigen-specific antibody responses are determined by ELISA as described above. Mouse dendritic cells are pulsed in vitro with the peptidogenic proteins that can generate a strong antibody response, and 24 hrs later the peptidogenic protein-derived peptides presented by MHCII are isolated and their masses analysed by liquid chromatography and mass spectrometry (LC/MS). These studies require large numbers (>$10^7$) of dendritic cells which are purified from mice previously injected with a mouse tumor line expressing FLT-3L, a cytokine that drives dendritic cell development in vivo (the spleens of these mice fill up with dendritic cells; Segura et al, 2009). To allow for peak identification and the quantiifcation of MHCII-peptides by mass spectrometry, the peptidogenic protein can be biosynthetically labeled with stable isotopes such as 13C and 15N (during production of the recombinant protein—see above) prior to feeding to the DCs (Hoedt et al 2014).

Example 9: Immunization Using Sequences Encoding a Mixture of Peptidogenic Proteins Methods of directly injecting polynucleotides into animals are well described in the art. See, for example, U.S. Pat. Nos. 5,676,954; 6,875,748; 5,661,133. Briefly, using the known degeneracy of the genetic code, polynucleotides encoding a mixture of peptidogenic proteins described herein can be synthesized using standard DNA synthesis techniques. The polynucleotide(s) can then be directly injected into the animal, such as, for example, mice. Specifically, a mixture of polynucleotides encoding the mixture of peptidogenic proteins can be injected into the quadriceps muscles of restrained awake mice (female 6-12 week old BALB/c or Nude, nu/nu, from Harlan Sprague Dawley, Indianapolis, Ind.). In one embodiment, 50 μg of a polynucleotide in 50 μl solution using a disposable sterile, plastic insulin syringe and 28G ½ needle (Becton-Dickinson, Franklin Lakes, N.J., Cat. No. 329430) fitted with a plastic collar cut from a micropipette tip can be used to inject the mice, as described in Hartikka, J., et al., Hum. Gene Ther. 7:1205-1217 (1996)).

Alternatively, 6-week old Sprague Dawley female mice (body weight 20-25 grams) can be given 5000 ppm ZnOSO4 in their drinking water beginning 24 hours prior to injection. This amount of zinc has been shown to be able to activate the metallothionein promoter. Each mouse is then injected intravenously through a tail vein puncture with a 25 gauge needle with 30 μg of polynucleotides encoding the mixture of peptidogenic proteins complexed with 150 μg liposome (Lipofection TM) in a total volume of 30 μl. In one embodiment, the polynucleotides mixture injected into the mice encodes for different peptidogenic proteins relating to the same starting protein. Alternatively, a library of peptidogenic proteins can be encoded by the mixture of polynucleotides, wherein the library relates to different starting proteins. Animal care should be maintained throughout the study and should be performed in compliance with the "Guide for the Use and Care of Laboratory Animals", Institute of Laboratory Animal Resources, Commission on Life Sciences, National Research Council, National Academy Press.

After the injected polynucleotide encoding the peptidogenic proteins are delivered into the cells in the animal, the peptidogenic proteins are then expressed in vivo. The peptidogenic proteins can then stimulate the production of antibodies specific to the peptidogenic proteins. These antibodies can be isolated and used as a polyclonal mixture or further isolated into single species or monoclonals. The process of the immune response and production of antibodies against foreign antigens in vivo are well known in the art. Unlike the traditional protocols of antibody generation, the platform invention described herein allows the simultaneously raising of a group of antibodies against multiple peptidogenic proteins (whether or not they rely on the same starting protein). This simultaneous production of antibodies to multiple proteins using a mixture of polynucleotides has the potential to change how antibody production is currently being performed.

Example 10: Immunization Using mRNA Encoding Peptidogenic Proteins

The methods of directly injecting in vitro transcribed (IVT) mRNA into animals are also well known in the art. See, Sahin et al., Nat Rev Drug Discov. 2014 October; 13(10):759-80; Kariko et al., Mol Ther, 2008 November; 16(11):1833-40; Kariko et al., Nucleic Acid Res, 2011, November; 39(21):e142; U.S. Pat. No. 6,511,832. For example, linearized DNA plasmid templates which encode a mixture of peptidogenic proteins can be used. All mRNAs can be designed to contain 5' and 3' untranslated regions, the open reading frames, and long poly(A) tails, which can help determine the translational activity and stability of the mRNA molecule after its transfer into cells.

For example, mRNAs (including a poly(A) tail) encoding peptidogenic proteins can be synthesized using triphosphate-derivatives of pseudouridine and 5-methylcytidine (m5C) (TriLink) to generate a modified nucleoside containing RNA. A 5'-cap can be added to the mRNAs by supplementing the transcription reactions with 6 mmol/l 3'-O-Me-m7GpppG, a nonreversible cap analog (New England Biolabs, Beverly, Mass.) and lowering the concentration of guanosine triphosphate (3.75 mmol/1). Purification of the transcripts can be performed by Turbo DNase (Ambion, Austin, Tex.) digestion followed by LiCl precipitation and 75% ethanol wash. The concentrations of RNA reconstituted in water can be determined by measuring the optical density at 260 nm. Efficient incorporation of modified nucleotides to the transcripts can be determined by HPLC analyses. All RNA samples can be analyzed by denaturing agarose gel electrophoresis for quality assurance. Lipofectin (Invitrogen, Carlsbad, Calif.) and mRNA are then complexed in phosphate buffer in order to enhance transfection. To assemble a 50 μl complex of RNA-lipofectin, first 0.4 μl potassium phosphate buffer (0.4 mol/1, pH 6.2) containing 10 μg/bovine serum albumin (Sigma, St. Louis, Mo.) is added to 6.7 μl DMEM, then 0.8 μl lipofectin is mixed in and the sample is incubated for 10 minutes. In a separate tube, 0.25-3 μg of RNA is added to DMEM to a final volume of 3.3 μl. Diluted RNA is added to the lipofectin mix and incubated for 10 minutes. Finally, the RNA-lipofectin complex is further diluted by adding 38.8 μl DMEM.

The RNA encoding the peptidogenic proteins can then be injected into the mouse models described herein. In general, a composition comprising 60 μl final volume with 1 μl lipofectin and different amounts of polynucleotides encoding the peptidogenic proteins are injected into the lateral vein using a 1-ml syringe with a 27G½ needle (Becton Dickinson, San Diego, Calif.). Alternatively, the polynucleotides can be injected via intramuscular, intradermal, intranasal, subcutaneous, intravenous, intratracheal, and intrathecal deliveries. After the polynucleotides are delivered into the cells, the peptidogenic proteins are synthesized in vivo.

The immune responses triggered by the peptidogenic proteins and the subsequent production of antibodies in the animals are described herein.

Example 11: Affinity Maturing Antibodies to Peptidogenic Protein Using Phage Display Once antibodies have been raised to the peptidogenic proteins by presenting and allowing the peptidogenic protein to undergo processing by an antigen presenting cell such as described in the Examples herein, the resulting antibodies can be matured using a display approach. For example, a library of phage displaying scFvs or Fabs derived from B cell mRNA encoding the target-specific antibodies can be screened in an assay to identify those phage displaying scFvs or Fabs that immunospecifically bind to a peptidogenic protein or to a starting protein. Phage displaying scFvs or Fabs that bound to immobilized peptidogenic protein or starting protein can be identified after panning on immobilized peptidogenic protein or starting protein and assessing by ELISA for binding to immobilized peptidogenic protein or starting protein. The peptidogenic protein or starting protein that is immobilized on plates for these assays can be purified from supernatants of Sf9 cells infected with a baculovirus expression construct as described in Moore et al., Science 285:260-263 or from supernatants from HEK293 cells. Each of the identified scFvs or Fabs can then be sequenced.

To determine the specificity of each of the unique scFvs or Fabs, a phage ELISA can be performed for each scFvs or Fabs against the peptidogenic protein or starting protein and control wells. Individual *E. coli* colonies containing a phagemid representing one of the unique scFvs or Fabs can be inoculated into 96-well plates containing 100 μl 2TYAG medium per well. Plates are incubated at 37° C. for 4 hours, shaking. M13K07 helper phage is then added to each well to a MOI of 10 and the plates are incubated for a further 1 hour at 37° C. The plates are centrifuged in a benchtop centrifuge at 2000 rpm for 10 minutes. The supernatant is removed and cell pellets are resuspended in 100 μl 2TYAK and incubated at 30° C. overnight, shaking.

The next day, plates are centrifuged at 2000 rpm for 10 min and the 100 μl phage-containing supernatant from each well are carefully transferred into a fresh 96-well plate. Twenty μl of 6×MPBS is added to each well, and incubated at room temperature for 1 hour to pre-block the phage prior to ELISA.

Flexible 96-well plates (Falcon) are coated overnight at 4° C. with a peptidogenic protein (directly or indirectly, at 1 mg/ml) in PBS, BSA (1 g/ml) in PBS, or PBS. After coating, the solutions are removed from the wells, and the plates are blocked for 1 hour at room temperature in MPBS. The plates are washed 3 times with PBS and then 50 μl of pre-blocked phage is added to each well. The plates are incubated at room temperature for 1 hour and then washed with 3 changes of PBST followed by 3 changes of PBS. To each well, 50 μl of an anti-gene VIII-HRP conjugate (Pharmacia) at a 1 to 5000 dilution in MPBS is added and the plates are incubated at room temperature for 1 hour. Each plate is washed three times with PBST followed by three times with PBS. Then 50 μl of an HRP-labelled anti-mouse antibody (DAKO EnVision) diluted 1/50 in 3% MPBS is added and incubated for 1 hour at room temperature. Each plate is then washed three times with PBST followed by three times with PBS. Fifty μl of TMB substrate is then added to each well, and incubated at room temperature for 30 minutes or until color development. The reaction is stopped by the addition of 25 μl of 0.5 M H2SO4. The signal generated is measured by reading the absorbance at 450 nm (A450) using a microtiter plate reader (Bio-Rad 3550).

Conversion of scFvs or Fabs to IgG1 format can be performed as follows. The VH domain and the VL domains of scFvs or Fabs that we wish to convert into IgG molecules can be cloned into vectors containing the nucleotide sequences of the appropriate heavy (human IgG1, IgG2, etc.) or light chain (human kappa or human lambda) constant regions such that a complete heavy or light chain molecule could be expressed from these vectors when transfected into an appropriate host cell. Further, when cloned heavy and light chains are both expressed in one cell line (from either one or two vectors), they can assemble into a complete functional antibody molecule that is secreted into the cell culture medium. Methods for converting scFvs or Fabs into conventional antibody molecules are well known within the art.

The purification of the IgG from the fermentation broth is performed using a combination of conventional techniques commonly used for antibody production. Typically the culture harvest is clarified to remove cells and cellular debris prior to starting the purification scheme. This would normally be achieved by using either centrifugation or filtration of the harvest. Following clarification, the antibody would typically be captured and significantly purified using affinity chromatography on Protein A Sepharose. The antibody is bound to Protein A Sepharose at basic pH and, following washing of the matrix, is eluted by a reduction of the pH. Further purification of the antibody is then achieved by gel filtration. As well as removing components with different molecular weights from the antibody this step can also be used to buffer exchange into the desired final formulation buffer.

Example 12: Assays Used to Characterize Antibodies and Measure Cross-Reactivity

Antibodies (whether cross-reacting or antibodies raised against the peptidogenic protein) (including scFvs or Fabs and other molecules comprising, or alternatively consisting of, antibody fragments or variants thereof) may be screened in a variety of assays, some of which are described below to identify those antibodies that bind to the peptidogenic protein and/or starting protein.

In one particular assay, antibodies (whether cross-reacting or antibodies raised against the peptidogenic protein) that bind to a biotinylated protein (whether the peptidogenic protein and/or starting protein) can be captured on streptavidin coated magnetic beads. This assay may be applied to identify antibodies (whether cross-reacting or antibodies raised against the peptidogenic protein) that neutralize and/or bind to the peptidogenic protein and/or starting protein. Additionally, antibodies may be assayed in neutralization assays described herein or otherwise known in the art. For example, where the target protein is BlyS, antibodies may be tested for their ability to inhibit the peptidogenic protein and/or starting protein from binding to IM9 cells. In this assay, labeled peptidogenic protein and/or starting protein (e.g., biotinylated) is incubated with antibodies to allow for the formation of protein-antibody complexes. Following incubation, an aliquot of the protein-antibody sample is added to IM9 cells. Binding may be determined using techniques known in the art. For example, the binding of biotinylated protein (whether the peptidogenic protein and/or starting protein) to IM9 cells may be detected using a fluorimeter following the addition of streptavidin-delfia.

Biotinylated protein, if it is not bound by antibodies that neutralize the protein, will bind to the cells and can be detected. Thus, an antibody that decreases the amount of biotinylated-protein that binds to IM9 cells (relative to a control sample in which the protein had been preincubated with an irrelevant antibody or no antibody at all) is identified as one that binds to and neutralizes the protein.

Other immunoassays which can be used to analyze cross-reactivity and/or characterize the antibodies raised against the peptidogenic protein include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, and protein A immunoassays, to name but a few. Such assays are routine and well known in the art (see, e.g., Ausubel et al, eds, 1994, Current Protocols in Molecular Biology, Vol. 1, John Wiley & Sons, Inc., New York.

Exemplary immunoassays are described briefly below (but are not intended by way of limitation) Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the cross-reacting antibody of interest to the cell lysate, incubating for a period of time (e.g., 1 to 4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a peptidogenic protein and/or a starting protein can be assessed by, e.g., western blot analysis or mass spectrometry. One of skill in the art would be knowledgeable as to the parameters that can be modified to increase the binding of the antibody to a peptidogenic protein and/or a starting protein and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., 32P or 1211) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

In a further example, ELISAs comprise preparing peptidogenic protein and/or a starting protein, coating the well of a 96-well microtiter plate (directly or indirectly) with the peptidogenic protein and/or a starting protein, washing away the peptidogenic protein and/or a starting protein that did not bind the wells, adding the antibody of interest conjugated to a detectable compound such as an enzymatic substrate (e.g., horseradish peroxidase or alkaline phosphatase) to the wells and incubating for a period of time, washing away unbound antibodies or non-specifically bound antibodies, and detecting the presence of the antibodies specifically bound to the peptidogenic protein and/or a starting protein coating the well. In ELISAs the antibody of interest does not have to be conjugated to a detectable compound; instead, a second antibody (which recognizes the antibody of interest) conjugated to a detectable compound may be added to the well.

Further, instead of coating the well with the antigen, the antibody may be coated to the well. In this case, the detectable molecule could be the peptidogenic protein and/or a starting protein conjugated to a detectable compound such as an enzymatic substrate (e.g., horseradish peroxidase or alkaline phosphatase). One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1. The binding affinity of an antibody to a peptidogenic protein and/or a starting protein and the off-rate of an antibody-protein interaction can be determined by competitive binding assays. One example of a competitive binding assay is a radioimmunoassay comprising the incubation of labeled peptidogenic protein and/or a starting protein (e.g., 3H or 1251) with the antibody of interest in the presence of increasing amounts of unlabeled peptidogenic protein and/or a starting protein, and the detection of the antibody bound to the labeled peptidogenic protein and/or a starting protein. The affinity of the antibody of the present invention for a peptidogenic protein and/or the starting protein and the binding off-rates can be determined from the data by Scatchard plot analysis. Competition with a second antibody can also be determined using radioimmunoassays. In this case, a peptidogenic protein and/or starting protein is incubated with an antibody of interest conjugated to a labeled compound (e.g., 3H or 1251) in the presence of increasing amounts of an unlabeled second anti-peptidogenic protein antibody.

In a preferred embodiment, BIAcore kinetic analysis can be used to determine the binding on and off rates of antibodies to peptidogenic protein and/or starting protein. BIAcore kinetic analysis comprises analyzing the binding and dissociation of peptidogenic protein and/or starting protein from chips with immobilized antibodies on their surface.

Example 13: Vaccination

Further, a mixture of peptidogenic proteins as described herein can be used as a vaccine. For example a concentration of 320 ug/mL in phosphate-buffered saline (PBS, 155 mM NaCl, 1 mM KH2PO4, 3 mM Na2HPO3) of the peptidogenic proteins are aseptically emulsified with an equal volume of Montanide ISA 51 to give a final vaccine concentration of 160 ug/mL. The emulsion is achieved by homogenizing the mixture in a volume of 200 mL in a 400-mL vessel at room temperature for 6 min at 6000 rpm using an Omni Mixer-ES homogenizer (Omni International, Warren-ton, VA). Each vaccine undergoes comprehensive quality control analyses to ensure general safety, purity, identity, integrity, and uniform water-in-oil droplet size. Stability of vaccines stored at 2-8° C. is evaluated regularly using mouse immunogenicity tests and physical and biochemical assays to verify the vaccine safety, potency, uniformity, purity, and integrity until 4-10 months after the termination of the human immunizations. The 160 ug/mL peptidogenic protein vaccines are diluted with the PBS/ISA 51 (the adjuvant control vaccine) to the final dose forms of 10 ug/mL or 40 ug/mL prior to immunizations. As a result of different degrees of dilution, these vaccines contained two different ratios of vaccine-containing vs. vaccine-free water droplets, namely ratios of 1:15 and 1:3 for the 10 ug/mL and 40 ug/mL formulations, respectively. The test and control vaccines may be highly viscous and require vortexing prior to and after manipulation to ensure homogeneity. The vaccine can be administered intramuscularly by needle and syringe. Vaccine-induced T-cell responses are further evaluated by means of a qualified intracellular cytokine staining assay. Peripheral-blood mononuclear cells are quantified to determine the proportion of total and memory CD4 and CD8 T cells producing interleukin-2, interferon-γ, or tumor necrosis factor (TNF).

Polynucleotides encoding a mixture of peptidogenic proteins can also be used as a vaccine by administering to a patient the polynucleotide described herein.

LITERATURE CITED

1. Starner N, et al., The Protein Capture Reagents Program Data Portal. (Submitted). 2014.
2. Paduch M, et al., Methods. 2013; 60(1):3-14. doi: 10.1016/j.ymeth.2012.12.010.
3. Acton T B, et al., Methods in Enzymology: Academic Press; 2005. p. 210-43.
4. Xiao R, et al., Journal of structural biology. 2010; 172(1):21-33.
5. DeKosky B J, Nat Biotech. 2013; 31(2):166-9. doi: 10.1038/nbt.2492.
6. Naso and Panavas, Current drug discovery technologies. 2014; 11(1):85-95. Epub 2013/09/12. PubMed PMID: 24020911.
7. Reddy S T et al. Current Opinion in Biotechnology. 2011; 22(4):584-9.
8. Vollmers C, et al., Proceedings of the National Academy of Sciences. 2013; 110(33):13463-8. doi: 10.1073/pnas.1312146110.
9. Georgiou G, et al., Nat Biotech. 2014; 32(2):158-68. doi: 10.1038/nbt.2782.
10. Sato S, et al., Nat Biotechnol. 2012; 30(11):1039-43. Epub 2012/11/10. doi: 10.1038/nbt.2406. PubMed PMID: 23138294.
11. Dobson C M. Nature. 2003; 426(6968):884-90.
12. Bowie, and Sauer Biochemistry. 1989; 28(18):7139-43. doi: 10.1021/bi00444a001.
13. Milla M E, et al., Nat Struct Mol Biol. 1994; 1(8):518-23.
14. Waldburger C D, et al., Nat Struct Mol Biol. 1995; 2(2):122-8.
15. Ascenzi P, et al., Current Protein and Peptide Science. 2003; 4(3):231-51. doi: 10.2174/1389203033487180.
16. Marks C, et al., Science. 1987; 235(4794):1370-3. doi: 10.1126/science.2435002.
17. Nilsson B et al., Journal of Biological Chemistry. 1991; 266(5):2970-7.
18. Betz S F, Protein Science. 1993; 2(10):1551-8. doi: 10.1002/pro.5560021002.
19. Eigenbrot and Kossiakoff, Protein Engineering. 1990; 3(7):591-8. doi: 10.1093/protein/3.7.591.
20. Hurle et al., Biochemistry. 1990; 29(18):4410-9. doi: 10.1021/bi00470a021.
21. Krokoszynska I, et al., Journal of Molecular Biology. 1998; 275(3):503-13. doi: 10.1006/jmbi.1997.1460.
22. Staley J P et al., Proceedings of the National Academy of Sciences. 1992; 89(5):1519-23. doi: 10.1073/pnas.89.5.1519.
23. Castro M J M et al., Biochemistry. 1996; 35(35):11435-46. doi: 10.1021/bi960515w.
24. Altman J D, et al., Protein Engineering. 1991; 4(5):593-600. doi: 10.1093/protein/4.5.593.
25. Cull and Schatz, Methods Enzymol. 2000; 326:430-40. Epub 2000/10/19. PubMed PMID: 11036656.
26. Fiorucci L et al., Histochem J. 1989; 21(12):721-30. doi: 10.1007/BF01002838.
27. Nori S L, et al., Peptides. 1992; 13(2):365-71. doi: http://dx.doi.org/10.1016/0196-9781(92)90122-J.
28. Savage M J, et al., Amyloid. 1995; 2(4):234-40. doi: doi:10.3109/13506129508999005.
29. Cheung W C et al., Nat Biotechnol. 2012; 30(5):447-52. Epub 2012/03/27. doi: 10.1038/nbt.2167. PubMed PMID: 22446692.
30. Kaminski D A et al., Frontiers in immunology. 2012; 3:302. Epub 2012/10/23. doi: 10.3389/fimmu.2012.00302. PubMed PMID: 23087687; PubMed Central PMCID: PMCPmc3467643.
31. Maecker H T et al., Nature reviews Rheumatology. 2012; 8(6):317-28. Epub 2012/06/01. doi: 10.1038/nrrheum.2012.66. PubMed PMID: 22647780; PubMed Central PMCID: PMCPmc3409841.
32. Toung J M et al., Genome research. 2011; 21(6):991-8. doi: 10.1101/gr.116335.110.
33. Young M M et al., Proceedings of the National Academy of Sciences. 2000; 97(11):5802-6. doi: 10.1073/pnas.090099097.
34. Goh C S et al., Nucleic Acids Research. 2003; 31(11): 2833-8. doi: 10.1093/nar/gkg397.
35. Glanville J, et al., Proceedings of the National Academy of Sciences. 2009; 106(48):20216-21. doi: 10.1073/pnas.0909775106.
36. Brochet X et al., Nucleic Acids Res. 2008; 36(Web Server issue):W503-8. Epub 2008/05/27. doi: 10.1093/nar/gkn316. PubMed PMID: 18503082; PubMed Central PMCID: PMCPmc2447746.
37. D'Angelo S., et al., mAbs. 2014; 6(1):160-72. Epub 2014/01/16. doi: 10.4161/mabs.27105. PubMed PMID: 24423623; PubMed Central PMCID: PMCPmc3929439.
38. Eng J K et al., Journal of the American Society for Mass Spectrometry. 1994; 5(11):976-89. doi: http://dx.doi.org/10.1016/1044-0305(94)80016-2.
39. Van Regenmortel MHV. Journal of Molecular Recognition. 2011; 24(5):741-53. doi: 10.1002/jmr.1116.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11384138B2). An electronic copy of the "Sequence Listing" will also be available from the USPTO upon request and payment of the fee set forth in 37 CFR 1.19(b)(3).

The invention claimed is:

1. A method of generating an immune response in an animal wherein said method comprises:

a. introducing a mixture of at least two different peptidogenic proteins derived from a starting protein, wherein each of the peptidogenic proteins has altered conformational dynamics as compared to the starting protein, wherein each of the peptidogenic proteins is similar in conformation to the starting protein, and wherein each of the peptidogenic proteins comprises replacement of at least one non-surface amino acid residue in the starting protein with a different amino acid residue to an animal; and b. generating an immune response in the animal.

2. The method of claim 1, wherein the conformational dynamics are altered by:

a. examining the 3-D structure of the starting protein, identifying non-surface amino acid residues of the starting protein and replacing at least one non-surface amino acid residue in the starting protein to generate the peptidogenic proteins; or b. examining a model of the 3-D structure of the starting protein, identifying non-surface amino acid residues of the starting protein and replacing at least one non-surface amino acid residue in the starting protein to generate the peptidogenic proteins; or c. comparing the pattern of conserved amino acid homology across proteins orthologous to the starting protein from different species to identify non-surface amino acid residues of the starting protein and replacing at least one non-surface amino acid residue in the starting protein to generate the peptidogenic proteins; or d. replacing at least one non-surface amino acid residue of the starting protein to generate the peptidogenic proteins; or e. replacing at least one non-surface amino acid residue with a smaller amino acid residue; or f. replacing at least one non-surface amino acid residue with an alanine or glycine; or g. eliminating at least one disulfide bond in the starting protein.

3. The method of claim 1, wherein at least 1, 2, 3, 4, 5, 6, 7, 8, 9, 10, 11, 12, 13, 14, 15, 16, 17, 18, 19, or 20 amino acids are replaced in the starting protein.

4. The method of claim 1, wherein the conformational dynamics of the starting protein are altered by replacing:

a. at least one non-surface threonine with a valine, alanine, glycine or serine; or b. at least one non-surface cysteine with alanine, valine, glycine, serine or threonine; or c. at least one non-surface valine with alanine, glycine, leucine or isoleucine; or d. at least one non-surface leucine with alanine, valine, glycine, or isoleucine; or e. at least one non-surface isoleucine with alanine, valine, leucine, or glycine; or f. at least one non-surface proline with methionine, alanine, valine, leucine, isoleucine, or glycine; or g. at least one non-surface methionine with alanine, valine, leucine, isoleucine, or glycine; or h. at least one non-surface phenylalanine with tyrosine, methionine, histidine, alanine, valine, leucine, isoleucine, or glycine; or i. at least one non-surface tyrosine with phenylalanine, methionine, histidine, alanine, valine, leucine, isoleucine, or glycine; or j. at least one non-surface tryptophan with tyrosine, phenylalanine, methionine, histidine, alanine, valine, leucine, isoleucine, or glycine; or k. at least one non-surface aspartic acid with glutamic acid, glutamine, asparagine, glycine, serine, threonine, alanine, valine, leucine, or isoleucine; or l. at least one non-surface asparagine with glycine, serine, threonine, alanine, valine, leucine, isoleucine, glutamine, glutamic acid, or aspartic acid; or m. at least one non-surface glutamic acid with aspartic acid, asparagine, glutamine, glycine, serine, threonine, alanine, valine, leucine, or isoleucine; or n. at least one non-surface glutamine with glutamic acid, aspartic acid, asparagine, glutamine, glycine, serine, threonine, alanine, valine, leucine, or isoleucine; or o. at least one non-surface lysine with arginine, histidine, glycine, serine, threonine, alanine, valine, methionine, leucine, or isoleucine; or p. at least one non-surface arginine with lysine, histidine, glycine, serine, threonine, alanine, valine, methionine, leucine, or isoleucine; or q. at least one non-surface histidine with phenylalanine, tyrosine, lysine, arginine, glycine, serine, threonine, alanine, valine, glutamine, asparagine, leucine, methionine or isoleucine; or r. at least one non-surface alanine with a glycine or proline; or s. at least one non-surface glycine with an alanine or proline; or t. at least one non-surface serine with an alanine or glycine; or u. at least one non-surface residue with a non-natural amino acid; or v. a combination of any of the above replacements.

5. The method of claim 1, wherein the altered conformational dynamics of the peptidogenic proteins is measured by:

a. a change in melting temperature as compared to the starting protein; or b. a change in Gibbs free energy of stabilization or proteolytic sensitivity assay; or c. a change in Gibbs free energy, wherein the change in Gibbs free energy of stabilization is measured by denaturant modulated equilibrium unfolding, wherein the denaturant is urea or guanidinium hydrochloride.

6. The method of claim 1, wherein similarity in conformation to the starting protein is measured by:

binding of a cross-reacting antibody to both the peptidogenic proteins and the starting protein; optionally wherein (a) binding of the cross-reactive antibody is measured by an immunoprecipitation assay, surface plasmon resonance, isothermal titration calorimetry, oblique-incidence reflective difference (OI-RD), western blots, radioimmunoassays, ELISA (enzyme linked immunosorbent assay), "sandwich" immunoassays, gel diffusion precipitin reactions, immunodiffusion assays, agglutination assays, complement-fixation assays, immunoradiometric assays, fluorescent immunoassays, and/or protein A immunoassays; and/or (b) the cross-reacting antibody has a dissociation constant (KD) to the starting protein and the peptidogenic proteins of less than or equal to $10^{-9}$M; and/or (c) the cross-reacting antibody has a dissociation constant (KD) to the starting protein and the peptidogenic proteins of less than or equal to $10^{-8}$M, less than or equal to $10^{-7}$M, or less than or equal to $10^{-6}$M.

7. The method of claim 1, wherein the starting protein is selected from:

a. an envelope glycoprotein of the human immunodeficiency virus (HIV), HIV gp120, HIV gp41, HIV gp160, an ebola antigen, a viral antigen, a bacterial antigen, a parasite antigen, an allergen, a venom, a toxin, a tumor-associated antigen, a transmembrane domain protein, a G-protein coupled receptor, an ion channel, a hepatitis C virus antigen, a hepatitis B virus antigen, a MERS-CoV antigen, a Zika virus antigen, an influenza virus antigen, a malaria antigen; and/or b. any one of the malaria antigens selected from MAL13P1.225, PF13 0203, PF11 0164, PFLO375W, PFI1270W, PF10 0104, PF13 0128, PF11 0058, PFA0490W, PF07 0087, PFB0570W, PF13 0180, PF11 0065, PF14 0678, PF13 0125, PF13 0141, PF14 0117, PF11 0098, PF14 0660, PFD0240C, PFE0080C, PFA0660W, PF11 0352, PF11 0055, PFB0475C, PF11 0302, PFA0210C, PF07 0089, PF14 0060, MAL8P1.17, MAL7P1.77, PF11 0099, PF07 0068, PF13 0201, PF07 0094, PF07 0006, PFLO770W, PFI1645C, PF14 0166, PFE0815W, PF11 0174, PFE0475W, PF11 0074, PFL1385C, PF14 0102, PF11 0212, PF07 0129, PFL2570W, PFL1070C, PFB0695C, PF11 0175, MAL13P1.22, PFLO035C, PFI0685W, PFD0425W, PF14 0293, PF14 0344, PFLO560C, PF07 0035, PFL1675C, PFC0435W, PFI1445W, PF13 0354, PFC0110W, PFC0120W, PF08 0078, PF14 0614, PF14 0051, PF11 0076, MAL13P1.262, PFC0640W, PFL2520W, PFCO282W, PF08 0004, PF11 0224, PF13 0272, MAL13P1.171, PFE1340W, PF14 0369, PF14 0178, PFLO870W, PFCO210C, PFI0500W, PF11 0069, PFD0355C, PFI0880C, PF11 0251, PFC0065C, PFC0925W, MAL13P1.121, PF13 0133, PFL2015W, PFD0440W, PFC0330W, PFD0430C, PF14 0462, PF07 0100, MAL7P1.23, PFL1835W, PF07 0047, PF14 0250, PFE0905W, PFA0180W, PFL1210W, PF14 0363, PFB0400W, PFI0920C, PF14 0094, PFA0125C, PF10 0372, PFL2315C, MAL13P1.271, MAL7P1.31, PF10 0317, PF07 0070, MAL7P1.64, PFI0935W, PFA0160C, PFB0465C, PF10 0208, PFB0760W, MAL13P1.206, PF14 0541, PFLO790W, PFL2410W, PF14 0440, PF11 0333, PF10 0242, PFC0590C, PF14 0342, MAL7P1.92, PF14 0593, MAL13P1.49, MAL13P1.172, PF08 0006, PFD1035W, PF11 0052, MAL13P1.79, PF10 0295, PFL1745C, PF14 0677, PFLO600W, PF08 0108, PF08 0081, PF14 0620, PFE0710W, PF11 0270, MAL7P1.149, PFC0810C, PF14 0249, PF13 0116, MAL13P1.60, PF11 0246, PFL2505C, PFB0405W, PF11 0256, PF08 0047, PFC0835C, PFI0605C, PF10 0127, PF11 0344, PF10 0130, PFL2395C, PF08 0008, PF14 0201, PFI1475W, PF13 0182, PF14 0495, or PF13 0277; and/or c. any one of the Targets selected from A4GCL9, A8T655, B2R7F8, B4DEZ9, B4DTR1, D4HNR6, D5RWT1, F8WCM5, G8EJ09, I6YE93, K9N5Q8, 000141, 000189, 000206, 000220, 000253, 000294, 000300, 000522, 000585, 000754, 014522, 014763, 014773, 014788, 014793, 014807, 014836, 014896, 014931, 014936, 014976, 014994, 015020, 015118, 015230, 015305, 015357, 015372, 015394, 015455, 015520, 043155, 043291, 043323, 043424, 043557, 043570, 043707, 043854, 043897, 043933, 060229, 060494, 060565, 060602, 060706, 060840, 060882, 075197, 075367, 075369, 075436, 075581, 075665, 075695, 075712, 075874, 075888, 075923, 075970, 076041, 076090, 094804, 095150, 095256, 095342, 095407, 095445, 095452, 095633, 095760, 095967, P00167, P00338, P00387, P00403, P00439, P00441, P00451, P00488, P00492, P00519, P00533, P00568, P00734, P00740, P00742, P00746, P00747, P00748, P00751, P00797, P00918, P00966, P00995, P01008, P01009, P01019, P01024, P01031, P01032, P01034, P01111, P01127, P01130, P01137, P01138, P01185, P01241, P01308, P01344, P01374, P01375, P01579, P01583, P01584, P01588, P01589, P01730, P01854, P01889, P01903, P01906, P01909, P01911, P01912, P01920, P02452, P02458, P02461, P02462, P02489, P02647, P02649, P02671, P02675, P02679, P02708, P02730, P02760, P02766, P02768, P02792, P03147, P03372, P03420, P03441, P03446, P03448, P03456, P03457, P03471, P03472, P03474, P03476, P03477, P03478, P03886, P03950, P03951, P04040, P04049, P04062, P04070, P04080, P04155, P04156, P04179, P04180, P04233, P04234, P04275, P04424, P04440, P04578, P04626, P04629, P04661, P04792, P04839, P05019, P05062, P05067, P05089, P05091, P05106, P05107, P05112, P05113, P05121, P05129, P05155, P05156, P05186, P05231, P05386, P05540, P05556, P05961, P05997, P06127, P06213, P06239, P06280, P06340, P06396, P06681, P06684, P06737, P06744, P06804, P06865, P07204, P07225, P07288, P07339, P07477, P07585, P07602, P07686, P07911, P07949, P07954, P08034, P08100, P08118, P08133, P08183, P08235, P08236, P08237, P08246, P08253, P08326, P08473, P08514, P08519, P08567, P08572, P08575, P08581, P08603, P08617, P08708, P08709, P08887, P09417, P09467, P09603, P09619, P09668, P09936, P09960, POCOL4, POCOLS, PODJI8, PODJI9, P10071, P10321, P10448, P10619, P10721, P10809, P10828, P10912, P11021, P11132, P11166, P11168, P11177, P11215, P11217, P11224, P11230, P11233, P11310, P11362, P11413, P11532, P11586, P11597, P11836, P12023, P12111, P12259, P12318, P12643, P12644, P12821, P12830, P12955, P13103, P13224, P13500, P13569, P13612, P13637, P13716, P13726, P13747, P13765, P13804, P13807, P14138, P14174, P14207, P14210, P14222, P14416, P14672, P14770, P14778, P14780, P14784, P14867, P14921, P14923, P15018, P15259, P15260, P15289, P15291, P15313, P15328, P15391, P15509, P15529, P15692, P15814, P15848, P15907, P15924, P15941, P16109, P16144, P16154, P16278, P16401, P16410, P16422, P16442, P16473, P16871, P16930, P17050, P17174, P17693, P17787, P17858, P17900, P17927, P17948, P18074, P18177, P18206, P18510, P19079, P19235, P19256, P19320, P19438, P19694, P19838, P19876, P20023, P20036, P20138, P20151, P20273, P20701, P20702, P20749, P20807, P20849, P20929, P20933, P21333, P21359, P21439, P21580, P21583, P21709, P21781, P21802, P21817, P21860, P21912, P22105, P22223, P22301, P22362, P22413, P22460, P22735, P22748, P23284, P23415, P23468, P23510, P23560, P23945, P23975, P24723, P24855, P25024, P25025, P25054, P25189, P25445, P26010, P26136, P26927, P27169, P27487, P27909, P27930, P27958, P28062, P28068, P28472, P28482, P28799, P28907, P28908, P29033, P29120, P29216, P29320, P29323, P29400, P29459, P29460, P29590, P29597, P29965, P30044, P30203, P30301, P30460, P30530, P30556, P31371, P31785, P31994, P31995, P31997, P32297, P32754, P33681, P33795, P34059, P34130, P35221, P35222, P35225, P35442, P35462, P35475, P35555, P35579, P35609, P35625, P35670, P35749, P35754, P35968, P35991, P36222, P36871, P36888, P36894, P36896, P36897, P36915, P36941, P36955, P37023, P37173, P38117, P39019, P39023, P39060, P39905, P40225, P40238, P40259, P40394, P41159, P41180, P41181, P41250, P42081, P42261, P42263, P42336, P42568, P42658, P42702, P42768, P43026, P43034, P43235, P43258, P43259, P43260, P43681, P44815, P45381, P45954, P46094, P46379, P46459, P46531, P46783, P46934, P46952, P47756, P48023, P48061, P48167, P48436, P48544, P48643, P49257, P49419, P49588, P49683, P49747, P49768, P49789, P49810, P50440, P50454, P50570, P50897, P50993, P51149, P51159, P51532, P51570, P51608, P51648, P51681, P51688, P51690, P51693, P51787, P51800, P51812, P51813, P52788, P52803, P53004, P53420, P53634, P54098, P54577, P54764, P54802, P54803, P54819, P55008, P55072, P55075, P55268, P55286, P55291, P55789, P56537, P57075, P57735, P58335, P59594, P60033, P60484, P60568, P60900, P60953, P61457, P61626, P61769, P61812, P61916, P62070, P62081, P62736, P62854, P62913, P63092, P63252, P67870, P68032, P68036, P68133, P68871, P69905, P78324, P78363, P78380, P78504, P78509, P78545, P80098, P82279, P84022, P98082, P98160, P98161, Q00653, Q00973, Q01484, Q01955, Q01968, Q02223, Q02297, Q02388, Q02413, Q02487, Q03154, Q03403, Q03426, Q03591, Q04446, Q04609, Q04656, Q04721, Q04771, Q04844, Q05397, Q05495, Q05586, Q06124, Q06187, Q07001, Q07108, Q07599, Q07954, Q07FI5, Q08048, Q08334, Q08345, Q08881, Q09428, Q09470, Q0A2R1, Q0A448, Q0ED31, Q0Z7S6, Q0ZME7, Q0ZNA6, Q12791, Q12809, Q12879, Q12965, Q13002, Q13009, Q13018, Q13093, Q13126, Q13224, Q13231, Q13253, Q13410, Q13421, Q13424, Q13478, Q13496, Q13501, Q13563, Q13614, Q13620, Q13651, Q13698, Q13753, Q13822, Q13835, Q13873, Q13936, Q14019, Q14103, Q14108, Q14114, Q14117, Q14126, Q14204, Q14315, Q14376, Q14563, Q14571, Q14573, Q14654, Q14833, Q14956, Q14974, Q15027, Q15046, Q15109, Q15116, Q15149, Q15223, Q15262, Q15303, Q15465, Q15582, Q15746, Q15822, Q15831, Q15833, Q15848, Q16288, Q16348, Q16515, Q16552, Q16566, Q16787, Q16827, Q189K3, Q189K5, Q18PE1, Q1HLC5, Q1HP67, Q1PHM6, Q28090, Q289M7, Q29974, Q29980, Q29983, Q2M1P5, Q2N0S5, Q2N0S6, Q30154, Q30201, Q32ZE1, Q3T906, Q3UV74, Q3ZC95, Q3ZLH8, Q46342, Q49DS8, Q4KMG0, Q53SF7, Q59FL8, Q59H50, Q5D862, Q5JWF2, Q5T2T1, Q5VV43, Q5VWQ8, Q5VYX0, Q67333, Q69994, Q6DQ33, Q6IQ55, Q6KF10, Q6PHW0, Q6Q1S2, Q6TXC0, Q6VMK1, Q6XV28, Q71U36, Q75760, Q7L0Q8, Q7LG56, Q7Z6G8, Q7Z6Z7, Q82559, Q84850, Q86UR5, Q86UX7, Q8IU80, Q8IWT1, Q8IZI9, Q8IZJ0, Q8IZP0, Q8IZU9, Q8J581, Q8JDI3, Q8N0W4, Q8N157, Q8N1C3, Q8N5C8, Q8N608, Q8NBP7, Q8NCM8, Q8NFY4, Q8NG31, Q8Q7Z9, Q8TDA6, Q8TDX5, Q8TEW8, Q8TF72, Q8WWA0, Q8WX93, Q8WXD0, Q8WXH0, Q8WXI7, Q91MA7, Q92185, Q92542, Q92597, Q92692, Q92736, Q92743, Q92765, Q92766, Q92796, Q92834, Q92838, Q92887, Q92956, Q93052, Q93099, Q969J5, Q96B97, Q96F46, Q96FE5, Q96HC4, Q96J02, Q96J92, Q96MS0, Q96P20, Q96PD4, Q96PX8, Q96QZ7, Q993A8, Q99466, Q99497, Q99877, Q99972, Q99985, Q9BQB4, Q9BUL8, Q9BWV1, Q9BXJ0, Q9BXM0, Q9BXR6, Q9BZ11, Q9C000, Q9D1H1, Q9DBR4, Q9EQF4, Q9GZV9, Q9H0F7, Q9H0U3, Q9H221, Q9H222, Q9H251, Q9H3Z4, Q9H4F8, Q9H6X2, Q9HB21, Q9HBA0, Q9HBE4, Q9HCE7, Q9HCK4, Q9HD26, Q9HDB5, Q9IGQ6, Q9J3E7, Q9NPF7, Q9NQ25, Q9NQ38, Q9NQC7, Q9NS40, Q9NVA2, Q9NVD7, Q9NY72, Q9NZ08, Q9NZN1, Q9NZQ7, Q9NZV8, Q9P1W8, Q9UBP0, Q9UBQ7, Q9UBV7, Q9UBX5, Q9UGJ0, Q9UGM3, Q9UHF4, Q9UHG0, Q9UHN1, Q9UHP7, Q9UIR5, Q9UKL4, Q9UKM7, Q9UKQ2, Q9ULV1, Q9ULV5, Q9UM47, Q9UM54, Q9UNA1, Q9UNG2, Q9UPW8, Q9W7Y7, Q9WFX3, Q9WMX2, Q9Y275, Q9Y281, Q9Y2Q5, Q9Y496, Q9Y4CO, Q9Y4J8, Q9Y5K2, Q9Y5K6, Q9Y6D5, Q9Y6N8, or Q9Y6Q6; and/or d. a tumor associated antigen selected from MAGE-A1, MAGE-A2, MAGE-A3, MAGE-A4, MAGE-A5, MAGE-A6, MAGE-A7, MAGE-A8, MAGE-A9, MAGE-A10, MAGE-A1 1, MAGE-A12, GAGE-I, GAGE-2, GAGE-3, GAGE-4, GAGE-5, GAGE-6, GAGE-7, GAGE-8, BAGE-I, RAGE-1, LB33/MUM-1, PRAME, NAG, MAGE-Xp2 (MAGE-B2), MAGE-Xp3 (MAGE-B3), MAGE-Xp4 (MAGE-B4), MAGE-C1/CT7, MAGE-C2, NY-ESO-I, LAGE-I, SSX-I, SSX-2(HOM-MEL-40), SSX-3, SSX-4, SSX-5, SCP-I and XAGE, melanocyte differentiation antigens, p53, ras, CEA, MUC1, PMSA, PSA, tyrosinase, Melan-A, MART-1, gp100, gp75, alpha-actinin-4, Bcr-Abl fusion protein, Casp-8, beta-catenin, cdc27, cdk4, cdkn2a, coa-1, dek-can fusion protein, EF2, ETV6-AML1 fusion protein, LDLR-fucosyltransferaseAS fusion protein, HLA-A2, HLA-All, hsp70-2, KIAAO205, Mart2, Mum-2, and 3, neo-PAP, myosin class I, OS-9, pml-RAR alpha fusion protein, PTPRK, K-ras, N-ras, Triosephosphate isomerase, GnTV, Herv-K-mel, NA-88, SP17, and TRP2-Int2, (MART-I), E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, alpha-fetoprotein, 13HCG, BCA225, BTAA, CA 125, CA 15-3 (CA 27.29\BCAA), CA 195, CA 242, CA-50, CAM43, CD68\KP1, CO-029, FGF-5, G250, Ga733 (EpCAM), HTgp-175, M344, MA-50, MG7-Ag, MOV18, NB\170K, NY-CO-1, RCAS1, SDCCAG16, TA-90 (Mac-2 binding protein\cyclophilin C-associated protein), TAAL6, TAG72, TLP, TPS, tyrosinase related proteins, TRP-1, TRP-2, or cytomegalovirus phosphoprotein 65 (pp65).

8. The method of claim 1, wherein the mixture of peptidogenic proteins is introduced into the animal by:

a. administering the mixture of peptidogenic proteins to the animal;
b. administering a mixture of polynucleotides encoding the mixture of peptidogenic proteins to the animal; and/or
c. administering to the animal antigen presenting cells transfected with the mixture of polynucleotides and/or placed in contact with the mixture of peptidogenic proteins.

9. The method of claim 1, wherein the peptidogenic proteins are derived:

a. from the same starting protein; or
b. from multiple starting proteins; or
c. from multiple related starting proteins.

10. The method of claim 8, wherein the mixture of peptidogenic proteins is introduced into the animal by administering a mixture of polynucleotides encoding the mixture of peptidogenic proteins to the animal, and wherein the polynucleotides:

a. are synthesized in vitro; or
b. comprise DNA; or
c. comprise in vitro transcribed (IVT) mRNA; or
d. comprise IVT mRNA comprising a poly(A) tail; or
e. comprise IVT mRNA comprising a 5' Cap, optionally wherein the polynucleotides are:
1) not associated with any targeting components; or
2) are associated with a targeting component capable of targeting the polynucleotides to a cell or an organ; or
3) are associated with a targeting component capable of targeting the polynucleotides to a cell or an organ, wherein the targeting component is a vector.

11. The method of claim 1 wherein the animal is a mammal, a human, mouse, rabbit, llama, or a cow.

12. The method of claim 8, wherein the animal is injected with the polynucleotides, wherein the polynucleotides are:

a. injected directly into the muscle of the animal; and/or
b. injected into the animal on multiple occasions.

13. The method of claim 1, wherein the immune response generates antibodies.

14. The method of claim 13, wherein the method further comprises isolating the antibodies.

15. The method of claim 14, wherein the antibodies are fully human antibodies, chimeric antibodies, humanized antibodies, monoclonal antibodies, and/or polyclonal antibodies.

16. The method of claim 13, wherein the method further comprises affinity maturing the antibodies, wherein the affinity maturation occurs by:

a. phage display, yeast display or ribosome display; or
b. a panning technique.

17. The method of claim 1, wherein the mixture of peptidogenic proteins further comprises the starting protein.

18. The method of claim 1, wherein each of the peptidogenic proteins has increased conformational dynamics as compared to the starting protein.

* * * * *

UNITED STATES PATENT AND TRADEMARK OFFICE

CERTIFICATE OF CORRECTION

PATENT NO. : 11,384,138 B2
APPLICATION NO. : 15/753321
DATED : July 12, 2022
INVENTOR(S) : Anderson et al.

It is certified that error appears in the above-identified patent and that said Letters Patent is hereby corrected as shown below:

In the Claims

In Claim 7, Column 187, Line 39 to Column 188, Line 13:
"b. anyone of the malaria antigens selected from MAL13P1.225, PF13 0203, PF11 0164, PFLO375W, PFI1270W, PF10 0104, PF13 0128, PF11 0058, PFA0490W, PF07 0087, PFB0570W, PF13 0180, PF11 0065, PF14 0678, PF13 0125, PF13 0141, PF14 0117, PF11 0098, PF14 0660, PFD0240C, PFE0080C, PFA0660W, PF11 0352, PF11 0055, PFB0475C, PF11 0302, PFA0210C, PF07 0089, PF14 0060, MAL8P1.17, MAL7P1.77, PF11 0099, PF07 0068, PF13 0201, PF07 0094, PF07 0006, PFLO770W, PFI1645C, PF14 0166, PFE0815W, PF11 0174, PFE0475W, PF11 0074, PFL1385C, PF14 0102, PF11 0212, PF07 0129, PFL2570W, PFL1070C, PFB0695C, PF11 0175, MAL13P1.22, PFLO035C, PFI0685W, PFD0425W, PF14 0293, PF14 0344, PFLO560C, PF07 0035, PFL1675C, PFC0435W, PFI1445W, PF13 0354, PFC0110W, PFC0120W, PF08 0078, PF14 0614, PF14 0051, PF11 0076, MALI 3P1.262, PFC0640W, PFL2520W, PFC0282W, PF08 0004, PF11 0224, PF13 0272, MALI 3P1.171, PFE1340W, PF14 0369, PF14 0178, PFLO870W, PFCO210C, PFI0500W, PF11 0069, PFD0355C, PFI0880C, PF11 0251, PFC0065C, PFC0925W, MAL13P1.121, PF13 0133, PFL2015W, PFD0440W, PFC0330W, PFD0430C, PF14 0462, PF07 0100, MAL7P1.23, PFL1835W, PF07 0047, PF14 0250, PFE0905W, PFA0180W, PFL1210W, PF14 0363, PFB0400W, PFI0920C, PF14 0094, PFA0125C, PF10 0372, PFL2315C, MALI 3P1.271, MAL7P1.31, PF10 0317, PF07 0070, MAL7P1.64, PFI0935W, PFA0160C, PFB0465C, PF10 0208, PFB0760W, MALI 3P1.206, PF14 0541, PFLO790W, PFL2410W, PF14 0440, PF11 0333, PF10 0242, PFC0590C, PF14 0342, MAL7P1.92, PF14 0593, MAL13P1.49, MAL13P1.172, PF08 0006, PFD1035W, PF11 0052, MAL13P1.79, PF10 0295, PFL1745C, PF14 0677, PFLO600W, PF08 0108, PF08 0081, PF14 0620, PFE0710W, PF11 0270, MAL7P1.149, PFC0810C, PF14 0249, PF13 0116, MAL13P1.60, PF11 0246, PFL2505C, PFB0405W, PF11 0256, PF08 0047, PFC0835C, PFI0605C, PF10 0127, PF11 0344, PF10 0130, PFL2395C, PF08 0008, PF14 0201, PFI1475W, PF13 0182, PF14 0495, or PF13 0277; and/or" should read
--b. any one of the malaria antigens selected from MAL13P1.225, PF13_0203, PF11_0164, PFL0375W, PFI1270W, PF10_0104, PF13_0128, PF11_0058, PFA0490W, PF07_0087, PFB0570W, PF13_0180, PF11_0065, PF14_0678, PF13_0125, PF13_0141, PF14_0117, PF11_0098, PF14_0660, PFD0240C, PFE0080C, PFA0660W, PF11_0352, PF11_0055, PFB0475C, PF11_0302, PFA0210C, Signed and Sealed this
Twenty-seventh Day of September, 2022

Katherine Kelly Vidal

Katherine Kelly Vidal
*Director of the United States Patent and Trademark Office*

PF07_0089, PF14_0060, MAL8P1.17, MAL7P1.77, PF11_0099, PF07_0068, PF13_0201, PF07_0094, PF07_0006, PFL0770W, PFI1645C, PF14_0166, PFE0815W, PF11_0174, PFE0475W, PF11_0074, PFL1385C, PF14_0102, PF11_0212, PF07_0129, PFL2570W, PFL1070C, PFB0695C, PF11_0175, MAL13P1.22, PFL0035C, PFI0685W, PFD0425W, PF14_0293, PF14_0344, PFL0560C, PF07_0035, PFL1675C, PFC0435W, PFI1445W, PF13_0354, PFC0110W, PFC0120W, PF08_0078, PF14_0614, PF14_0051, PF11_0076, MAL13P1.262, PFC0640W, PFL2520W, PFC0282W, PF08_0004, PF11_0224, PF13_0272, MAL13P1.171, PFE1340W, PF14_0369, PF14_0178, PFL0870W, PFC0210C, PFI0500W, PF11_0069, PFD0355C, PFI0880C, PF11_0251, PFC0065C, PFC0925W, MAL13P1.121, PF13_0133, PFL2015W, PFD0440W, PFC0330W, PFD0430C, PF14_0462, PF07_0100, MAL7P1.23, PFL1835W, PF07_0047, PF14_0250, PFE0905W, PFA0180W, PFL1210W, PF14_0363, PFB0400W, PFI0920C, PF14_0094, PFA0125C, PF10_0372, PFL2315C, MAL13P1.271, MAL7P1.31, PF10_0317, PF07_0070, MAL7P1.64, PFI0935W, PFA0160C, PFB0465C, PF10_0208, PFB0760W, MALI 3P1.206, PF14_0541, PFL0790W, PFL2410W, PF14_0440, PF11_0333, PF10_0242, PFC0590C, PF14_0342, MAL7P1.92, PF14_0593, MAL13P1.49, MALI 3P1.172, PF08_0006, PFD1035W, PF11_0052, MAL13P1.79, PF10_0295, PFL1745C, PF14_0677, PFL0600W, PF08_0108, PF08_0081, PF14_0620, PFE0710W, PF11_0270, MAL7P1.149, PFC0810C, PF14_0249, PF13_0116, MAL13P1.60, PF11_0246, PFL2505C, PFB0405W, PF11_0256, PF08_0047, PFC0835C, PFI0605C, PF10_0127, PF11_0344, PF10_0130, PFL2395C, PF08_0008, PF14_0201, PFI1475W, PF13_0182, PF14_0495, or PF13_0277; and/or--

In Claim 7, Column 188, Lines 16 to 28:
"000141, 000189, 000206, 000220, 000253, 000294, 000300, 000522, 000585, 000754, 014522, 014763, 014773, 014788, 014793, 014807, 014836, 014896, 014931, 014936, 014976, 014994, 015020, 015118, 015230, 015305, 015357, 015372, 015394, 015455, 015520, 043155, 043291, 043323, 043424, 043557, 043570, 043707, 043854, 043897, 043933, 060229, 060494, 060565, 060602, 060706, 060840, 060882, 075197, 075367, 075369, 075436, 075581, 075665, 075695, 075712, 075874, 075888, 075923, 075970, 076041, 076090, 094804, 095150, 095256, 095342, 095407, 095445, 095452, 095633, 095760, 095967," should read
--O00141, O00189, O00206, O00220, O00253, O00294, O00300, O00522, O00585, O00754, O14522, O14763, O14773, O14788, O14793, O14807, O14836, O14896, O14931, O14936, O14976, O14994, O15020, O15118, O15230, O15305, O15357, O15372, O15394, O15455, O15520, O43155, O43291,O43323, O43424, O43557, O43570, O43707, O43854, O43897, O43933, O60229, O60494, O60565, O60602, O60706, O60840, O60882, O75197, O75367, O75369, O75436, O75581, O75665, O75695, O75712, O75874, O75888, O75923, O75970, O76041, O76090, O94804, O95150, O95256, O95342, O95407, O95445, O95452, O95633, O95760, O95967,--

In Claim 7, Column 188, Line 59:
"POCOL4, POCOLS, PODJI8, PODJI9," should read
--P0C0L4, P0C0L5, P0DJI8, P0DJI9,--

In Claim 7, Column 190, Line 44:
"MAGE-A1 1" should read --MAGE-A11--

In Claim 10, Column 191, Line 30:
"in vitro" should read -- *in vitro* --
In Claim 10, Column 191, Line 32:

"in vitro" should read -- *in vitro* --